United States Patent
Kimura et al.

(10) Patent No.: US 7,737,141 B2
(45) Date of Patent: Jun. 15, 2010

(54) PRODRUG OF CINNAMIDE COMPOUND

(75) Inventors: Teiji Kimura, Tsukuba (JP); Koki Kawano, Tsukuba (JP); Noritaka Kitazawa, Tsukuba (JP); Nobuaki Sato, Tsukuba (JP); Toshihiko Kaneko, Tsukuba (JP); Koichi Ito, Tsukuba (JP); Mamoru Takaishi, Tsukuba (JP); Ikuo Kushida, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 532 days.

(21) Appl. No.: 11/878,556

(22) Filed: Jul. 25, 2007

(65) Prior Publication Data
US 2009/0048213 A1 Feb. 19, 2009

Related U.S. Application Data

(60) Provisional application No. 60/820,761, filed on Jul. 28, 2006, provisional application No. 60/869,259, filed on Dec. 8, 2006.

(30) Foreign Application Priority Data

Jul. 28, 2006 (JP) ............................. 2006-206007
Dec. 8, 2006 (JP) ............................. 2006-331274

(51) Int. Cl.
A61K 31/535 (2006.01)
A61K 31/44 (2006.01)
C07D 413/14 (2006.01)
C07D 221/02 (2006.01)

(52) U.S. Cl. .............. 514/232.2; 514/233.2; 514/235.5; 514/235.8; 514/299; 514/306; 544/131; 544/127; 544/139; 544/111; 546/183

(58) Field of Classification Search .............. 514/235.5, 514/299, 233.2, 235.8, 306, 232.2; 544/131, 544/127, 139, 111; 546/183
See application file for complete search history.

(56) References Cited

U.S. PATENT DOCUMENTS

| 4,910,200 | A | 3/1990 | Curtze et al. |
| 5,281,626 | A | 1/1994 | Oinuma et al. |
| 5,563,162 | A | 10/1996 | Oku et al. |
| 5,985,856 | A | 11/1999 | Stella et al. |
| 6,235,728 | B1 | 5/2001 | Golik et al. |
| 6,306,870 | B1 | 10/2001 | Bombrun et al. |
| 7,053,087 | B1 | 5/2006 | Beatch et al. |
| 7,138,414 | B2 | 11/2006 | Schoenafinger et al. |
| 7,300,936 | B2 | 11/2007 | Parker et al. |
| 7,314,940 | B2 | 1/2008 | Graczyk et al. |
| 7,618,960 | B2 | 11/2009 | Kimura et al. |
| 7,667,041 | B2 | 2/2010 | Kimura et al. |
| 2001/0051642 | A1 | 12/2001 | Ahn |
| 2002/0128263 | A1 | 9/2002 | Mutel et al. |
| 2003/0195201 | A1 | 10/2003 | Bo et al. |
| 2003/0208082 | A1 | 11/2003 | Mutel et al. |
| 2003/0225070 | A1 | 12/2003 | Mutel et al. |
| 2004/0034096 | A1 | 2/2004 | Jolidon et al. |
| 2004/0038969 | A1 | 2/2004 | Doherty et al. |
| 2004/0063770 | A1 | 4/2004 | Ahn et al. |
| 2004/0087798 | A1 | 5/2004 | Yamada |
| 2004/0127494 | A1 | 7/2004 | Parker et al. |
| 2004/0127555 | A1 | 7/2004 | Snow et al. |
| 2004/0152743 | A1 | 8/2004 | Schoenafinger et al. |
| 2004/0192743 | A1 | 9/2004 | Mjalli et al. |
| 2004/0235864 | A1 | 11/2004 | Graczyk et al. |
| 2005/0070538 | A1 | 3/2005 | Cheng et al. |
| 2005/0131043 | A1 | 6/2005 | Mutel et al. |
| 2005/0187277 | A1 | 8/2005 | Mjalli et al. |
| 2006/0004013 | A1 | 1/2006 | Kimura et al. |
| 2007/0117798 | A1 | 5/2007 | Kimura et al. |
| 2007/0117839 | A1 | 5/2007 | Kimura et al. |
| 2007/0219181 | A1 | 9/2007 | Kimura et al. |
| 2008/0070902 | A1 | 3/2008 | Kimura et al. |
| 2008/0085894 | A1 | 4/2008 | Parker et al. |
| 2008/0096892 | A1 | 4/2008 | Cheng et al. |
| 2008/0280948 | A1 | 11/2008 | Baumann et al. |
| 2009/0048213 | A1 | 2/2009 | Kimura et al. |
| 2009/0048448 | A1 | 2/2009 | Kushida et al. |
| 2009/0203916 | A1 | 8/2009 | Kushida et al. |
| 2009/0270623 | A1 | 10/2009 | Shimomura et al. |

FOREIGN PATENT DOCUMENTS

DE 3 541 716 A1 5/1987

(Continued)

OTHER PUBLICATIONS

Official Action dated Jul. 4, 2008, which issued in corresponding Russian Patent Application No. 2006146070.

(Continued)

*Primary Examiner*—Rebecca L Anderson
(74) *Attorney, Agent, or Firm*—Birch, Stewart, Kolasch & Birch, LLP

(57) ABSTRACT

The present invention provides a most suitable prodrug of a cinnamide compound. The prodrug is represented by Formula (I)

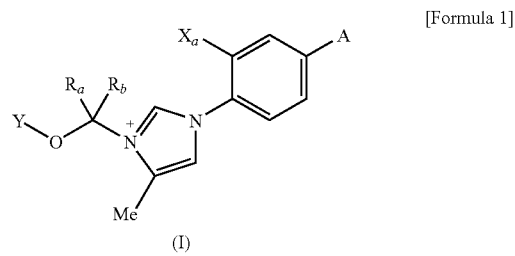

wherein $R_a$ and $R_b$ each denote a C1-6 alkyl group or the like; $X_a$ denotes a methoxy group or a fluorine atom; Y denotes a phosphono group or the like; and A denotes a cyclic lactam derivative.

22 Claims, No Drawings

FOREIGN PATENT DOCUMENTS

| | | |
|---|---|---|
| EP | 0 219 756 | 4/1987 |
| EP | 1 264 820 | 12/2002 |
| EP | 0 973 768 B1 | 7/2003 |
| EP | 1 757 591 A1 | 2/2007 |
| EP | 1 808 432 A1 | 7/2007 |
| EP | 1 953 151 A1 | 8/2008 |
| EP | 1 953 158 A1 | 8/2008 |
| GE | P 2006 3920 B | 5/2006 |
| GE | P-20084571 B | 12/2008 |
| JP | 3-206042 A | 9/1991 |
| JP | 8-283219 A | 10/1996 |
| JP | 10-510512 A | 10/1998 |
| JP | 11-228548 A | 8/1999 |
| JP | 3176365 B2 | 4/2001 |
| JP | 2001-508767 A | 7/2001 |
| JP | 2001-527083 A | 12/2001 |
| JP | 2003-206280 A | 7/2003 |
| JP | 2004-531519 A | 10/2004 |
| JP | 2005-518371 A | 6/2005 |
| JP | 2005-526807 A | 9/2005 |
| JP | 2005-531596 A | 10/2005 |
| JP | 2005-533092 A | 11/2005 |
| JP | 7-2780 A | 12/2005 |
| JP | 2006-502247 A | 1/2006 |
| JP | 2007-504282 T | 3/2007 |
| RU | 2001126135 A | 7/2003 |
| WO | WO-91/12237 A1 | 8/1991 |
| WO | WO-96/10559 A1 | 4/1996 |
| WO | WO-97/43287 | 11/1997 |
| WO | WO-98/03166 A1 | 1/1998 |
| WO | WO-98-24785 A1 | 6/1998 |
| WO | WO-00/07993 A1 | 2/2000 |
| WO | WO-00/50391 A1 | 8/2000 |
| WO | WO-00/51981 A1 | 9/2000 |
| WO | WO-01/68585 A1 | 9/2001 |
| WO | WO-01/81312 A2 | 11/2001 |
| WO | WO-03/053912 A1 | 7/2003 |
| WO | WO-03/082292 A1 | 10/2003 |
| WO | WO-03/101927 A1 | 12/2003 |
| WO | WO-2004/007429 | 1/2004 |
| WO | WO-2004/007455 A1 | 1/2004 |
| WO | WO-2005/020921 A2 | 3/2005 |
| WO | WO-2005/063754 A1 | 7/2005 |
| WO | WO-2005/115990 A1 | 8/2005 |
| WO | WO-2006/046575 A1 | 5/2006 |
| WO | WO-2006/112550 A2 | 10/2006 |
| WO | WO-2007/034282 A2 | 3/2007 |
| WO | WO-2007/060810 A1 | 5/2007 |
| WO | WO-2007/102580 A1 | 9/2007 |
| WO | WO-2008/013213 A1 | 1/2008 |
| WO | WO-2008/097538 A1 | 8/2008 |
| WO | WO-2008/137139 A1 | 11/2008 |
| WO | WO-2008/156580 A1 | 12/2008 |
| WO | WO-2009/020580 A1 | 2/2009 |

OTHER PUBLICATIONS

Official Action issued on Nov. 14, 2008, in corresponding Russian Patent Application No. 2006146070.

T. A. Comery, The Journal of Neuroscience, Sep. 28, 2005, 25(39): 8898-8902.

T. A. Comery et al., Society for Neuroscience Annual Meeting (2003), Abstracts, Program No. 525.21.

Official Action issued Jan. 22, 2010, in Peruvian Patent Application No. 001480-2006.

Office Action issued Jan. 19, 2010, in copending U.S. Appl. No. 11/596,723.

J. G. Varnes et al., Bioorganic & Medicinal Chemistry Letters, 14 (2004) 1645-1649.

H. Stark et al., Pharmazie 52 (1997), vol. 6, pp. 419-423.

M. Kajbaf et al., Journal of Chromatography, 575 (1992) 75-85.

S. L. Marcus, Cancer Research, 45, 112-115, Jan. 1995.

H. L. Yale, J. Med. Chem., 1966, 9(1), 42-46.

S. M. Catalano et al., "The Role of Amyloid-Beta Derived Diffusible Ligands (ADDLs) in Alzheimer's Disease," Current Topics in Medicinal Chemistry, vol. 6, 597-608 (2006).

Search Report issued May 27, 2009, in connection with Georgia Patent Application No. AP 2006 010709 (with English translation).

Yuesong Gong et al.; Proceeding National Academy of Science, vol. 100, No. 18, pp. 10417-10422, Sep. 2, 2003.

Christoph Hock et al.; Neuron, vol. 38, No. 4, pp. 547-554, May 22, 2003.

Joseph T. Jarrett et al.; Biochemistry; vol. 32, No. 18, pp. 4693-4697, May 11, 1993.

George G. Glenner et al.; Biochemical and Biophysical Research Communications; vol. 120, No. 3, pp. 885-890, May 16, 1984.

Colin L. Masters et al.; Proceeding National Academy of Science; vol. 82, No. 12, pp. 4245-4249, Jun. 1985.

Gunnar K. Gouras et al.; American Journal of Pathology, vol. 156, No. 1, pp. 15-20, Jan. 2000.

D. Scheuner et al.; Nature Medicine, vol. 2, No. 8, pp. 864-870, Aug. 1996.

Mark S. Forman et al.; The Journal of Biological Chemistry; vol. 272, No. 51, pp. 32247-32253, Dec. 19, 1997.

Mark S. Shearman et al.; Biochemistry; vol. 39, No. 30, pp. 8698-8704, 2000.

Huw D. Lewis et al.; Biochemistry, vol. 42, No. 24, pp. 7580-7586, 2003.

Thomas A. Lanz et al., The Journal of Pharmacology and Experimental Therapeutics; vol. 39, No. 1, pp. 49-55, 2004.

Gwendolyn T. Wong et al.; The Journal of Biological Chemistry, vol. 279, No. 13, pp. 12876-12882, Mar. 26, 2004.

John P. Blass; Journal of Neuroscience Research, vol. 66, No. 1, pp. 851-856, 2001.

Genevieve Evin et al.; NeuroReport; vol. 13, No. 5, pp. 719-723, Apr. 16, 2002.

Osamu Yasuhara et al.; Neuroscience Letters, vol. 171, Nos. 1 and 2, pp. 63-66, 1994.

Jan T. Teller et al.; Nature Medicine, vol. 2, No. 1, pp. 93-95, Jan. 1996.

Takahiko Tokuda et al.; Annals Neurology, vol. 41, No. 2, pp. 271-273, Feb. 1997.

Yorihide Hayashi et al.; Brain Research; vol. 789, No. 2, pp. 307-314, 1998.

Helene Barelli et al.; Molecular Medicine, vol. 3, No. 10, pp. 695-707, Oct. 1997.

Michael E. Calhoun et al.; Proceeding National Academy of Science, vol. 96, No. 24, pp. 14088-14093, Nov. 23, 1999.

B. Dermaut et al.; Brain, vol. 124, No. 12, pp. 2383-2392, 2001.

P. Cras et al.; Acta Neuropathol, vol. 96, No. 3, pp. 253-260, 1998.

Martin C. Herzig et al.; Nature Neuroscience, vol. 7, No. 9, pp. 954-960, Sep. 2004.

Sjoerd G. Van Duinen et al.; Proceeding National Academy of Science, vol. 84, No. 16, pp. 5991-5994, Aug. 1987.

Efrat Levy et al.; Science, vol. 248, No. 4959, pp. 1124-1126, 1990.

Simon M. Laws et al.; Neurobiology of Aging, vol. 23, No. 1, pp. 55-58, 2002.

E. Vaucher et al.; Experimental Neurology, vol. 175, No. 2, pp. 398-406, 2002.

Dave Morgan et al.; Nature, vol. 408, No. 6815, pp. 982-985, Dec. 2000.

Paula M. Moran et al.; Proceeding National Academy of Science, vol. 92, No. 12, pp. 5341-5345, 2002.

Milla Koistinaho et al.; Proceeding National Academy of Science, vol. 99, No. 3, pp. 1610-1615, Feb. 5, 2002.

Fangyi Zhang et al.; The Journal of Neuroscience, vol. 17, No. 20, pp. 7655-7661, Oct. 15, 1997.

Marcin Sadowski et al.; Neurochemical Research, vol. 29, No. 6, pp. 1257-1266, Jun. 2004.

S. O'Riordan et al.; Neurology, vol. 59, No. 7, pp. 1108-1110, Oct. 2002.

Jochen Gehrmann et al.; Glia; vol. 15, No. 2, pp. 141-151, 1995.

Wanda F. Reynolds et al.; Experimental Neurology, vol. 155, No. 1, pp. 31-41, 1999.

Douglas H. Smith et al.; NeuroMolecular Medicine, vol. 4, No. 1 and 2, pp. 59-72, 2003.

Miho Matsubara-Tsutsui et al.; American Journal of Medical Genetics, vol. 114, No. 3, pp. 292-298, 2002.

Marina D. Kirkitadze et al.; Journal of Neuroscience Research, vol. 69, No. 5, pp. 567-577, 2002.

Bernd O. Evert at al.; The Journal of Neuroscience, vol. 21, No. 15, pp. 5389-5396, Aug. 1, 2001.

D.M.A. Mann et al.; Neuroscience Letters, vol. 109, No. 1 and 2, pp. 68-75, 1990.

James Primavera et al.; Journal of Alzheimer's Disease, vol. 1, No. 3, pp. 183-193, 1999.

Benoit I. Giasson at al.; NeuroMolecular Medicine, vol. 4, No. 1 and 2, pp. 49-58, 2003.

Eliezer Masliah et al.; Proceeding National Academy of Science; vol. 98, No. 21, pp. 12245-12250, Oct. 9, 2001.

Marta Barrachina et al.; Neurochemistry International; vol. 46, No. 3, pp. 253-260, 2005.

M.L. Schmidt et al.; Acta Neuropathol, vol. 95, No. 2, pp. 117-122, 1998.

H. Ito et al.; Neuropathology and Applied Neurobiology, vol. 17, No. 5, pp. 365-373, 1991.

S.M. Rosso et al.; Annals of the New York Academy of Science, vol. 920, pp. 115-119, 2000.

M. Tolnay et al.; Neuropathology and Applied Neurobiology, vol. 25, No. 4, pp. 295-305, 1999.

Lee-Way Jin et al.; American Journal of Pathology, vol. 164, No. 3, pp. 975-985, Mar. 2004.

Shoichi Sasaki et al.; Acta Neuropathol, vol. 97, No. 5, pp. 463-468, 1999.

A. Tamaoka et al.; Journal of Neurology, vol. 247, No. 8, pp. 633-635, 2000.

Ronald L. Hamilton et al.; Acta Neuropathol, vol. 107, No. 6, pp. 515-522, 2004.

Bradley J. Turner et al.; Neurochemical Research, vol. 29, No. 12, pp. 2281-2286, 2004.

Roy O. Weller; Journal of Neuropathology and Experimental Neurology, vol. 57, No. 10, pp. 885-894, Oct. 1998.

Gerald D. Silverberg et al.; Lancet Neurology, vol. 2, No. 8, pp. 506-511, Aug. 2003.

Roy O. Weller et al.; Annals of the New York Academy of Science, vol. 903, pp. 110-117, 2000.

H.Y. Yow et al.; Neuropathology and Applied Neurobiology; vol. 28, p. 149, 2002.

Roy O. Weller et al.; Annals of the New York Academy of Science, vol. 977, pp. 162-168, 2002.

Margaret J. Smith et al.; Annals of Neurology, vol. 49, No. 1, pp. 125-129, 2001.

Richard Crook et al.; Nature Medicine, vol. 4, No. 4, pp. 452-455, Apr. 1998.

Craig S. Atwood, Brain Research Review; vol. 43, No. 1, pp. 164-178, 2003.

Jonathan D. Lowenson et al.; Trends in Cardiovascular Medicine, vol. 4, No. 1, pp. 3-8, 1994.

Andrew B. Singleton et al.; vol. 123, No. 12, pp. 2467-2474, 2000.

W.F. Gattaz et al.; Journal of Neural Transmission, vol. 111, No. 5, pp. 591-601, 2004.

A. Assini et al.; Neurology, vol. 63, No. 5, pp. 828-831, 2004.

Guido R.Y. DeMeyer et al.; Circulation Research, vol. 90, No. 11, pp. 1197-1204, 2002.

Masahiko Kato et al., Chem. Pharm. Bull., 42 (12), 2546-2555 (1994).

The International Search Report for International Appl. No. PCT/JP2008/053887, mailed Sep. 19, 2008.

An Office Action from Russian Patent Appl. No. 2008125426/04(030920), date Jun. 1, 2009.

An Office Action from U.S. Appl. No. 11/715,440, dated Jul. 16, 2009.

An Office Action from U.S Appl. No. 12/200,731, dated Jul. 30, 2009.

Guiroy, Acta Neuropathol (1991) 82:87-92.

Ross, J. Med. Chem., 1973, vol. 16, No. 4, 347-352.

Office Action dated Sep. 16, 2008, that issued in connection with copending U.S. Appl. No. 11/594,150.

Office Action dated Jul. 11, 2008, that issued in connection with copending U.S. Appl. No. 11/136,355.

Georgia Office Action in Application No. 87447 issued Oct. 1, 2009, and translation.

PRODRUG OF CINNAMIDE COMPOUND

RELATED APPLICATIONS

The present application claims priority from U.S. provisional application Ser. No. 60/820,761 filed on Jul. 28, 2006, U.S. provisional application Ser. No. 60/869,259 filed on Dec. 8, 2006, Japanese patent application no. 2006-206007 filed on Jul. 28, 2006, and from Japanese patent application no. 2006-331274 filed on Dec. 8, 2006, which are expressly incorporated herein by reference.

BACKGROUND OF THE INVENTION (1) Field of the Invention

The present invention relates to novel prodrugs of cinnamide compounds and drugs containing the same as active ingredients. The prodrugs and the drugs are useful for treating diseases caused by amyloid β (hereinafter referred to as Aβ), which are represented by Alzheimer's disease, and are suitable for oral or parenteral administration. More specifically, the present invention relates to novel prodrugs of cinnamide compounds, pharmacologically acceptable salts thereof, and drugs containing the same as active ingredients, wherein water solubility of the cinnamide compounds is increased by converting the imidazole moiety of cinnamide compound molecules into a quaternary salt form.

(2) Description of Related Art

Aβ proteins, which are metabolites of amyloid precursor proteins (hereinafter referred to as APP), are thought to be highly involved in alteration or exfoliation of nerve cells and also in expression of dementia. The main components of the Aβ proteins are Aβ40 consisting of 40 amino acids and Aβ42 having additional two amino acids at the C-terminal of the Aβ40. These Aβ40 and Aβ42 are highly aggregative and are main components of senile plaques. Further, it is known that mutation in APP or a presenilin gene, which is observed in familial Alzheimer's disease, increases the amounts of these Aβ40 and Aβ42. Therefore, a compound which can inhibit the synthesis of Aβ40 and Aβ42 from APP is expected as a therapeutic or preventive agent for diseases caused by Aβ, such as Alzheimer's disease. The present inventors have found cinnamide compounds as non-peptide compounds inhibiting the synthesis of Aβ40 and Aβ42 and having excellent drug activity (for example, International Publication No. WO05/115990).

Generally, in some compounds, the usefulness as a drug is restricted by their low water solubility. For example, it is broadly known that some azole compounds, which are famous antifungal agents, have low water solubility and thereby are prevented from development as parenteral agents.

A method for solving this problem is disclosed in U.S. Pat. No. 6,235,728, for example. According to this, the water solubility of an azole antifungal agent can be increased by binding a phosphonooxymethyl group to the azole moiety. In addition, prodrugs having a similar phosphonooxymethyl group or derivatives thereof represented by the following formula are disclosed in Yasutsugu Ueda and 21 others, Phosphonomethyl Prodrugs of the Broad Spectrum antifungal Azole, Ravuconazole: Synthesis and Biological Properties. Bioorganic & Medicinal Chemistry Letters 2003, 13, 3669-3672.

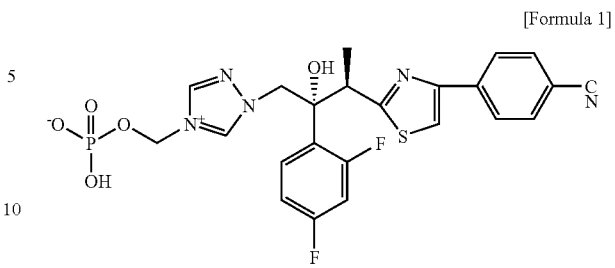

[Formula 1]

Further, Professor Stella Valentino's team from the University of Kansas discloses in International Publication No. WO99/33846 (Claims, page 48, lines 3 to 10) the compound represented by the formula (VIa),

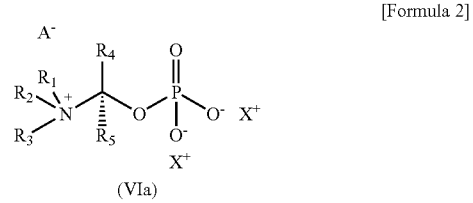

[Formula 2]

wherein, $R^1$, $R^2$ and $R^3$ represent substituents containing the tertiary or secondary amine of a parent compound, and $R^4$ and $R^5$ are an organic or an inorganic residue. This compound is generally described as having an external anion (A) associated with a quaternary amine center and an external cation associated with a phosphate dual anionic charge (page 18, line 28 to page 24, line 11 in the specification). Among such compounds, examples of medicinal compounds having a quaternary amine classified as an aromatic species are illustrated in the specification at page 22, line 1 to page 23, line 3. Illustrated examples include, for instance, miconazole having an imidazolyl group.

However, this publication lacks any disclosure either in the illustrated compounds or in the compounds described in the Examples of a cinnamide derivative containing an imidazolyl group, which is a characteristic feature of the present invention, and fails to either disclose or suggest the compound according to the present invention.

In addition, in International Publication No. WO98/43970, compounds, for example, represented by the following formula are disclosed as prodrugs of antifungal compounds,

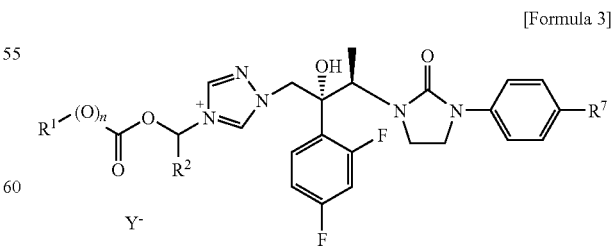

[Formula 3]

wherein $R^1$ denotes an alkyl group or the like, $R^2$ denotes a hydrogen atom, an alkyl group, or the like, and $R^7$ denotes a triazolyl group, a tetrazolyl group, or the like.

As described above, though quaternary ammonium prodrugs of azole antifungal agents have been reported, quaternary salt prodrugs of phenylimidazole derivatives which are commonly observed in a cinnamide compound structure have not been reported yet.

BRIEF SUMMARY OF THE INVENTION

As described above, cinnamide compounds which inhibit the synthesis of Aβ40 and Aβ42 from APP are expected as therapeutic or preventive agents for diseases caused by Aβ, such as Alzheimer's disease. That is, prodrugs of cinnamide compounds of which usefulness as drugs is further enhanced by increasing the water solubility of the cinnamide compounds are expected.

Therefore, an object of the present invention to provide a prodrug of a cinnamide compound and a drug containing the same as an active ingredient, wherein the water solubility of the cinnamide compound is increased, and the usefulness of the cinnamide compound as a drug is further enhanced.

The present inventors have conducted intensive studies and have found the fact that the water solubility of a cinnamide compound can be highly improved by introducing a quaternary salt into the imidazole moiety of the cinnamide compound molecule. Thus, the present invention has been completed.

The present invention provides 1) a compound represented by Formula (I) or its pharmacologically acceptable salt:

[Formula 4]

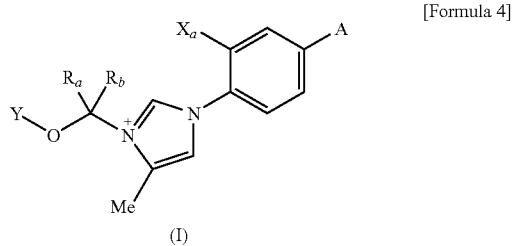

(I)

wherein $R_a$ and $R_b$ are the same or different and each denote a hydrogen atom or a C1-6 alkyl group;

$X_a$ denotes a methoxy group or a fluorine atom;

Y denotes —CO—(O)$_n$—$R_c$.$M_a^-$, wherein $R_c$ denotes a C1-6 alkyl group, 6- to 14-membered aromatic hydrocarbon ring group, 5- to 14-membered aromatic heterocyclic group, 6- to 14-membered non-aromatic hydrocarbon ring group, or 5- to 14-membered non-aromatic heterocyclic group which may be substituted with the same or different 1 to 5 substituents selected from Substituent Group A1; n is 0 or 1; and $M_a^-$ denotes an anion, —P(=O) (O$R_d$)$_2$.$M_a^-$, wherein $R_d$ denotes a C1-6 alkyl group which may be substituted with the same or different 1 to 3 substituents selected from Substituent Group A2, and $M_a^-$ denotes an anion, —P(=O) (OH)$_2$.$M_a^-$, wherein $M_a^-$ denotes an anion, —P(=O) (—O$^-$) (OH), or —P(=O)(—O$^-$)(—O$^-$.$M_b^+$), wherein $M_b^+$ denotes a cation;

A is represented by Formula (A-1):

[Formula 5]

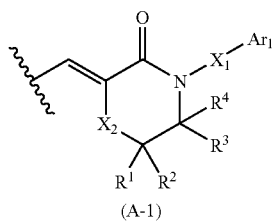

(A-1)

wherein (a) $R^1$, $R^2$, $R^3$, and $R^4$ are the same or different and each denote a hydrogen atom or a C1-6 alkyl group, $X_1$ denotes a C1-6 alkylene group which may be substituted with 1 to 3 hydroxy or C1-6 alkyl groups which may be substituted with 1 to 3 hydroxy groups, $X_2$ denotes an oxygen atom or a methylene group which may be substituted with 1 or 2 C1-6 alkyl groups, and $Ar_1$ denotes —$X_{1-a}$—$Ar_{1-a}$, wherein $Ar_{1-a}$ denotes a 6- to 14-membered aromatic hydrocarbon ring or 5- to 14-membered aromatic heterocyclic group which may be substituted with the same or different 1 to 3 substituents selected from Substituent Group A2, and $X_{1-a}$ denotes a single bond or an oxygen atom; or (b) $R^1$, $R^2$, $R^3$, $R^4$, and $X_2$ are the same as defined above, and $Ar_1$-$X_1$— denotes a C3-8 cycloalkyl group which has a methylene group which may be substituted with an oxygen atom condensed with a benzene ring which may be substituted with the same or different 1 to 3 substituents selected from Substituent Group A2, or A is represented by Formula (A-2):

[Formula 6]

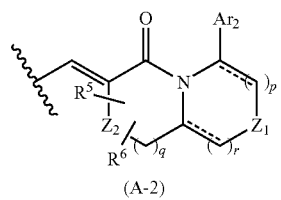

(A-2)

wherein ⚌ denotes a single bond or a double bond; $Ar_2$ denotes a 6- to 14-membered aromatic hydrocarbon ring or 5- to 14-membered aromatic heterocyclic group which may be substituted with the same or different 1 to 3 substituents selected from Substituent Group A2; $R^5$ and $R^6$ are the same or different and each denote a substituent selected from Substituent Group A2; $Z_1$ and $Z_2$ are the same or different and each denote a methylene or vinylene group which may be substituted with the same or different 1 or 2 substituents selected from Substituent Group A2, an oxygen atom, or an imino group which may be substituted with a C1-6 alkyl or C1-6 acyl group; and p, q, and r are the same or different and each denote an integer of 0 to 2, wherein Substituent Group A1 consists of (1) hydroxy groups, (2) cyano groups, (3) C3-8 cycloalkoxy groups, (4) C1-6 alkoxy groups which may be each substituted with 1 to 3 substituents selected from the group consisting of halogen atoms, hydroxy groups, cyano groups, C3-8 cycloalkyl groups, and C3-8 cycloalkoxy groups, (5) amino groups which may be each substituted with 1 or 2 C1-6 alkyl groups which may be each substituted with 1 to 3 halogen atoms, (6) carbamoyl groups which may be each substituted with 1 or 2 C1-6 alkyl groups which may be each substituted with 1 to 3 halogen atoms, (7) carboxyl groups, (8) pyridinyl groups, and (9) sugar residues; and Substituent Group A2 consists of (1) halogen atoms, (2) hydroxy groups, (3) cyano groups, (4) C3-8 cycloalkyl groups, (5) C3-8 cycloalkoxy groups, (6) C1-6 alkyl groups which may be each substituted with 1 to 3 substituents selected from the group consisting of halogen atoms, hydroxy groups, cyano groups, C3-8 cycloalkyl groups, C1-6 alkoxy groups, and C3-8 cycloalkoxy groups, (7) C1-6 alkoxy groups which may be each substituted with 1 to 3 substituents selected from the group consisting of halogen atoms, hydroxy groups, cyano groups, C3-8 cycloalkyl groups, and C3-8 cycloalkoxy groups, (8) amino groups which may be each substituted with 1 or 2 C1-6 alkyl groups which may be each substituted with 1 to 3 halogen atoms, and (9) carbamoyl groups which may be each substituted with 1 or 2 C1-6 alkyl groups which may be each substituted with 1 to 3 halogen atoms.

The present invention further provides:

2) the compound or its pharmacologically acceptable salt according to the above 1), in which $X_a$ denotes a methoxy group;

3) the compound or its pharmacologically acceptable salt according to the above 1), in which $X_a$ denotes a fluorine atom;

4) the compound or its pharmacologically acceptable salt according to the above 1), in which Y denotes —P(=O) $(OH)_2 \cdot M_a^-$, wherein $M_a^-$ denotes an anion, —P(=O)(—O$^-$)(OH), or —P(=O)(—O$^-$)(—O$^- \cdot M_b^+$), wherein $M_b^+$ denotes a cation;

5) the compound or its pharmacologically acceptable salt according to the above 1), in which $Ar_1$ denotes a 6- to 14-membered aromatic hydrocarbon ring or 5- to 14-membered aromatic heterocyclic group which may be substituted with the same or different 1 to 3 substituents selected from the aforementioned Substituent Group A2;

6) the compound or its pharmacologically acceptable salt according to the above 1), in which $Ar_1$ denotes a phenyl or pyridinyl group which may be substituted with the same or different 1 to 3 substituents selected from the aforementioned Substituent Group A2;

7) the compound or its pharmacologically acceptable salt according to the above 1), in which $Ar_1$ denotes a phenyl group, a pyridinyl group, or a phenyl or pyridinyl group which has been substituted with 1 to 3 halogen atoms;

8) the compound or its pharmacologically acceptable salt according to the above 1), in which $X_1$ denotes =CH—CH (OH)—$R^7$, wherein $R^7$ denotes a C1-6 alkyl group);

9) the compound or its pharmacologically acceptable salt according to the above 1), in which $X_2$ denotes a methylene group;

10) the compound or its pharmacologically acceptable salt according to the above 1), in which $X_2$ denotes an oxygen atom;

11) the compound or its pharmacologically acceptable salt according to the above 1), in which $Z_1$ and $Z_2$ are the same or different and each denote an oxygen atom or a methylene group which may be substituted with 1 or 2 of C1-6 alkyl groups, halogen atoms, and hydroxy groups; and $R^5$ and $R^6$ are the same or different and each denote a C1-6 alkyl group, a halogen atom, or a hydrogen atom;

12) the compound or its pharmacologically acceptable salt according to the above 11), in which $Z_1$ and $Z_2$ are the same or different and each denote a methylene group which may be substituted with 1 or 2 of C1-6 alkyl groups, halogen atoms, and hydroxy groups; and p, q, and r are each 1;

13) the compound or its pharmacologically acceptable salt according to the above 11), in which $Z_1$ and $Z_2$ are the same or different and each denote a methylene group which may be substituted with 1 or 2 of C1-6 alkyl groups, halogen atoms, and hydroxy groups; p and q are each 1; and r is 0;

14) the compound or its pharmacologically acceptable salt according to the above 11), in which $Z_1$ denotes a methylene group which may be substituted with 1 or 2 of C1-6 alkyl groups, halogen atoms, and hydroxy groups; $Z_2$ denotes an oxygen atom; and p, q, and r are each 1;

15) the compound or its pharmacologically acceptable salt according to the above 11), in which $Z_1$ denotes an oxygen atom; $Z_2$ denotes a methylene group which may be substituted with 1 or 2 of C1-6 alkyl groups, halogen atoms, and hydroxy groups; and p, q, and r are each 1;

16) the compound or its pharmacologically acceptable salt according to the above 11), in which $Z_1$ denotes an oxygen atom; $Z_2$ denotes an oxygen atom; and p, q, and r are each 1;

17) the compound or its pharmacologically acceptable salt according to the above 11), in which $Ar_2$ denotes a phenyl group which has been substituted with 1 to 3 halogen atoms;

18) the compound or its pharmacologically acceptable salt according to the above 11), in which $Ar_2$ denotes a phenyl group which has been substituted with 2 or 3 halogen atoms;

19) the compound or its pharmacologically acceptable salt according to the above 1), in which $R^5$ and $R^6$ are the same or different and each denote 1 or 2 of C1-6 alkyl groups, halogen atoms, and hydrogen atoms;

20) the compound or its pharmacologically acceptable salt according to the above 1), which is selected from the following group consisting of:

1) 3-{4-{1-[(S)-1-(4-fluorophenyl)ethyl]-2-oxopiperidin-(3E)-ylidenemethyl}-2-methoxyphenyl}-5-methyl-1-(phosphonooxymethyl)-3H-imidazol-1-ium trifluoroacetate, 2) 1-acetoxymethyl-3-{4-{1-[(S)-1-(4-fluorophenyl)ethyl]-2-oxopiperidin-(3E)-ylidenemethyl}-2-methoxyphenyl}-5-methyl-3H-imidazol-1-ium iodide, 3) 3-{4-{1-[(1R,2R)-2-hydroxy-1-(3,4,5-trifluorophenyl)propyl]-2-oxopiperidin-(3E)-ylidenemethyl}-2-methoxyphenyl}-5-methyl-1-(phosphonooxymethyl)-3H-imidazol-1-ium trifluoroacetate, 4) 3-[2-fluoro-4-[(S)-4-[(1R,2R)-2-hydroxy-1-(3,4,5-trifluorophenyl)propyl]-6-methyl-3-oxomorpholin-(2Z)-ylidenemethyl]phenyl]-5-methyl-1-phosphonooxymethyl-3H-imidazol-1-ium trifluoroacetate, 5) 3-{2-methoxy-4-[(3S,8aS)-5-oxo-3-(3,4,5-trifluorophenyl)hexahydroindolizin-(6E)-ylidenemethyl]phenyl}-5-methyl-1-phosphonooxymethyl-3H-imidazol-1-ium trifluoroacetate, 6) 3-{4-{(S)-4-[(S)-1-(2,6-difluoropyridin-3-yl)ethyl]-6-methyl-3-oxomorpholin-(2Z)-ylidenemethyl}-2-methoxyphenyl}-5-methyl-1-phosphonooxymethyl-3H-imidazol-1-ium chloride, 7) 3-{4-[(3S,8aS)-3-(4-chlorophenyl)-5-oxohexahydroindolizin-(6E)-ylidenemethyl]-2-methoxyphenyl}-5-methyl-1-(phosphonooxymethyl)-3H-imidazol-1-ium trifluoroacetate, 8) 3-{4-{(S)-4-[(1R,2R)-1-(3,4-difluorophenyl)-2-hydroxypropyl]-6-methyl-3-oxomorpholin-(2Z)-ylidenemethyl}-2-fluorophenyl}-5-methyl-1-phosphonooxymethyl-3H-imidazol-1-ium trifluoroacetate, 9) 3-{2-methoxy-4-[(6S,9aS)-4-oxo-6-(3,4,5-trifluorophenyl)hexahydroquinolizin-(3E)-ylidenemethyl]phenyl}-5-methyl-1-(phosphonooxymethyl)-3H-imidazol-1-ium trifluoroacetate, 10) 3-{2-methoxy-4-[(4R,9aS)-6-oxo-4-(3,4,5-trifluorophenyl)hexahydropyrido[2,1-c][1,4]oxazin-(7E)-ylidenemethyl]phenyl}-5-methyl-1-phosphonooxymethyl-3H-imidazol-1-ium trifluoroacetate, 11) 3-{4-{(S)-4-[(1R,2R)-2-hydroxy-1-(3,4,5-trifluorophenyl)propyl]-6-methyl-3-oxomorpholin-(2Z)-ylidenemethyl}-2-methoxyphenyl}-5-methyl-1-(phosphonooxymethyl)-3H-imidazol-1-ium_trifluoroacetate, 12) 3-{4-[(6S,9aR)-6-(4-chlorophenyl)-4-oxohexahydroquinolizin-(3E)-ylidenemethyl]-2-methoxyphenyl}-5-methyl-1-phosphonooxymethyl-3H-imidazol-1-ium trifluoroacetate, 13) 3-{2-methoxy-4-[(1S,6R,9aR)-1-methyl-4-oxo-6-(3,4,5-trifluorophenyl)tetrahydro[1,4]-oxazino[3,4-c][1,4]oxazine-(3Z)-ylidenemethyl]phenyl}-5-methyl-1-phosphonooxymethyl-3H-imidazole-1-ium trifluoroacetate,
14) 3-{4-[(1S,6R,9aR)-6-(4-chlorophenyl)-1-methyl-4-oxotetrahydro[1,4]oxazino[3,4-c][1,4]oxazine-(3Z)-ylidenemethyl]-2-methoxyphenyl}-5-methyl-1-phosphonooxymethyl-3H-imidazole-1-ium trifluoroacetate,
15) 3-{2-methoxy-4-[(1S,6S,8aR)-1-methyl-4-oxo-6-(3,4,5-trifluorophenyl)tetrahydropyrrolo[2,1-c][1,4]oxazine-(3Z)-ylidenemethyl]phenyl}-5-methyl-1-phosphonooxymethyl-3H-imidazole-1-ium trifluoroacetate,
16) 3-{4-[(1S,6R,9aR)-6-(3,4-difluorophenyl)-1-methyl-4-oxotetrahydro[1,4]oxazino[3,4-c][1,4]oxazine-(3Z)-ylidenemethyl]-2-methoxyphenyl}-5-methyl-1-phosphonooxymethyl-3H-imidazole-1-ium trifluoroacetate, and
17) 3-{4-[(6R,9aR)-1,1-dimethyl-4-oxo-6-(3,4,5-trifluorophenyl)tetrahydro[1,4]oxazino[3,4-c][1,4]oxazine-(3Z)-ylidenemethyl]-2-methoxyphenyl}-5-methyl-1-phosphonooxymethyl-3H-imidazole-1-ium trifluoroacetate;

21) the compound according to the above 1), which is selected from the following group consisting of:
1) 1-{4-[(E)-{1-[(1S)-1-(4-fluorophenyl)ethyl]-2-oxopiperidin-3-ylidene}methyl]-2-methoxyphenyl}-4-methyl-1H-imidazol-3-iomethyl monohydrogen phosphate,
2) 1-{4-[(E)-{1-[(1R,2R)-2-hydroxy-1-(3,4,5-trifluorophenyl)propyl]-2-oxopiperidin-3-ylidene}methyl]-2-methoxyphenyl}-4-methyl-1H-imidazol-3-iomethyl monohydrogen phosphate,
3) 1-{2-fluoro-4-[(Z)-{(6S)-4-[(1R,2R)-2-hydroxy-1-(3,4,5-trifluorophenyl)propyl]-6-methyl-3-oxomorpholin-2-ylidene}methyl]phenyl}-4-methyl-1H-imidazol-3-iomethyl monohydrogen phosphate,
4) 1-(2-methoxy-4-{(E)-[(3S,8aS)-5-oxo-3-(3,4,5-trifluorophenyl)hexahydroindolizin-6(5H)-ylidene]methyl}phenyl)-4-methyl-1H-imidazol-3-iomethyl monohydrogen phosphate,
5) 1-{4-[(Z)-{(6S)-4-[(1S)-1-(2,6-difluoropyridin-3-yl)ethyl]-6-methyl-3-oxomorpholin-2-ylidene}methyl]-2-methoxyphenyl}-4-methyl-1H-imidazol-3-iomethyl monohydrogen phosphate,
6) 1-(4-{(E)-[(3S,8aS)-3-(4-chlorophenyl)-5-oxohexahydroindolizin-6(5H)-ylidene]methyl}-2-methoxyphenyl)-4-methyl-1H-imidazol-3-iomethyl monohydrogen phosphate,
7) 1-{4-[(Z)-{(6S)-4-[(1R,2R)-1-(3,4-difluorophenyl)-2-hydroxypropyl]-6-methyl-3-oxomorpholin-2-ylidene}methyl]-2-fluorophenyl}-4-methyl-1H-imidazol-3-iomethyl monohydrogen phosphate,
8) 1-(2-methoxy-4-{(E)-[(6S,9aS)-4-oxo-6-(3,4,5-trifluorophenyl)hexahydro-2H-quinolizin-3(4H)-ylidene]methyl}phenyl)-4-methyl-1H-imidazol-3-iomethyl monohydrogen phosphate,
9) 1-(2-methoxy-4-{(E)-[(4R,9aS)-6-oxo-4-(3,4,5-trifluorophenyl)hexahydropyrido[2,1-c][1,4]oxazin-7(6H)-ylidene]methyl}phenyl)-4-methyl-1H-imidazol-3-iomethyl monohydrogen phosphate,
10) 1-{4-[(Z)-{(6S)-4-[(1R,2R)-2-hydroxy-1-(3,4,5-trifluorophenyl)propyl]-6-methyl-3-oxomorpholin-2-ylidene}methyl]-2-methoxyphenyl}-4-methyl-1H-imidazol-3-iomethyl monohydrogen phosphate,
11) 1-(4-{(E)-[(6S,9aR)-6-(4-chlorophenyl)-4-oxohexahydro-2H-quinolizin-3(4H)-ylidene]methyl}-2-methoxyphenyl)-4-methyl-1H-imidazol-3-iomethyl monohydrogen phosphate,
12) 1-(2-methoxy-4-{(Z)-[(1S,6R,9aR)-1-methyl-4-oxo-6-(3,4,5-trifluorophenyl)tetrahydro-1H-[1,4]oxazino[3,4-c][1,4]oxazin-3(4H)-ylidene]methyl}phenyl)-4-methyl-1H-imidazol-3-iomethyl monohydrogen phosphate,
13) 1-(4-{(Z)-[(1S,6R,9aR)-6-(4-chlorophenyl)-1-methyl-4-oxotetrahydro-1H-[1,4]oxazino[3,4-c][1,4]oxazin-3(4H)-ylidene]methyl}-2-methoxyphenyl)-4-methyl-1H-imidazol-3-iomethyl monohydrogen phosphate,
14) 1-(2-methoxy-4-{(Z)-[(1S,6S,8aR)-1-methyl-4-oxo-6-(3,4,5-trifluorophenyl)tetrahydro-1H-pyrrolo[2,1-c][1,4]oxazin-3(4H)-ylidene]methyl}phenyl)-4-methyl-1H-imidazol-3-iomethyl monohydrogen phosphate,
15) 1-(4-{(Z)-[(1S,6R,9aR)-6-(3,4-difluorophenyl)-1-methyl-4-oxotetrahydro-1H-[1,4]oxazino[3,4-c][1,4]oxazin-3(4H)-ylidene]methyl}-2-methoxyphenyl)-4-methyl-1H-imidazol-3-iomethyl monohydrogen phosphate and
16) 1-(4-{(Z)-[(6R,9aR)-1,1-dimethyl-4-oxo-6-(3,4,5-trifluorophenyl)tetrahydro-1H-[1,4]oxazino[3,4-c][1,4]oxazin-3(4H)-ylidene]methyl}-2-methoxyphenyl)-4-methyl-1H-imidazol-3-iomethyl monohydrogen phosphate;
22) a drug containing a compound or its pharmacologically acceptable salt according to any one of the above 1) to 21) as an active ingredient;
23) the drug according to the above 22), in which the drug is a preventive or therapeutic agent for a disease caused by amyloid-beta; and
24) the drug according to the above 23), in which the disease caused by amyloid-beta is Alzheimer's disease, senile dementia, Down syndrome, or amyloidosis.

DETAILED DESCRIPTION OF THE INVENTION

The compound represented by Formula (I) or its pharmacologically acceptable salt according to the present invention is a prodrug of a cinnamide compound of which water solubility is increased by converting the imidazole moiety of the cinnamide compound molecule to a quaternary salt form. The prodrug can be converted into an active cinnamide compound in vitro and in vivo and is a novel compound which is not disclosed in any literatures and is very useful as a preventive or therapeutic agent for diseases caused by Aβ.

Meanings of symbols, terms, and the like used in this specification will now be described, and the present invention will be described in detail.

Herein, a structural formula of a compound sometimes represents a certain isomer for convenience of description. However, compounds of the present invention may include all possible isomers, such as structurally possible geometric isomers, optical isomers generated due to the presence of asymmetric carbons, stereoisomers, tautomers, and mixtures of isomers, and are not limited to formulae being used for the convenience of description, and may be either of two isomers or a mixture of both isomers. Thus, compounds of the present invention may be either optically active compounds having an asymmetric carbon atom in their molecules or their racemates, and are not restricted to either of them but include both. Furthermore, compounds of the present invention may exhibit crystalline polymorphism, but likewise are not restricted to any one of these but may be in any one of these crystal forms, or exist as a mixture of two or more crystal forms, or may be amorphous forms. Compounds of the present invention also may be in anhydrous forms or solvated forms.

Herein, "diseases caused by Aβ" are wide-ranging, of which examples include Alzheimer's disease (for example, see Klein W L and seven others, Alzheimer's disease-affected brain: Presence of oligomeric Aβ ligands (ADDLs) suggests a molecular basis for reversible memory loss. Proceeding National Academy of Science USA, 2003, Sep. 2, 100(18), 10417-10422; Nitsch R M and 16 others, Antibodies against β-amyloid slow cognitive decline in Alzheimer's disease. Neuron, 2003, May 22, 38(4), 547-554; Jarrett J T and two others, The carboxy terminus of the β amyloid protein is critical for the seeding of amyloid formation: Implications for the pathogenesis of Alzheimer's disease. Biochemistry, 1993, May 11, 32(18), 4693-4697; Glenner G G and another, Alzheimer's disease: initial report of the purification and characterization of a novel cerebrovascular amyloid protein. Biochemical and biophysical research communications, 1984, May 16, 120(3), 885-890; Masters CL and six others, Amyloid plaque core protein in Alzheimer disease and Down syndrome. Proceeding National Academy of Science USA, 1985, June, 82(12), 4245-4249; Gouras G K and 11 others, Intraneuronal Aβ42 accumulation in human brain. American Journal of pathology, 2000, January, 156(1), 15-20; Scheuner D and 20 others, Secreted amyloid β-protein similar to that in the senile plaques of Alzheimer's disease is increased in vivo by the presenilin 1 and 2 and APP mutations linked to familial Alzheimer's disease. Nature Medicine, 1996, Aug. 2(8), 864-870; Forman M S and four others, Differential effects of the Swedish mutant amyloid precursor protein on β-amyloid accumulation and secretion in neurons and normeuronal cells. The Journal of biological chemistry, 1997, Dec. 19, 272(51), 32247-32253), senile dementia (for example, see Blass J P, Brain metabolism and brain disease: Is metabolic deficiency the proximate cause of Alzheimer dementia?. Journal of Neuroscience Research, 2001, Dec. 1, 66(5), 851-856), frontotemporal dementia (for example, see Evin G and 11 others, Alternative transcripts of presenilin-1 associated with frontotemporal dementia. Neuroreport, 2002, Apr. 16, 13(5), 719-723), Pick disease (for example, see Yasuhara O and three others, Accumulation of amyloid precursor protein in brain lesions of patients with Pick disease. Neuroscience Letters, 1994, Apr. 25, 171(1-2), 63-66), Down disease (for example, see Teller J K and ten others, Presence of soluble amyloid β-peptide precedes amyloid plaque formation in Down's syndrome, Nature Medicine, 1996, Jan. 2(1), 93-95; Tokuda T and six others, Plasma levels of amyloid β proteins Aβ1-40 and Aβ1-42(43) are elevated in Down's syndrome. Annals of Neurology, 1997, Feb. 41(2), 271-273), cerebrovascular angiopathy (for example, see Hayashi Y and nine others, Evidence for presenilin-1 involvement in amyloid angiopathy in the Alzheimer's disease-affected brain. Brain Research, 1998, Apr. 13, 789(2), 307-314; Barelli H and 15 others, Characterization of new polyclonal antibodies specific for 40 and 42 amino acid-long amyloid β peptides: their use to examine the cell biology of presenilins and the immunohistochemistry of sporadic Alzheimer's disease and cerebral amyloid angiopathy cases. Molecular Medicine, 1997, Oct. 3(10), 695-707; Calhoun M E and ten others, Neuronal overexpression of mutant amyloid precursor protein results in prominent deposition of cerebrovascular amyloid. Proceeding National Academy of Science USA, 1999, Nov. 23, 96(24), 14088-14093; Dermaut B, et al., Cerebral amyloid angiopathy is a pathogenic lesion in Alzheimer's Disease due to a novel presenilin-1 mutation. Brain, 2001, December 124 (12), 2383-2392), hereditary cerebral hemorrhage with amyloidosis (Dutch type) (for example, see Crass P. and nine others, Presenile Alzheimer dementia characterized by amyloid angiopathy and large amyloid core type senile plaques in the APP 692Ala→Gly mutation. Acta Neuropathologica (Berl), 1998, Sep. 96(3), 253-260; Herzig M C and 14 others, Aβ is targeted to the vasculature in a mouse model of hereditary cerebral hemorrhage with amyloidosis. Nature Neuroscience, 2004, Sep. 7(9), 954-960; van Duinen S G and five others, Hereditary cerebral hemorrhage with amyloidosis in patients of Dutch origin is related to Alzheimer disease. Proceeding National Academy of Science USA, 1987, Aug. 84(16), 5991-5994; Levy E and eight others, Mutation of the Alzheimer's disease amyloid gene in hereditary cerebral hemorrhage, Dutch type. Science, 1990, Jun. 1, 248(4959), 1124-1126), cognitive impairment (for example, see Laws S M and seven others, Association between the presenilin-1 mutation Glu318Gly and complaints of memory impairment. Neurobiology of Aging, 2002, January-February, 23(1), 55-58), memory and learning disorders (for example, see Vaucher E and five others, Object recognition memory and cholinergic parameters in mice expressing human presenilin 1 transgenes. Experimental Neurology, 2002, Jun. 175(2), 398-406; Morgan D and 14 others, Aβ peptide vaccination prevents memory loss in an animal model of Alzheimer's disease. Nature, 2000, Dec. 21-28, 408(6815), 982-985; Moran P M and three others, Age-related learning deficits in transgenic mice expressing the 751-amino acid isoform of human β-amyloid precursor protein. Proceeding National Academy of Science USA, 1995, Jun. 6, 92(12), 5341-5345), amyloidosis and cerebral ischemia (for example, see Laws S M and seven others, Association between the presenilin-1 mutation Glu318Gly and complaints of memory impairment. Neurobiology of Aging, 2002, January-February, 23(1), 55-58; Koistinaho M and ten others, β-Amyloid precursor protein transgenic mice that harbor diffuse Aβ deposits but do not form plaques show increased ischemic vulnerability: Role of inflammation. Proceeding National Academy of Science USA, 2002, Feb. 5, 99(3), 1610-1615; Zhang F and four others, Increased susceptibility to ischemic brain damage in transgenic mice overexpressing the amyloid precursor protein. The Journal of neuroscience, 1997, Oct. 15, 17(20), 7655-7661), cerebrovascular dementia (for example, see Sadowski M and six others, Links between the pathology of Alzheimer's disease and vascular dementia. Neurochemical Research, 2004, Jun. 29(6), 1257-1266), opthalmoplegia (for example, see O'Riordan S and seven others, Presenilin-1 mutation (E280G), spastic paraparesis, and cranial MRI white-matter abnormalities. Neurology, 2002, Oct. 8, 59(7), 1108-1110), multiple sclerosis (for example, see Gehrmann J and four others Amyloid precursor protein (APP) expression in multiple sclerosis lesions. Glia, 1995, Oct. 15(2), 141-151; Reynolds W F and six others, Myeloperoxidase polymorphism is associated with gender specific risk for Alzheimer's disease. Experimental Neurology, 1999, Jan. 155(1), 31-41), head injury and skull injury (for example, see Smith D H and four others, Protein accumulation in traumatic brain injury. NeuroMolecular Medicine, 2003, 4(1-2), 59-72), apraxia (for example, see Matsubara-Tsutsui M and seven others, Molecular evidence of presenilin 1 mutation in familial early onset dementia. American Journal of Medical Genetics, 2002, Apr. 8, 114(3), 292-298), prion diseases, familial amyloid neuropathy, and triplet repeat diseases (for example, see Kirkitadze M D, et al., Paradigm shifts in Alzheimer's disease and other neurodegenerative disorders: the emerging role of oligomeric assemblies. Journal of Neuroscience Research, 2002, Sep. 1, 69(5), 567-577; Evert B O and eight others, Inflammatory genes are upreglulated in expanded ataxin-3-expressing cell lines and spinocerebellar ataxia type 3 brains. The Journal of Neuroscience, 2001, Aug. 1, 21(15), 5389-5396; Mann D M and another, Deposition of amyloid (A4) protein within the brains of persons with dementing disorders other than Alzheimer's disease and Down's syndrome. Neuroscience Letters, 1990, Feb. 5, 109(1-2) 68-75), Parkinson's disease (for example, see Primavera J and four others, Brain accumulation of amyloid-β in Non-Alzheimer Neurodegeneration. Journal of Alzheimer's Disease, 1999, Oct. 1(3), 183-193), dementia with Lewy bodies (for example, see Giasson B I and two others, Interactions of amyloidogenic proteins. NeuroMolecular Medicine, 2003, 4(1-2), 49-58; Masliah E and six, β-Amyloid peptides enhance α-synuclein accumulation and neuronal deficits in a transgenic mouse model linking Alzheimer's disease and Parkinson's disease: Proceeding National Academy of Science USA, 2001, Oct. 9, 98(21), 12245-12250; Barrachina M and six others, Amyloid-β deposition in the cerebral cortex in Dementia with Lewy bodies is accompanied by a relative increase in AβPP mRNA isoforms containing the Kunitz protease inhibitor. Neurochemistry International, 2005, Feb. 46(3), 253-260; Primavera J and four others, Brain accumulation of amyloid-β in Non-Alzheimer Neurodegeneration. Journal of Alzheimer's Disease, 1999, Oct. 1(3), 183-193), parkinsonism-dementia complex (for example, see Schmidt M L and six others, Amyloid plaques in Guam amyotrophic lateral sclerosis/parkinsonism-dementia complex contain species of Aβ similar to those found in the amyloid plaques of Alzheimer's disease and pathological aging. Acta Neuropathologica (Berl), 1998, Feb. 95(2), 117-122; Ito H and three others, Demonstration of β amyloid protein-containing neurofibrillary tangles in parkinsonism-dementia complex on Guam. Neuropathology and applied neurobiology, 1991, Oct. 17(5), 365-373), frontotemporal dementia-parkinsonism linked to chromosome 17 (for example, see Rosso S M and three others, Coexistent tau and amyloid pathology in hereditary frontotemporal dementia with tau mutations. Annals of the New York academy of sciences, 2000, 920, 115-119), dementia with argyrophilic grains (for example, see Tolnay M and four others, Low amyloid (Aβ) plaque load and relative predominance of diffuse plaques distinguish argyrophilic grain disease from Alzheimer's disease. Neuropathology and applied neurobiology, 1999, Aug. 25(4), 295-305), Niemann-Pick disease (for example, see Jin L W and three others, Intracellular accumulation of amyloidogenic fragments of amyloid-β precursor protein in neurons with Niemann-Pick type C defects is associated with endosomal abnormalities. American Journal of Pathology, 2004, Mar. 164(3), 975-985), amyotrophic lateral sclerosis (for example, see Sasaki S and another, Immunoreactivity of β-amyloid precursor protein in amyotrophic lateral sclerosis. Acta Neuropathologica (Berl), 1999, May 97(5), 463-468; Tamaoka A and four others, Increased amyloid β protein in the skin of patients with amyotrophic lateral sclerosis. Journal of Neurology, 2000, Aug. 247(8), 633-635; Hamilton R L and another, Alzheimer disease pathology in amyotrophic lateral sclerosis. Acta Neuropathologica, 2004, Jun. 107(6), 515-522; Turner B J and six others, Brain β-amyloid accumulation in transgenic mice expressing mutant superoxide dismutase 1. Neurochemical Research, 2004, Dec. 29(12), 2281-2286), hydrocephalus (for example, see Weller R O, Pathology of cerebrospinal fluid and interstitial fluid of the CNS: Significance for Alzheimer disease, prion disorders and multiple sclerosis. Journal of Neuropathology and Experimental Neurology, 1998, Oct. 57(10), 885-894; Silverberg G D and four others, Alzheimer's disease, normal-pressure hydrocephalus, and senescent changes in CSF circulatory physiology: a hypothesis. Lancet neurology, 2003, Aug. 2(8), 506-511; Weller R O and three others, Cerebral amyloid angiopathy: Accumulation of Aβ in interstitial fluid drainage pathways in Alzheimer's disease. Annals of the New York academy of sciences, 2000, Apr. 903, 110-117; Yow H Y and another, A role for cerebrovascular disease in determining the pattern of β-amyloid deposition in Alzheimer's disease. Neurology and applied neurobiology, 2002, 28, 149; Weller R O and four others, Cerebrovascular disease is a major factor in the failure of elimination of Aβ from the aging human brain. Annals of the New York academy of sciences, 2002, Nov. 977, 162-168), paraparesis (for example, see O'Riordan S and seven others, Presenilin-1 mutation (E280G), spastic paraparesis, and cranial MRI white-matter abnormalities. Neurology, 2002, Oct. 8, 59(7), 1108-1110; Matsubara-Tsutsui M and seven others, Molecular evidence of presenilin 1 mutation in familial early onset dementia. American Journal of Medical Genetics, 2002, Apr. 8, 114(3), 292-298; Smith M J and 11 others, Variable phenotype of Alzheimer's disease with spastic paraparesis. Annals of Neurology, 2001, 49(1), 125-129; Crook R and 17 others, A variant of Alzheimer's disease with spastic pararesis and unusual plaques due to deletion of exon 9 of presenilin 1. Nature Medicine, 1998, Apr. 4(4), 452-455), progressive supranuclear palsy (for example, see Barrachina M and six others, Amyloid-β deposition in the cerebral cortex in Dementia with Lewy bodies is accompanied by a relative increase in AβPP mRNA isoforms containing the Kunitz protease inhibitor. Neurochemistry International, 2005, Feb. 46(3), 253-260; Primavera J and four others, Brain accumulation of amyloid-β in Non-Alzheimer Neurodegeneration. Journal of Alzheimer's Disease, 1999, Oct. 1(3), 183-193), cerebral hemorrhage (for example, see Atwood C S and three others, Cerebrovascular requirement for sealant, anti-coagulant and remodeling molecules that allow for the maintenance of vascular integrity and blood supply. Brain Research Reviews, 2003, Sep. 43(1), 164-178; Lowenson J D and two others, Protein aging: Extracellular amyloid formation and intracellular repair. Trends in cardiovascular medicine, 1994, 4(1), 3-8), convulsion (for example, see Singleton A B and 13 others, Pathology of early-onset Alzheimer's disease cases bearing the Thr113-114ins presenilin-1 mutation. Brain, 2000, December 123(Pt 12), 2467-2474), mild cognitive impairment (for example, see Gattaz W F and four others, Platelet phospholipase A2 activity in Alzheimer's disease and mild cognitive impairment. Journal of Neural Transmission, 2004, May 111(5), 591-601; Assini A and 14 others, Plasma levels of amyloid β-protein 42 are increased in women with mild cognitive impairment. Neurology, 2004, Sep. 14, 63(5), 828-831), and arteriosclerosis (for example, see De Meyer G R and eight others, Platelet phagocytosis and processing of β-amyloid precursor protein as a mechanism of macrophage activation in atherosclerosis. Circulation Research, 2002, Jun. 14, 90(11), 1197-1204).

Here, the term "C1-6 alkyl group" refers to a linear or branched alkyl group having 1 to 6 carbon atoms, and preferable examples of the group include a methyl group, an ethyl group, an n-propyl group, an i-propyl group, an n-butyl group, an i-butyl group, a tert-butyl group, an n-pentyl group, an i-pentyl group, a neopentyl group, an n-hexyl group, a 1-methylpropyl group, a 1,2-dimethylpropyl group, a 1-ethylpropyl group, a 1-methyl-2-ethylpropyl group, a 1-ethyl-2-methylpropyl group, a 1,1,2-trimethylpropyl group, a 1-methylbutyl group, a 2-methylbutyl group, a 1,1-dimethylbutyl group, a 2,2-dimethylbutyl group, a 2-ethylbutyl group, a 1,3-dimethylbutyl group, a 2-methylpentyl group, and a 3-methylpentyl group.

The term "6- to 14-membered aromatic hydrocarbon ring group" refers to a monocyclic, bicyclic, or tricyclic aromatic hydrocarbon ring group having 6 to 14 carbon atoms, and preferable examples of the group include a phenyl group, an indenyl group, a naphthyl group, an azulenyl group, a heptalenyl group, a biphenyl group, a fluorenyl group, a phenalenyl group, a phenanthrenyl group, and an anthracenyl group.

The term "5- to 14-membered aromatic heterocyclic group" refers to a monocyclic, bicyclic, or tricyclic aromatic heterocyclic group having 5 to 14 carbon atoms, and preferable examples of the group include (1) nitrogen-containing aromatic heterocyclic groups such as a pyrrolyl group, a pyridyl group, a pyridazinyl group, a pyrimidinyl group, a pyrazinyl group, a pyrazolinyl group, an imidazolyl group, an indolyl group, an isoindolyl group, an indolizinyl group, a purinyl group, an indazolyl group, a quinolyl group, an isoquinolyl group, a quinolizinyl group, a phthalazinyl group, a naphthyridinyl group, a quinoxalinyl group, a quinazolinyl group, a cinnolinyl group, a pteridinyl group, an imidazotriazinyl group, a pyrazinopyridazinyl group, an acridinyl group, a phenantridinyl group, a carbazolyl group, a perimidinyl group, a phenanthrolinyl group, and a phenacyl group, (2) sulfur-containing aromatic heterocyclic groups such as a thienyl group and a benzothienyl group, (3) oxygen-containing aromatic heterocyclic groups such as a furyl group, a pyranyl group, a cyclopentapyranyl group, a benzofuranyl group, and an isobenzofuranyl group, and (4) aromatic heterocyclic groups each containing two or more different atoms selected from the group consisting of a nitrogen atom, a sulfur atom, and an oxygen atom, such as a thiazolyl group, an isothiazolyl group, a benzthiazolinyl group, a benzthiadiazolyl group, a phenothiazinyl group, an isoxazolyl group, a furazanyl group, a phenoxazinyl group, a pyrazolooxazolyl group, an imidazothiazolyl group, a thienofuryl group, a furopyrrolyl group, and a pyridooxazinyl group.

The term "6- to 14-membered non-aromatic hydrocarbon ring group" refers to a cyclic aliphatic hydrocarbon group having 6 to 14 carbon atoms, and examples of the group include a cyclopropyl group, a cyclobutyl group, a cyclopentyl group, a cyclohexyl group, a cycloheptyl group, a cyclooctyl group, a spiro[3,4]octanyl group, a decanyl group, an indanyl group, a 1-acenaphthenyl group, a cyclopentacyclooctenyl group, a benzocyclooctenyl group, an indenyl group, a tetrahydronaphthyl group, a 6,7,8,9-tetrahydro-5H-benzocycloheptenyl group, and a 1,4-dihydronaphthalenyl group.

The term "5- to 14-membered non-aromatic heterocyclic group" refers to not only a 5- to 14-membered non-aromatic heteromonocyclic group but also a saturated heterocyclic group condensed with an aromatic hydrocarbon ring group and a saturated hydrocarbon ring or saturated heterocyclic group condensed with an aromatic heterocyclic group, in which 1) the number of atoms forming a ring is 5 to 14; 2) the atoms forming the ring contain 1 to 5 heteroatoms such as nitrogen, oxygen, and sulfur atoms; and 3) the ring may contain one or more of carbonyl groups, double bonds, or triple bonds. Examples of the 5- to 14-membered non-aromatic heterocyclic group include an azetidinyl ring, a pyrrolidinyl ring, a piperidinyl ring, an azepanyl ring, an azokanyl ring, a tetrahydrofuranyl ring, a tetrahydropyranyl ring, a morpholinyl ring, a thiomorpholinyl ring, a piperazinyl ring, a thiazolidinyl ring, a dioxanyl ring, an imidazolinyl ring, a thiazolinyl ring, a 1,2-benzopyranyl ring, an isochromanyl ring, a chromanyl ring, an indolinyl ring, an isoindolinyl ring, an azaindanyl group, an azatetrahydronaphthyl group, an azachromanyl group, a tetrahydrobenzofuranyl group, a tetrahydrobenzothienyl group, a 2,3,4,5-tetrahydro-benzo[b]thienyl group, a 3,4-dihydro-2H-benzo[b][1,4]dioxepinyl group, an indan-1-onyl group, a 6,7-dihydro-5H-cyclopentapyradinyl group, a 6,7-dihydro-5H-[1]pyridinyl group, a 5,6-dihydro-4H-cyclopenta[b]thienyl group, a 4,5,6,7-tetrahydro-benzo[b]thienyl group, a 3,4-dihydro-2H-naphthale-1-onyl group, a 2,3-dihydro-isoindol-1-onyl group, a 3,4-dihydro-2H-isoquinolin-1-onyl group, and 3,4-dihydro-2H-benzo[1,4]oxapinyl group.

The term "C1-6 alkylene group" refers to an alkylene group having 1 to 6 carbon atoms, and examples of the group include a methylene group, an ethylene group, a propylene group, a butylene group, and a pentylene group.

The term "C1-6 acyl group" refers to a group in which a hydrogen atom of an alkyl group having 1 to 6 carbon atoms has been substituted with a carbonyl group, and examples of the C1-6 acyl group include an acetyl group, a propionyl group, and a butynyl group.

The term "C3-8 cycloalkyl group condensed with a benzene ring" refers to, for example, a group represented by the following formulae:

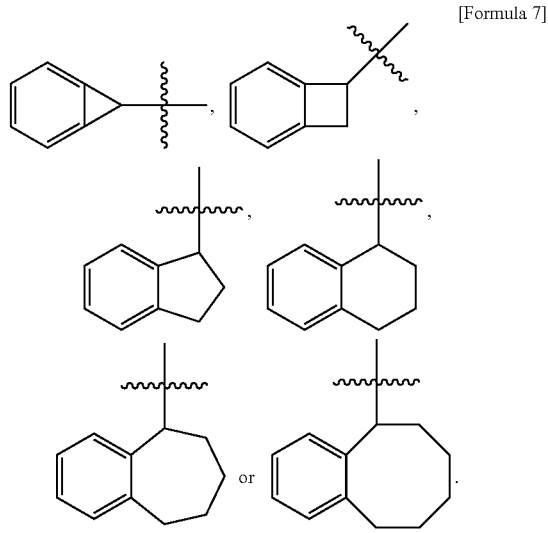

[Formula 7]

In these formulae, the benzene ring may be substituted with the same or different 1 to 3 substituents selected from Substituent Group A2 below, and one methylene group of the C3-8 cycloalkyl group may be substituted with an oxygen atom.

In the aforementioned Formula (A-2), the term "$Z_1$ denotes a methylene group, a vinylene group, or an oxygen atom, or an imino group which may be substituted with a C1-6 alkyl group or a C1-6 acyl group" refers to a ring structure containing the methylene group, vinylene group, oxygen atom, or imino group. The ring structure can be specifically shown, for example, by the following formulae:

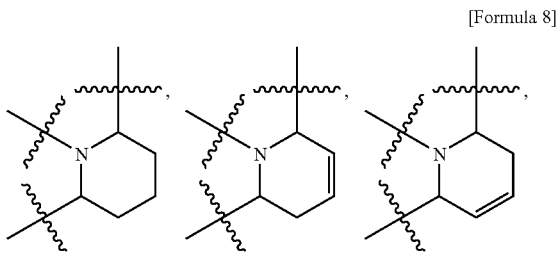

[Formula 8]

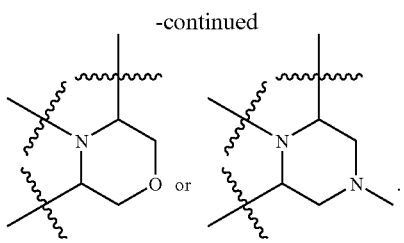

In these formulae, the methylene group and the vinylene group of the ring structure may be each substituted with the same or different 1 or 2 substituents selected from Substituent Group A2.

In Formula (A-2), the term "$Z_2$ denotes a methylene group, a vinylene group, or an oxygen atom, or an imino group which may be substituted with a C1-6 alkyl group or a C1-6 acyl group" refers to a ring structure containing the methylene group, vinylene group, n oxygen atom, or imino group. The ring structure can be specifically shown, for example, by the following formulae:

[Formula 9]

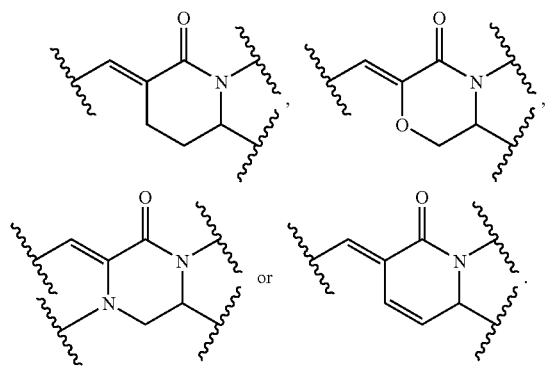

In these formulae, the methylene group and the vinylene group of the ring structure may be each substituted with the same or different 1 or 2 substituents selected from Substituent Group A2.

In Formula (A-2), when $Z_1$ or $Z_2$ denotes "an imino group which may be substituted with a C1-6 alkyl group or a C1-6 acyl group", the imino group moiety can be further specifically shown, for example, by the following formulae:

[Formula 10]

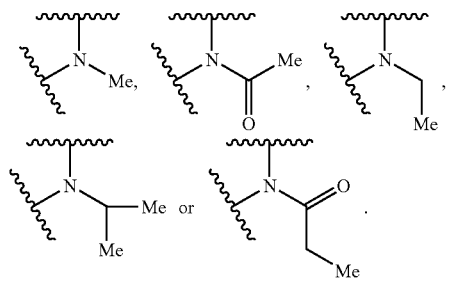

Substituent Group A1 consists of (1) hydroxy groups, (2) cyano groups, (3.) C3-8 cycloalkoxy groups, (4) C1-6 alkoxy groups which may be each substituted with 1 to 3 substituents selected from the group consisting of halogen atoms, hydroxy groups, cyano groups, C3-8 cycloalkyl groups, and C3-8 cycloalkoxy groups, (5) amino groups which may be each substituted with 1 or 2 C1-6 alkyl groups which may be each substituted with 1 to 3 halogen atoms, (6) carbamoyl groups which may be each substituted with 1 or 2 C1-6 alkyl groups which may be each substituted with 1 to 3 halogen atoms, (7) carboxyl groups, (8) pyridinyl groups, and (9) sugar residues; and Substituent Group A2 consists of (1) halogen atoms, (2) hydroxy groups, (3) cyano groups, (4) C3-8 cycloalkyl groups, (5) C3-8 cycloalkoxy groups, (6) C1-6 alkyl groups which may be each substituted with 1 to 3 substituents selected from the group consisting of halogen atoms, hydroxy groups, cyano groups, C3-8 cycloalkyl groups, C1-6 alkoxy groups, and C3-8 cycloalkoxy groups, (7) C1-6 alkoxy groups which may be each substituted with 1 to 3 substituents selected from the group consisting of halogen atoms, hydroxy groups, cyano groups, C3-8 cycloalkyl groups, and C3-8 cycloalkoxy groups, (8) amino groups which may be each substituted with 1 or 2 C1-6 alkyl groups which may be each substituted with 1 to 3 halogen atoms, and (9) carbamoyl groups which may be each substituted with 1 or 2 C1-6 alkyl groups which may be each substituted with 1 to 3 halogen atoms.

Here, the term "halogen atom" refers to a fluorine, chlorine, bromine, or iodine atom, and preferably a fluorine, chlorine, or bromine atom.

The term "C3-8 cycloalkyl group" refers to a cyclic alkyl group having 3 to 8 carbon atoms, and preferable examples of the group include a cyclopropyl group, a cyclobutyl group, a cyclopentyl group, a cyclohexyl group, a cycloheptyl group, and a cyclooctyl group.

The term "C3-8 cycloalkoxy group" refers to a group in which a hydrogen atom of the cyclic alkyl group having 3 to 8 carbon atoms has been substituted with an oxygen atom, and preferable examples of the group include a cyclopropoxy group, a cyclobutoxy group, a cyclopentoxy group, a cyclohexoxy group, a cycloheptyloxy group, and a cyclooctyloxy group.

The term "C1-6 alkyl group" is the same as defined above, and preferable examples of the group are the same as defined above.

Preferable examples of the "C1-6 alkyl group which may be substituted with 1 to 3 substituents selected from the group consisting of halogen atoms, hydroxy groups, cyano groups, C3-8 cycloalkyl groups, C1-6 alkoxy groups, and C3-8 cycloalkoxy groups" include a methyl group, a trifluoromethyl group, a hydroxymethyl group, a cyanomethy group, an ethyl group, 2-hydroxyethyl group, an n-propyl group, an i-propyl group, a 3-hydroxy-n-propyl group, a tert-butyl group, an n-pentyl group, an i-pentyl group, a neopentyl group, an n-hexyl group, a 1-methylpropyl group, a 1,2-dimethylpropyl group, a 1-ethylpropyl group, a 1-methyl-2-ethylpropyl group, a 1-ethyl-2-methylpropyl group, a 1,1,2-trimethylpropyl group, a 1-methylbutyl group, a 2,2-dimethylbutyl group, a 2-ethylbutyl group, a 2-methylpentyl group, and a 3-methylpentyl group.

The term "C1-6 alkoxy group" refers to a group in which a hydrogen atom of the alkyl group having 1 to 6 carbon atoms has been substituted with an oxygen atom, and preferable examples of the group include a methoxy group, an ethoxy group, an n-propoxy group, an i-propoxy group, an n-butoxy group, an i-butoxy group, a sec-butoxy group, a tert-butoxy group, an n-pentoxy group, an i-pentoxy group, a sec-pentoxy group, a tert-pentoxy group, an n-hexoxy group, an i-hexoxy group, a 1,2-dimethylpropoxy group, a 2-ethylpropoxy group, a 1-methyl-2-ethylpropoxy group, a 1-ethyl-2-methylpropoxy group, a 1,1,2-trimethylpropoxy group, a 1,1-dimethylbutoxy group, a 2,2-dimethylbutoxy group, a 2-ethylbutoxy group, a 1,3-dimethylbutoxy group, a 2-methylpentoxy group, a 3-methylpentoxy group, and a hexyloxy group.

The term "amino group which may be substituted with 1 or 2 C1-6 alkyl groups" refers to an amino group in which hydrogen atoms may be substituted with 1 or 2 alkyl groups having 1 to 6 carbon atoms, and preferable examples of the substituted amino group include a methylamino group, a dimethyl amino group, an ethylamino group, a diethylamino group, an n-propylamino group, and a di-n-propylamino group.

The term "C1-6 alkyl group which may be substituted with 1 to 3 halogen atoms" refers to an alkyl group having 1 to 6 carbon atoms and in which hydrogen atoms may be substituted with 1 to 3 halogen atoms. Preferable examples of the substituted alkyl group include a trifluoromethyl group.

The term "carbamoyl group which may be substituted with 1 or 2 C1-6 alkyl groups" refers to a carbamoyl group in which hydrogen atoms may be substituted with 1 or 2 alkyl groups having 1 to 6 carbon atoms, and preferable examples of the substituted carbamoyl group include a methylcarbamoyl group, a dimethylcarbamoyl group, an ethylcarbamoyl group, a diethylcarbamoyl group, an n-propylcarbamoyl group, and a di-n-propylcarbamoyl group.

The term "C1-6 alkoxy group (the C1-6 alkoxy group may be substituted with 1 to 3 halogen atoms" refers to an alkoxy group having 1 to 6 carbon atoms and in which hydrogen atoms may be substituted with 1 to 3 halogen atoms, and preferably examples of the substituted C1-6 alkoxy group include a trifluoromethoxy group.

The term "sugar residues" is a generic term referring to sugars including monosaccharides such as glucose and fructose, disaccharides such as sucrose, trisaccharides, oligosaccharides, and polysaccharides.

The term "methylene group which may be substituted with 1 or 2 of C1-6 alkyl groups, halogen atoms, and hydroxy groups" refers to a group which can be specifically shown, for example, by the following formulae:

[Formula 11]

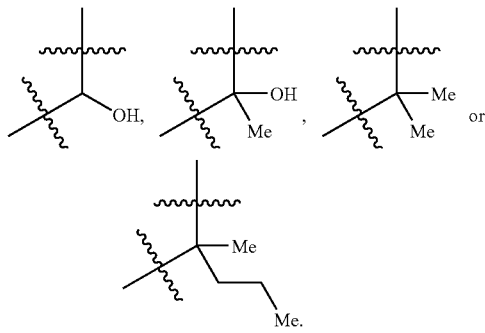

In Formula (I), when Y is —CO—(O)$_n$—R$_c$.M$_a^-$, —P(=O) (OR$_d$)$_2$.M$_a^-$, or —P(=O) (OH)$_2$.M$_a^-$, the "M$_a^-$" refers to an anion which is obtained by removing a proton from an organic or inorganic acid. Examples of the organic acid include acetic acid, trifluoroacetic acid, propionic acid, methanesulfonic acid, benzenesulfonic acid, toluenesulfonic acid, and trifluoromethane-sulfonic acid. Examples of the inorganic acid include hydrochloric acid, sulfuric acid, phosphoric acid, hydrofluoric acid, hydrobromic acid, hydroiodic acid, and water. Specifically, examples of the "M$_a^-$" include a chlorine ion, a bromine ion, an iodine ion, HSO$_3^-$, HSO$_4^-$, H$_2$PO$_4^-$, and OH$^-$.

In Formula (I), when Y is —P(=O) (—O$^-$) (—O$^-$.M$_b^+$), the "M$_b^+$" denotes a cation, namely, a positively charged atom or atom group. Examples of the cation include a sodium ion, a potassium ion, and a quaternary ammonium ion.

In this specification, the term "pharmacologically acceptable salt" refers to a salt of the compound represented by Formula (I) which becomes a preventive or therapeutic agent for diseases caused by Aβ, and the salt is not specifically limited as long as it is pharmaceutically acceptable. Preferable examples of the pharmaceutically acceptable salt include salts with hydrohalogenic acids (for example, hydrofluoride, hydrochloride, hydrobromide, and hydroiodide), with inorganic acids (for example, sulfate, nitrate, perchlorate, phosphate, carbonate, and bicarbonate), with organic carboxylic acids (for example, acetate, oxalate, maleate, tartrate, fumarate, and citrate), with organic sulfonic acids (for example, methanesulfonate, trifluoromethanesulfonate, ethanesulfonate, benzenesulfonate, toluenesulfonate, and camphorsulfonate), with amino acids (for example, aspartate and glutamate), with quaternary amines, with alkali metals (for example, a sodium salt and a potassium salt), and with alkaline earth metals (for example, a magnesium salt and a calcium salt).

The compounds represented by Formula (I) according to the present invention will now be described.

Among the compounds represented by Formula (I),
preferred is a compound or a pharmacologically acceptable salt thereof in which R$_a$ and R$_b$ are each a hydrogen atom or a C1-6 alkyl group.

Among the compounds represented by Formula (I),
preferred is a compound or a pharmacologically acceptable salt thereof in which X$_a$ is a methoxy group or a fluorine atom.

Among the compounds represented by Formula (I),
preferred is a compound or a pharmacologically acceptable salt thereof in which Y is —CO—(O)$_n$—R$_c$.M$_a^-$, wherein R$_c$ denotes a C1-6 alkyl, 6- to 14-membered aromatic hydrocarbon ring, 5- to 14-membered aromatic heterocyclic, 6- to 14-membered non-aromatic hydrocarbon ring, or 5- to 14-membered non-aromatic heterocyclic group which may be substituted with the same or different 1 to 5 substituents selected from Substituent Group A1; n is 0 or 1; and M$_a^-$ denotes an anion, —P(=O) (OR$_d$)$_2$.M$_a^-$, wherein R$_d$ denotes a C1-6 alkyl group which may be substituted with the same or different 1 to 3 substituents selected from Substituent Group A2, and M$_a^-$ denotes an anion, —P(=O) (OH)$_2$.M$_a^-$, wherein M$_a^-$ denotes an anion, —P(=O) (—O$^-$) (OH), or —P(=O) (—O$^-$) (—O$^-$.M$_b^+$), wherein M$_b^+$ denotes a cation;

more preferred is a compound or a pharmacologically acceptable salt thereof in which Y is —P(=O) (OR$_d$)$_2$.M$_a^-$, wherein R$_d$ denotes a C1-6 alkyl group which may be substituted with the same or different 1 to 3 substituents selected from Substituent Group A2, and M$_a^-$ denotes an anion, —P(=O) (OH)$_2$.M$_a^-$, wherein M$_a^-$ denotes an anion, —P(=O) (—O$^-$) (OH), or —P(=O) (—O$^-$) (—O$^-$. M$_b^+$), wherein M$_b^+$ denotes a cation; and most preferred is a compound or a pharmacologically acceptable salt thereof in which Y is —P(=O) (OH)$_2$.M$_a^-$, wherein M$_a^-$ denotes an anion, —P(=O) (—O$^-$) (OH), or —P(=O) (—O$^-$) (—O$^-$.M$_b^+$), wherein M$_b^+$ denotes a cation.

Among the compounds represented by Formula (I), when Y is —CO—(O)$_n$—R$_c$.M$_a^-$,
preferred is a compound or a pharmacologically acceptable salt thereof in which R$_c$ denotes a C1-6 alkyl group which may be substituted with the same or different 1 to 5 substituents selected from Substituent Group A1; and more preferred is a compound or a pharmacologically acceptable salt thereof in which $R_c$ denotes a C1-6 alkyl group which may be substituted with the same or different 1 to 5 substituents selected from the group consisting of (1) hydroxy groups, (2) amino groups which may be each substituted with 1 or 2 C1-6 alkyl groups which may be each substituted with 1 to 3 halogen atoms, (3) carboxyl groups, (4) pyridinyl groups, and (5) C1-6 alkyl groups which may be each substituted with 1 to 5 sugar residues.

Among the compounds represented by Formula (I), when Y is $-P(=O) (OR_d)_2 \cdot M_a^-$, preferred is a compound or a pharmacologically acceptable salt thereof in which $R_d$ is a C1-6 alkyl group which may be substituted with the same or different 1 to 3 substituents selected from Substituent Group A2; and more preferred is a compound or a pharmacologically acceptable salt thereof in which $R_d$ is a C1-6 alkyl group which may be substituted with 1 to 3 hydroxy or C1-6 alkyl groups.

Among the compounds represented by Formula (I), preferred is a compound or a pharmacologically acceptable salt thereof in which A is represented by Formulae (A-1) or (A-2).

Among the compounds represented by Formula (I), when A is represented by Formula (A-1), preferred is a compound or a pharmacologically acceptable salt thereof in which $R^1$, $R^2$, $R^3$, and $R^4$ are each a hydrogen atom or a C1-6 alkyl group.

Among the compounds represented by Formula (I), when A is represented by Formula (A-1), preferred is a compound or a pharmacologically acceptable salt thereof in which $X_1$ is a C1-6 alkylene group which may be substituted with 1 to 3 hydroxy or C1-6 alkyl groups which may be substituted with 1 to 3 hydroxy groups; and more preferred is a compound or a pharmacologically acceptable salt thereof in which $X_1$ is $=CH-CH(OH)-R^7$, wherein $R^7$ is a C1-6 alkyl group).

Among the compounds represented by Formula (I), when A is represented by Formula (A-1), preferred is a compound or a pharmacologically acceptable salt thereof in which $Ar_1$ is $-X_{1-a}-Ar_{1-a}$, wherein $Ar_{1-a}$ denotes a 6- to 14-membered aromatic hydrocarbon ring or 5- to 14-membered aromatic heterocyclic group which may be substituted with 1 to 3 substituents selected from Substituent Group A2, and $X_{1-a}$ denotes a single bond or an oxygen atom;

more preferred is a compound or a pharmacologically acceptable salt thereof in which $Ar_1$ is a phenyl or pyridinyl group which may be substituted with 1 to 3 halogen atoms; and most preferred is a compound or a pharmacologically acceptable salt thereof in which $Ar_1$ is a phenyl group which may be substituted with 1 to 3 halogen atoms.

Among the compounds represented by Formula (I), when A is represented by Formula (A-2), preferred is a compound or a pharmacologically acceptable salt thereof in which $R^5$ and $R^6$ are the same or different groups selected from Substituent Group A2 below; and more preferred is a compound or a pharmacologically acceptable salt thereof in which $R^5$ and $R^6$ are the same or different and are each a hydrogen atom or a C1-6 alkyl group.

Among the compounds represented by Formula (I), when A is represented by Formula (A-2), preferred is a compound or a pharmacologically acceptable salt thereof in which $Z_1$ and $Z_2$ are the same or different and each denote a methylene or vinylene group which may be substituted with 1 or 2 substituents selected from Substituent Group A2, an oxygen atom, or an imino group which may be substituted with a C1-6 alkyl group or a C1-6 acyl group;

more preferred is a compound or a pharmacologically acceptable salt thereof in which $Z_1$ and $Z_2$ are the same or different and each denote an oxygen atom or a methylene group which may be substituted with 1 or 2 substituents selected from Substituent Group A2; and most preferred is a compound or a pharmacologically acceptable salt thereof in which $Z_1$ and $Z_2$ are the same or different and each denote an oxygen atom or a methylene group which may be substituted with 1 or 2 C1-6 alkyl groups or halogen atoms.

Among the compounds represented by Formula (I), when A is represented by Formula (A-2), preferred is a compound or a pharmacologically acceptable salt thereof in which $Ar_2$ is a 6- to 14-membered aromatic hydrocarbon ring or 5- to 14-membered aromatic heterocyclic group which may be substituted with 1 to 3 substituents selected from Substituent Group A2; and more preferred is a compound or a pharmacologically acceptable salt thereof in which $Ar_2$ is a phenyl group which is substituted with 1 to 3 halogen atoms.

Among the compounds represented by Formula (I), when A is represented by Formula (A-2), preferred is a compound or a pharmacologically acceptable salt thereof in which p, q, and r are the same or different and each denote an integer of 0 to 2; and more preferred is a compound or a pharmacologically acceptable salt thereof in which p, q, and r are each 1; or p and q are each 1 and r denotes 0.

In the present invention, preferable examples of the compounds represented by Formula (I) or pharmacologically acceptable salts thereof include the following compounds:

1) 3-{4-{1-[(S)-1-(4-fluorophenyl)ethyl]-2-oxopiperidin-(3E)-ylidenemethyl}-2-methoxyphenyl}-5-methyl-1-(phosphonooxymethyl)-3H-imidazol-1-ium trifluoroacetate, 2) 1-acetoxymethyl-3-{4-{1-[(S)-1-(4-fluorophenyl)ethyl]-2-oxopiperidin-(3E)-ylidenemethyl}-2-methoxyphenyl}-5-methyl-3H-imidazol-1-ium iodide, 3) 3-{4-{1-[(1R,2R)-2-hydroxy-1-(3,4,5-trifluorophenyl)propyl]-2-oxopiperidin-(3E)-ylidenemethyl}-2-methoxyphenyl}-5-methyl-1-(phosphonooxymethyl)-3H-imidazol-1-ium trifluoroacetate, 4) 3-[2-fluoro-4-[(S)-4-[(1R,2R)-2-hydroxy-1-(3,4,5-trifluorophenyl)propyl]-6-methyl-3-oxomorpholin-(2Z)-ylidenemethyl]phenyl]-5-methyl-1-phosphonooxymethyl-3H-imidazol-1-ium trifluoroacetate, 5) 3-{2-methoxy-4-[(3S,8aS)-5-oxo-3-(3,4,5-trifluorophenyl)hexahydroindolizin-(6E)-ylidenemethyl]phenyl}-5-methyl-1-phosphonooxymethyl-3H-imidazol-1-ium trifluoroacetate, 6) 3-{4-{(S)-4-[(S)-1-(2,6-difluoropyridin-3-yl)ethyl]-6-methyl-3-oxomorpholin-(2Z)-ylidenemethyl}-2-methoxyphenyl}-5-methyl-1-phosphonooxymethyl-3H-imidazol-1-ium chloride, 7) 3-{4-[(3S,8aS)-3-(4-chlorophenyl)-5-oxohexahydroindolizin-(6E)-ylidenemethyl]-2-methoxyphenyl}-5-methyl-1-(phosphonooxymethyl)-3H-imidazol-1-ium trifluoroacetate, 8) 3-{4-{(S)-4-[(1R,2R)-1-(3,4-difluorophenyl)-2-hydroxypropyl]-6-methyl-3-oxomorpholin-(2Z)-ylidenemethyl}-2-fluorophenyl}-5-methyl-1-phosphonooxymethyl-3H-imidazol-1-ium trifluoroacetate, 9) 3-{2-methoxy-4-[(6S,9aS)-4-oxo-6-(3,4,5-trifluorophenyl)hexahydroquinolizin-(3E)-ylidenemethyl]phenyl}-5-methyl-1-(phosphonooxymethyl)-3H-imidazol-1-ium trifluoroacetate,
10) 3-{2-methoxy-4-[(4R,9aS)-6-oxo-4-(3,4,5-trifluorophenyl)hexahydropyrido[2,1-c][1,4]oxazin-(7E)-ylidenemethyl]phenyl}-5-methyl-1-phosphonooxymethyl-3H-imidazol-1-ium trifluoroacetate,
11) 3-{4-{(S)-4-[(1R,2R)-2-hydroxy-1-(3,4,5-trifluorophenyl)propyl]-6-methyl-3-oxomorpholin-(2Z)-ylidenemethyl}-2-methoxyphenyl}-5-methyl-1-(phosphonooxymethyl)-3H-imidazol-1-ium_trifluoroacetate,
12) 3-{4-[(6S,9aR)-6-(4-chlorophenyl)-4-oxohexahydroquinolizin-(3E)-ylidenemethyl]-2-methoxyphenyl}-5-methyl-1-phosphonooxymethyl-3H-imidazol-1-ium trifluoroacetate,
13) 3-{2-methoxy-4-[(1S,6R,9aR)-1-methyl-4-oxo-6-(3,4,5-trifluorophenyl)tetrahydro[1,4]-oxazino[3,4-c][1,4]oxazine-(3Z)-ylidenemethyl]phenyl}-5-methyl-1-phosphonooxymethyl-3H-imidazole-1-ium trifluoroacetate,
14) 3-{4-[(1S,6R,9aR)-6-(4-chlorophenyl)-1-methyl-4-oxotetrahydro[1,4]oxazino[3,4-c][1,4]oxazine-(3Z)-ylidenemethyl]-2-methoxyphenyl}-5-methyl-1-phosphonooxymethyl-3H-imidazol-1-ium trifluoroacetate,
15) 3-{2-methoxy-4-[(1S,6S,8aR)-1-methyl-4-oxo-6-(3,4,5-trifluorophenyl)tetrahydropyrrolo[2,1-c][1,4]oxazine-(3Z)-ylidenemethyl]phenyl}-5-methyl-1-phosphonooxymethyl-3H-imidazole-1-ium trifluoroacetate,
16) 3-{4-[(1S,6R,9aR)-6-(3,4-difluorophenyl)-1-methyl-4-oxotetrahydro[1,4]oxazino[3,4-c][1,4]oxazine-(3Z)-ylidenemethyl]-2-methoxyphenyl}-5-methyl-1-phosphonooxymethyl-3H-imidazole-1-ium trifluoroacetate, and
17) 3-{4-[(6R,9aR)-1,1-dimethyl-4-oxo-6-(3,4,5-trifluorophenyl)tetrahydro[1,4]oxazino[3,4-c][1,4]oxazine-(3Z)-ylidenemethyl]-2-methoxyphenyl}-5-methyl-1-phosphonooxymethyl-3H-imidazole-1-ium trifluoroacetate.

In the present invention, preferable examples of the compounds represented by Formula (I) include the following compounds:
1) 1-{4-[(E)-{1-[(1S)-1-(4-fluorophenyl)ethyl]-2-oxopiperidin-3-ylidene}methyl]-2-methoxyphenyl}-4-methyl-1H-imidazol-3-iomethyl monohydrogen phosphate,
2) 1-{4-[(E)-{1-[(1R,2R)-2-hydroxy-1-(3,4,5-trifluorophenyl)propyl]-2-oxopiperidin-3-ylidene}methyl]-2-methoxyphenyl}-4-methyl-1H-imidazol-3-iomethyl monohydrogen phosphate,
3) 1-{2-fluoro-4-[(Z)-{(6S)-4-[(1R,2R)-2-hydroxy-1-(3,4,5-trifluorophenyl)propyl]-6-methyl-3-oxomorpholin-2-ylidene}methyl]phenyl}-4-methyl-1H-imidazol-3-iomethyl monohydrogen phosphate,
4) 1-(2-methoxy-4-{(E)-[(3S,8aS)-5-oxo-3-(3,4,5-trifluorophenyl)hexahydroindolizin-6(5H)-ylidene]methyl}phenyl)-4-methyl-1H-imidazol-3-iomethyl monohydrogen phosphate,
5) 1-{4-[(Z)-{(6S)-4-[(1S)-1-(2,6-difluoropyridin-3-yl)ethyl]-6-methyl-3-oxomorpholin-2-ylidene}methyl]-2-methoxyphenyl}-4-methyl-1H-imidazol-3-iomethyl monohydrogen phosphate,
6) 1-(4-{(E)-[(3S,8aS)-3-(4-chlorophenyl)-5-oxohexahydroindolizin-6(5H)-ylidene]methyl}-2-methoxyphenyl)-4-methyl-1H-imidazol-3-iomethyl monohydrogen phosphate,
7) 1-{4-[(Z)-{(6S)-4-[(1R,2R)-1-(3,4-difluorophenyl)-2-hydroxypropyl]-6-methyl-3-oxomorpholin-2-ylidene}methyl]-2-fluorophenyl}-4-methyl-1H-imidazol-3-iomethyl monohydrogen phosphate,
8) 1-(2-methoxy-4-{(E)-[(6S,9aS)-4-oxo-6-(3,4,5-trifluorophenyl)hexahydro-2H-quinolizin-3(4H)-ylidene]methyl}phenyl)-4-methyl-1H-imidazol-3-iomethyl monohydrogen phosphate,
9) 1-(2-methoxy-4-{(E)-[(4R,9aS)-6-oxo-4-(3,4,5-trifluorophenyl)hexahydropyrido[2,1-c][1,4]oxazin-7(6H)-ylidene]methyl}phenyl)-4-methyl-1H-imidazol-3-iomethyl monohydrogen phosphate,
10) 1-{4-[(Z)-{(6S)-4-[(1R,2R)-2-hydroxy-1-(3,4,5-trifluorophenyl)propyl]-6-methyl-3-oxomorpholin-2-ylidene}methyl]-2-methoxyphenyl}-4-methyl-1H-imidazol-3-iomethyl monohydrogen phosphate,
11) 1-(4-{(E)-[(6S,9aR)-6-(4-chlorophenyl)-4-oxohexahydro-2H-quinolizin-3(4H)-ylidene]methyl}-2-methoxyphenyl)-4-methyl-1H-imidazol-3-iomethyl monohydrogen phosphate,
12) 1-(2-methoxy-4-{(Z)-[(1S,6R,9aR)-1-methyl-4-oxo-6-(3,4,5-trifluorophenyl)tetrahydro-1H-[1,4]oxazino[3,4-c][1,4]oxazin-3(4H)-ylidene]methyl}phenyl)-4-methyl-1H-imidazol-3-iomethyl monohydrogen phosphate,
13) 1-(4-{(Z)-[(1S,6R,9aR)-6-(4-chlorophenyl)-1-methyl-4-oxotetrahydro-1H-[1,4]oxazino[3,4-c][1,4]oxazin-3(4H)-ylidene]methyl}-2-methoxyphenyl)-4-methyl-1H-imidazol-3-iomethyl monohydrogen phosphate,
14) 1-(2-methoxy-4-{(Z)-[(1S,6S,8aR)-1-methyl-4-oxo-6-(3,4,5-trifluorophenyl)tetrahydro-1H-pyrrolo[2,1-c][1,4]oxazin-3(4H)-ylidene]methyl}phenyl)-4-methyl-1H-imidazol-3-iomethyl monohydrogen phosphate,
15) 1-(4-{(Z)-[(1S,6R,9aR)-6-(3,4-difluorophenyl)-1-methyl-4-oxotetrahydro-1H-[1,4]oxazino[3,4-c][1,4]oxazin-3(4H)-ylidene]methyl}-2-methoxyphenyl)-4-methyl-1H-imidazol-3-iomethyl monohydrogen phosphate and
16) 1-(4-{(Z)-[(6R,9aR)-1,1-dimethyl-4-oxo-6-(3,4,5-trifluorophenyl)tetrahydro-1H-[1,4]oxazino[3,4-c][1,4]oxazin-3(4H)-ylidene]methyl}-2-methoxyphenyl)-4-methyl-1H-imidazol-3-iomethyl monohydrogen phosphate.

Among the compounds represented by Formula (I), preferable aspects have been described above, but the pharmaceutical active ingredients for drugs according to the present invention are not limited to the compounds specifically described herein and can be selected from the maximum range of compounds represented by Formula (I).

Methods for manufacturing compounds represented by Formula (I) according to the present invention will now be described. Compounds represented by Formula (I) can be synthesized according to, for example, a general manufacturing method 1 or 2 described below.

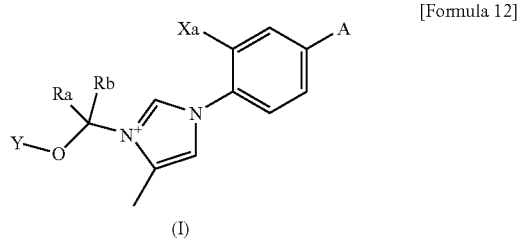

[Formula 12]

(I)

(wherein A, $X_a$, Y, $R_a$, and $R_b$ are the same as defined above.)
In addition, for properly manufacturing compounds according to the present invention, a protective group suitable for each process, which is known to those skilled in the art (see, for example, T. Greene, et al., "Protective Groups in Organic Synthesis", John Wiley & Sons, Inc., NY, 1999), is selected and protection of functional groups and deprotection of the protecting groups may be optionally performed.

(General Manufacturing Method 1)

A typical "General Manufacturing Method 1" for the compound represented by Formula (I) according to the present invention will now be described.

[Formula 13]

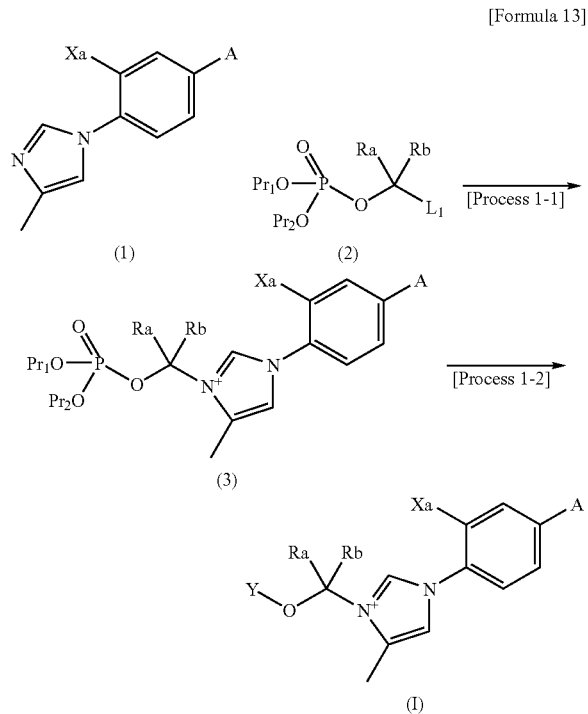

wherein A, $X_a$, Y, $R_a$, and $R_b$ are the same as defined above, $L_1$ denotes a halogen such as a fluorine atom, a chlorine atom, a bromine atom, or an iodine atom; or a sulfonate group such as a methanesulfonate, a p-toluenesulfonate, or a trifluoromethanesulfonate, $Pr_1$ and $Pr_2$ each denote a protecting group for a hydroxy group (for example, an alkyl group such as a methyl group, an ethyl group, an allyl group, a benzyl group, a triphenylmethyl group, a tert-butyl group, a propionitrile group, a trichloroethyl group, or a trimethylsilylethyl group; an aryl group such as a phenyl group or a quinolinyl group; or a silyl group such as a tert-butyldimethylsilyl group or a tert-butyldiphenylsilyl group), and $M_1^-$ denotes an anion of a halogen atom such as a fluorine atom, a chlorine atom, a bromine atom, or an iodine atom; or an anion of an organic acid such as methanesulfonic acid or benzenesulfonic acid.

The above-mentioned "General Manufacturing Method 1" is an exemplary method for producing a compound of Formula (I) by condensing a compound (1) and a compound (2) according to "Process 1-1" and then subjecting the obtained compound (3) to the deprotection reaction in "Process 1-2".

(Preparation of Compound of Formula (I))

The compound of Formula (I) can be prepared by deprotecting the compound (3) according to "Process 1-2". That is, though the deprotection reaction in "Process 1-2" varies depending on the starting material, no specific limitation is imposed upon it as long as the reaction is conducted under conditions similar to those in this reaction. The reaction can be carried out by a known method disclosed in many publications. Examples of the method include i) acid hydrolysis, ii) base hydrolysis, iii) hydrogenolysis, iv) reductive decomposition, v) photodecomposition, and vi) elimination reaction (for example, see T. Greene, et al., Protective Groups in Organic Synthesis, John Wiley & Sons, Inc., NY, 1999, 660-700).

In the case of i) acid hydrolysis, for example, preferably, a compound (3) is stirred in a solvent in the presence of 1.0 to 100.0 molar equivalents of an acid with respect to the compound (3). This reaction is particularly preferable when $Pr_1$ and $Pr_2$ are a tert-butyl group. The acid used in this reaction varies depending on the starting material, but is not specifically limited. Preferable examples of the acid include organic acids such as trifluoroacetic acid and methanesulfonic acid; inorganic acids such as hydrochloric acid, hydrobromic acid, and sulfuric acid; and Lewis acids such as boron trichloride, boron tribromide, and boron triiodide. The solvent to be used is not specifically limited as long as the solvent can dissolve the starting material and the used acid to certain degrees, but preferable examples of the solvent include ethyl acetate, toluene, acetonitrile, THF (tetrahydrofuran), 1,4-dioxane, ethanol, methanol, propanol, methylene chloride, chloroform, water, and a mixture thereof. In some cases, an acid is used as the solvent. The reaction temperature should be a temperature which is sufficient for completing the reaction without promoting formation of undesired by-products and is preferably, for example, ice-cooling to 100° C. This reaction completes in 1 to 24 hours, and the progress of the reaction can be monitored by known chromatography technology. Undesired by-products can be removed by commonly used chromatography technology and/or technology known to those skilled in the art, such as crystallization.

In the case of ii) base hydrolysis, for example, preferably, a compound (3) is stirred in a solvent in the presence of 1.0 to 100.0 molar equivalents of a base with respect to the compound (3). The base used in this reaction varies depending on the starting material, but is not specifically limited. Preferable examples of the base include sodium hydroxide, potassium hydroxide, lithium hydroxide, and ammonia. The solvent to be used is not specifically limited as long as the solvent can dissolve the starting material and the used base to certain degrees, but preferable examples of the solvent include tetrahydrofuran, 1,4-dioxane, ethanol, methanol, propanol, water, and a mixture thereof. The reaction temperature should be a temperature which is sufficient for completing the reaction without promoting formation of undesired by-products and is preferably, for example, room temperature to 150° C. This reaction completes in 1 to 24 hours, and the progress of the reaction can be monitored by known chromatography technology. Undesired by-products can be removed by commonly used chromatography technology and/or technology known to those skilled in the art, such as crystallization.

In the case of iii) hydrogenolysis, for example, preferably, a compound (3) is stirred in a solvent in the presence of 0.01 to 0.5 molar equivalents of a metal catalyst with respect to the compound (3) under hydrogen atmosphere of normal pressure to 5 MPa or in the presence of a hydrogen donor. The metal catalyst used in this reaction varies depending on the starting material, but is not specifically limited. Preferable examples of the metal catalyst include palladium-carbon, rhodium-carbon, ruthenium-carbon, palladium hydroxide, and platinum oxide. The hydrogen donor varies depending on the starting material, but is not specifically limited. Preferable examples of the hydrogen donor include formic acid, ammonium formate, and 1,4-cyclohexadiene. The solvent to be used varies depending on the starting material and the used metal catalyst, but is not specifically limited. Preferable examples of the solvent include ethyl acetate, chloroform, methylene chloride, toluene, tetrahydrofuran, dioxane, ethanol, methanol, propanol, water, and a mixture thereof. The reaction temperature should be a temperature which is sufficient for completing the reaction without promoting formation of undesired by-products and is preferably, for example, room temperature to 100° C. This reaction completes in 1 to 24 hours, and the progress of the reaction can be monitored by known chromatography technology. Undesired by-products can be removed by commonly used chromatography technology and/or technology known to those skilled in the art, such as crystallization.

In the case of iv) reductive decomposition, for example, preferably, a compound (3) is stirred in a solvent in the presence of 1.0 to 10.0 molar equivalents of a metal reagent with respect to the compound (3). This reaction is particularly preferable when $Pr_1$ and $Pr_2$ are a trichloroethyl group. The metal reagent used in this reaction varies depending on the starting material, but is not specifically limited. Preferable examples of the metal reagent include sodium, zinc, copper, iron, mercury, and a mixture complex thereof. The solvent to be used varies depending on the starting material and the used metal reagent, but is not specifically limited. Preferable examples of the solvent include DMF (dimethylformamide), tetrahydrofuran, 1,4-dioxane, acetonitrile, liquid ammonia, and a mixture thereof. The reaction temperature should be a temperature which is sufficient for completing the reaction without promoting formation of undesired by-products and is preferably, for example, −78° C. to 100° C. This reaction completes in 1 to 24 hours, and the progress of the reaction can be monitored by known chromatography technology. Undesired by-products can be removed by commonly used chromatography technology and/or technology known to those skilled in the art, such as crystallization.

In the case of v) photodecomposition, for example, preferably, a compound (3) is stirred in a solvent under light irradiation. A light source used in this reaction varies depending on the starting material, but is not specifically limited. Preferable examples of the light source include an ultraviolet source such as a mercury lamp. The solvent to be used varies depending on the starting material, but is not specifically limited. Preferable examples of the solvent include toluene, ethanol, methanol, propanol, and a mixture thereof. In some cases, 1.0 to 100.0 molar equivalents of a base such as pyridine with respect to the compound (3) is added for efficiently promoting the reaction. The reaction temperature should be a temperature which is sufficient for completing the reaction without promoting formation of undesired by-products and is preferably, for example, −78 to 100° C. This reaction completes in 1 to 24 hours, and the progress of the reaction can be monitored by known chromatography technology. Undesired by-products can be removed by commonly used chromatography technology and/or technology known to those skilled in the art, such as crystallization.

In the case of vi) elimination reaction, for example, preferably, a compound (3) is stirred in a solvent in the presence of 1.0 to 10.0 molar equivalents of an eliminating agent with respect to the compound (3). The eliminating agent used in this reaction varies depending on the starting material, but is not specifically limited. Preferable examples of the eliminating agent include bases such as triethylamine, diisopropylethylamine, and lutidine (which are particularly preferable when $Pr_1$ and $Pr_2$ are a propionitrile group); fluorine anion reagents such as tetrabutylammonium fluoride, pyridinium fluoride, and hydrogen fluoride (which are particularly preferable when $Pr_1$ and $Pr_2$ are a trimethylsilylethyl group, tert-butyldimethylsilyl group, or a tert-butyldiphenylsilyl group); and halogen anion groups such as trimethylsilyl iodide, trimethylsilyl bromide, sodium iodide, and potassium iodide (which are particularly preferable when $Pr_1$ and $Pr_2$ are a methyl ethyl, benzyl, or phenyl group). The solvent to be used varies depending on the starting material, but is not specifically limited. Preferable examples of the solvent include tetrahydrofuran, dimethylformamide, 1,4-dioxane, methylene chloride, chloroform, acetonitrile, toluene, ethanol, methanol, propanol, ethyl acetate, water, and a mixture thereof. The reaction temperature should be a temperature which is sufficient for completing the reaction without promoting formation of undesired by-products and is preferably, for example, −78 to 100° C. This reaction completes in 1 to 24 hours, and the progress of the reaction can be monitored by known chromatography technology. Undesired by-products can be removed by commonly used chromatography technology and/or technology known to those skilled in the art, such as crystallization.

The compounds obtained by the above-described methods can be changed to compounds represented by Formula (I) each having a desired anion $M_a^-$ by ion exchange according to need. The ion exchange is preferably performed, for example, by using an anion exchange resin or treating the compound with an organic acid (preferably, for example, acetic acid, trifluoroacetic acid, benzenesulfonic acid, methanesulfonic acid, citric acid, or maleic acid) or with an inorganic acid (preferably, for example, hydrochloric acid, hydrobromic acid, hydroiodic acid, sulfuric acid, nitric acid, or phosphoric acid). In addition, the compounds obtained by the above-described methods can be changed to compounds represented by Formula (I) in a bipolar ionic structure can be obtained by subjecting the compounds to reverse-phase chromatography (the carrier is preferably, for example, C18 silica gel). Further, the compounds represented by Formula (I) in a bipolar ionic structure can be changed to compounds represented by Formula (I) each having a desired anion $M_b^+$ by, for example, treating the compound with an alkali metal salt (preferably, for example, sodium hydroxide, potassium hydroxide, or lithium hydroxide) or with an alkaline earth metal salt (preferably, for example, calcium hydroxide, magnesium hydroxide, magnesium oxide, calcium oxide, magnesium chloride, or calcium chloride).

(Preparation of Compound (3))

The compound (3) can be prepared by condensing a compound (1) and a compound (2) according to "Process 1-1". That is, though "Process 1-1" varies depending on the starting material, no specific limitation is imposed upon it as long as the reaction is conducted under conditions similar to those in this reaction. The process can be carried out by known methods which are disclosed in many publications (see, for example, Jikken Kagaku Koza (Experimental Methods of Chemistry), vol. 20, Yuki Gosei (Organic Synthesis) [II], edited by the Chemical Society of Japan, Maruzen Co., Ltd., July 1992, 284-288). For example, the process is preferably carried out by stirring a compound (1) and 1.0 to 5.0 molar equivalents of a compound (2) with respect to the compound (1) in a solvent in the presence of 0.1 to 10.0 molar equivalents of a base with respect to the compound (1). The base used in this reaction varies depending on the starting material, but is not specifically limited. Preferable examples of the base include organic amines such as diisopropylethylamine, triethylamine, pyridine, lutidine, and 1,8-diazabicyclo[5,4,0]undecene; alkali metal hydrides such as sodium hydride and lithium hydride; alkali metal salts such as sodium hydroxide, potassium hydroxide, sodium carbonate, potassium carbonate, and cesium carbonate; and alkaline earth metal hydroxides. The solvent to be used is not specifically limited as long as the solvent can dissolve the starting material and the used base to certain degrees. Preferable examples of the solvent include dimethoxyethane, 1,4-dioxane, tetrahydrofuran, dimethylformamide, dimethylsulfoxide, acetone, methylethylketone, acetonitrile, methylene chloride, chloroform, ethanol, methanol, propanol, water, and a mixture thereof. In some cases, the reaction is carried out in the absence of a solvent. The reaction temperature should be a temperature which is sufficient for completing the reaction without promoting formation of undesired by-products and is preferably, for example, ice-cooling to 100° C. This reaction completes in 1 to 24 hours, and the progress of the reaction can be monitored by known chromatography technology. Undesired by-products can be removed by commonly used chromatography technology and/or technology known to those skilled in the art, such as crystallization.

(Preparation of Compound (1))

The compound (1) can be prepared by a known method disclosed in International Publication No. WO05/115990 or any methods in Reference Examples 1 to 6 described below or modified methods thereof.

Reference Example 1 the starting material, no specific limitation is imposed upon it as long as the reaction is conducted under conditions similar to those in this reaction. The reaction can be carried out by a known method disclosed in many publications (for example, Jikken Kagaku Koza (Experimental Methods of Chemistry), vol. 19, Yuki Gosei (Organic Synthesis) [I], edited by the Chemical Society of Japan, Maruzen Co., Ltd., June 1992, 194-226). The reaction is preferably carried out by, for example, i) treating the aldol adduct (7a) with an acid (for example, Jikken Kagaku Koza (Experimental Methods of Chemistry), vol. 19, Yuki Gosei (Organic Synthesis) [I], edited by the Chemical Society of Japan, Maruzen Co., Ltd., June 1992, 194-196), or ii) converting an alcohol group of the aldol adduct (7a) into a leaving group such as a sulfonate ester group or a halogen atom and then treating the aldol adduct (7a) with a base (for example, Jikken Kagaku Koza (Experimental Methods of Chemistry), vol. 19, Yuki Gosei (Organic Synthesis) [I], edited by the Chemical Society of Japan, Maruzen Co., Ltd., June 1992, 198-205).

In the above-mentioned method i), the acid, solvent, and temperature conditions vary depending on the starting material, but are not specifically limited. For example, 0.1 to 10 molar equivalents of an acid such as hydrochloric acid, sul-

[Formula 14]

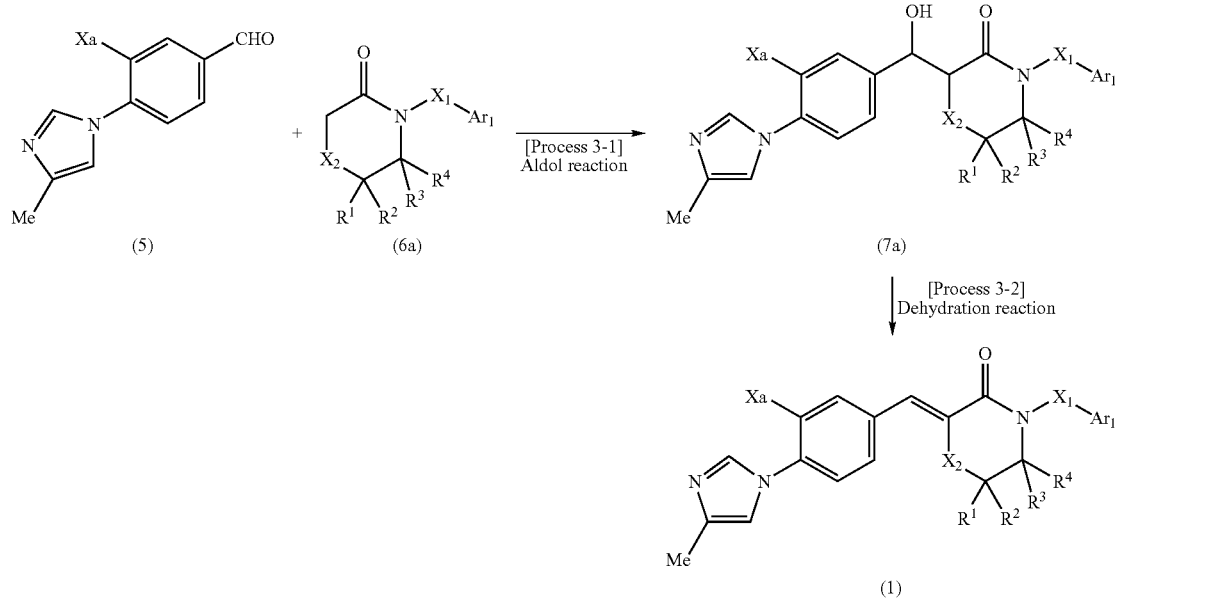

[wherein $R^1$, $R^2$, $R^3$, $R^4$, $X_1$ (the $X_1$ may have a protecting group when it contains a hydroxy group), $X_a$, $X_2$, and $Ar_1$ are the same as defined above].

The "Reference Example 1" is an exemplary method for preparing a compound (1) by subjecting an aldehyde compound (5) and 0.3 to 3.0 molar equivalents of an amide compound (6a) with respect to the aldehyde compound (5) to aldol reaction in "Process 3-1" to obtain an aldol adduct (7a) and then subjecting the resulting aldol adduct to dehydration reaction.

(Conversion of Aldol Adduct (7a) into Compound (1))

The aldol adduct (7a) can be converted into the compound (1) by dehydration reaction in "Process 3-2". That is, though the dehydration reaction in "Process 3-2" varies depending on furic acid, phosphoric acid, potassium hydrosulfuric acid, oxalic acid, p-toluenesulfonic acid, boron trifluoride ether complex, thionyl chloride, or aluminium oxide is used with respect to the aldol adduct (7a). Though the reaction may be performed in the absence of a solvent in some cases, a solvent or solvent mixture which can dissolve the starting material to a certain degree without inhibiting the reaction is used. Preferable examples of the solvent include water, acetone, dimethylsulfoxide, and hexamethylphosphoroamide. Further, in some cases, 0.1 to 10 molar equivalents of a combination of an acid and an organic base such as pyridine with respect to the aldol adduct (7a) improves the reaction rate and the reaction yield. The reaction temperature should be a temperature which is sufficient for completing the reaction without promoting formation of undesired by-products and is preferably, for example, room temperature to 200° C. This reaction preferably completes in 0.5 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

In the above-mentioned method ii), preferable examples of the leaving group include an acetyl group, a methanesulfonate ester group, a p-toluenesulfonate ester group, a chlorine atom, a bromine atom, and an iodine atom. The process for conversion into these leaving groups varies depending on the starting material, but is not specifically limited and can be performed according to a method which is known to those skilled in the art. Preferable examples of the solvent include halogenated solvents such as methylene chloride and chloroform, nonpolar solvents such as toluene and benzene, ether solvents such as tetrahydrofuran and ethylene glycol dimethyl ether, and solvent mixtures thereof. In addition, for example, 1.0 to 10.0 molar equivalents of an acetylating agent, a sulfonic acid-esterifying agent, or a halogenating agent with respect to the aldol adduct (7a) can be used. Examples of the acetylating agent include acetyl chloride and acetic anhydride. Examples of the sulfonic acid-esterifying agent include methanesulfonate chloride and p-toluenesulfonate chloride. Examples of the halogenating agent include thionyl chloride. The reaction temperature should be a temperature which is sufficient for completing the reaction without promoting formation of undesired by-products and is preferably, for example, −78 to 100° C. This reaction preferably completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization. The second process, namely, the elimination reaction, is preferably performed in, for example, a halogenated solvent such as methylene chloride; a nonpolar solvent such as toluene; a polar solvent such as acetonitrile, dimethylformamide, or dimethylsulfoxide; an ether solvent such as tetrahydrofuran or ethylene glycol dimethyl ether; or a solvent mixture thereof. Preferably, 0.1 to 10 molar equivalents of a base with respect to the aldol adduct (7a) is used. Examples of the base include organic bases such as diazabicycloundecene, pyridine, 4-dimethylaminopyridine, and triethylamine; quaternary ammonium salts such as tetrabutylammonium hydroxide; alkali metal salts of alcohols such as sodium methoxide and potassium tert-butoxide; alkali metal hydroxides such as sodium hydroxide; alkali metal carbonates such as lithium carbonate and potassium carbonate; and organic metal reagents such as lithium diisopropylamide.

In addition, an organic base such as pyridine can be used as a solvent. The reaction temperature should be a temperature which is sufficient for completing the reaction without promoting formation of undesired by-products and is preferably, for example, −78 to 100° C. This reaction preferably completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

(Preparation of Aldol Adduct (7a))

The aldol adduct (7a) can be prepared, for example, by using an aldehyde compound (5) and an amide compound (6a) according to "Process 3-1". That is, though the aldol reaction in "Process 3-1" varies depending on the starting material, no specific limitation is imposed upon it as long as the reaction is conducted under conditions similar to those in this reaction. The reaction can be carried out by a method known to those skilled in the art (see, for example, Jikken Kagaku Koza (Experimental Methods of Chemistry), vol. 20, Yuki Gosei (Organic Synthesis) [II], edited by the Chemical Society of Japan, Maruzen Co., Ltd., July 1992, 94-100). For example, the aldol reaction is carried out by i) preferably enolating an amide compound (6a) with 1.0 to 5.0 molar equivalents of a base such as lithium diisopropylamide, sodium hydride, or sodium methoxide with respect to the amide compound (6a) and then reacting the resulting alkali metal enolate with an aldehyde compound (5) (see, for example, Jikken Kagaku Koza (Experimental Methods of Chemistry), vol. 20, Yuki Gosei (Organic Synthesis) [II], edited by the Chemical Society of Japan, Maruzen Co., Ltd., July 1992, 97-98), or ii) enolating an amide compound (6a) with 1.0 to 5.0 molar equivalents of a base such as lithium diisopropylamide, sodium hydride, or sodium methoxide with respect to the amide compound (6a), preferably reacting the resulting alkali metal enolate with, for example, a silicon halide reagent such as trimethylchlorosilane or tert-butyldimethylchlorosilane, and then preferably reacting the resulting silyl enol ether with an aldehyde compound (5), for example, in the presence of a Lewis acid such as titanium tetrachloride or boron trifluoride (see, for example, Jikken Kagaku Koza (Experimental Methods of Chemistry), vol. 20, Yuki Gosei (Organic Synthesis) [II], edited by the Chemical Society of Japan, Maruzen Co., Ltd., July 1992, 96-97).

The solvent to be used and the reaction temperature vary depending on the starting material, but are not specifically limited. Preferable examples of the solvent or solvent mixture which can dissolve the starting material to a certain degree without inhibiting the reaction include ether solvents such as tetrahydrofuran, 1,4-dioxane, and diethyl ether; halogenated solvents such as methylene chloride, 1,2-dichloroethane, and chloroform; and nonpolar solvents such as toluene and xylene. The reaction temperature should be a temperature which is sufficient for completing the reaction without promoting formation of undesired by-products and is preferably, for example, −78° C. to room temperature. This reaction preferably completes in 0.5 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

(Preparation of Aldehyde Compound (5))

The aldehyde compound (5) can be prepared by a known method disclosed in International Publication No. WO05/115990.

(Preparation of Amide Compound (6a))

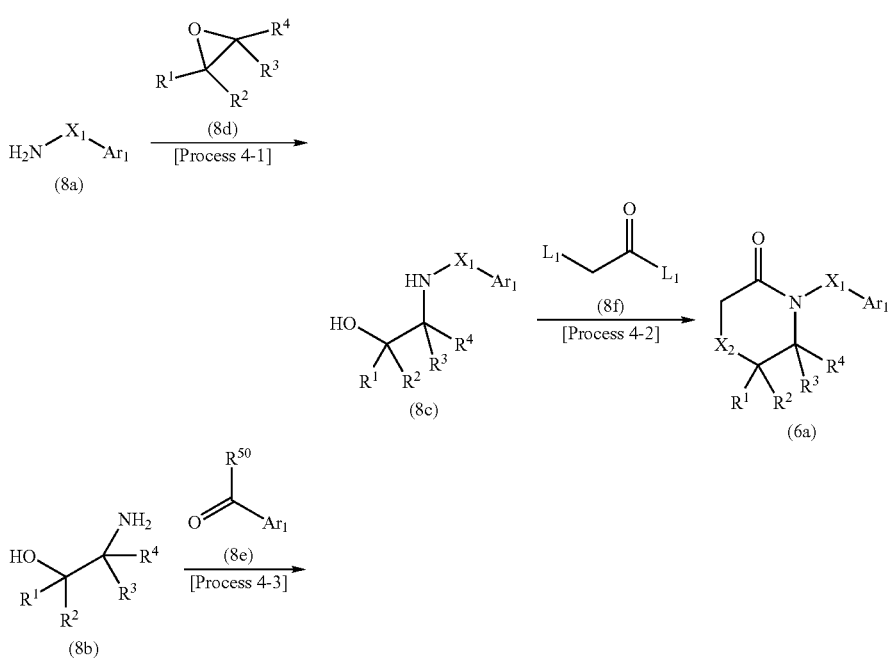

[Formula 15]

[wherein $L_1$, $R^1$, $R^2$, $R^3$, $R^4$, $R^{50}$, $X_1$ (the $X_1$ may have a protecting group when it contains a hydroxy group), $X_2$, and $Ar_1$ are the same as defined above, $R^{50}$ denotes a C1-6 alkyl group which may have protecting groups when it contains 1 to 3 hydroxy groups.].

The above-mentioned reaction formulae are exemplary methods for preparing the amide compound (6a). That is, (i) an amine compound (8a) as the starting material, which is commercially available or is prepared by a method known to those skilled in the art, is converted into a compound (8c) according to "Process 4-1" and then an oxomorpholine ring is formed in "Process 4-2", or (ii) when at least one substituent of the $X_1$ is a hydrogen atom, a compound (8b) as the starting material, which is commercially available or is prepared by a method known to those skilled in the art, is converted into a compound (8c) according to "Process 4-3" and then an oxomorpholine ring is formed in "Process 4-2".

(Conversion of Compound (8c) into Amide Compound (6a))

Though "Process 4-2" varies depending on the starting material, no specific limitation is imposed upon it as long as the reaction is conducted under conditions similar to those in this reaction. The process can be carried out by a method known to those skilled in the art. For example, preferably, the reaction is efficiently performed by vigorously agitating a compound (8c) and 1.0 to 10 molar equivalents of a compound (8f) with respect to the compound (8c) in a two-phase reaction solvent of an organic solvent and a basic aqueous solution. The solvent to be used and the reaction temperature vary depending on the starting material, but are not specifically limited. Preferably, the solvent dissolves the starting material to a certain degree without inhibiting the reaction. Preferable examples of the solvent include ether solvents such as diethyl ether; halogenated solvents such as methylene chloride, 1,2-dichloroethane, and chloroform; and nonpolar solvents such as toluene and xylene. Preferable examples of the basic aqueous solution include solutions of alkali metal salts such as sodium hydroxide, potassium hydroxide, sodium carbonate, potassium carbonate, cesium carbonate, and sodium hydrogencarbonate. The reaction temperature should be a temperature which is sufficient for completing the reaction without promoting formation of undesired by-products and is preferably, for example, −78° C. to room temperature. This reaction preferably completes in 0.5 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

In addition, in some cases, the reaction may be efficiently progressed by stirring a compound (8c) and 1.0 to 10 molar equivalents of a compound (8f) with respect to the compound (8c) under basic conditions. The solvent to be used and the reaction temperature vary depending on the starting material, but are not specifically limited. Preferably, the solvent dissolves the starting material to a certain degree without inhibiting the reaction. Preferable examples of the solvent include ether solvents such as diethyl ether and tetrahydrofuran; halogenated solvents such as methylene chloride, 1,2-dichloroethane, and chloroform; and nonpolar solvents such as toluene and xylene. The base to be used varies depending on the starting material, but is not specifically limited. The amount of the base is preferably 1.0 to 10 molar equivalents to the compound (5c). Preferable examples of the base include alkali metal salts such as sodium hydroxide, potassium hydroxide, sodium carbonate, potassium carbonate, cesium carbonate, and sodium hydrogencarbonate; and organic bases such as diazacycloundecene, pyridine, 4-dimethylaminopyridine, and triethylamine. The reaction temperature should be a temperature which is sufficient for completing the reaction without promoting formation of undesired by-products and is preferably, for example, −78° C. to room temperature. This reaction preferably completes in 0.5 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

(Preparation of Compound (8f))

The compound (8f) is commercially available or can be prepared by a method known to those skilled in the art. Preferable examples of the compound (8f) include chloroacetyl chloride and bromoacetyl bromide.

(Preparation of Compound (8c))

The compound (8c) is commercially available or can be prepared by a method known to those skilled in the art. For example, preferably, the compound (8c) is prepared (i) according to "Process 4-1" using an amine compound (8a) as the starting material, which is commercially available or prepared by a method known to those skilled in the art, or (ii) according to "Process 4-3" using a compound (8b) as the starting material, which is commercially available or prepared by a method known to those skilled in the art.

(Conversion of Compound (8a) into Compound (8c))

Though "Process 4-1" varies depending on the starting material, no specific limitation is imposed upon it as long as the reaction is conducted under conditions similar to those in this reaction. The process can be carried out by a method known to those skilled in the art. For example, ring-opening reaction is preferably performed by using a compound (8a) and 1.0 to 10 molar equivalents of an oxirane compound (8d) with respect to the compound (8a). The solvent to be used and the reaction temperature vary depending on the starting material, but are not specifically limited. Preferably, the solvent or solvent mixture dissolves the starting material to a certain degree without inhibiting the reaction. Preferable examples of the solvent include ether solvents such as diethyl ether; halogenated solvents such as methylene chloride, 1,2-dichloroethane, and chloroform; and nonpolar solvents such as toluene and xylene. In addition, in some cases, favorable results can be obtained in the absence of a solvent. The reaction temperature should be a temperature which is sufficient for completing the reaction without promoting formation of undesired by-products and is preferably, for example, room temperature to 300° C. This reaction preferably completes in 0.5 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization. In addition, in some cases, the reaction may be efficiently progressed by adding, for example, a Lewis acid such as boron trifluoride, titanium tetraisopropoxide, or lithium perchlorate (see, for example, Synthesis, 2004, 10, 1563-1565).

(Preparation of Compound (8a))

The compound (8a) is commercially available or can be prepared by a method known to those skilled in the art. When the compound (8a) is not commercially available, it can be prepared according to a method which is published and known to those skilled in the art (see, for example, Jikken Kagaku Koza (Experimental Methods of Chemistry), vol. 14, Yuki-Kagobutsu no Gosei to Hannou (Synthesis and Reaction of Organic Compound) [III], edited by the Chemical Society of Japan, Maruzen Co., Ltd., February 1978, 1332-1399). For example, preferably, the compound (8a) can be prepared by i) converting a corresponding carbonyl derivative into a compound (8a) by reductive amination; ii) reducing a corresponding carbonyl derivative into an alcohol derivative, subjecting the alcohol derivative to displacement reaction known to those skilled in the art to obtain an amine equivalent (preferably, for example, an azido group or imido group), and then converting the amine equivalent into a compound (8a) by a method known to those skilled in the art; iii) converting a corresponding carbonyl derivative into an oxime derivative, and then reducing the oxime derivative into a compound (8a) by a method known to those skilled in the art; iv) converting a corresponding olefin compound into an alcohol derivative by oxidation, subjecting the alcohol derivative to displacement reaction known to those skilled in the art to obtain an amine equivalent (preferably, for example, an azido group or imido group), and then converting the amine equivalent into a compound (8a) by a method known to those skilled in the art; or v) converting a corresponding olefin compound into an amino alcohol derivative by addition reaction, and then converting the amino alcohol derivative into a compound (8a) by a method known to those skilled in the art. The compound (8a) may be an optically active substance which is commercially available or prepared by a method known to those skilled in the art (see, for example, Chem. Rev., 1994, 94, 2483-2547; Tetrahedron Letters, 1996, 37, 3219-3222, Organic Letters, 2000, 2, 2821-2824). By using such a substance as the starting material, the compound according to the present invention can be prepared as an optically active compound.

(Preparation of Oxirane Compound (8d))

The oxirane compound (8d) is commercially available or can be prepared by a method known to those skilled in the art. When the compound (8d) is not commercially available, it can be prepared according to a method which is published and known to those skilled in the art (see, for example, Jikken Kagaku Koza (Experimental Methods of Chemistry), vol. 14, Yuki-Kagobutsu no Gosei to Hannou (Synthesis and Reaction of Organic Compound) [I], edited by the Chemical Society of Japan, Maruzen Co., Ltd., November 1977, 567-611).

The compound (8d) may be an optically active substance which is commercially available or prepared by a method known to those skilled in the art (see, for example, K. B. Sharpless, et al., Comprehensive Organic Synthesis, vol. 7, Chapter 3-2, B. M. Trost, Pergamon, 1991). By using such a substance as the starting material, the compound according to the present invention can be prepared as an optically active compound.

(Conversion of Compound (8b) into Compound (8c))

Though "Process 4-3" varies depending on the starting material, no specific limitation is imposed upon it as long as the reaction is conducted under conditions similar to those in this reaction. The process can be carried out by a method known to those skilled in the art. For example, the "Process 4-3" is preferably performed by reductive amination of a compound (8b) and a carbonyl compound (8e) (see, for example, Jikken Kagaku Koza (Experimental Methods of Chemistry), vol. 14, Yuki-Kagobutsu no Gosei to Hannou (Synthesis and Reaction of Organic Compound) [III], edited by the Chemical Society of Japan, Maruzen Co., Ltd., February 1978, 1380-1384). For example, an imine derivative is prepared by preferably subjecting a carbonyl compound (8e) and 0.5 to 5.0 molar equivalents of a compound (8b) with respect to the carbonyl compound (8e) to dehydration by heating under reflux, more preferably, in the presence of an acid catalyst (preferably, for example, 0.01 to 0.5 molar equivalents with respect to the carbonyl compound (8e)), for example, a typical inorganic acid such as hydrochloric acid or sulfuric acid, an organic acid such as methanesulfonic acid, p-toluenesulfonic acid, or camphorsulfonic acid, or an organic acid salt such as pyridinium or p-toluenesulfonate. The prepared imine derivative is reduced with, preferably, for example, 1.0 to 10 molar equivalents of a metal hydride such as lithium aluminium hydride or sodium borohydride to obtain a desired amine derivative. Alternatively, a carbonyl compound (8e) is treated in an inert solvent such as tetrahydrofuran, preferably, in the presence of a Lewis acid catalyst such as titanium tetraisopropoxide (preferably, for example, 0.01 to 0.5 molar equivalents with respect to the carbonyl compound (8e)) and then the resulting compound is reduced with 1.0 to 10 molar equivalents of a metal hydride such as sodium borohydride with respect to the carbonyl compound (8e). Alternatively, for example, a desired amine derivative is preferably prepared by reducing a carbonyl compound (8e) and, preferably, 0.5 to 5.0 molar equivalents of a compound (8b) with respect to the carbonyl compound (8e), preferably, in an inert solvent such as dichloromethane, 1,2-dichloroethane, tetrahydrofuran, methanol or ethanol with, preferably, 1.0 to 10 molar equivalents of a metal hydride such as sodium triacetoxy borohydride or sodium cyano borohydride with respect to the carbonyl compound (8e). Further, it is preferable to add 1.0 to 10 molar equivalents of an acidic substance such as acetic acid or hydrochloric acid with respect to the carbonyl compound (8e) in order to efficiently perform the reaction. The reaction temperature varies depending on the starting material, but is not specifically limited. The reaction temperature should be a temperature which is sufficient for completing the reaction without promoting formation of undesired by-products and is preferably, for example, room temperature to 100° C. This reaction preferably completes in 0.5 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

(Preparation of Compound (8b))

The compound (8b) is commercially available or can be prepared by a method known to those skilled in the art. When the compound (8b) is not commercially available, it can be prepared according to a method which is published and known to those skilled in the art (see, for example, Jikken Kagaku Koza (Experimental Methods of Chemistry), vol. 14, Yuki-Kagobutsu no Gosei to Hannou (Synthesis and Reaction of Organic Compound) [III], edited by the Chemical Society of Japan, Maruzen Co., Ltd., February 1978, 1332-1399). The compound (8b) may be an optically active substance which is commercially available or prepared by a method known to those skilled in the art (see, for example, Tetrahedron Letters, 1996, 37, 3219-3222). By using such a substance as the starting material, the compound according to the present invention can be prepared as an optically active compound.

(Preparation of Carbonyl Compound (8e))

The compound (8e) is commercially available or can be prepared by a method known to those skilled in the art. When the compound (8e) is not commercially available, it can be prepared according to a method which is published and known to those skilled in the art (see, for example, Jikken Kagaku Koza (Experimental Methods of Chemistry), vol. 14, Yuki-Kagobutsu no Gosei to Hannou (Synthesis and Reaction of Organic Compound) [II], edited by the Chemical Society of Japan, Maruzen Co., Ltd., December 1977, 633-875).

Reference Example 2

[Formula 16]

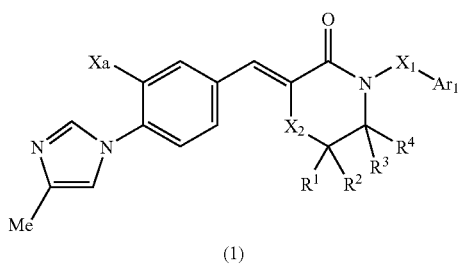

(1)

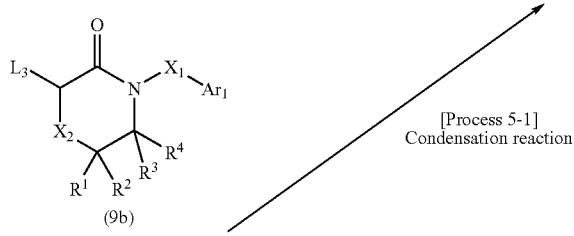

(9b)

[Process 5-1]
Condensation reaction

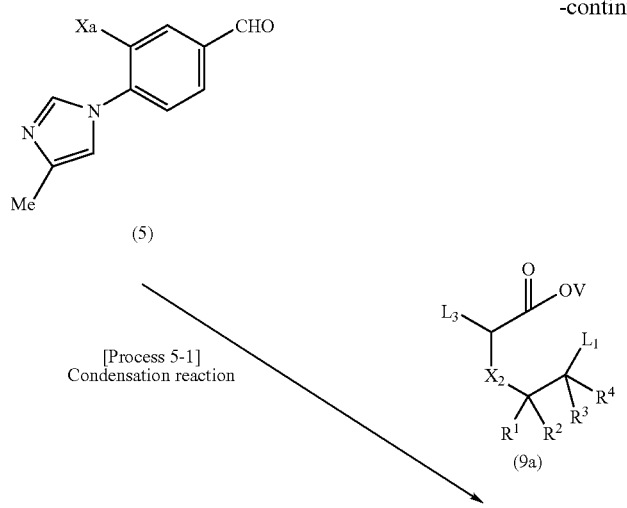

(5)

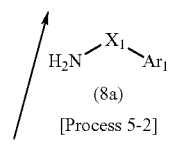

(8a)

[Process 5-2]

[Process 5-1]
Condensation reaction

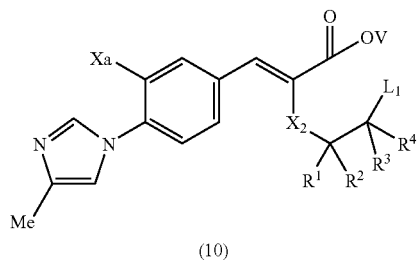

(9a)

(10)

(wherein $Ar_1$, $R^1$, $R^2$, $R^3$, $R^4$, $L_1$, $X_a$, $X_1$, and $X_2$ are the same as defined above; $L_3$ denotes a triphenylphosphonium group, a phosphite ester group, or a silyl group; and V denotes a protecting group for a carboxyl group, such as a methyl group, an ethyl group, a benzyl group, an allyl group, a triphenylmethyl group, a tert-butyl group, or a tert-butyldimethylsilyl group).

The "Reference Example 2" is an exemplary method for preparing a compound (1) by subjecting an aldehyde compound (5) and an amide compound (9b) to a condensation reaction according to "Process 5-1"; or preparing a compound (1) by subjecting an aldehyde compound (5) and an ester compound (9a) to a condensation reaction according to "Process 5-1" to obtain a compound (10) and then reacting the obtained compound (10) with an amine compound (8a) according to "Process 5-2".

(Process 5-1)

Though the condensation reaction in "Process 5-1" varies depending on the starting material, no specific limitation is imposed upon it as long as the reaction is conducted under conditions similar to those in this reaction. The reaction can be carried out by a known method disclosed in many publications. For example, the Wittig reaction, the Horner-Emmons reaction, or the Peterson reaction (for example, Jikken Kagaku Koza (Experimental Methods of Chemistry), vol. 19, Yuki Gosei (Organic Synthesis) [I], edited by the Chemical Society of Japan, Maruzen Co., Ltd., June 1992, 57-85) is preferable.

The Wittig reaction is preferably performed, for example, by stirring a compound (9b) and 0.8 to 1.5 molar equivalents of an aldehyde compound (5) with respect to the compound (9b) in a solvent in the presence of 1.0 to 5.0 molar equivalents of a base with respect to the compound (9b). Herein, $L_3$ is a triphenylphosphonium halide salt. In this reaction, i) a compound (9b) and a base are treated first to form a phosphonium ylide, and then an aldehyde (5) is added thereto; or ii) a base is added to a mixture of a compound (9b) and an aldehyde compound (5). The reaction is similarly performed using a compound (9a) instead of the compound (9b). This reaction is preferably carried out in the presence of a solvent from the viewpoints of operational ease and stirring efficiency. The solvent varies depending on the starting material and the used base, but is not specifically limited as long as the solvent can dissolve the starting material to a certain degree without inhibiting the reaction. Preferable examples of the solvent include polar solvents such as nitromethane, acetonitrile, 1-methyl-2-pyrrolidone, N,N-dimethylformamide, and dimethylsulfoxide; ether solvents such as tetrahydrofuran, 1,4-dioxane, and 1,2-dimethoxyethane; nonpolar solvents such as benzene, toluene, and xylene; alcohol solvents such as ethanol and methanol; halogenated solvents such as chloroform and dichloromethane; water; and solvent mixtures. The base varies depending on the starting material and the used solvent. Preferable examples of the base include alkali metal hydroxides such as sodium hydroxide, potassium hydroxide, and lithium hydroxide; alkali metal carbonates such as sodium carbonate, potassium carbonate, and sodium hydrogencarbonate; alkali metal salts of alcohols such as sodium methoxide and potassium tert-butoxide; organic bases such as triethylamine, pyridine, and diazabicyclononene; organic metals such as butyl lithium and lithium diisobutylamide; and alkali metal hydrides such as sodium hydride. The reaction temperature should be a temperature which is sufficient for completing the reaction without promoting formation of undesired by-products and is preferably, for example, −78 to 150° C. This reaction completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

The Horner-Emmons reaction is preferably performed, for example, by stirring a compound (9b) and 0.8 to 1.5 molar equivalents of an aldehyde compound (5) with respect to the compound (9b) in a solvent in the presence of 1.0 to 5.0 molar equivalents of a base with respect to the compound (9b). Herein, $L_3$ is a phosphite ester. In this reaction, i) a compound (9b) and a base are treated first to form a carbanion, and then an aldehyde compound (5) is added thereto; or ii) a base is added to a mixture of a compound (9b) and an aldehyde compound (5). The reaction is similarly performed using a compound (9a) instead of the compound (9b). This reaction is preferably carried out in the presence of a solvent from the viewpoints of operational ease and stirring efficiency. The solvent varies depending on the starting material and the used base, but is not specifically limited as long as the solvent can dissolve the starting material to a certain degree without inhibiting the reaction. Preferable examples of the solvent include polar solvents such as 1-methyl-2-pyrrolidone, N,N-dimethylformamide, and dimethylsulfoxide; ether solvents such as tetrahydrofuran, 1,4-dioxane, and 1,2-dimethoxyethane; nonpolar solvents such as benzene, toluene, and xylene; alcohol solvents such as ethanol and methanol; water; and solvent mixtures thereof. The base varies depending on the starting material and the used solvent. Preferable examples of the base include alkali metal hydroxides such as sodium hydroxide, potassium hydroxide, and lithium hydroxide; alkali metal carbonates such as sodium carbonate, potassium carbonate, and sodium hydrogencarbonate; alkali metal salts of alcohols such as sodium methoxide and potassium tert-butoxide; organic bases such as triethylamine, pyridine, and diazabicyclononene; organic metals such as butyl lithium and lithium diisobutylamide; alkali metal hydrides such as sodium hydride; and alkali metal ammonium salts such as sodium amide. The reaction temperature should be a temperature which is sufficient for completing the reaction without promoting formation of undesired by-products and is preferably, for example, −78 to 150° C. This reaction completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

The Peterson reaction is preferably performed, for example, by stirring a compound (9b) and 0.8 to 1.5 molar equivalents of an aldehyde compound (5) with respect to the compound (9b) in a solvent in the presence of 1.0 to 5.0 molar equivalents of a base with respect to the compound (9b). Herein, $L_3$ is a silyl group. In this reaction, i) a compound (9b) and a base are treated first to form a carbanion, and then an aldehyde (5) is added thereto; or ii) a base is added to a mixture of a compound (9b) and an aldehyde compound (5). The reaction is similarly performed using a compound (9a) instead of the compound (9b). This reaction is preferably carried out in the presence of a solvent from the viewpoints of operational ease and stirring efficiency. The solvent varies depending on the starting material and the used base, but is not specifically limited as long as the solvent can dissolve the starting material to a certain degree without inhibiting the reaction. Preferable examples of the solvent include polar solvents such as 1-methyl-2-pyrrolidone, N,N-dimethylformamide, and dimethylsulfoxide; ether solvents such as tetrahydrofuran, 1,4-dioxane, and 1,2-dimethoxyethane; nonpolar solvents such as benzene, toluene, and xylene; alcohol solvents such as ethanol and methanol; water; and solvent mixtures thereof. The base varies depending on the starting material and the used solvent. Preferable examples of the base include alkali metal hydroxides such as sodium hydroxide, potassium hydroxide, and lithium hydroxide; alkali metal carbonates such as sodium carbonate, potassium carbonate, and sodium hydrogencarbonate; alkali metal salts of alcohols such as sodium methoxide and potassium tert-butoxide; organic bases such as triethylamine, pyridine, and diazabicyclononene; organic metals such as butyl lithium and lithium diisobutylamide; alkali metal hydrides such as sodium hydride; and alkali metal ammonium salts such as sodium amide. The reaction temperature should be a temperature which is sufficient for completing the reaction without promoting formation of undesired by-products and is preferably, for example, −78 to 150° C. This reaction completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

(Process 5-2)

"Process 5-2" is an exemplary method for preparing a compound (1) by condensing a compound (10) and an amine compound (8a). This process is performed, for example, by i) deprotecting the protecting group of a compound (10) by a method known to those skilled in the art (for example, T. Greene, et al., Protective Groups in Organic Synthesis, John Wiley & Sons, Inc., NY, 1981), then subjecting the compound (10) to dehydration condensation with an amine compound (8a) by a method known to those skilled in the art (for example, Jikken Kagaku Koza (Experimental Methods of Chemistry), vol. 14, Yuki-Kagobutsu no Gosei to Hannou (Synthesis and Reaction of Organic Compound) [II], edited by the Chemical Society of Japan, Maruzen Co., Ltd., February 1978, 1136-1162; Yuki Kagaku Jikken no Tebiki (Guide to Organic Chemistry Experiment) (4), Kagaku Dojin, September 1990, 27-52), and converting the resulting compound into the compound (1) under basic conditions; or ii) subjecting the compound (10) to coupling reaction with an amine compound (8a) by a method known to those skilled in the art, and deprotecting the protecting group followed by intramolecular amidation to be converted into the compound (1). Further, in this process, the compound (10) and the amine compound (8a) are converted into the compound (1) in one step by selecting optimum conditions.

(Preparation of Amide Compound (9b))

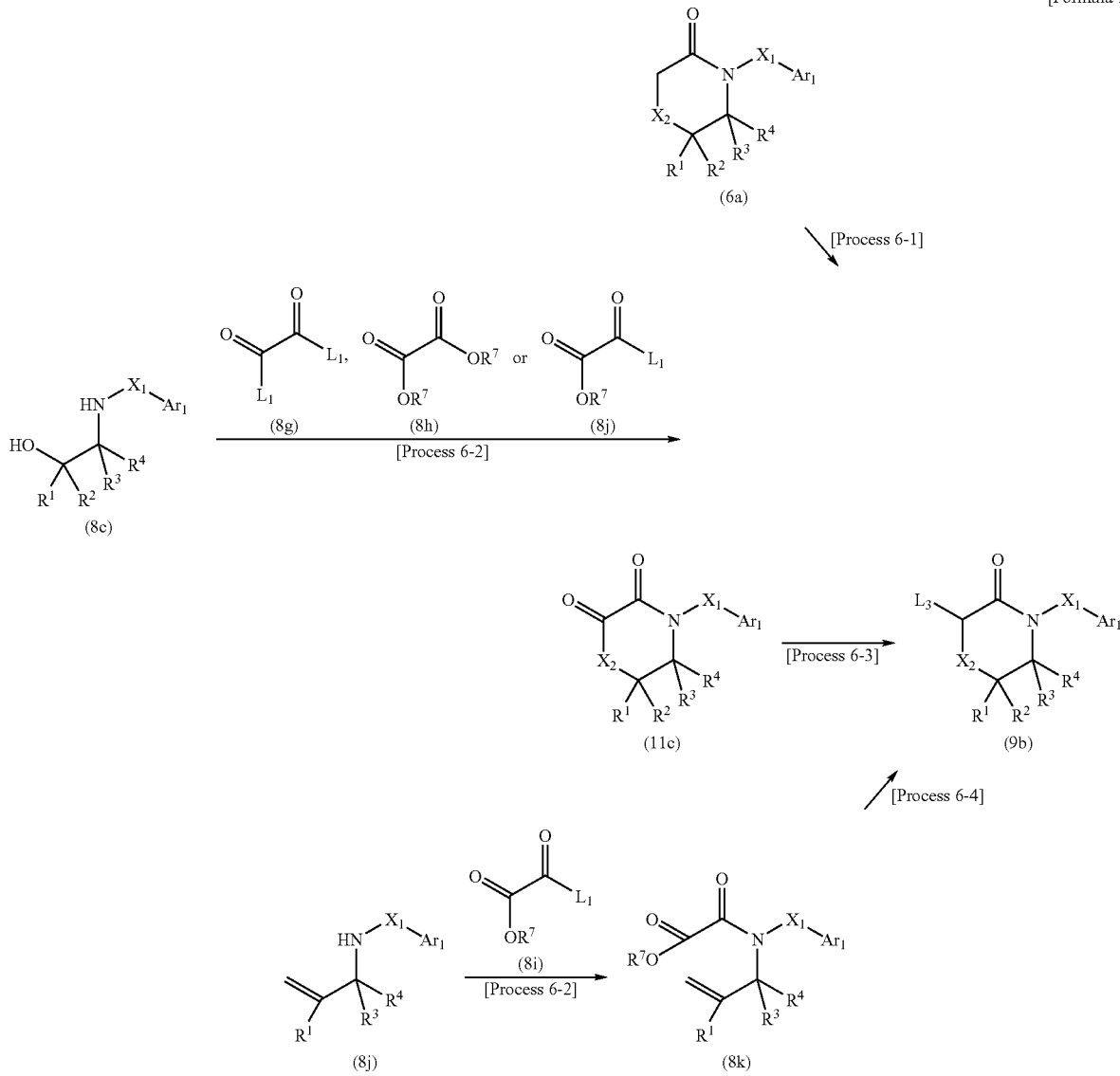

[Formula 17]

(wherein $Ar_1$, $L_1$, $L_3$, $R^1$, $R^2$, $R^3$, $R^4$, $X_1$, and $X_2$ are the same as defined above; and $R^7$ denotes a lower alkyl group).

The above-mentioned reaction formulae are exemplary methods for preparing the amide compound (9b). That is, though the amide compound (9b) varies depending on the starting material, it can be prepared by a method known to those skilled in the art. For example, preferably, the amide compound (9b) is prepared according to "Process 6-1" using an amide compound (6a) as the starting material; or a compound (8c) as the starting material is converted into a compound (11c) according to "Process 6-2" and then the amide compound (9b) is prepared from the compound (11c) according to "Process 6-3"; or a compound (8j) as the starting material is converted into a compound (8k) according to "Process 6-2" and then the amide compound (9b) is prepared from the compound (8k) according to "Process 6-4".

(Conversion of Amide Compound (6a) into Amide Compound (9b))

Though "Process 6-1" varies depending on the starting material, no specific limitation is imposed upon it as long as the reaction is conducted under conditions similar to those in this reaction. The process can be carried out by a method known to those skilled in the art. For example, "Process 6-1" is preferably i) the Wittig reaction (here, $L_3$ is a triphenylphosphonium group) in which an amide compound (6a) is halogenated by a method known to those skilled in the art (see, for example, Jikken Kagaku Koza (Experimental Methods of Chemistry), vol. 19, Yuki Gosei (Organic Synthesis) [I], edited by the Chemical Society of Japan, Maruzen Co., Ltd., June 1992, 430-438) and then the halogenated amide compound is reacted with a triphenylphosphine (see, for example, Organic Reaction, 1965, 14, 270). Alternatively, "Process 6-1" is ii) the Horner-Emmons reaction (here, $L_3$ is a phosphite ester) in which an amide compound (6a) is halogenated by a method known to those skilled in the art (see, for example, Jikken Kagaku Koza (Experimental Methods of Chemistry), vol. 19, Yuki Gosei (Organic Synthesis) [I], edited by the Chemical Society of Japan, Maruzen Co., Ltd., June 1992, 430-438) and then an amide compound (9b) is prepared by the Arbuzov reaction (see, for example, Chemical Review, 1981, 81, 415) using alkyl phosphite or by the Becker reaction (see, for example, Journal of the American Chemical Society, 1945, 67, 1180) using a metal phosphonite. Further, in "Process 6-1", the amide compound (9b) can be prepared by using an amide compound (6a) and chlorophosphate in the presence of a base (see, for example, Journal of Organic Chemistry, 1989, 54, 4750). Alternatively, "Process 6-1" is iii) the Peterson reaction (here, $L_3$ is a silyl group) in which the compound (9b) is prepared by using an amide compound (6a) and trialkylsilyl chloride in the presence of a base (see, for example, Journal of Organometallic Chemistry, 1983, 248, 51).

(Conversion of Amide Compound (11c) into Amide Compound (9b))

Though "Process 6-3" varies depending on the starting material, no specific limitation is imposed upon it as long as the reaction is conducted under conditions similar to those in this reaction. The process can be carried out by a method known to those skilled in the art. For example, "Process 6-3" is preferably performed by reducing an ester carbonyl moiety into an alcohol group (see, for example, Jikken Kagaku Koza (Experimental Methods of Chemistry), vol. 26, Yuki Gosei (Organic Synthesis) [VIII], edited by the Chemical Society of Japan, Maruzen Co., Ltd., April 1992, 159-266) and then converting it into a halogen compound (see, for example, Jikken Kagaku Koza (Experimental Methods of Chemistry), vol. 14, Yuki-Kagobutsu no Gosei to Hannou (Synthesis and Reaction of Organic Compound) [I], edited by the Chemical Society of Japan, Maruzen Co., Ltd., November 1977, 331-450) to obtain a Wittig reagent (9b) (see, for example, Organic Reaction, 1965, 14, 270), or by the Arbuzov reaction (see, for example, Chemical Review, 1981, 81, 415) to obtain a Horner-Emmons reagent (9b). Alternatively, the alcohol can be converted into a Wittig reagent (9b) by reacting it with a triaryl phosphorus hydrogen bromide (see, for example, Synth. Commun. 1996, 26, 3091-3095; Tetrahedron Lett., 2001, 42, 1309-1331).

(Preparation of Amide Compound (11c))

An amide compound (11c) varies depending on the starting material, but can be prepared by a method known to those skilled in the art. For example, an amide compound (11c) can be preferably prepared by using a compound (8c) as a starting material according to "Process 6-2". Preferably, for example, this reaction is efficiently progressed by vigorously agitating a compound (8c) and 1.0 to 10 molar equivalents of a compound (8g) with respect to the compound (8c) in a two-phase reaction solvent of an organic solvent and a basic aqueous solution. The solvent to be used and the reaction temperature vary depending on the starting material, but are not specifically limited. Preferably, the solvent or solvent mixture dissolves the starting material to a certain degree without inhibiting the reaction. Preferable examples of the organic solvent include ether solvents such as diethyl ether; halogenated solvents such as methylene chloride, 1,2-dichloroethane, and chloroform; and nonpolar solvents such as toluene and xylene. The basic aqueous solution is preferably used at not less than 1.0 molar equivalents, and preferable examples of which include aqueous solutions of alkali metal salts such as sodium hydroxide, potassium hydroxide, sodium carbonate, potassium carbonate, cesium carbonate, and sodium hydrogencarbonate. The reaction temperature should be a temperature which is sufficient for completing the reaction without promoting formation of undesired by-products and is preferably, for example, $-78°$ C. to room temperature. This reaction preferably completes in 0.5 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

Alternatively, "Process 6-2" may be performed by reacting a compound (8c) and preferably 1.0 to 5.0 molar equivalents of a compound (8g) with respect to the compound (8c) in the presence of a base such as an organic amine (preferably, at 1.0 to 5.0 molar equivalents to the compound (8c)). Preferable examples of the organic amine include triethylamine, isopropylethylamine, and pyridine. The solvent to be used and the reaction temperature vary depending on the starting material, but are not specifically limited. Preferably, the solvent dissolves the starting material to a certain degree without inhibiting the reaction. Preferable examples of the organic solvent include ether solvents such as diethyl ether; halogenated solvents such as methylene chloride, 1,2-dichloroethane, and chloroform; and nonpolar solvents such as toluene and xylene. The reaction temperature should be a temperature which is sufficient for completing the reaction without promoting formation of undesired by-products and is preferably, for example, $-78$ to $100°$ C. This reaction preferably completes in 0.5 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

Alternatively, "Process 6-2" may be efficiently performed by heating a compound (8c) and 1.0 to 20 molar equivalents of a compound (8h: $R^7$ denotes a lower alkyl group) with respect to the compound (8c). The solvent to be used and the reaction temperature vary depending on the starting material, but are not specifically limited. Preferably, the solvent or solvent mixture dissolves the starting material to a certain degree without inhibiting the reaction. Preferable examples of the organic solvent include ether solvents such as diethyl ether; halogenated solvents such as methylene chloride, 1,2-dichloroethane, and 1,2-dichlorobenzene; nonpolar solvents such as toluene and xylene; polar solvents such as dimethylformamide and N-methylpyrrolidone; and alcohol solvents such as methanol, ethanol, 2-propanol, and tert-butanol. In addition, the reaction may also be efficiently progressed in the absence of a solvent. The reaction temperature should be a temperature which is sufficient for completing the reaction without promoting formation of undesired by-products and is preferably, for example, 50 to $200°$ C. This reaction preferably completes in 0.5 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

Alternatively, "Process 6-2" may be efficiently performed by using a compound (8c) and 1.0 to 5.0 molar equivalents of a compound (8i) with respect to the compound (8c) under the above-described reaction conditions or a combination thereof. In addition, this process may be efficiently progressed by the addition of a quaternary ammonium phase transfer catalyst such as tetrabutylammonium chloride or benzyltriethylammonium chloride or the addition of an acidic compound such as p-toluenesulfonic acid or camphorsulfonic acid.

(Preparation of Compounds (8g), (8h), and (8i))

Compounds (8g), (8h), and (8i) are commercially available or are prepared by methods known to those skilled in the art. When the compounds (8g), (8h), and (8i) are not commercially available, these compounds can be prepared by esterifying or halogenating corresponding oxalic acid derivatives by methods known to those skilled in the art.

(Conversion of Compound (8k) into Oxomorpholine Compound (9b))

Though "Process 6-4" varies depending on the starting material, no specific limitation is imposed upon it as long as the reaction is conducted under conditions similar to those in this reaction. The process can be carried out by a method known to those skilled in the art. For example, a compound (8k) is converted into a hemiacetal derivative by oxidative cleavage and intramolecular cyclization of the olefin moiety and, after the conversion into a halogen compound (see, for example, Jikken Kagaku Koza (Experimental Methods of Chemistry), vol. 14, Yuki-Kagobutsu no Gosei to Hannou (Synthesis and Reaction of Organic Compound) [I], edited by the Chemical Society of Japan, Maruzen Co., Ltd., November 1977, 331-450), the halogen compound is converted into a Wittig reagent (9b) (see, for example, Organic Reaction, 1965, 14, 270); or by the Arbuzov reaction (see, for example, Chemical Review, 1981, 81, 415) to obtain a Horner-Emmons reagent (9b). Further, the hemiacetal derivative can be converted into a Wittig reagent (9b) by the reaction with a triaryl phosphorus hydrogen bromide (see, for example, Synth. Commun. 1996, 26, 3091-3095; Tetrahedron Lett., 2001, 42, 1309-1331). Though the oxidative cleavage of an olefin moiety varies depending on the starting material, no specific limitation is imposed upon it as long as the reaction is conducted under conditions similar to those in this reaction. The reaction can be carried out by known methods disclosed in many publications. For example, ozone oxidation is preferable (see, for example, Jikken Kagaku Koza (Experimental Methods of Chemistry), vol. 15, Sanka to Kangen (oxidation and Reduction) [I-2], edited by the Chemical Society of Japan, Maruzen Co., Ltd., September 1976, 563-603). The oxidative cleavage and the intramolecular cyclization can proceed successively under appropriate reaction conditions to efficiently prepare the compound (9b).

(Preparation of Compound (8k))

For example, a compound (8k) can be preferably prepared by using a compound (8j) and 1.0 to 5.0 molar equivalents of a compound (81) with respect to the compound (8j) according to the above-described "Process 6-2".

(Preparation Compound (8j))

A compound (8j) is commercially available or is prepared by a method known to those skilled in the art. When the compound (8j) is not commercially available, for example, intramolecular hydroamination of an amine or sulfonylamide compound having an arenyl group using a metal catalyst is preferable for binding $R^4$ and $X_1$ to form a nitrogen-containing heterocycle (see, for example, Journal of the American Chemical Society, 2003, 125, 11956; Tetrahedron Lett., 1998, 39, 5421-5424). Though this reaction varies depending on the starting material, no specific limitation is imposed upon it as long as the reaction is conducted under conditions similar to those in this reaction. Preferably, 0.001 to 0.1 molar equivalents of a palladium complex with respect to the starting material is used as the metal catalyst. Examples of the palladium complex include palladium(II) acetate, dichlorobis (triphenylphosphine)palladium(II), tetrakis(triphenylphosphine)palladium(0), and allylpalladium chloride dimmer. In addition, for example, by the addition of 0.001 to 0.1 molar equivalents of a phosphorus ligand with respect to the starting material, the reaction may be efficiently progressed. Examples of the phosphorus ligand include 2,2'-bis(diphenylphosphino)-1,1'-binaphthyl and 1,1'-bis(diphenylphosphino)ferrocene. Further, for example, the reaction may be efficiently progressed by the addition of 0.001 to 10 molar equivalents of hydrochloric acid or acetic acid with respect to the starting material. The solvent to be used and the reaction temperature vary depending on the starting material, but are not specifically limited. Preferably, the solvent or solvent mixture dissolves the starting material to a certain degree without inhibiting the reaction. Preferable examples of the organic solvent include ether solvents such as diethyl ether and tetrahydrofuran; halogenated solvents such as methylene chloride and 1,2-dichloroethane; nonpolar solvents such as toluene and xylene; polar solvents such as dimethylformamide and N-methylpyrrolidone; and alcohol solvents such as methanol, ethanol, 2-propanol and tert-butanol. The reaction temperature should be a temperature which is sufficient for completing the reaction without promoting formation of undesired by-products and is preferably, for example, 50 to 200° C. This reaction preferably completes in 0.5 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

(Preparation of Compound (9a))

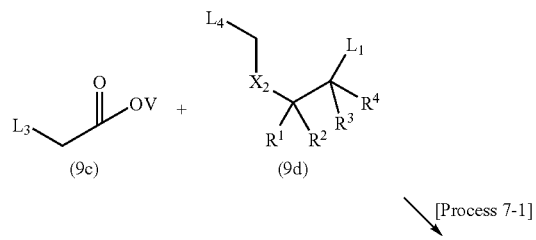

[Formula 18]

[Process 7-1]

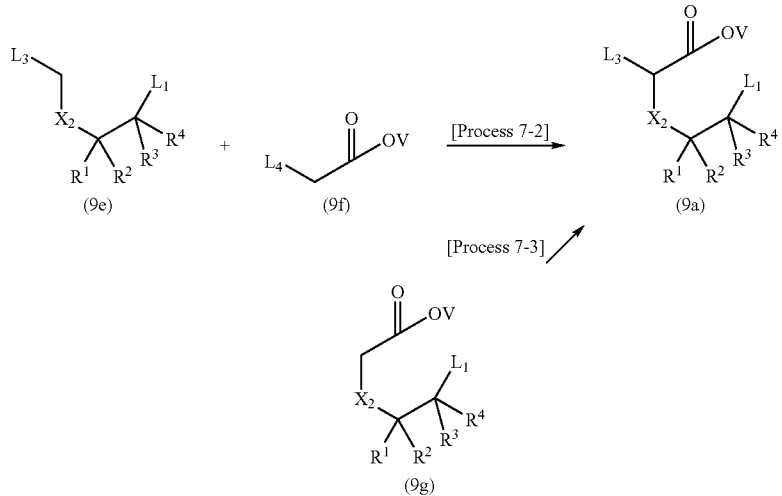

(wherein the $R^1$, $R^2$, $R^3$, $R^4$, V, $L_1$, $L_3$, and $X_2$ are the same as defined above, and $L_4$ is the same as defined $L_1$).

The above-mentioned reaction formulae are exemplary methods for preparing the compound (9a). That is, a compound (9a) is commercially available or can be prepared according to the above-mentioned reaction formulae which are known to those skilled in the art (see, for example, C. Patois, et al., Synth. Commun., 1991, 22, 2391; J. A. Jackson, et al., J. Org. Chem., 1989, 20, 5556). For example, in "Process 7-1", a phosphonate ester compound (9c) is treated with 1.0 to 2.0 molar equivalents of a compound (9d) with respect to the phosphonate ester compound (9c) under basic conditions to obtain a desired compound (9a). Alternatively, in "Process 7-2", a compound (9e) is treated with 1.0 to 2.0 molar equivalents of an ester compound (9f) with respect to the compound (9e) under basic conditions to obtain a desired compound (9a). In addition, a desired compound (9a) can be obtained from a compound (9g) according to "Process 7-3", which is similar to "Process 7-1".

The base used in this process varies depending on the starting material, but is not limited. For example, 1.0 to 1.5 molar equivalents of a base with respect to the starting material is preferably used. Examples of the base include sodium hydride, n-butyl lithium, lithium diisopropylamide, lithium bis(trimethylsilyl)amide, and sodium bis(trimethylsilyl)amide. The solvent used in this process varies depending on the starting material, but is not specifically limited as long as the solvent can dissolve the starting material to a certain degree without inhibiting the reaction. Preferable examples of the solvent include hexane, toluene, diethylether, tetrahydrofuran, N,N-dimethylformamide, hexamethylphosphoric triamide, and the above-mentioned solvent mixtures. The reaction temperature should be a temperature which is sufficient for completing the reaction without promoting formation of undesired by-products and is preferably, for example, −78 to 150° C. This reaction completes in 1 to 24 hours under appropriate reaction conditions, and the progress of the reaction can be monitored by known chromatography technology. Undesired by-products can be removed by commonly used chromatography technology and/or technology known to those skilled in the art, such as crystallization.

The phosphonate ester compound (9c), compound (9d), compound (9e), ester compound (9f), and compound (9g) are commercially available or can be prepared by methods which are known to those skilled in the art.

Reference Example 3

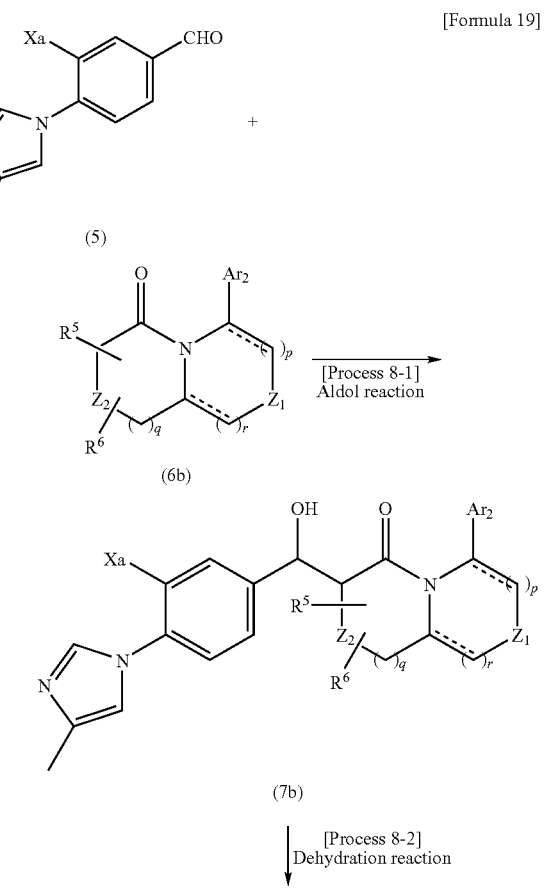

-continued

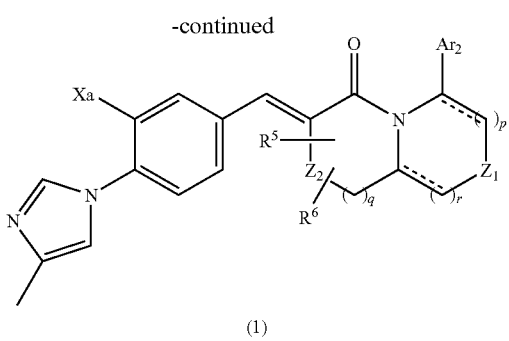

(1)

(wherein ⇌ denotes a single bond or a double bond, $Ar_2$, $Z_1$, $Z_2$, $R^5$, $R^6$, $X_a$, p, q, and r are the same as defined above).

(Preparation of Compound (1))

A compound (1) can be prepared using an aldol adduct (7b) according to "Process 8-2". That is, though the dehydration reaction in "Process 8-2" varies depending on the starting material, no specific limitation is imposed upon it as long as the reaction is conducted under conditions similar to those in this reaction. The reaction can be carried out by known a method disclosed in many publications (see, for example, Jikken Kagaku Koza (Experimental Methods of Chemistry), vol. 19, Yuki Gosei (Organic Synthesis) [I], edited by the Chemical Society of Japan, Maruzen Co., Ltd., June 1992, 194-226). For example, i) an aldol adduct (7b) is preferably treated with 0.1 to 100.0 molar equivalents of an acid with respect to the aldol adduct (7b) (see, for example, Jikken Kagaku Koza (Experimental Methods of Chemistry), vol. 19, Yuki Gosei (Organic Synthesis) [I], edited by the Chemical Society of Japan, Maruzen Co., Ltd., June 1992, 194-196); or ii) an alcohol group of an aldol adduct (7b) is converted into a carboxylate ester group such as an acetyl group, a sulfonate ester group, or a leaving group such as a halogen atom, and then the resulting product is preferably treated with 1.0 to 10.0 molar equivalents of a base with respect to the resulting product (see, for example, Jikken Kagaku Koza (Experimental Methods of Chemistry), vol. 19, Yuki Gosei (Organic Synthesis) [I], edited by the Chemical Society of Japan, Maruzen Co., Ltd., June 1992, 198-205).

In the above-mentioned process i), the acid, solvent, and temperature condition to be used vary depending on the starting material, but are not specifically limited. Preferable examples of the acid include hydrochloric acid, sulfuric acid, phosphoric acid, potassium hydrosulfuric acid, oxalic acid, p-toluenesulfonic acid, boron trifluoride ether complex, thionyl chloride, and aluminium oxide. Though the reaction may be performed in the absence of a solvent in some cases, a solvent or solvent mixture which can dissolve the starting material to a certain degree without inhibiting the reaction is used. Preferable examples of the solvent include nonpolar solvents such as toluene and benzene; polar solvents such as acetone, dimethylsulfoxide, and hexamethylphosphoroamide; halogenated solvents such as chloroform and methylene chloride; and water. Further, in some cases, a combination of an acid and an organic base such as pyridine improves the reaction rate and the reaction yield. The reaction temperature should be a temperature which is sufficient for completing the reaction without promoting formation of undesired by-products and is preferably, for example, room temperature to 200° C. This reaction preferably completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

In the above-mentioned process ii), preferable examples of the leaving group include an acetyl group, a methanesulfonate ester group, a p-toluenesulfonate ester group, a chlorine atom, a bromine atom, and an iodine atom. The process for conversion into these leaving groups varies depending on the starting material, but is not specifically limited and can be performed according to a method which is known to those skilled in the art. Preferably, the process is carried out using 1.0 to 10.0 molar equivalents of an acylating agent, a sulfonating agent, or a halogenating agent with respect to the aldol adduct (7b) in a solvent or solvent mixture. Preferable examples of the solvent include halogenated solvents such as methylene chloride and chloroform, nonpolar solvents such as toluene and benzene, ether solvents such as tetrahydrofuran and ethylene glycol dimethyl ether. Examples of the acylating agent include acetyl chloride and acetic anhydride. Examples of the sulfonating agent include methanesulfonate chloride and p-toluenesulfonate chloride. Examples of the halogenating agent include thionyl chloride. In addition, in this process, a desired compound may be efficiently prepared by using a base such as pyridine or triethylamine, for example, at 1.0 to 10 molar equivalents with respect to the aldol adduct (7b) or as a solvent. The reaction temperature should be a temperature which is sufficient for completing the reaction without promoting formation of undesired by-products and is preferably, for example, −78 to 100° C. This reaction preferably completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization. The second process, namely, the elimination reaction, is preferably performed in, for example, a halogenated solvent such as methylene chloride or chloroform; a nonpolar solvent such as toluene or benzene; a polar solvent such as acetonitrile, dimethylformamide, or dimethylsulfoxide; an ether solvent such as tetrahydrofuran or ethylene glycol dimethyl ether; or a solvent mixture thereof. Preferable examples of the base include organic bases such as diazabicycloundecene, pyridine, 4-dimethylaminopyridine, and triethylamine; quaternary ammonium salts such as tetrabutylammonium hydroxide; alkali metal salts of alcohols such as sodium methoxide and potassium tert-butoxide; alkali metal hydroxides such as sodium hydroxide; alkali metal carbonates such as lithium carbonate and potassium carbonate; and organic metal reagents such as lithium diisopropylamide. These bases are preferably used at 1.0 to 10.0 molar equivalents to the resulting product. Further, an organic base such as pyridine can be used as a solvent. The reaction temperature should be a temperature which is sufficient for completing the reaction without promoting formation of undesired by-products and is preferably, for example, −78 to 100° C. This reaction preferably completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

(Preparation of Aldol Adduct (7b))

An aldol adduct (7b) can be prepared by, for example, using an aldehyde compound (5) and 1.0 to 5.0 molar equivalents of a lactam compound (6b) with respect to the aldehyde compound (5) according to "Process 8-1". That is, though the aldol reaction in "Process 8-1" varies depending on the starting material, no specific limitation is imposed upon it as long as the reaction is conducted under conditions similar to those in this reaction. The reaction can be carried out by a method known to those skilled in the art (for example, Jikken Kagaku Koza (Experimental Methods of Chemistry), vol. 20, Yuki Gosei (Organic Synthesis) [II], edited by the Chemical Society of Japan, Maruzen Co., Ltd., July 1992, 94-100). For example, the aldol reaction is preferably performed by i) enolating a lactam compound (6b) with 1.0 to 5.0 molar equivalents of a base (preferably, for example, lithium diisopropylamide, butyl lithium, sodium amide, sodium hydride, sodium methoxide, or potassium tert-butoxide) with respect to the lactam compound (6b) into an alkali metal enolate and then reacting the resulting alkali metal enolate with an aldehyde compound (5) (see, for example, Jikken Kagaku Koza (Experimental Methods of Chemistry), vol. 20, Yuki Gosei (Organic Synthesis) [II], edited by the Chemical Society of Japan, Maruzen Co., Ltd., July 1992, 97-98); or ii) enolating a lactam compound (6b) with 1.0 to 5.0 molar equivalents of a base (preferably, for example, lithium diisopropylamide, butyl lithium, sodium amide, sodium hydride, sodium methoxide, or potassium tert-butoxide) with respect to the lactam compound (6b) into an alkali metal enolate, then reacting the resulting alkali metal enolate with a silicon halide reagent (preferably, for example, trimethylchlorosilane or tert-butyldimethylchlorosilane) to obtain a silyl enol ether, and then reacting the resulting silyl enol ether with an aldehyde compound (5), for example, in the presence of 0.05 to 5.0 molar equivalents of a Lewis acid (preferably, for example, titanium tetrachloride or boron trifluoride) with respect to the lactam compound (6b) (see, for example, Jikken Kagaku Koza (Experimental Methods of Chemistry), vol. 20, Yuki Gosei (Organic Synthesis) [II], edited by the Chemical Society of Japan, Maruzen Co., Ltd., July 1992, 96-97). The solvent to be used and the reaction temperature vary depending on the starting material, but are not specifically limited. Preferable examples of the solvent or solvent mixture which can dissolve the starting material to a certain degree without inhibiting the reaction include ether solvents such as tetrahydrofuran, 1,4-dioxane, and diethyl ether; halogenated solvents such as methylene chloride, 1,2-dichloroethane, and chloroform; and nonpolar solvents such as toluene and benzene. The reaction temperature should be a temperature which is sufficient for completing the reaction without promoting formation of undesired by-products and is preferably, for example, −78° C. to room temperature. This reaction preferably completes in 0.5 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

(Preparation of Lactam Compound (6b))

[Formula 20]

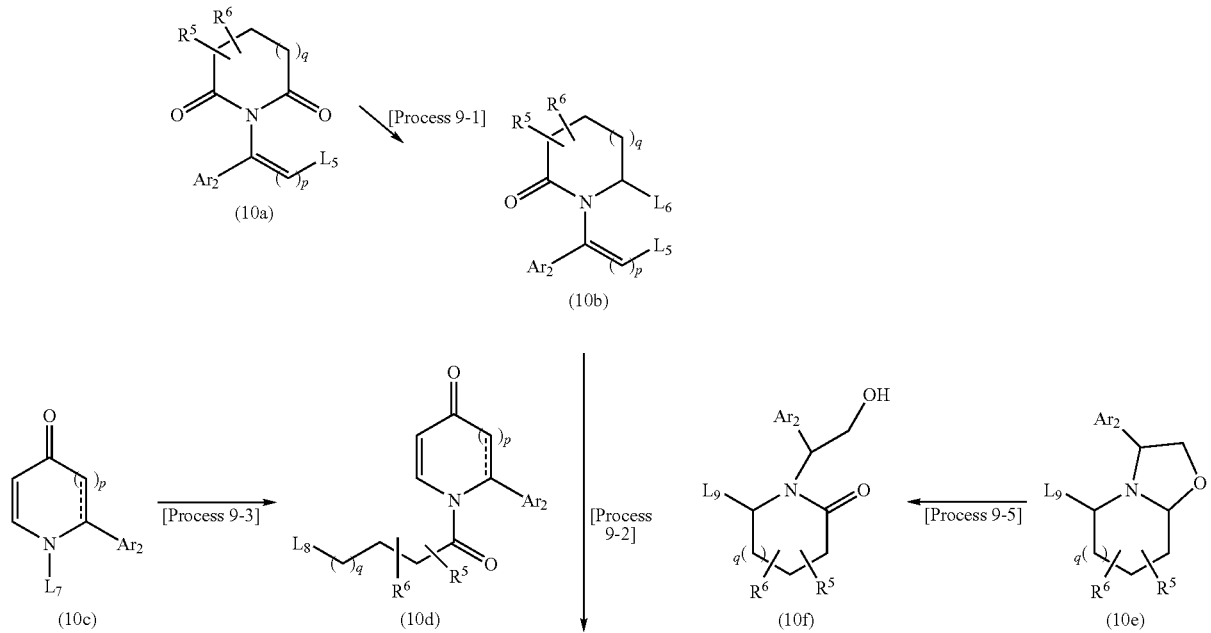

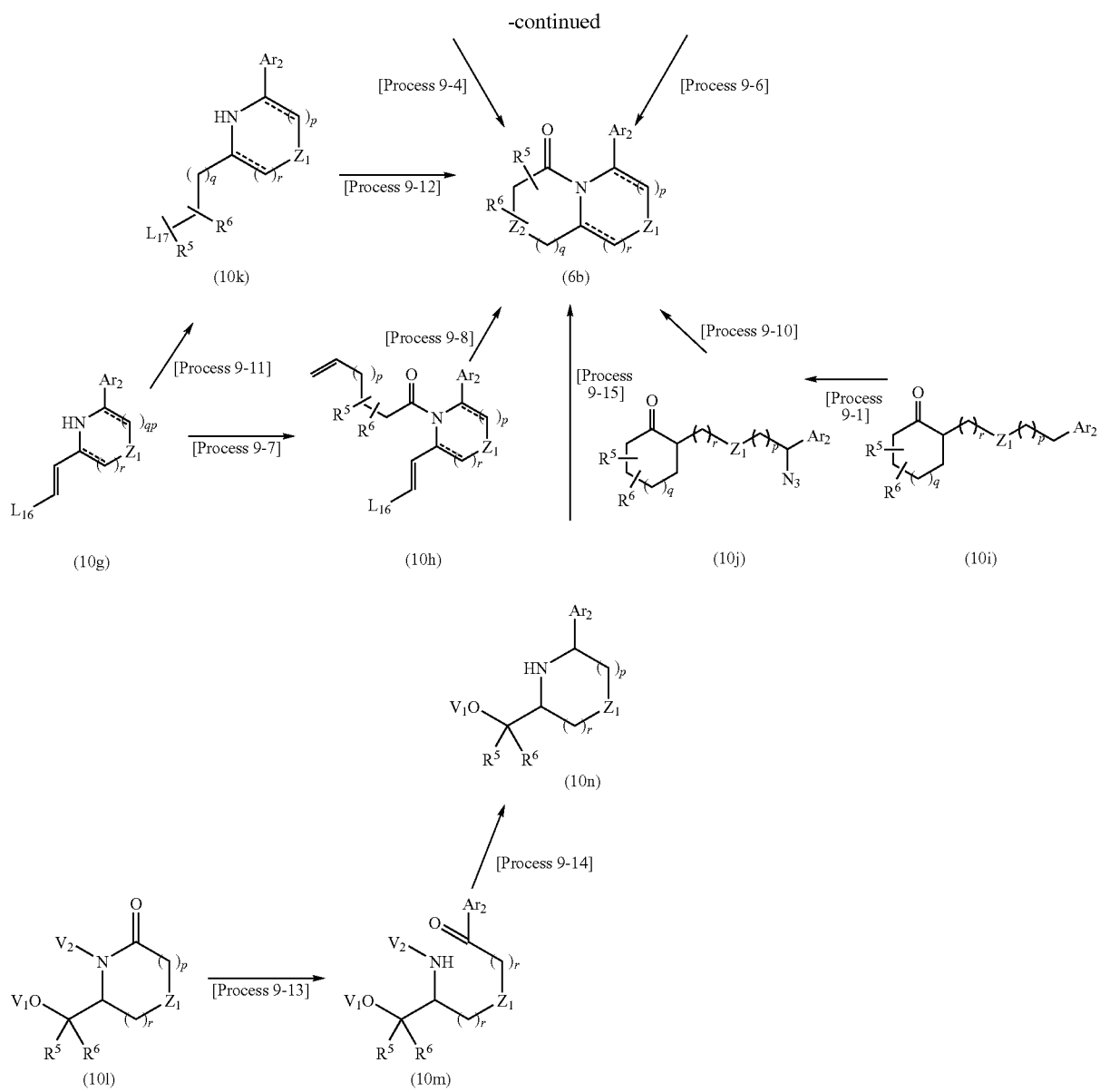

(wherein ⚌ denotes a single bond or a double bond, $Ar_2$, $L_1$, $Z_1$, $Z_2$, $R^5$, $R^6$, p, q, and r are the same as defined above; $L_5$ denotes an alkyl ester group such as a methyl ester or ethyl ester group, an alkyl ketone group such as an acetyl, an araalkyl ketone group such as phenylmethylketone, an arylketone such as a benzoyl group; $L_6$ denotes an alkoxy group such as a methoxy or ethoxy group; $L_7$ denotes a carbamate protecting group such as a methylcarbamate, benzylcarbamate, or tert-butylcarbamate group, or an amide protecting group such as an acetyl group; $L_8$ denotes a halogen atom such as a bromine or iodine atom; $L_9$ denotes a nitrile, an alkyl ester group such as methyl ester group, or an alkyl ketone group such as an acetyl group; $L_{16}$ denotes a hydrogen atom, an alkyl group such as a methyl or ethyl group, a phenyl group which may be substituted with 1 to 3 substituents selected from the aforementioned Substituent Group A1, an ester group such as a methyl ester or ethyl ester group, a phosphate ester group such as dimethyl phosphate or diethyl phosphate, an alkylsulfonyl group such as a methylsulfonyl group, or an arylsulfonyl group such as a phenylsulfonyl group; $L_{17}$ denotes an alkyl ketone group such as an acetyl group, an aryl ketone group such as a benzoyl group, an alkyl ester group such as a formyl, methyl ester, or ethyl ester group, or an aryl ester group such as a phenyl ester group); $V_1$ donates a hydrogen or a protecting group of hydroxyl group such as benzyl, methoxymethyl, tert-butyldimethylsilyl or tert-butyldiphenylsilyl group; and $V_2$ denotes a hydrogen, a carbamate protecting group such as a methylcarbamate, benzylcarbamate, or tert-butylcarbamate group, or an amide protecting group such as an acetyl group).

The above-mentioned reaction formulae are exemplary methods for preparing the lactam compound (6b). That is, (i) a lactam compound (6b) is prepared by using an imido compound (10a) which is commercially available or prepared by a method known to those skilled in the art (see, for example, Tetrahedron: Asymmetry, 1998, 9, 4361) as the starting material, converting the imido compound (10a) into an alkoxy lactam compound (10b) according to "Process 9-1", and then successively conducting carbon-adding reaction and ring-closing reaction in "Process 9-2"; (ii) a lactam compound (6b) is prepared by using a 4-pyridone compound (10c) which is commercially available or prepared by a method known to those skilled in the art (see, for example, Tetrahedron Letters, 1986, 27, 4549) as the starting material, converting the 4-pyridone compound (10c) into an acylated compound (10d) according to "Process 9-3", and then conducting ring-closing reaction in "Process 9-4"; (iii) a lactam compound (6b) is prepared by using an oxazolidine compound (10e) which is commercially available or prepared by a method known to those skilled in the art (see, for example, European Journal of Organic Chemistry, 2004, 23, 4823) as the starting material, converting the oxazolidine compound (10e) into an amide alcohol compound (10f) according to "Process 9-5", and then conducting ring-closing reaction in "Process 9-6"; (iv) a lactam compound (6b) is prepared by using a vinyl-substituted cyclic amine compound (10g) which is commercially available or prepared by a method known to those skilled in the art (see, for example, Tetrahedron Letters, 1998, 39, 5421; Tetrahedron Letters, 2004, 45, 4895) as the starting material, converting the vinyl-substituted cyclic amine compound (10g) into an acylated compound (10h) according to "Process 9-7", and then conducting ring-closing reaction in "Process 9-8"; (v) a lactam compound (6b) is prepared by using a cycloalkyl ketone compound (10i) which is commercially available or prepared by a method known to those skilled in the art (see, for example, Journal of the Organic Chemistry, 2001, 66, 886) as the starting material, converting the cycloalkyl ketone compound (10i) into an azidated compound (10j) according to "Process 9-9", and then conducting ring-closing reaction in "Process 9-10"; (vi) a lactam compound (6b) is prepared by using a vinyl-substituted cyclic amine compound (10g) as the starting material, converting the vinyl-substituted cyclic amine (10g) into a compound (10k) according to "Process 9-11", and the conducting ring-closing reaction in "Process 9-12"; or (vii) a lactam compound is prepared by using a compound (101) which is commercially available or prepared by a method known to those skilled in the art as the starting material, converting the compound (10i) into a compound (10m) according to "Process 9-13", conducting deprotection of the nitrogen atom and intramolecular reductive amination to obtain a compound (10n) in "Process 9-14", and conducting deprotection of the oxygen atom and ring-closing reaction in "Process 9-15".

(Conversion of Imido Compound (10a) into Alkoxy Lactam Compound (10b))

Though the partial reduction of an the imido group in "Process 9-1" varies depending on the starting material, the reaction can be performed by a method known to those skilled in the art under conditions similar to those in this reaction. For example, a desired alkoxy lactam compound (10b) can be preferably prepared by reacting an imido compound (10a) and 1.0 to 5.0 molar equivalents of sodium borohydride with respect to the imido compound (10a) in an alcohol solvent such as methanol (see, for example, Jikken Kagaku Koza (Experimental Methods of Chemistry), vol. 26, Yuki Gosei (Organic Synthesis) [VIII], edited by the Chemical Society of Japan, Maruzen Co., Ltd., April 1992, 207-237); or reacting an imido compound (10a) and 1.0 to 5.0 molar equivalents of borane with respect to the imido compound (10a) in an ether solvent such as tetrahydrofuran (see, for example, Jikken Kagaku Koza (Experimental Methods of Chemistry), vol. 26, Yuki Gosei (Organic Synthesis) [VIII], edited by the Chemical Society of Japan, Maruzen Co., Ltd., April 1992, 237-248) and then in an alcohol solvent such as methanol in the presence of 0.1 to 10.0 molar equivalents of an inorganic acid such as sulfuric acid with respect to the imido compound (10a). Alternatively, for example, a desired alkoxy lactam compound (10b) can be preferably prepared in one step by reacting an imido compound (10a) and 1.0 to 5.0 molar equivalents of sodium borohydride with respect to the imido compound (10a) in the presence of 0.1 to 5.0 molar equivalents of an inorganic acid such as sulfuric acid with respect to the imido compound (10a) in an alcohol solvent such as methanol (see, for example, Tetrahedron: Asymmetry, 1998, 9, 4361). The reaction temperature should be a temperature which is sufficient for completing the reaction without promoting formation of undesired by-products and is preferably, for example, −78 to 100° C. This reaction completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

(Conversion of Alkoxy Lactam Compound (10b) into Lactam Compound (6b))

In "Process 9-2", a desired lactam compound (6b) can be prepared by treating $L_5$ of an alkoxy lactam compound (10b) with a Wittig reagent (see, for example, Jikken Kagaku Koza (Experimental Methods of Chemistry), vol. 24, Yuki Gosei (Organic Synthesis) [VII], edited by the Chemical Society of Japan, Maruzen Co., Ltd., September 1992, 254-262) or with a Grignard reagent (see, for example, Jikken Kagaku Koza (Experimental Methods of Chemistry), vol. 24, Yuki Gosei (Organic Synthesis) [VI], edited by the Chemical Society of Japan, Maruzen Co., Ltd., September 1991, 59-72) or with an alkyl lithium reagent (see, for example, Jikken Kagaku Koza (Experimental Methods of Chemistry), vol. 24, Yuki Gosei (Organic Synthesis) [VI], edited by the Chemical Society of Japan, Maruzen Co., Ltd., September 1991, 9-51) to convert into an olefin derivative, and then treating with an acid such as hydrochloric acid. For example, a desired lactam compound (6b) can be obtained with a high yield by stirring an alkoxy lactam compound (10b) and 1.0 to 10.0 molar equivalents of a Grignard reagent such as trimethylsilylmethyl magnesium chloride with respect to the alkoxy lactam compound (10b) in the presence of 1.0 to 10.0 molar equivalents of cerium chloride with respect to the alkoxy lactam compound (10b) in an ether solvent such as tetrahydrofuran, and then treating the resulting olefin derivative with an inorganic acid such as hydrochloric acid (see, for example, Tetrahedron: Asymmetry, 1998, 9, 4361). The reaction temperature should be a temperature which is sufficient for completing the reaction without promoting formation of undesired by-products and is preferably, for example, −78 to 100° C. This reaction preferably completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

(Conversion of 4-pyridone Compound (10c) into Acylated Compound (10d))

In "Process 9-3", deprotection reaction of an amine moiety is followed by amidation reaction. The deprotection reaction of a compound (10c) can be performed by a method disclosed in many publications (see, for example, T. W. Green, Protective Groups in Organic Synthesis, John Wiley & Sons, Inc., 1981). An amine compound can be obtained from a corresponding carbamate compound (for example, preferably, a tert-butyl carbamate compound, a benzyl carbamate compound, or a 9-fluorenylmethyl carbamate compound), or an amine compound can be obtained from a corresponding amide compound (for example, preferably, a formamide compound, an acetamide compound, or a trifluoroacetamide compound). Though the conditions for this deprotection reaction vary depending on the starting material, no specific limitation is imposed upon it as long as the reaction is conducted under conditions similar to those in this reaction, and a known method can be used. This reaction preferably completes in 1 to 24 hours under appropriate reaction conditions, and the progress of the reaction can be monitored by known chromatography technology. Undesired by-products can be removed by commonly used chromatography technology and/or technology known to those skilled in the art, such as crystallization. Though the amidation reaction varies depending on the starting material, no specific limitation is imposed upon it as long as the reaction is conducted under conditions similar to those in this reaction. The reaction can be performed by a known method disclosed in many publications (see, for example, Jikken Kagaku Koza (Experimental Methods of Chemistry), vol. 14, Yuki-Kagobutsu no Gosei to Hannou (Synthesis and Reaction of Organic Compound) [II], edited by the Chemical Society of Japan, Maruzen Co., Ltd., February 1978, 1136-1162). For example, preferably, i) an amine compound and 1.0 to 5.0 molar equivalents of an acid halide compound with respect to the amine compound are reacted under basic conditions (see, for example, Jikken Kagaku Koza (Experimental Methods of Chemistry), vol. 14, Yuki-Kagobutsu no Gosei to Hannou (Synthesis and Reaction of Organic Compound) [II], edited by the Chemical Society of Japan, Maruzen Co., Ltd., February 1978, 1142-1145), or ii) an amine compound and 1.0 to 5.0 molar equivalents of carboxylic acid compound with respect to the amine compound are reacted using 1.0 to 5.0 molar equivalents of a condensing agent with respect to the amine compound (Yuki Kagaku Jikken no Tebiki (Guide to Organic Chemistry Experiment) (4), Kagaku Dojin, September 1990, 27-52).

In the above-mentioned i), the base to be used varies depending on the starting material, but is not specifically limited. For example, 1.0 to 100.0 molar equivalents of a base with respect to the amine compound is preferably used. Preferable examples of the base include pyridine, triethylamine, N,N-diisopropylethylamine, lutidine, quinoline, and isoquinoline. The solvent to be used is not specifically limited as long as it can dissolve the starting material to a certain degree without inhibiting the reaction, and preferable example of which include tetrahydrofuran and 1,4-dioxane. In addition, a base may be used as a solvent in some cases. Alternatively, a two-layer distribution system of an alkali aqueous solution as a base and a halogenated solvent may be used. The alkali aqueous solution is preferably, for example, an aqueous solution of sodium hydroxide or potassium hydroxide. The halogenated solvent is preferably, for example, methylene chloride or 1,2-dichloroethane. The reaction temperature should be a temperature which is sufficient for completing the reaction without promoting formation of undesired by-products and is preferably, for example, ice-cooling to 100° C. This reaction preferably completes in 1 to 24 hours under appropriate reaction conditions, and the progress of the reaction can be monitored by known chromatography technology. Undesired by-products can be removed by commonly used chromatography technology and/or technology known to those skilled in the art, such as crystallization.

In the above-mentioned ii), the condensing agent to be used varies depending on the starting material, but is not specifically limited. Preferable examples of the condensing agent include 1,3-dicyclohexylcarbodiimide, 1-ethyl-3-(3'-dimethylaminopropyl)carbodiimide, benzotriazol-1-yloxytris (dimethylamino)phosphonium hexafluorophosphonate, diethylcyanophosphonate, and bis(2-oxo-3-oxazolidinyl) phosphinic chloride. Preferably, 1.0 to 2.0 molar equivalents of a condensing agent with respect to a used carboxylic acid is used. In addition, in order to efficiently progress the reaction, for example, 1.0 to 2.0 molar equivalents of N-hydroxysuccinimide or N-hydroxybenzotriazole with respect to the used carboxylic acid compound may be added. This reaction is preferably carried out in the presence of a solvent from the viewpoints of operational ease and stirring efficiency. The solvent to be used varies depending on the starting material and the used condensing agent, but is not specifically limited as long as the solvent can dissolve the starting material to a certain degree without inhibiting the reaction. Preferable examples of the solvent include halogenated solvents such as methylene chloride and 1,2-dichloroethane and polar solvents such as tetrahydrofuran and N,N-dimethylformamide. The reaction temperature should be a temperature which is sufficient for completing the reaction without promoting formation of undesired by-products and is preferably, for example, ice-cooling to 100° C. This reaction preferably completes in 1 to 24 hours under appropriate reaction conditions, and the progress of the reaction can be monitored by known chromatography technology. Undesired by-products can be removed by commonly used chromatography technology and/or technology known to those skilled in the art, such as crystallization.

(Conversion of Acylated Compound (10d) into Lactam Compound (6b))

"Process 9-4" is cyclization reaction through radical formation. That is, for example, a desired lactam compound (6b) can be obtained with a high yield by reacting an compound (10d) and, preferably, 1.0 to 2.0 molar equivalents of an alkyl-tin reagent such as tributyl tin with respect to the compound (10d), preferably, in the presence of 0.1 to 1.0 molar equivalents of a radical initiator such as 2,2-azobis(isobutylnitrile) with respect to the compound (10d) in a nonpolar solvent such as toluene. The reaction temperature should be a temperature which is sufficient for completing the reaction without promoting formation of undesired by-products and is preferably, for example, 50 to 150° C. This reaction preferably completes in 1 to 24 hours under appropriate reaction conditions, and the progress of the reaction can be monitored by known chromatography technology. Undesired by-products can be removed by commonly used chromatography technology and/or technology known to those skilled in the art, such as crystallization. In addition, after the formation of the ring, $Z_1$ can be variously converted utilizing the ketone group by a method known to those skilled in the art (for example, by reductive reaction (see, for example, Jikken Kagaku Koza (Experimental Methods of Chemistry), vol. 26, Yuki Gosei (Organic Synthesis) [VIII], edited by the Chemical Society of Japan, Maruzen Co., Ltd., April 1992, 159-266); addition reaction (see, for example, Jikken Kagaku Koza (Experimental Methods of Chemistry), vol. 25, Yuki Gosei (Organic Synthesis) [VII], edited by the Chemical Society of Japan, Maruzen Co., Ltd., September 1991, 9-72); or addition and dehydration reaction (see, for example, Jikken Kagaku Koza (Experimental Methods of Chemistry), vol. 19, Yuki Gosei (Organic Synthesis) [I], edited by the Chemical Society of Japan, Maruzen Co., Ltd., June 1992, 57-85)).

(Conversion of Oxazolidine Compound (10e) into Amide Alcohol Compound (10f))

"Process 9-5" is oxidative cleavage reaction of an oxazolidine ring to convert a compound (10e) into an amide alcohol compound (10f). That is, a desired amide alcohol compound (10f) can be obtained with a high yield, for example, by preferably reacting a compound (10e) and 2.0 to 10.0 molar equivalents of potassium permanganate with respect to the compound (10e) in a water-containing solvent such as a mixture of water and acetone (see, for example, European Journal of Organic Chemistry, 2004, 23, 4823); or, for example, by preferably reacting a compound (10e) and 1.0 to 10.0 molar equivalents of bromine with respect to the compound (10e) in a halogenated solvent such as methylene chloride (see, for example, Synlett. 1994, 2, 143). The solvent used in this process varies depending on the starting material and the used oxidizing agent, but is not specifically limited as long as the solvent can dissolve the starting material to a certain degree without inhibiting the reaction. The reaction temperature should be a temperature which is sufficient for completing the reaction without promoting formation of undesired by-products and is preferably, for example, ice-cooling to 100° C. This reaction preferably completes in 1 to 24 hours under appropriate reaction conditions, and the progress of the reaction can be monitored by known chromatography technology. Undesired by-products can be removed by commonly used chromatography technology and/or technology known to those skilled in the art, such as crystallization.

(Conversion of Amide Alcohol Compound (10f) into Lactam Compound (6b))

In "Process 9-6", the conversion of $L_9$ of an amide alcohol compound (10f) into an alcohol or an amine is followed by cyclization reaction. That is, the conversion of $L_9$ of an amide alcohol compound (10f) into an alcohol varies depending on the starting material, but can be carried by a method known to those skilled in the art under conditions similar to those in this reaction (see, for example, Jikken Kagaku Koza (Experimental Methods of Chemistry), vol. 20, Yuki Gosei Hannou (Organic Synthesis Reaction) [II], edited by the Chemical Society of Japan, Maruzen Co., Ltd., July 1992, 1-30). In addition, the conversion of $L_9$ of an amide alcohol compound (10f) into an amine varies depending on the starting material, but can be carried out by a method known to those skilled in the art under conditions similar to those in this reaction (see, for example, Jikken Kagaku Koza (Experimental Methods of Chemistry), vol. 20, Yuki Gosei Hannou (Organic Synthesis Reaction) [II], edited by the Chemical Society of Japan, Maruzen Co., Ltd., July 1992, 279-318). The ring-closing reaction of the alcohol or the amine varies depending on the starting material, but can be carried out by a method known to those skilled in the art under conditions similar to those in this reaction (see, for example, Journal of Fluorine Chemistry, 1997, 2, 119; Scientia Pharmaceutica, 1996, 64, 3). For example, a lactam compound (6b) can be obtained with a high yield by preferably heating the alcohol in the presence or absence of a solvent in the presence of 0.1 to 10 molar equivalents of an organic acid such as p-toluenesulfonic acid or camphorsulfonic acid or an inorganic acid such as sulfuric acid or hydrochloric acid with respect to the alcohol. The ring-closing reaction of the amine varies depending on the starting material, but can be carried out by a method known to those skilled in the art under conditions similar to those in this reaction (see, for example, Petrochemia, 1990, 30, 56; International Publication No. WO03/076386; Tetrahedron Letters, 1982, 23, 229). For example, a lactam compound (6b) can be obtained with a high yield by preferably stirring the amine in a solvent such as tetrahydrofuran, toluene, methylene chloride, or dimethylformamide in the presence of 0.1 to 1.0 molar equivalents of an organic metal such as tetrakistriphenylphosphine palladium or tristriphenylphosphine ruthenium with respect to the amine. The solvent used in this process varies depending on the starting material and the used reagent, but is not specifically limited as long as the solvent can dissolve the starting material to a certain degree without inhibiting the reaction. The reaction temperature should be a temperature which is sufficient for completing the reaction without promoting formation of undesired by-products and is preferably, for example, ice-cooling to 100° C. This reaction preferably completes in 1 to 24 hours under appropriate reaction conditions, and the progress of the reaction can be monitored by known chromatography technology. Undesired by-products can be removed by commonly used chromatography technology and/or technology known to those skilled in the art, such as crystallization.

(Conversion of Vinyl-Substituted Cyclic Amine Compound (10g) into Acylated Compound (10h))

An acylated compound (10h) is prepared according to "Process 9-7" using a vinyl-substituted cyclic amine compound (10g) as the starting material. That is, "Process 9-7" is the same method as the aforementioned "Process 9-3".

(Conversion of Acylated Compound (10h) into Lactam Compound (6b))

In "Process 9-8", the ring-closing metathesis reaction is followed by modification of a double bond. The ring-closing metathesis reaction varies depending on the starting material, but can be carried out by a method known to those skilled in the art under conditions similar to those in this reaction (see, for example, Comprehensive Organometallic Chemistry, 1982, 8, 499; Angewandte Chemie International Edition, 2000, 39, 3012). The modification of a double bond is preferably carried out by, for example, i) catalytic hydrogenation (see, for example, Jikken Kagaku Koza (Experimental Methods of Chemistry), vol. 26, Yuki Gosei Hannou (Organic Synthesis Reaction) [VIII], edited by the Chemical Society of Japan, Maruzen Co., Ltd., April 1992, 251-266); ii) hydroboration (see, for example, Jikken Kagaku Koza (Experimental Methods of Chemistry), vol. 26, Yuki Gosei Hannou (Organic Synthesis Reaction) [VII], edited by the Chemical Society of Japan, Maruzen Co., Ltd., September 1991, 83-134); or iii) oxidation of a carbon-carbon double bond (see, for example, Jikken Kagaku Koza (Experimental Methods of Chemistry), vol. 26, Yuki Gosei Hannou (Organic Synthesis Reaction) [V], edited by the Chemical Society of Japan, Maruzen Co., Ltd., October 1991, 237-267).

For example, the ring-closing metathesis reaction is preferably performed by stirring an acylated compound (10h) in a solvent in the presence of 0.01 to 0.2 molar equivalents of a metal catalyst with respect to the acylated compound (10h). Preferable examples of the solvent include halogenated solvents such as methylene chloride and chloroform; ether solvents such as tetrahydrofuran, 1,4-dioxane, and 1,2-dimethoxyethane; nonpolar solvents such as benzene, toluene, and xylene; and solvent mixtures thereof. The metal catalyst to be used varies depending on the starting material and solvent, but preferable examples of which include ruthenium catalysts such as bis(tricyclohexylphosphine)benzylidene ruthenium(IV) dichloride, benzylidene[1,3-bis(2,4,6-trimethylphenyl)-2-imidazolidinylidene]dichloro-(tricyclohexylphosphine)ruthenium(IV), [1,3-bis-(2,4,6-trimethylphenyl)-2-imidazolidinylidene]dichloro(ortho-isopropoxyphenylmethylidene)ruthenium(IV), bis(tricyclohexylphosphine)-3-phenyl-1H-inden-1-ylidene ruthenium (II) dichloride; and molybdenum catalysts such as 2,6-diisopropylphenylimide neophylidene biphen molybdenum(VI) and 2,6-diisopropylphenylimide neophylidene molybdenum(VI) bis(hexafluoro-tert-butoxide). The reaction temperature should be a temperature which is sufficient for completing the reaction without promoting formation of undesired by-products and is preferably, for example, room temperature to 100° C. This reaction preferably completes in 1 to 24 hours under appropriate reaction conditions, and the progress of the reaction can be monitored by known chromatography technology. Undesired by-products can be removed by commonly used chromatography, extraction, and/or technology known to those skilled in the art, such as crystallization.

(Conversion of Cycloalkyl Ketone Compound (10i) into Azido Compound (10j))

In "Process 9-9", i) halogenation reaction of the alpha-position of an aromatic ring (—$CH_2$—$Ar_2$) is followed by ii) introduction reaction of an azido group.

The halogenation reaction in the above-mentioned i) varies depending on the starting material, but can be carried out by a method known to those skilled in the art under conditions similar to those in this reaction (see, for example, Jikken Kagaku Koza (Experimental Methods of Chemistry), vol. 19, Yuki Gosei Hannou (Organic Synthesis Reaction) [I], edited by the Chemical Society of Japan, Maruzen Co., Ltd., June 1992, 422-458). For example, a cycloalkyl ketone compound (10i) and 1.0 to 2.0 molar equivalents of a halogenating agent with respect to the cycloalkyl ketone compound (10i) are preferably stirred in a solvent. Preferable examples of the halogenating agent include N-bromosuccimide and bromide. Further, in some cases, the reaction may be significantly enhanced by adding, for example, 0.01 to 0.5 molar equivalents of a radical initiator such as benzoyl peroxide or 2,2-azobis(isobutylonitrile) with respect to the cycloalkyl ketone compound (10i) or 0.01 to 0.5 molar equivalents of an acid catalyst such as hydrobromic acid with respect to the cycloalkyl ketone compound (10i). The solvent to be used varies depending on the starting material, but is not specifically limited as long as it can dissolve the starting material to a certain degree without inhibiting the reaction. Preferable examples of the solvent include carbon tetrachloride and benzene. The reaction temperature should be a temperature which is sufficient for completing the reaction without promoting formation of undesired by-products and is preferably, for example, room temperature to 150° C. This reaction preferably completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

The azidation reaction in the above-mentioned ii) varies depending on the starting material, but can be carried out by a method known to those skilled in the art under conditions similar to those in this reaction (see, for example, Jikken Kagaku Koza (Experimental Methods of Chemistry), vol. 20, Yuki Gosei Hannou (Organic Synthesis Reaction) [II], edited by the Chemical Society of Japan, Maruzen Co., Ltd., July 1992, 415-420). For example, a halogenated compound and 1.0 to 5.0 molar equivalents of an azidating agent with respect to the halogenated compound are stirred in a solvent. Preferable examples of the azidating agent include sodium azide and trimethylsilyl azide. Further, in some cases, the reaction may be significantly enhanced by using, for example, 0.1 to 5.0 molar equivalents of a quaternary amine salt such as tetrabutylammonium fluoride with respect to the azidating agent. The solvent to be used varies depending on the starting material, but is not specifically limited as long as it can dissolve the starting material to a certain degree without inhibiting the reaction. Preferable examples of the solvent include ether solvents such as tetrahydrofuran and dioxane; halogenated solvents such as chloroform and methylene chloride; nonpolar solvents such as benzene and toluene; and polar solvents such as acetone, acetonitrile, dimethylformamide, and N-methylpyrrolidine. The reaction temperature should be a temperature which is sufficient for completing the reaction without promoting formation of undesired by-products and is preferably, for example, room temperature to 150° C. This reaction preferably completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

(Conversion of Azido Compound (10j) into Lactam Compound (6b))

In "Process 9-10", a lactam compound (6b) is prepared by transfer reaction by stirring an azido compound (10j) in a solvent in the presence of 1.0 to 10.0 molar equivalents of an acid with respect to the azido compound (10j). That is, this process varies depending on the starting material, but can be carried out by a method known to those skilled in the art under conditions similar to this reaction (see, for example, Journal of the Organic Chemistry, 2001, 66, 886). Preferable examples of the acid include trifluoromethanesulfonic acid, trifluoroacetic acid, sulfuric acid, and hydrochloric acid. This reaction may be carried out using the acid as the solvent, but is preferably carried out in the presence of a solvent from the viewpoints of operational ease and stirring efficiency. The solvent to be used varies depending on the starting material, but is not specifically limited as long as it can dissolve the starting material to a certain degree without inhibiting the reaction. Preferable solvents include halogenated solvents such as chloroform and methylene chloride, and nonpolar solvents such as benzene and toluene. The reaction temperature should be a temperature which is sufficient for completing the reaction without promoting formation of undesired by-products and is preferably, for example, −78 to 50° C. This reaction preferably completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

(Conversion of Vinyl-Substituted Cyclic Amine Compound (10 g) into Compound (10k))

The compound (10k) is prepared according to "Process 9-11" by using a vinyl-substituted cyclic amine compound (10g) as a starting material. That is, in "Process 9-11", reductive reaction of a double bond is followed by carbon-adding reaction. The reductive reaction of a double bond can be carried out by a method disclosed in many publications, preferably, for example, by i) catalytic hydrogenation (see, for example, Jikken Kagaku Koza (Experimental Methods of Chemistry), vol. 26, Yuki Gosei Hannou (Organic Synthesis Reaction) [VIII], edited by the Chemical Society of Japan, Maruzen Co., Ltd., April 1992, 251-266), or ii) reduction with a metal and a metal salt (see, for example, Jikken Kagaku Koza (Experimental Methods of Chemistry), vol. 26, Yuki Gosei Hannou (Organic Synthesis Reaction) [VIII], edited by the Chemical Society of Japan, Maruzen Co., Ltd., April 1992, 165-1856).

In the above-mentioned i), a compound (10g) and a hydrogen source are stirred in a solvent in the presence of 0.01 to 0.5 molar equivalents of a metal catalyst with respect to the compound (10g). The metal catalyst to be used varies depending on the starting material, but is not specifically limited. Preferable examples of the metal catalyst include palladium-carbon, rhodium-carbon, ruthenium-carbon, palladium hydroxide, platinum oxide, Raney nickel, and a Wilkinson catalyst. The hydrogen source varies depending on the starting material and the used metal catalyst, but is not specifically limited. Preferable examples of the hydrogen source include a hydrogen gas, formic acid, ammonium formate, and cyclohexadiene. The solvent to be used varies depending on the starting material and the used metal catalyst, but is not specifically limited. Preferable examples of the solvent include methanol, ethanol, ethyl acetate, toluene, tetrahydrofuran, 1,4-dioxane, chloroform, methylene chloride, water, and mixtures thereof. Further, in order to efficiently progress the reaction, an organic acid, inorganic acid, or organic base may be optionally added. The reaction temperature should be a temperature which is sufficient for completing the reaction without promoting formation of undesired by-products and is preferably, for example, room temperature to 150° C. This reaction preferably completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

In the above-mentioned ii), a compound (10g) is stirred in a solvent in the presence of 1.0 to 10.0 molar equivalents of a metal or metal salt with respect to the compound (10g). The metal or metal salt to be used varies depending on the starting material, but is not specifically limited. Preferable examples of the metal or metal salt include alkali metals such as lithium and sodium; alkaline earth metals such as magnesium and calcium; and salts thereof. The solvent to be used varies depending on the starting material and the used metal, but is not specifically limited. Preferable examples of the solvent include ammonia, methanol, ethanol, tert-butanol, tetrahydrofuran, 1,4-dioxane, diethyl ether, water, and mixtures thereof. The reaction temperature should be a temperature which is sufficient for completing the reaction without promoting formation of undesired by-products and is preferably, for example, −78 to 100° C. This reaction preferably completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

The carbon-adding reaction following the reduction of a double bond can be carried out by a method disclosed in many publications. Preferable examples of the method include i) Wittig reaction, ii) Horner-Emmons reaction, and iii) Peterson reaction (see, for example, Jikken Kagaku Koza (Experimental Methods of Chemistry), vol. 19, Yuki Gosei (Organic Synthesis) [I], edited by the Chemical Society of Japan, Maruzen Co., Ltd., June 1992, 57-85).

The Wittig reaction is preferably performed, for example, by stirring an aldehyde compound derived from a compound (10g) and 1.0 to 3.0 molar equivalents of a known Wittig reagent with respect to the aldehyde compound in a solvent in the presence of 1.0 to 5.0 molar equivalents of a base with respect to the aldehyde compound. The solvent to be used varies depending on the starting material and the used base, but is not specifically limited as long as the solvent can dissolve the starting material to a certain degree without inhibiting the reaction. Preferable examples of the solvent include polar solvents such as nitromethane, acetonitrile, 1-methyl-2-pyrrolidone, N,N-dimethylformamide, and dimethylsulfoxide; ether solvents such as tetrahydrofuran, 1,4-dioxane, and 1,2-dimethoxyethane; nonpolar solvents such as benzene, toluene, and xylene; alcohol solvents such as ethanol and methanol; halogenated solvents such as chloroform and methylene chloride; water; and solvent mixtures thereof. The base to be used varies depending on the starting material and the used solvent. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine, and diazabicyclononene; organic metals such as butyl lithium and lithium diisobutylamide; and alkali metal hydrides such as sodium hydride. The reaction temperature should be a temperature which is sufficient for completing the reaction without promoting formation of undesired by-products and is preferably, for example, −78 to 150° C. This reaction completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

The Horner-Emmons reaction is preferably performed, for example, by stirring an aldehyde compound derived from a compound (10 g) and 1.0 to 3.0 molar equivalents of a known Horner-Emmons reagent with respect to the aldehyde compound in a solvent in the presence of 1.0 to 5.0 molar equivalents of a base with respect to the aldehyde compound. The solvent to be used varies depending on the starting material and the used base, but is not specifically limited as long as the solvent can dissolve the starting material to a certain degree without inhibiting the reaction. Preferable examples of the solvent include polar solvents such as 1-methyl-2-pyrrolidone, N,N-dimethylformamide, and dimethylsulfoxide; ether solvents such as tetrahydrofuran, 1,4-dioxane, and 1,2-dimethoxyethane; nonpolar solvents such as benzene, toluene, and xylene; alcohol solvents such as ethanol and methanol; water; and solvent mixtures thereof. The base to be used varies depending on the starting material and the used solvent. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine, and diazabicyclononene; organic metals such as butyl lithium and lithium diisobutylamide; alkali metal hydrides such as sodium hydride; and alkali metal ammonium salts such as sodium amide. The reaction temperature should be a temperature which is sufficient for completing the reaction without promoting formation of undesired by-products and is preferably, for example, −78 to 150° C. This reaction completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

The Peterson reaction is preferably performed, for example, by stirring an aldehyde compound derived from a compound (10g) and 1.0 to 3.0 molar equivalents of a known Peterson reagent with respect to the aldehyde compound in a solvent in the presence of 1.0 to 5.0 molar equivalents of a base with respect to the aldehyde compound. The solvent to be used varies depending on the starting material and the used base, but is not specifically limited as long as the solvent can dissolve the starting material to a certain degree without inhibiting the reaction. Preferable examples of the solvent include polar solvents such as 1-methyl-2-pyrrolidone, N,N-dimethylformamide, and dimethylsulfoxide; ether solvents such as tetrahydrofuran, 1,4-dioxane, and 1,2-dimethoxyethane; nonpolar solvents such as benzene, toluene, and xylene; alcohol solvents such as ethanol and methanol; water; and solvent mixtures thereof. The base to be used varies depending on the starting material and the solvent. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine, and diazabicyclononene; organic metals such as butyl lithium and lithium diisobutylamide; alkali metal hydrides such as sodium hydride; and alkali metal ammonium salts such as sodium amide. The reaction temperature should be a temperature which is sufficient for completing the reaction without promoting formation of undesired by-products and is preferably, for example, −78 to 150° C. This reaction completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

(Conversion of Compound (10k) into Lactam Compound (6b))

The lactam compound (6b) can be prepared according to "Process 9-12" by intramolecular amidation using a compound (10k) as the starting material. That is, "Process 9-12" is the same method as the aforementioned "Process 9-3".

(Conversion of Compound (10l) into Compound (10m))

In "Process 9-13", a compound (10m) is prepared by subjecting a compound (10l) to nucleophilic reaction of an organic metal reagent which is commercially available or is prepared by a method known to those skilled in the art. That is, this process varies depending on the starting material, but can be carried out by a method known to those skilled in the art under conditions similar to those in this reaction (see, for example, Jikken Kagaku Koza (Experimental Methods of Chemistry), vol. 25, Yuki Gosei (Organic Synthesis) [VII], edited by the Chemical Society of Japan, Maruzen Co., Ltd., September 1991, 9-72). For example, a compound (10l) and 0.5 to 5.0 molar equivalents of an organic metal reagent with respect to the compound (10l) are stirred in a solvent. The solvent to be used varies depending on the starting material, but is not specifically limited. A solvent or solvent mixture preferably dissolves the starting material to a certain degree without inhibiting the reaction is preferable, and examples of which include ether solvents such as diethyl ether and tetrahydrofuran; halogenated solvents such as methylene chloride, 1,2-dichloroethane, and chloroform; nonpolar solvents such as benzene, toluene, and xylene. The reaction temperature varies depending on the starting material, but is not specifically limited. Preferably, the reaction temperature should be a temperature which is sufficient for completing the reaction without promoting formation of undesired by-products and is preferably, for example, −78 to 50° C. This reaction completes in 0.5 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization. Further, for example, a compound (10l) having a carbonyl group formed by $R^5$ and $R^6$ may be preferably used as a starting material.

(Conversion of Compound (10m) into Compound (10n))

In "Process 9-14", two steps are performed. That is, deprotection of a protecting group of a nitrogen atom in a compound (10m) by a method known to those skilled in the art (see, for example, T. Greene, et al., Protective Groups in Organic Synthesis, John Wiley & Sons, Inc., NY, 1981) is followed by intramolecular reductive amination (see, for example, Jikken Kagaku Koza (Experimental Methods of Chemistry), vol. 14, Yuki-Kagobutsu no Gosei to Hannou (Synthesis and Reaction of Organic Compound) [III], edited by the Chemical Society of Japan, Maruzen Co., Ltd., February 1978, 1380-1384). Further, this process can be preferably performed, for example, by using a compound (10m) having a carbonyl group formed by $R^5$ and $R^6$ may be used as a starting material.

(Conversion of Compound (10n) into Compound (6b))

In "Process 9-15", a deprotection step of a protecting group $V_1$ of a compound (10n) is followed by an oxomorpholine ring-closing step. The deprotection step can be performed by a method known to those skilled in the art (see, for example, T. Greene, et al., Protective Groups in Organic Synthesis, John Wiley & Sons, Inc., NY, 1981). In addition, for example, when $R^5$ and $R^6$ are each a hydrogen atom, a compound (10m) may be prepared as an ester derivative (formation of a carbonyl group by $R^5$ and $R^6$), and then reduction reaction may be performed by a method known to those skilled in the art. The oxomorpholine ring-closing step is the same as the aforementioned "Process 4-2".

Reference Example 4

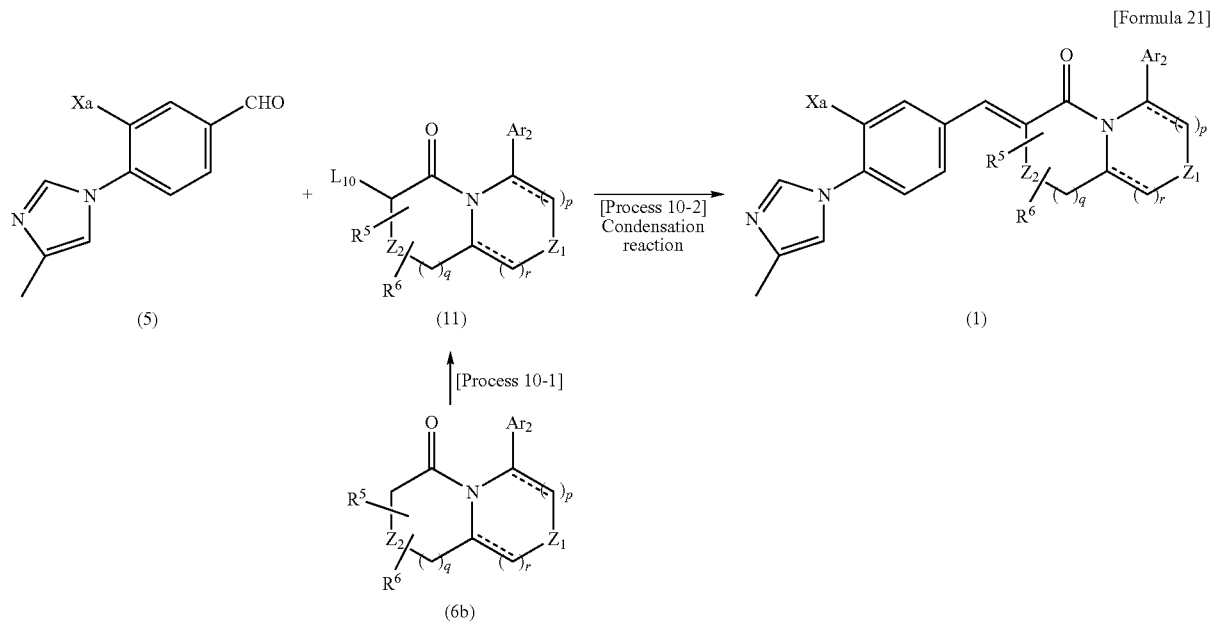

[Formula 21]

(wherein ⚌ denotes a single bond or a double bond; $Ar_2$, $Z_1$, $Z_2$, $R^5$, $R^6$, $X_a$, p, q, and r are the same as defined above; $L_{10}$ denotes a phosphonic acid ester group such as a diethylphosphonyl group, a phosphonium salt such as triphenylphosphonium bromide, a silyl group such as a trimethylsilyl group, an ester group such as a methyl ester or ethyl ester group, or a carboxyl group).

The aforementioned "Reference example 4" is an exemplary method for preparing a compound (1) by introduction of a leaving group $L_{10}$ into a lactam compound (6b) according to "Process 10-1" and then condensation reaction with an aldehyde compound (5) in "Process 10-2".

(Preparation of Compound (1))

Though the condensation reaction in "Process 10-2" varies depending on the starting material, no specific limitation is imposed upon it as long as the reaction is conducted under conditions similar to those in this reaction. The condensation reaction can be carried out by a method disclosed in many publications. For example, the Wittig reaction, the Horner-Emmons reaction, the Peterson reaction, or the Knoevenagel reaction (see, for example, Jikken Kagaku Koza (Experimental Methods of Chemistry), vol. 19, Yuki Gosei (Organic Synthesis) [I], edited by the Chemical Society of Japan, Maruzen Co., Ltd., June 1992, 57-85), is preferable.

The Wittig reaction is preferably performed, for example, by stirring a compound (11) (here, $L_{10}$ denotes a phosphonium salt), 0.5 to 2.0 molar equivalents of an aldehyde compound (5) with respect to the compound (11), and 1.0 to 5.0 molar equivalents of a base with respect to the compound (11) in a solvent. In this reaction, a compound (11) and a base are treated first to form a phosphonium ylide, and then an aldehyde (5) is added thereto; or a base is added to a mixture of a compound (11) and an aldehyde compound (5). The solvent to be used varies depending on the starting material and the used base, but is not specifically limited as long as the solvent can dissolve the starting material to a certain degree without inhibiting the reaction. Preferable examples of the solvent include polar solvents such as nitromethane, acetonitrile, 1-methyl-2-pyrrolidone, N,N-dimethylformamide, and dimethylsulfoxide; ether solvents such as tetrahydrofuran, 1,4-dioxane, and 1,2-dimethoxyethane; nonpolar solvents such as benzene, toluene, and xylene; alcohol solvents such as ethanol and methanol; halogenated solvents such as chloroform and methylene chloride; water; and solvent mixtures thereof. The base to be used varies depending on the starting material and the used solvent, and preferable examples of which include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine, and diazabicyclononene; organic metals such as butyl lithium and lithium diisobutylamide; and alkali metal hydrides such as sodium hydride. The reaction temperature should be a temperature which is sufficient for completing the reaction without promoting formation of undesired by-products and is preferably, for example, −78 to 150° C. This reaction completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

The Horner-Emmons reaction is preferably performed, for example, by stirring a compound (11) (here, $L_{10}$ denotes a phosphonic acid ester group), 0.5 to 2.0 molar equivalents of an aldehyde compound (5) with respect to the compound (11), and 1.0 to 5.0 molar equivalents of a base with respect to the compound (11) in a solvent. In this reaction, a compound (11) and a base are treated first to form a carbanion, and then an aldehyde compound (5) is added thereto; or a base is added to a mixture of a compound (11) and an aldehyde compound (5). The solvent to be used varies depending on the starting material and the used base, but is not specifically limited as long as the solvent can dissolve the starting material to a certain degree without inhibiting the reaction. Preferable examples of the solvent include polar solvents such as 1-methyl-2-pyrrolidone, N,N-dimethylformamide, and dimethylsulfoxide; ether solvents such as tetrahydrofuran, 1,4-dioxane, and 1,2-dimethoxyethane; nonpolar solvents such as benzene, toluene, and xylene; alcohol solvents such as ethanol and methanol; water; and solvent mixtures thereof. The base to be used varies depending on the starting material and the used solvent, and preferable examples of which include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine, and diazabicyclononene; organic metals such as butyl lithium and lithium diisobutylamide; alkali metal hydrides such as sodium hydride; and alkali metal ammonium salts such as sodium amide. The reaction temperature should be a temperature which is sufficient for completing the reaction without promoting formation of undesired by-products and is preferably, for example, −78 to 150° C. This reaction completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

The Peterson reaction is preferably performed, for example, by stirring a compound (11) (here, $L_{10}$ denotes a silyl group), 0.5 to 2.0 molar equivalents of an aldehyde compound (5) with respect to the compound (11), and 1.0 to 5.0 molar equivalents of a base with respect to the compound (11) in a solvent. In this reaction, a compound (11) and a base are treated first to form a carbanion, and then an aldehyde (5) is added thereto; or a base is added to a mixture of a compound (11) and an aldehyde compound (5). The solvent to be used varies depending on the starting material and the used base, but is not specifically limited as long as the solvent can dissolve the starting material to a certain degree without inhibiting the reaction. Preferable examples of the solvent include polar solvents such as 1-methyl-2-pyrrolidone, N,N-dimethylformamide, and dimethylsulfoxide; ether solvents such as tetrahydrofuran, 1,4-dioxane, and 1,2-dimethoxyethane; nonpolar solvents such as benzene, toluene, and xylene; alcohol solvents such as ethanol and methanol; water; and solvent mixtures thereof. The base to be used varies depending on the starting material and the used solvent, an preferable examples of which include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine, and diazabicyclononene; organic metals such as butyl lithium and lithium diisobutylamide; alkali metal hydrides such as sodium hydride; and alkali metal ammonium salts such as sodium amide. The reaction temperature should be a temperature which is sufficient for completing the reaction without promoting formation of undesired by-products and is preferably, for example, −78 to 150° C. This reaction completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

The Knoevegagel reaction is preferably performed, for example, by stirring a compound (11) (here, $L_{10}$ denotes an ester or carboxyl group), 0.5 to 2.0 molar equivalents of an aldehyde compound (5) with respect to the compound (11), and 1.0 to 5.0 molar equivalents of a base with respect to the compound (11) in a solvent. In this reaction, a compound (11) and a base are treated first to form a carbanion, and then an aldehyde (5) is added thereto; or a base is added to a mixture of a compound (11) and an aldehyde compound (5). The solvent to be used varies depending on the starting material and the used base, but is not specifically limited as long as the solvent can dissolve the starting material to a certain degree without inhibiting the reaction. Preferable examples of the solvent include polar solvents such as 1-methyl-2-pyrrolidone, N,N-dimethylformamide, and dimethylsulfoxide; ether solvents such as tetrahydrofuran, 1,4-dioxane, and 1,2-dimethoxyethane; nonpolar solvents such as benzene, toluene, and xylene; alcohol solvents such as ethanol and methanol; water; and solvent mixtures thereof. The base to be used varies depending on the starting material and the solvent, and preferable examples of which include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine, and diazabicyclononene; organic metals such as butyl lithium and lithium diisobutylamide; alkali metal hydrides such as sodium hydride; and alkali metal ammonium salts such as sodium amide. The reaction temperature should be a temperature which is sufficient for completing the reaction without promoting formation of undesired by-products and is preferably, for example, −78 to 150° C. This reaction completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

(Preparation of Compound (11))

The compound (11) can be prepared according to "Process 10-1" by using a lactam compound (6b) as a starting material. For example, i) a Wittig reagent (11) (here, $L_{10}$ is a phosphonium salt) can be prepared by halogenating a lactam compound (6b) by a method known to those skilled in the art (see, for example, Jikken Kagaku Koza (Experimental Methods of Chemistry), vol. 19, Yuki Gosei (Organic Synthesis) [I], edited by the Chemical Society of Japan, Maruzen Co., Ltd., June 1992, 430-438) and then reacting the halogenated compound with an organic phosphorus compound such as triphenylphosphine (see, for example, Organic Reaction, 1965, 14, 270); ii) a Horner-Emmons reagent (11) (here, $L_{10}$ is a phosphonic acid ester group) can be prepared by halogenating a lactam compound (6b) by a method known to those skilled in the art (see, for example, Jikken Kagaku Koza (Experimental Methods of Chemistry), vol. 19, Yuki Gosei (Organic Synthesis) [I], edited by the Chemical Society of Japan, Maruzen Co., Ltd., June 1992, 430-438) and then subjecting the halogenated compound to the Arbuzov reaction using alkyl phosphite (see, for example, Chemical Review, 1981, 81, 415) or to the Becker reaction using metal phosphonite (see, for example, Journal of the American Chemical Society, 1945, 67, 1180). Alternatively, the Horner-Emmons reagent (11) can be prepared by treating a lactam compound (6b) and chlorophosphate in the presence of a base (see, for example, Journal of Organic Chemistry, 1989, 54, 4750); iii) a Peterson reagent (11) (here, $L_{10}$ is a silyl group) can be prepared by treating a lactam compound (6b) and trialkylsilyl chloride in the presence of a base (see, for example, Journal of Organometallic Chemistry, 1983, 248, 51); and iv) a compound (11) of an ester or carboxylic acid derivative (here, $L_{10}$ is an ester or carboxyl group) can be prepared by treating a lactam compound (6b) with a diester carbonate, a halogenated carbonate ester, or carbon dioxide in the presence of a base (see, for example, Jikken Kagaku Koza (Experimental Methods of Chemistry), vol. 22, Yuki Gosei (Organic Synthesis) [IV], edited by the Chemical Society of Japan, Maruzen Co., Ltd., June 1992, 14-30 and 54-71).

Reference Example 5

(Preparation of Compound (1))

In the above-mentioned i), a compound (1) can be prepared from an amide compound (13) according to "Process 11-3". In "Process 11-3", ring-closing metathesis reaction is followed by modification of a double bond. That is, ring-closing metathesis reaction as a first step varies depending on the starting material, but can be carried out by a method known to those skilled in the art under conditions similar to those in this reaction (see, for example, Comprehensive Organometallic Chemistry, 1982, 8, 499; Angewandte Chemie International

[Formula 22]

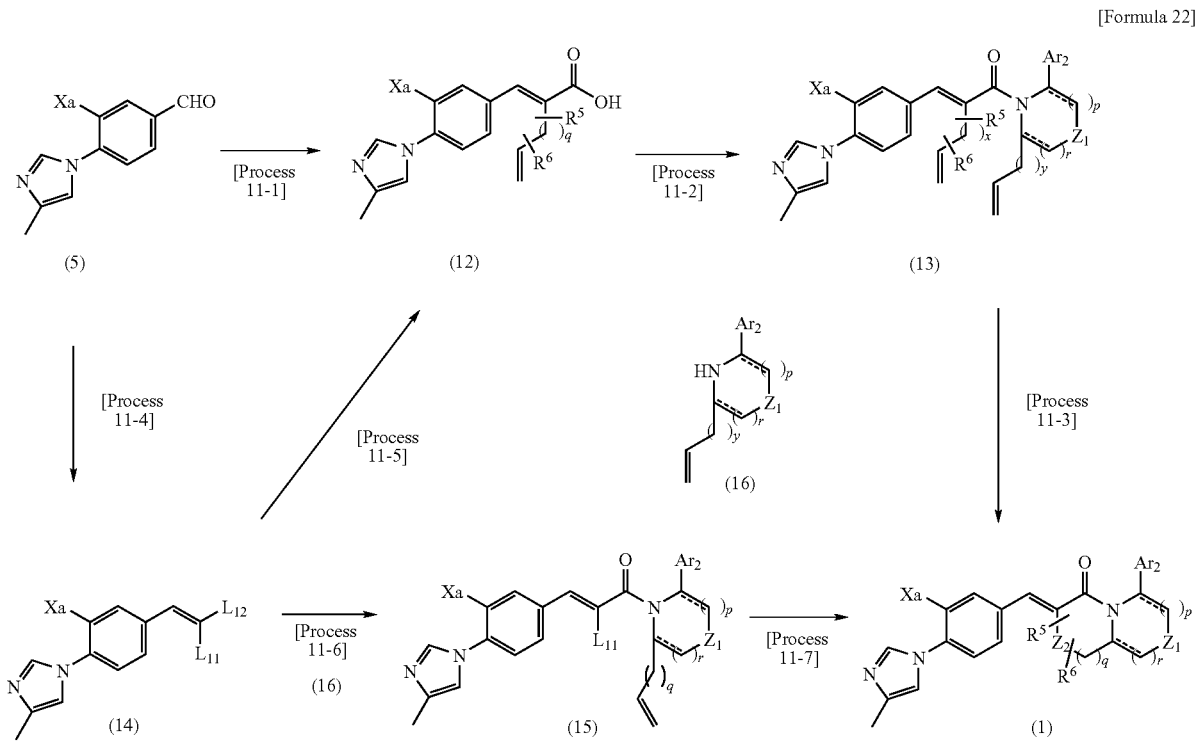

(wherein ⹀ denotes a single bond or a double bond; $Ar_2$, $Z_1$, $Z_2$, $R^5$, $R^6$, p, q, $X_a$, and r are the same as defined above; x and y each denote an integer of 0 to 2; $L_{11}$ denotes a halogen atom such as chlorine, bromine, or iodine, or a sulfonate ester group such as a triflate group; and $L_{12}$ denotes an ester group such as a methyl ester or ethyl ester group, or carboxylic acid).

The aforementioned "Reference Example 5" is an exemplary method for preparing a compound (1) by i) preparing a compound (12) from an aldehyde compound (5) according to "Process 11-1" or "Process 11-5" through "Process 11-4", converting the compound (12) into an amide compound (13) by condensation reaction with an amine compound (16), and subjecting the amide compound (13) to ring-closing metathesis reaction followed by modification of a double bond in "Process 11-3"; or by ii) preparing a compound (14) from an aldehyde compound (5) according to "Process 11-4", converting the compound (14) into an amide compound (15) in "Process 11-6", and subjecting the amide compound (15) to the Heck reaction followed by modification of a double bond in "Process 11-7".

Edition, 2000, 39, 3012). A second step, i.e., modification of a double bond, can be performed by, for example, i) catalytic hydrogenation (see, for example, Jikken Kagaku Koza (Experimental Methods of Chemistry), vol. 26, Yuki Gosei Hannou (Organic Synthesis Reaction) [VIII], edited by the Chemical Society of Japan, Maruzen Co., Ltd., April 1992, 251-266); ii) hydroboration (see, for example, Jikken Kagaku Koza (Experimental Methods of Chemistry), vol. 26, Yuki Gosei Hannou (Organic Synthesis Reaction) [VII], edited by the Chemical Society of Japan, Maruzen Co., Ltd., September 1991, 83-134); or iii) oxidation of a carbon-carbon double bond (see, for example, Jikken Kagaku Koza (Experimental Methods of Chemistry), vol. 26, Yuki Gosei Hannou (Organic Synthesis Reaction) [V], edited by the Chemical Society of Japan, Maruzen Co., Ltd., October 1991, 237-267).

In the ring-closing metathesis reaction, intermolecular ring-closing is performed by, for example, stirring an amide compound (13) in a solvent in the presence of 0.01 to 0.2 molar equivalents of a metal catalyst with respect to the amide compound (13). Preferable examples of the solvent to be used include halogenated solvents such as methylene chloride and chloroform; ether solvents such as tetrahydrofuran, 1,4-dioxane, and 1,2-dimethoxyethane; nonpolar solvents such as benzene, toluene, and xylene; and solvent mixtures thereof. The metal catalyst to be used varies depending on the starting material and the solvent, but preferable examples of which include ruthenium catalysts such as bis(tricyclohexylphosphine)-benzylidene ruthenium(IV) dichloride, benzylidene [1,3-bis(2,4,6-trimethylphenyl)-2-imidazolidinylidene]-dichloro-(tricyclohexylphosphine)ruthenium(IV), [1,3-bis (2,4,6-trimethylphenyl)-2-imidazolidinylidene]dichloro (ortho-isopropoxyphenylmethylidene)ruthenium(IV), bis (tricyclohexylphosphine)-3-phenyl-1H-inden-1-ylidene ruthenium (II) dichloride; and molybdenum catalysts such as 2,6-diisopropylphenylimide neophylidene biphen molybdenum(VI) and 2,6-diisopropylphenylimide neophylidene molybdenum(VI) bis(hexafluoro-tert-butoxide). The reaction temperature should be a temperature which is sufficient for completing the reaction without promoting formation of undesired by-products and is preferably, for example, room temperature to 100° C. This reaction preferably completes in 1 to 24 hours under appropriate reaction conditions, and the progress of the reaction can be monitored by known chromatography technology. Undesired by-products can be removed by commonly used chromatography, extraction, and/or technology known to those skilled in the art, such as crystallization.

The modification of a double bond is preferably performed by, for example, catalytic hydrogenation. For example, a ring-closed compound obtained by the ring-closing metathesis reaction is subjected to reduction reaction, preferably, in the presence of 0.01 to 0.2 molar equivalents of a metal catalyst with respect to the ring-closed compound, preferably, in a hydrogen flow at 1 to 10 atm. This reaction is preferably carried out in the presence of a solvent from the viewpoints of operational ease and stirring efficiency. Preferable examples of the solvent to be used include alcohol solvents such as ethanol and methanol; halogenated solvents such as methylene chloride and chloroform; ether solvents such as tetrahydrofuran, 1,4-dioxane, and 1,2-dimethoxyethane; nonpolar solvents such as benzene, toluene, and xylene; polar solvents such as ethyl acetate and acetonitrile; and solvent mixtures thereof. The metal catalyst to be used varies depending on the starting material and the solvent, and preferable examples of which include platinum, platinum oxide, platinum black, Raney nickel, and palladium-carbon. The reaction temperature should be a temperature which is sufficient for completing the reaction without promoting formation of undesired by-products and is preferably, for example, room temperature to 100° C. This reaction preferably completes in 1 to 24 hours under appropriate reaction conditions, and the progress of the reaction can be monitored by known chromatography technology. Undesired by-products can be removed by commonly used chromatography, extraction, and/or technology known to those skilled in the art, such as crystallization.

In the above-mentioned ii), a compound (1) can be prepared from an amide compound (15) according to "Process 11-7". In "Process 11-7", the Heck reaction is followed by modification of a double bond. That is, a first step, i.e., the Heck reaction, varies depending on the starting material, but can be carried out by a method known to those skilled in the art under conditions similar to those in this reaction (see, for example, Jikken Kagaku Koza (Experimental Methods of Chemistry), vol. 19, Yuki Gosei Hannou (Organic Synthesis Reaction) [I], edited by the Chemical Society of Japan, Maruzen Co., Ltd., June 1992, 123-132). A second step, i.e., modification of a double bond, can be performed by, for example, i) catalytic hydrogenation (see, for example, Jikken Kagaku Koza (Experimental Methods of Chemistry), vol. 26, Yuki Gosei Hannou (Organic Synthesis Reaction) [VIII], edited by the Chemical Society of Japan, Maruzen Co., Ltd., April 1992, 251-266); ii) hydroboration (see, for example, Jikken Kagaku Koza (Experimental Methods of Chemistry), vol. 26, Yuki Gosei Hannou (Organic Synthesis Reaction) [VII], edited by the Chemical Society of Japan, Maruzen Co., Ltd., September 1991, 83-134); or iii) oxidation of a carbon-carbon double bond (see, for example, Jikken Kagaku Koza (Experimental Methods of Chemistry), vol. 26, Yuki Gosei Hannou (Organic Synthesis Reaction) [V], edited by the Chemical Society of Japan, Maruzen Co., Ltd., October 1991, 237-267).

The Heck reaction can be preferably performed by, for example, stirring a compound (15) in a solvent in the presence of 0.01 to 0.2 molar equivalents of a transition metal catalyst with respect to the compound (15). The solvent to be used varies depending on the starting material and the used transition metal catalyst, but is not specifically limited as long as the solvent can dissolve the starting material to a certain degree without inhibiting the reaction. Preferable examples of the solvent include acetonitrile, tetrahydrofuran, 1,4-dioxane, 1,2-dimethoxyethane, benzene, toluene, xylene, 1-methyl-2-pyrrolidone, and N,N-dimethylformamide. The reaction temperature should be a temperature which is sufficient for completing the coupling reaction and is preferably, for example, room temperature to 150° C. This reaction is performed preferably in an inert gas atmosphere, more preferably in a nitrogen or argon atmosphere. Preferable examples of the transition metal catalyst are palladium complexes, and more preferable examples are known palladium complexes such as palladium(II) acetate, dichlorobis(triphenylphosphine)palladium(II), tetrakis(triphenylphosphine)palladium (0), and tris(dibenzylideneacetone)dipalladium(0). In addition, it is preferable to optionally add, for example, 1.0 to 5.0 molar equivalents of a phosphorus ligand with respect to the used transition metal catalyst, in order to efficiently progress the reaction. Preferable examples of the phosphorus ligand include triphenylphosphine, tri-o-tolylphosphine, tri-tert-butylphosphine, and 2-(di-tert-butylphosphino)biphenyl. Further, a favorable result may be obtained in the presence of a base. The base to be used is not specifically limited as long as it can be used in coupling reaction similar to this reaction. For example, 0.1 to 5.0 molar equivalents of a base with respect to the compound (15) is preferably used. Preferable examples of the base include triethylamine, N,N-diisopropylethylamine, N,N-dicyclohexylmethylamine, and tetrabutylammonium chloride. This reaction preferably completes in 1 to 24 hours under appropriate reaction conditions, and the progress of the reaction can be monitored by known chromatography technology.

(Preparation of Amide Compound (13))

Though the amidation reaction in "Process 11-2" varies depending on the starting material, no specific limitation is imposed upon it as long as the reaction is conducted under conditions similar to those in this reaction. The reaction can be carried out by a known method disclosed in many publications (see, for example, Jikken Kagaku Koza (Experimental Methods of Chemistry), vol. 14, Yuki-Kagobutsu no Gosei to Hannou (Synthesis and Reaction of Organic Compound) [II], edited by the Chemical Society of Japan, Maruzen Co., Ltd., February 1978, 1136-1162). Preferably, for example, i) a compound (12) is converted into an acid halide compound, and then the acid halide compound is reacted with an amine compound (16) under basic conditions (see, for example, Jikken Kagaku Koza (Experimental Methods of Chemistry), vol. 14, Yuki-Kagobutsu no Gosei to Hannou (Synthesis and Reaction of Organic Compound) [II], edited by the Chemical Society of Japan, Maruzen Co., Ltd., February 1978, 1142-1145); or ii) a compound (12) is reacted with an amine compound (16) using a condensing agent (see, for example, Yuki Kagaku Jikken no Tebiki (Guide to Organic Chemistry Experiment) (4), Kagaku Dojin, September 1990, 27-52).

In the above-mentioned i), for example, the conversion reaction of a compound (12) into an acid halide compound is preferably carried out by stirring the compound (12) in a solvent in the presence of 1.0 to 10.0 molar equivalents of a halogenating agent with respect to the compound (12). The halogenating agent to be used varies depending on the starting material, but is not specifically limited. Preferable examples of the halogenating agent include thionyl chloride, phosphorus pentachloride, and oxalyl chloride. The solvent to be used is not specifically limited as long as the solvent can dissolve the starting material to a certain degree without inhibiting the reaction. Preferable examples of the solvent include methylene chloride, chloroform, and toluene. In addition, in some cases, the reaction is efficiently progressed by optionally adding an organic base such as pyridine or dimethylformamide at 0.1 to 1.0 molar equivalents with respect to the compound (12). The reaction temperature should be a temperature which is sufficient for completing the reaction without promoting formation of undesired by-products and is preferably, for example, ice-cooling to 150° C. This reaction preferably completes in 1 to 24 hours under appropriate reaction conditions, and the progress of the reaction can be monitored by known chromatography technology. Undesired by-products can be removed by commonly used chromatography and/or technology known to those skilled in the art, such as crystallization.

The coupling reaction sequentially performed is, for example, carried out by preferably stirring the acid halide compound and 1.0 to 5.0 molar equivalents of an amine compound (16) with respect of the acid halide compound in a solvent in the presence of 1.0 to 100.0 molar equivalents of a base with respect to the acid halide compound. The base to be used varies depending on the starting material, but is not specifically limited. Preferable examples of the base include pyridine, triethylamine, N,N-diisopropylethylamine, lutidine, quinoline, and isoquinoline. The solvent to be used is not specifically limited as long as it can dissolve the starting material to a certain degree without inhibiting the reaction. Preferable examples of the solvent include methylene chloride, chloroform, toluene, tetrahydrofuran, and 1,4-dioxane. Further, in some cases, a base may be used as the solvent. Alternatively, a two-layer distribution system of an alkali aqueous solution as a base and a halogenated solvent can be used. The alkali aqueous solution is preferably, for example, an aqueous solution of sodium hydroxide or potassium hydroxide. The halogenated solvent is preferably, for example, methylene chloride or 1,2-dichloroethane. The reaction temperature should be a temperature which is sufficient for completing the reaction without promoting formation of undesired by-products and is preferably, for example, ice-cooling to 100° C. This reaction preferably completes in 1 to 24 hours under appropriate reaction conditions, and the progress of the reaction can be monitored by known chromatography technology. Undesired by-products can be removed by commonly used chromatography and/or technology known to those skilled in the art, such as crystallization.

In the above-mentioned ii), for example, a compound (12) and 1.0 to 5.0 molar equivalents of an amine compound (16) with respect to the compound (12) are stirred in a solvent in the presence of 1.0 to 5.0 molar equivalents of a condensing agent with respect to the compound (12). The condensing agent to be used varies depending on the starting material, but is not specifically limited. Preferable examples of the condensing agent include 1,3-dicyclohexylcarbodiimide, 1-ethyl-3-(3'-dimethylaminopropyl)carbodiimide, benzotriazol-1-yloxytris(dimethylamino)phosphonium hexafluorophosphonate, diethylcyanophosphonate, and bis(2-oxo-3-oxazolidinyl)phosphinic chloride. In addition, in order to efficiently progress the reaction, for example, 1.0 to 2.0 molar equivalents of N-hydroxysuccinimide or N-hydroxybenzotriazole with respect to the compound (12) may be added. This reaction is preferably carried out in the presence of a solvent from the viewpoints of operational ease and stirring efficiency. The solvent to be used varies depending on the starting material and the used condensing agent, but is not specifically limited as long as the solvent can dissolve the starting material to a certain degree without inhibiting the reaction. Preferable examples of the solvent include halogenated solvents such as methylene chloride and 1,2-dichloroethane and polar solvents such as tetrahydrofuran and N,N-dimethylformamide. The reaction temperature should be a temperature which is sufficient for completing the reaction without promoting formation of undesired by-products and is preferably, for example, ice-cooling to 100° C. This reaction preferably completes in 1 to 24 hours under appropriate reaction conditions, and the progress of the reaction can be monitored by known chromatography technology. Undesired by-products can be removed by commonly used chromatography technology and/or technology known to those skilled in the art, such as crystallization.

(Preparation of Amine Compound (16))

The amine compound (16) is commercially available or can be prepared by a method known to those skilled in the art (see, for example, Tetrahedron Letters, 1998, 39, 5421).

(Preparation of Compound (12))

The compound (12) can be prepared i) from an aldehyde compound (5) according to "Process 11-1", or ii) by converting an aldehyde compound (5) into a compound (14) according to "Process 11-4" (here, $L_{12}$ denotes an ester group) and then into a compound (12) according to "Process 11-5".

(Conversion of Aldehyde Compound (5) into Compound (12))

In "Process 11-1", an aldehyde compound (5) is converted into a cinnamate ester compound in a first step, and then the ester group is hydrolyzed into a carboxylic acid group in a second step. The cinnamate ester compound can be prepared from an aldehyde compound (5) and various Horner-Emmons reagents by a method known to those skilled in the art (see, for example, W. S. Wadsworth Jr., Organic Reactions, 1997, 25, 73). For example, a cinnamate ester compound can be prepared with a high yield by using an aldehyde compound (5) and preferably 1.0 to 2.0 molar equivalents of a Horner-Emmons reagent and 1.0 to 5.0 molar equivalents of a base with respect to the aldehyde compound (5). The Horner-Emmons reagent can be prepared by a method known to those skilled in the art. For example, the Horner-Emmons reagent is prepared by alkylation of commercially available trialkyl phosphonoacetate (see, for example, Synthetic Communication, 1991, 22, 2391), or by the Arbuzov reaction of an alpha-halogeno-acetic acid derivative using alkyl phosphite (see, for example, Chemical Review, 1981, 81, 415), or by the Becker reaction using metal phosphonite (see, for example, Journal of the American Chemical Society, 1945, 67, 1180). Preferable examples of the solvent to be used include polar solvents such as 1-methyl-2-pyrrolidone, N,N-dimethylformamide, and dimethylsulfoxide; ether solvents such as tetrahydrofuran, 1,4-dioxane, and 1,2-dimethoxyethane; nonpolar solvents such as benzene, toluene, and xylene; alcohol solvents such as ethanol and methanol; water; and solvent mixtures thereof. The base to be used varies depending on the starting material and the solvent, and preferable examples of which include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine, and diazabicyclononene; organic metals such as butyl lithium and lithium diisobutylamide; alkali metal hydrides such as sodium hydride; and alkali metal ammonium salts such as sodium amide. The reaction temperature should be a temperature which is sufficient for completing the reaction without promoting formation of undesired by-products and is preferably, for example, −78 to 150° C. This reaction completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization. In the hydrolysis reaction into a compound (12) using a cinnamate ester compound as a starting material, a deprotection method known to those skilled in the art can be used (see, for example, T. W. Green, "Protective Groups in Organic Synthesis", John Wiley & Sons, Inc., 1981, 154-186).

(Conversion of Compound (14) into Compound (12))

The compound (12) can be prepared by coupling a compound (14) as a starting material with a corresponding alkene compound according to "Process 11-5". That is, the coupling reaction in "Process 11-5" can be carried out by a method known to those skilled in the art. For example, the Heck reaction (see, for example, R. F. Heck, Org. Reactions, 1982, 27, 345), the Suzuki reaction (see, for example, A. Suzuki, Chem. Rev., 1995, 95, 2457), and the Stille coupling reaction (see, for example, J. K. Stille, Angew. Chem. Int. Ed. Engl., 1986, 25, 508) are preferable.

In the Heck reaction, for example, coupling reaction of a halogenated or triflate compound (14) with an alkene compound at, preferably, 1.0 to 5.0 molar equivalents with respect to the compound (14) is performed in the presence of 0.01 to 0.2 molar equivalents of a transition metal catalyst with respect to the compound (14). This reaction is preferably performed in the presence of a solvent from the viewpoints of operational ease and efficient stirring. The solvent to be used varies depending on the starting material and the used transition metal catalyst, but is not specifically limited as long as the solvent can dissolve the starting material to a certain degree without inhibiting the reaction. Preferable examples of the solvent include acetonitrile, tetrahydrofuran, 1,4-dioxane, 1,2-dimethoxyethane, benzene, toluene, xylene, 1-methyl-2-pyrrolidone, and N,N-dimethylformamide. The reaction temperature should be a temperature which is sufficient for completing the coupling reaction and is preferably, for example, room temperature to 150° C. This reaction is performed preferably in an inert gas atmosphere, more preferably in a nitrogen or argon atmosphere. For example, the transition metal catalyst is preferably a palladium complex, more preferably a known palladium complex such as palladium(II) acetate, dichlorobis-(triphenylphosphine)palladium (II), tetrakis(triphenylphosphine)palladium(0), or tris(dibenzylideneacetone)dipalladium(0). In addition, in order to efficiently progress the reaction, a phosphorus ligand may be optionally added. Preferable examples of the phosphorus ligand include triphenylphosphine, tri-o-tolylphosphine, tri-tert-butylphosphine, and 2-(di-tert-butylphosphino)biphenyl. Further, a favorable result may be obtained in the presence of a base. The base to be used is not specifically limited as long as it can be used in coupling reaction similar to this reaction. Preferable examples of the base include triethylamine, N,N-diisopropylethylamine, N,N-dicyclohexylmethylamine, and tetrabutylammonium chloride. This reaction preferably completes in 1 to 24 hours under appropriate reaction conditions, and the progress of the reaction can be monitored by known chromatography technology.

In the Suzuki reaction, for example, coupling reaction of a halogenated or triflate compound (14) with a boronic acid compound or boronate ester compound at 1.0 to 5.0 molar equivalents with respect to the compound (14) is performed in the presence of 0.01 to 0.5 molar equivalents of a transition metal catalyst with respect to the compound (14). This reaction is preferably performed in the presence of a solvent from the viewpoints of operational ease and efficient stirring. The solvent to be used varies depending on the starting material and the used transition metal catalyst, but is not specifically limited as long as the solvent can dissolve the starting material to a certain degree without inhibiting the reaction. Preferable examples of the solvent include acetonitrile, tetrahydrofuran, 1,4-dioxane, 1,2-dimethoxyethane, benzene, toluene, xylene, 1-methyl-2-pyrrolidone, N,N-dimethylformamide, water, and solvent mixtures thereof. The reaction temperature should be a temperature which is sufficient for completing the coupling reaction and is preferably, for example, room temperature to 200° C. This reaction is performed preferably in an inert gas atmosphere, more preferably in a nitrogen or argon atmosphere. For example, the transition metal catalyst is preferably a known palladium complex, more preferably a known palladium complex such as palladium(II) acetate, dichlorobis(triphenylphosphine)-palladium(II), tetrakis(triphenylphosphine)palladium(0), or tris(dibenzylideneacetone)dipalladium(0). In addition, in order to efficiently progress the reaction, a phosphorus ligand may be optionally added. Preferable examples of the phosphorus ligand include triphenylphosphine, tri-o-tolylphosphine, tricyclohexylphosphine, and tri-tert-butylphosphine. Further, in order to efficiently progress the reaction, a quaternary ammonium salt, preferably, for example, tetrabutylammonium chloride or tetrabutylammonium bromide can be optionally added. Further, a favorable result may be obtained in the presence of a base. The base varies depending on the starting material and the used solvent, but is not specifically limited. Preferable examples of the base include sodium hydroxide, barium hydroxide, potassium fluoride, cesium fluoride, sodium carbonate, potassium carbonate, cesium carbonate, and potassium phosphate. This reaction preferably completes in 1 to 24 hours under appropriate reaction conditions, and the progress of the reaction can be monitored by known chromatography technology.

In the Stille coupling reaction, for example, a halogenated or a triflate compound (14) and 1.0 to 10.0 molar equivalents of trialkyltin compound with respect to the compound (14) are stirred in a solvent in the presence of 0.01 to 0.2 molar equivalents of a transition metal catalyst with respect to the compound (14). In order to efficiently progress the reaction, for example, 0.1 to 5.0 molar equivalents of a copper(I) halide and/or lithium chloride with respect to the compound (14) may be optionally used. Preferable examples of the solvent used in this reaction include toluene, xylene, N,N-dimethylformamide, N,N-dimethylacetoamide, 1-methyl-2-pyrrolidone, and dimethylsulfoxide. The reaction temperature should be a temperature which is sufficient for completing the coupling reaction and is preferably, for example, room temperature to 100° C. The transition metal catalyst to be used is a palladium complex, preferably, for example, a known palladium complex such as palladium(II) acetate, dichlorobis (triphenylphosphine)palladium(II), tetrakis(triphenylphosphine)palladium(0), or tris(dibenzylideneacetone)dipalladium(0); and more preferably tetrakis(triphenylphosphine)palladium(0) or tris(dibenzylideneacetone)dipalladium(0). This reaction is preferably performed in an inert gas atmosphere, more preferably in nitrogen or argon atmosphere. This reaction preferably completes in 1 to 24 hours under appropriate reaction conditions, and the progress of the reaction can be monitored by known chromatography technology.

(Conversion of Compound (5) into Compound (14))

The compound (14) can be prepared according to "Process 11-4" by subjecting a compound (5) as a starting material and phosphoacetate halide to the Horner-Emmons reaction (see, for example Organic Letter, 2000, 2, 1975).

(Conversion of Compound (14) into Compound (15))

The compound (15) can be prepared according to "Process 11-6" using a compound (14) as a starting material. "Process 11-6" and the preparation of an amine compound to be used are the same as those in the aforementioned "Process 11-2".

(wherein $\rightleftharpoons$ denotes a single bond or a double bond; $Ar_2$, $Z_1$, $Z_2$, $R^5$, $R^6$, p, q, $X_a$, and r are the same as defined above; $L_{12}$ denotes a halogen atom such as a chlorine or bromine atom or a sulfonate ester group such as a mesyl or tosyl group; $L_{13}$ denotes a phosphonic acid ester group such as a diethyl phosphonyl group; $L_{14}$ and $L_{15}$ each denote a hydroxy group, a hydroxy group having a protecting group, an amino group, or an amino group having a protecting group; and $V_3$ denotes an ester group such as a methyl ester or ethyl ester group or a carboxylic acid group).

The aforementioned "Reference Example 6" is an exemplary method for preparing a compound (1) by preparing a compound (18) from an aldehyde compound (5) and a Horner-Emmons reagent (17) according to "Process 12-1", amidating the compound (18) in "Process 12-2", forming a lactam ring according to "Process 12-3", and lastly forming a second ring in "Process 12-4".

(Preparation of Compound (1))

The compound (1) can be prepared from a lactam compound (21) according to "Process 12-4". In "Process 12-4",

[Formula 23]

deprotection reaction of an alcohol group or an amine group of $L_{14}$ and $L_{15}$ of the compound (21) is followed by ring-closing reaction. The deprotection reaction can be performed by a method disclosed in many publications (see, for example, T. W. Green, Protective Groups in Organic Synthesis, John Wiley & Sons, Inc., 1981). Though the ring-closing reaction varies depending on the starting material, no specific limitation is imposed upon it as long as the reaction is conducted under conditions similar to those in this reaction. The reaction can be carried out by a method known to those skilled in the art. For example, the ring-closing reaction is preferably performed by i) the formation of cyclic ether from diol (see, for example, Journal of Fluorine Chemistry, 1997, 2, 119; Scientia Pharmaceutica, 1996, 64, 3); or ii) the formation of a cyclic amine from aminoalcohol (Petrochemia, 1990, 30, 56; International Publication No. WO03/076386; Tetrahedron Letters, 1982, 23, 229). More preferably, for example, a compound (1) can be obtained with a high yield by heating a compound to be deprotected in the presence of 0.1 to 10 molar equivalents (with respect to the compound) of an organic acid such as p-toluenesulfonic acid or camphorsulfonic acid or an inorganic acid such as sulfuric acid or hydrochloric acid in presence or absence of a solvent; or heating a compound to be deprotected in the presence of 0.1 to 1.0 molar equivalents (with respect to the compound) of an organic metal such as tetrakistriphenylphosphine palladium or tristriphenylphosphine ruthenium. The solvent used in this process varies depending on the starting material and the used reagent, but is not specifically limited as long as the solvent can dissolve the starting material to a certain degree without inhibiting the reaction. Preferable examples of the solvent include methylene chloride, chloroform, 1,4-dioxane, 1,2-dimethoxyethane, dimethylsulfoxide, toluene, tetrahydrofuran, dimethylformamide, ethanol, methanol, water, and solvent mixtures thereof. The reaction temperature should be a temperature which is sufficient for completing the reaction without promoting formation of undesired by-products and is preferably, for example, ice-cooling to 100° C. This reaction preferably completes in 1 to 24 hours under appropriate reaction conditions, and the progress of the reaction can be monitored by known chromatography technology. Undesired by-products can be removed by commonly used chromatography technology and/or technology known to those skilled in the art, such as crystallization.

(Preparation of Lactam Compound (21))

The lactam compound (21) can be prepared by using a cinnamide compound (20) as a starting material and by cyclizing the cinnamide compound (20) with simultaneous elimination of $L_{12}$ according to "Process 12-3". That is, for example, a desired lactam compound (21) can be obtained with a high yield by treating a compound (20) with 1.0 to 5.0 molar equivalents of a base with respect to the compound (20). This reaction is preferably carried out in the presence of a solvent from the viewpoints of operational ease and stirring efficiency. The solvent to be used varies depending on the starting material and the used base, but is not specifically limited as long as the solvent can dissolve the starting material to a certain degree without inhibiting the reaction. Preferable examples of the solvent include polar solvents such as 1-methyl-2-pyrrolidone, N,N-dimethylformamide, and dimethylsulfoxide; ether solvents such as tetrahydrofuran, 1,4-dioxane, and 1,2-dimethoxyethane; nonpolar solvents such as benzene, toluene, and xylene; alcohol solvents such as ethanol and methanol; water; and solvent mixtures thereof. The base to be used varies depending on the starting material and the solvent, and preferable examples of which include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine, and diazabicyclononene; organic metals such as butyl lithium and lithium diisobutylamide; alkali metal hydrides such as sodium hydride; and alkali metal ammonium salts such as sodium amide. The reaction temperature should be a temperature which is sufficient for completing the reaction without promoting formation of undesired by-products and is preferably, for example, −78 to 150° C. This reaction preferably completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization.

(Preparation of Cinnamide Compound (20))

The cinnamide compound (20) can be prepared by amidation reaction according to "Process 12-2" using a compound (18) and, for example, 1.0 to 5.0 molar equivalents of an amine compound (19) with respect to the compound (18). Though the amidation reaction varies depending on the starting material, no specific limitation is imposed upon it as long as the reaction is conducted under conditions similar to those in this reaction. The reaction can be performed by a known method disclosed in many publications (see, for example, Jikken Kagaku Koza (Experimental Methods of Chemistry), vol. 14, Yuki-Kagobutsu no Gosei to Hannou (Synthesis and Reaction of Organic Compound) [II], edited by the Chemical Society of Japan, Maruzen Co., Ltd., February 1978, 1136-1162). Preferably, for example, i) a compound (18) is converted into an acid halide, and then the acid halide is reacted with an amine compound (19) under basic conditions (see, for example, Jikken Kagaku Koza (Experimental Methods of Chemistry), vol. 14, Yuki-Kagobutsu no Gosei to Hannou (Synthesis and Reaction of Organic Compound) [II], edited by the Chemical Society of Japan, Maruzen Co., Ltd., February 1978, 1142-1145); or ii) a compound (18) is reacted with an amine compound (19) using a condensing agent (see, for example, Yuki Kagaku Jikken no Tebiki (Guide to Organic Chemistry Experiment) (4), Kagaku Dojin, September 1990, 27-52).

In the above-mentioned i), for example, the conversion reaction of a compound (18) into an acid halide is preferably carried out by stirring a compound (18) in a solvent in the presence of 1.0 to 10.0 molar equivalents of a halogenating agent with respect to the compound (18). The halogenating agent to be used varies depending on the starting material, but is not specifically limited. Preferable examples of the halogenating agent include thionyl chloride, phosphorus pentachloride, and oxalyl chloride. The solvent to be used is not specifically limited as long as the solvent can dissolve the starting material to a certain degree without inhibiting the reaction. Preferable examples of the solvent include methylene chloride, chloroform, and toluene. In addition, in some cases, the reaction is efficiently progressed by optionally adding an organic base such as pyridine or dimethylformamide at 0.1 to 1.0 molar equivalents with respect to the compound (18). The reaction temperature should be a temperature which is sufficient for completing the reaction without promoting formation of undesired by-products and is preferably, for example, ice-cooling to 150° C. This reaction preferably completes in 1 to 24 hours under appropriate reaction conditions, and the progress of the reaction can be monitored by known chromatography technology. Undesired by-products can be removed by commonly used chromatography and/or technology known to those skilled in the art, such as crystallization.

The coupling reaction sequentially performed is, for example, carried out by preferably stirring the acid halide and 1.0 to 5.0 molar equivalents of an amine compound (19) with respect of the acid halide in a solvent in the presence of 1.0 to 100.0 molar equivalents of a base with respect to the acid halide. The base to be used varies depending on the starting material, but is not specifically limited, and preferable examples of which include pyridine, triethylamine, N,N-diisopropylethylamine, lutidine, quinoline, and isoquinoline. The solvent to be used is not specifically limited as long as it can dissolve the starting material to a certain degree without inhibiting the reaction. Preferable examples of the solvent include methylene chloride, chloroform, toluene, tetrahydrofuran, and 1,4-dioxane. Further, in some cases, a base can be used as the solvent. Alternatively, a two-layer distribution system of an alkali aqueous solution as a base and a halogenated solvent can be used. Preferable examples of the alkali aqueous solution include aqueous solutions of sodium hydroxide and potassium hydroxide. Preferable examples of the halogenated solvent include methylene chloride and 1,2-dichloroethane. The reaction temperature should be a temperature which is sufficient for completing the reaction without promoting formation of undesired by-products and is preferably, for example, ice-cooling to 100° C. This reaction preferably completes in 1 to 24 hours under appropriate reaction conditions, and the progress of the reaction can be monitored by known chromatography technology. Undesired by-products can be removed by commonly used chromatography and/or technology known to those skilled in the art, such as crystallization.

In the above-mentioned ii), for example, a compound (18) and 1.0 to 5.0 molar equivalents of an amine compound (19) with respect to the compound (18) are stirred in a solvent in the presence of 1.0 to 5.0 molar equivalents of a condensing agent with respect to the compound (18). The condensing agent to be used varies depending on the starting material, but is not specifically limited. Preferable examples of the condensing agent include 1,3-dicyclohexylcarbodiimide, 1-ethyl-3-(3'-dimethylaminopropyl)carbodiimide, benzotriazol-1-yloxytris(dimethylamino)phosphonium hexafluorophosphonate, diethylcyanophosphonate, and bis(2-oxo-3-oxazolidinyl)phosphinic chloride. In addition, in order to efficiently progress the reaction, for example, 1.0 to 2.0 molar equivalents of N-hydroxysuccinimide or N-hydroxybenzotriazole with respect to the compound (18) may be added. This reaction is preferably carried out in the presence of a solvent from the viewpoints of operational ease and stirring efficiency. The solvent to be used varies depending on the starting material and the used condensing agent, but is not specifically limited as long as the solvent can dissolve the starting material to a certain degree without inhibiting the reaction. Preferable examples of the solvent include halogenated solvents such as methylene chloride and 1,2-dichloroethane and polar solvents such as tetrahydrofuran and N,N-dimethylformamide. The reaction temperature should be a temperature which is sufficient for completing the reaction without promoting formation of undesired by-products and is preferably, for example, ice-cooling to 100° C. This reaction preferably completes in 1 to 24 hours under appropriate reaction conditions, and the progress of the reaction can be monitored by known chromatography technology. Undesired by-products can be removed by commonly used chromatography technology and/or technology known to those skilled in the art, such as crystallization.

(Preparation of Amine Compound (19))

The amine compound (19) is commercially available or can be prepared by a method known to those skilled in the art. When the amine compound (19) is not commercially available, the compound can be prepared by, for example, converting a corresponding aldehyde group into a vinyl group and then aminohydroxylating the vinyl group (see, for example, Journal of the American Chemical Society, 2001, 123, 1862).

(Preparation of Compound (18))

In "Process 12-1", condensation reaction of an aldehyde compound (5) and a Horner-Emmons reagent (17) to synthesize a cinnamate ester compound is followed by deprotection of the ester group into a carboxylic acid. That is the Horner-Emmons reaction can be performed using an aldehyde compound (5) as a starting material by a method known to those skilled in the art (see, for example, Jikken Kagaku Koza (Experimental Methods of Chemistry), vol. 19, Yuki Gosei (Organic Synthesis) [I], edited by the Chemical Society of Japan, Maruzen Co., Ltd., June 1992, 57-85). Preferably, a desired cinnamate ester compound can be obtained by the reaction of an aldehyde compound (5) with 1.0 to 5.0 molar equivalents of a Horner-Emmons reagent (17) with respect to the aldehyde compound (5) in the presence of 1.0 to 5.0 molar equivalents of a base with respect to the aldehyde compound (5). The solvent to be used varies depending on the starting material and the used reagent, but is not specifically limited. Preferable examples of the solvent include polar solvents such as 1-methyl-2-pyrrolidone, N,N-dimethylformamide, and dimethylsulfoxide; ether solvents such as tetrahydrofuran, 1,4-dioxane, and 1,2-dimethoxyethane; nonpolar solvents such as benzene, toluene, and xylene; alcohol solvents such as ethanol and methanol; water; and solvent mixtures thereof. The base to be used varies depending on the starting material and the solvent, and preferable examples of which include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine, and diazabicyclononene; organic metals such as butyl lithium and lithium diisobutylamide; alkali metal hydrides such as sodium hydride; and alkali metal ammonium salts such as sodium amide. The reaction temperature should be a temperature which is sufficient for completing the reaction without promoting formation of undesired by-products and is preferably, for example, −78 to 150° C. This reaction completes in 1 to 24 hours under appropriate reaction conditions, and the progress of the reaction can be monitored by known chromatography technology. Undesired by-products can be removed by commonly used chromatography technology, extraction, and/or technology known to those skilled in the art, such as crystallization. In the hydrolysis reaction into a compound (18) using the cinnamate ester compound as a starting material, a deprotection method known to those skilled in the art can be used (see, for example, T. W. Green, "Protective Groups in Organic Synthesis", John Wiley & Sons, Inc., 1981, 154-186). For example, the compound (18) can be obtained with a high yield by, for example, treating a cinnamate ester compound in an alcohol solvent such as methanol or ethanol in the presence of 1.0 to 50.0 molar equivalents of an alkali metal hydroxide such as sodium hydroxide or potassium hydroxide with respect to the cinnamate ester compound.

(Preparation of Compound (17))

The compound (17) is commercially available. When the compound (17) is not commercially available, the compound (17) can be prepared by a method known to those skilled in the art. For example, a compound (17) can be prepared by alkylation of commercially available trialkyl phosphonoacetate (see, for example, Synthetic Communication, 1991, 22, 2391), or by the Arbuzov reaction of an alpha-halogeno-acetic acid derivative using alkyl phosphite (see, for example, Chemical Review, 1981, 81, 415), or by the Becker reaction using metal phosphonite (see, for example, Journal of the American Chemical Society, 1945, 67, 1180).

(Preparation of Compound (5))

The compound (5) is commercially available or can be prepared by a method known to those skilled in the art (see, Tetrahedron Letters, 2002, 43, 3793-3794; Synthetic Communications, 1984, 14, 857-864).

(General Manufacturing Method 2)

A typical "General Manufacturing Method 2" of a compound represented by Formula (I) according to the present invention will now be described.

[Formula 24]

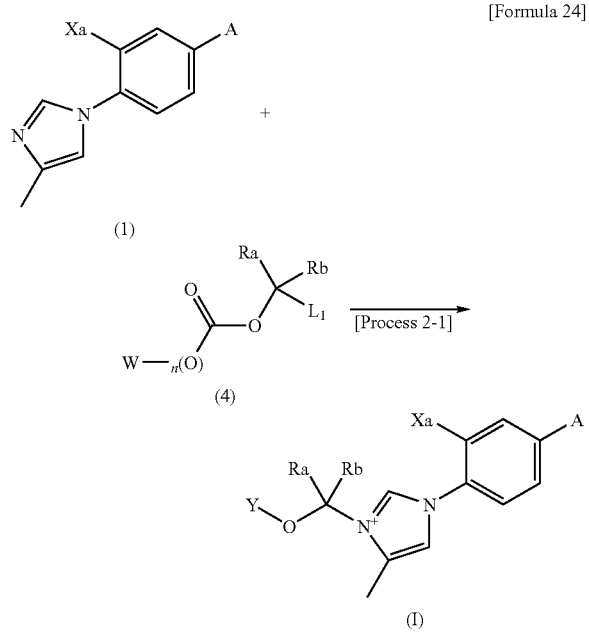

(wherein A, $X_a$, Y, $R_a$, $R_b$, n, and $L_1$ are the same as defined above; and W denotes a C1-6 alkyl, 6- to 14-membered aromatic hydrocarbon ring, 5- to 14-membered aromatic heterocyclic, 6- to 14-membered non-aromatic hydrocarbon ring, or 5- to 14-membered non-aromatic heterocyclic group which may be substituted with a substituent and may optionally have a protecting group).

The "General Manufacturing Method 2" is an exemplary method for manufacturing a compound of Formula (I) by condensing a compound (1) and a compound (4) according to "Process 2-1".

(Preparation of Compound of Formula (I))

The compound of Formula (I) can be prepared according to "Process 2-1". "Process 2-1" is the same as the aforementioned "Process 1-1". In addition, when W has a protecting group, the protecting group can be properly deprotected by a method known to those skilled in the art (see, for example, T. Greene, et al., Protective Groups in Organic Synthesis, John Wiley & Sons, Inc., NY, 1999) to obtain a desired compound of Formula (I). The compound obtained by the above-mentioned method can be introduced into a compound having a desired anion $M_a^-$ of Formula (I) by ion exchange according to need. The ion exchange can be preferably performed, for example, by using an anion-exchange resin or by treating the compound with an organic acid (for example, acetic acid, trifluoroacetic acid, benzenesulfonic acid, methanesulfonic acid, citric acid, or maleic acid) or an inorganic acid (preferably, for example, hydrochloric acid, hydrobromic acid, hydroiodic acid, sulfuric acid, nitric acid, or phosphoric acid).

(Preparation of Compound (4))

The compound (4) is commercially available or can be prepared by a method known to those skilled in the art (see, Synthesis, 1971, 11, 588-590; Synthetic Communications, 1994, 24, 767-772; JP-A-05-194517).

The compound represented by Formula (I) or its pharmacologically acceptable salt according to the present invention has excellent solubility. The present invention provides a therapeutic or preventive agent for neurodegenerative diseases caused by Aβ, particularly, for Alzheimer's disease and Down syndrome, as a prodrug of a cinnamide compound having activity inhibiting Aβ synthesis.

In the compound according to the present invention, the solubility of a parent cinnamide compound is improved and physiologically active parent compound is released enzymatically or nonenzymatically. That is, the compound of the invention functions as a prodrug.

The preventive or therapeutic agent for diseases caused by Aβ according to the present invention can be formulated by commonly used methods. Preferable examples of dosage forms include tablets, powders, subtle granules, granules, coated tablets, capsules, syrups, troches, inhalants, suppositories, injections, ointments, ophthalmic solutions, ophthalmic ointments, nasal drops, ear drops, cataplasms, and lotions. For formulation, commonly used additives such as an excipient, a binder, a disintegrator, a lubricant, a colorant, and a corrigent, and also, according to need, a stabilizer, an emulsifier, a sorbefacient, a surfactant, a pH adjuster, a preservative, and an antioxidant, may be used, and components generally used as ingredients for pharmaceuticals can be blended to formulate by a commonly used method. Examples of the components include animal and plant oils such as soybean oil, beef tallow, and synthetic glycerides; hydrocarbons such as liquid paraffin, squalane, and solid paraffin; ester oils such as octyldodecyl myristate and isopropyl myristate; higher alcohols such as cetostearyl alcohol and behenyl alcohol; silicone resins; silicone oils; surfactants such as polyoxyethylene fatty acid ester, sorbitan fatty acid ester, glycerine fatty acid ester, polyoxyethylene sorbitan fatty acid ester, polyoxyethylene hydrogenated castor oil, and polyoxyethylene polyoxypropylene block copolymer; water-soluble polymers such as hydroxyethyl cellulose, polyacrylate, carboxyvinyl polymers, polyethylene glycol, polyvinylpyrrolidone, and methylcellulose; lower alcohols such as ethanol and isopropanol; polyols such as glycerine, propylene glycol, dipropylene glycol, and sorbitol; sugars such as glucose and sucrose; inorganic powders such as silica, aluminium magnesium silicate, and aluminium silicate; and purified water. Examples of the excipient include lactose, corn starch, white sugar, glucose, mannitol, sorbitol, crystalline cellulose, and silicon dioxide. Examples of the binder include polyvinyl alcohol, polyvinyl ether, methylcellulose, ethylcellulose, gum Arabic, tragacanth, gelatin, shellac, hydroxypropyl methylcellulose, hydroxypropylcellulose, polyvinylpyrrolidone, polypropylene glycol/polyoxyethylene block polymer, and meglumine. Examples of the disintegrator include starch, agar, gelatin powders, crystalline cellulose, calcium carbonate, sodium hydrogencarbonate, calcium citrate, dextrin, pectin, and carboxymethylcellulose calcium. Examples of the lubricant include magnesium stearate, talc, polyethylene glycol, silica, and hydrogenated plant oil. Examples of the colorant are those approved as additives to pharmaceuticals. Examples of the corrigent include cocoa powder, menthol, aromatic powder, peppermint oil, borneol, and cinnamon powder.

Oral formulations of a compound or a salt or hydrate thereof according to the present invention are formed by adding additives such as an excipient and further, according to need, a binder, a disintegrator, a lubricant, a colorant, and a corrigent to the compound or the salt or hydrate thereof as an active ingredient and then formulating the mixture into powders, subtle granules, granules, tablets, coated tablets, capsules, and the like by commonly used methods. In the case of a tablet or granule, coating such as sugar coating may be optionally applied to them according to need. In the case of syrup or injection formulation, a pH adjuster, a solubilizer, a tonicity adjusting agent, and the like and further a solubilizing agent and a stabilizer are added to the formulation according to need and the syrup or injection formulation is formed in the usual manner. In the case of an external preparation, the formulation method is not particularly limited and the external preparation can be manufactured in the usual manner. Various base materials commonly used for pharmaceuticals, quasi drugs, or cosmetics can be used. Examples of the base materials include animal and plant oils, mineral oils, ester oils, waxes, higher alcohols, fatty acids, silicone oils, surfactants, phospholipids, alcohols, polyols, water-soluble polymers, clay minerals, and purified water. Further, a pH adjuster, an antioxidant, a chelating agent, a preservative/fungicide, a colorant, a flavoring, or the like may also be added, according to need. In addition, ingredients having differentiation-inducing effect, such as a blood flow increasing agent, a bactericide, an anti-inflammatory agent, a cell stimulant, a vitamin, an amino acid, a humectant, or a keratolytic agent may be blended, according to need. The administration amount of a therapeutic/preventive agent according to the present invention varies depending on the degree of symptom, age, sex, body weight, administration mode, type of the salt, concrete type of the disease and other factors. A typical amount per day for an adult is about 30 μg to 10 g, preferably 100 μg to 5 g, more preferably 1 mg to 1 g for oral administration, and about 30 μg to 1 g, preferably 100 μg to 500 mg, more preferably 100 μg to 30 mg for injection administration, as a compound represented by Formula (I) or its pharmacologically acceptable salt which is administered in a single or multiple doses.

The present invention will now be described in further detail with reference to Examples and Test Examples. These are meant to illustrate the preventive or therapeutic agents of the present invention for diseases caused by Aβ, but in no way to limit the agents to the particular Examples below. Many variations of the present invention are possible for those skilled in the art according to not only the Examples and Test Examples but also the appended claims for performing the invention to its full. Such variations are within the scope of the claims of the invention.

The following symbols are used in the Examples below.

THF: tetrahydrofuran

DMF: N,N'-dimethylformamide

DME: ethylene glycol dimethylether

IPEA: diisopropylethylamine

EDC: 1-ethyl-3-(3-dimethylaminopropyl)carbodiimide hydrochloride

HOBT: 1-hydroxybenzotriazol

LAH: lithium aluminium hydride

BOPCl: N,N-bis(2-oxo-3-oxazolidinyl)phosphinic chloride

Grubbs catalyst second generation: tricyclohexylphosphine [1,3-bis(2,4,6-trimethylphenyl)-4,5-dihydroimidazol-2-ylidene][benzylidene]-ruthenium(IV) dichloride TMED: N,N,N',N'-tetramethylethylenediamine TMSI: trimethylsilyl iodide t: tertiary s: secondary DMSO: dimethylsulfoxide AIBN: 2,2-azobisisobutyronitrile NMP: 1-methyl-2-pyrrolidone

EXAMPLES

Example 1

Synthesis of 3-{4-{1-[(S)-1-(4-fluorophenyl)ethyl]-2-oxopiperidin-(3E)-ylidenemethyl}-2-methoxyphenyl}-5-methyl-1-(phosphonooxymethyl)-3H-imidazol-1-ium trifluoroacetate

[Formula 25]

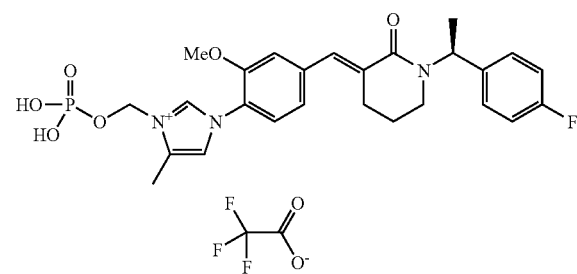

In nitrogen atmosphere, (E)-1-[(1S)-1-(4-fluorophenyl)ethyl]-3-[3-methoxy-4-(4-methyl-1H-imidazol-1-yl)benzylidene]piperidin-2-one (CAS Registry No. 870843-42-8, 200 mg) was added to an acetone solution (4 mL) of chloromethyl di-tert-butylphosphate (CAS Registry No. 229625-50-7, 185 mg), sodium iodide (214 mg), and diisopropylethylamine (21 μL). The resulting reaction solution was stirred at 60° C. for 1 hr and then concentrated under reduced pressure. To the residue, and methylene chloride (0.2 mL) and trifluoroacetic acid (0.3 mL) were added. The resulting solution was stirred at room temperature for 2.5 hr and then concentrated. A 25% acetonitrile aqueous solution of the obtained residue was subjected to reversed phase C18 silica gel column chromatography (developing solvent: 30% acetonitrile aqueous solution containing 0.1% trifluoroacetic acid). The objective fraction was concentrated and then lyophilized to give 247 mg of the title compound. The physical property values of this compound were as follows:

$^1$H-NMR (CD$_3$OD) δ (ppm): 1.58 (d, J=7.2 Hz, 3H), 1.63-1.90 (m, 2H), 2.53 (s, 3H), 2.80-2.90 (m, 2H), 2.95-3.05 (m, 1H), 3.35-3.42 (m, 1H), 3.92 (s, 3H), 5.94 (d, J=12.8 Hz, 2H), 6.08 (q, J=7.2 Hz, 1H), 7.10 (t, J=8.8 Hz, 2H), 7.22 (d, J=8.0 Hz, 1H), 7.32 (s, 1H), 7.38 (dd, J=8.8, 5.2 Hz, 2H), 7.58 (d, J=8.0 Hz, 1H), 7.68 (d, J=1.6 Hz, 1H), 7.80 (s, 1H), 9.42 (d, J=1.6 Hz, 1H).

Example 2

Synthesis of 1-{4-{(E)-1-{[(S)-1-(4-fluorophenyl)ethyl]-2-oxopiperidin-3-ylidene}methyl}-2-methoxyphenyl}-4-methyl-1H-imidazol-3-iomethyl monohydrogenphosphate

[Formula 26]

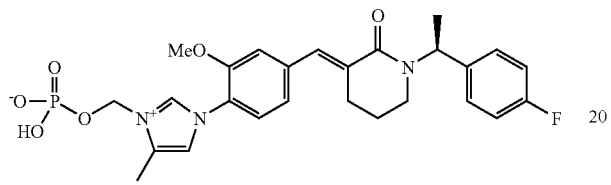

An aqueous solution (4 mL) of 3-{4-{1-[(S)-1-(4-fluorophenyl)ethyl]-2-oxopiperidin-(3E)-ylidenemethyl}-2-methoxyphenyl}-5-methyl-1-(phosphonooxymethyl)-3H-imidazol-1-ium trifluoroacetate (150 mg) obtained in Example 1 was subjected to reversed phase C18 silica gel column chromatography (developing solvent: 100% water to 35% acetonitrile aqueous solution). The objective fraction was concentrated and then lyophilized to give 112 mg of the title compound. The physical property values of this compound were as follows:

$^1$H-NMR (CD$_3$OD) δ (ppm): 1.59 (d, J=7.2 Hz, 3H), 1.63-1.90 (m, 2H), 2.53 (s, 3H), 2.78-2.85 (m, 2H), 2.95-3.04 (m, 1H), 3.35-3.42 (m, 1H), 3.96 (s, 3H), 5.88 (d, J=12.8 Hz, 2H), 6.09 (q, J=7.2 Hz, 1H), 7.10 (t, J=8.8 Hz, 2H), 7.21 (dd, J=8.0, 1.2 Hz, 1H), 7.31 (d, J=1.2 Hz, 1H), 7.38 (dd, J=8.8, 5.2 Hz, 2H), 7.59 (d, J=8.0 Hz, 1H), 7.65 (d, J=1.6 Hz, 1H), 7.80 (s, 1H), 9.38 (d, J=1.6 Hz, 1H).

Example 3

Synthesis of 1-acetoxymethyl-3-[4-{1-[(S)-1-(4-fluorophenyl)ethyl]-2-oxopiperidin-(3E)-ylidenemethyl]-2-methoxyphenyl}-5-methyl-3H-imidazol-1-ium iodide

[Formula 27]

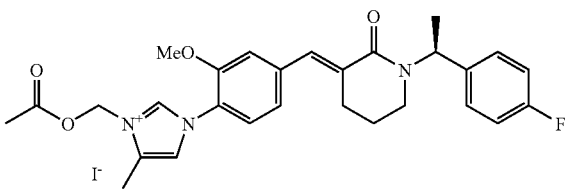

Sodium iodide (54 mg) and IPEA (0.05 mL) were added to a DME solution (2 mL) of (E)-1-[(1S)-1-(4-fluorophenyl)ethyl]-3-[3-methoxy-4-(4-methyl-1H-imidazol-1-yl)benzylidene]piperidin-2-one (CAS Registry No. 870843-42-8, 100 mg) and chloromethyl acetate (0.03 mL), and the resulting reaction solution was stirred at 80° C. for 1 hr. The reaction solution was allowed to cool to room temperature, and the precipitated solid was collected by filtration. The obtained solid was washed with diethylether and dried in air to give 70 mg of the title compound. The physical property values of this compound were as follows:

ESI-MS; m/z 492 [M$^+$]. $^1$H-NMR (CD$_3$OD) δ (ppm): 1.59 (d, J=7.2 Hz, 3H), 1.63-1.80 (m, 2H), 2.17 (s, 3H), 2.52 (s, 3H), 2.79-2.86 (m, 2H), 2.94-3.03 (m, 1H), 3.20-3.41 (m, 1H), 3.96 (s, 3H), 6.09 (q, J=7.2 Hz, 1H), 6.19 (s, 2H), 7.10 (t, J=8.8 Hz, 2H), 7.22 (brd, J=8.0 Hz, 1H), 7.32 (brs, 1H), 7.38 (dd, J=8.8, 5.2 Hz, 2H), 7.57 (d, J=8.0 Hz, 1H), 7.70 (s, 1H), 7.80 (brs, 1H).

Example 4

Synthesis of 3-{4-{1-[(1R,2R)-2-hydroxy-1-(3,4,5-trifluorophenyl)propyl]-2-oxopiperidin-(3E)-ylidenemethyl}-2-methoxyphenyl}-5-methyl-1-(phosphonooxymethyl)-3H-imidazol-1-ium trifluoroacetate

[Formula 28]

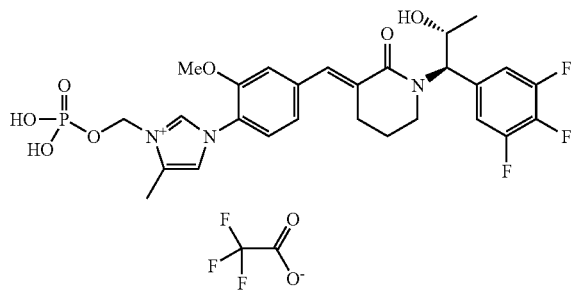

Synthesis of 1,2,3-trifluoro-5-((E)-propenyl)benzene

In nitrogen atmosphere, tetrakistriphenyl-phosphine palladium(0) (4.66 g) and cesium fluoride (21.4 g) were added to a solution mixture of dioxane (95 mL) and water (5 mL) of 1-bromo-3,4,5-trifluorobenzene (8.5 g), trans-1-propen-1-ylboronic acid (4.1 g). The resulting reaction solution was stirred at 80° C. for 5 hr and cooled to room temperature. To the reaction solution, hexane and water were added. The precipitated insoluble matter was removed by filtration, and the organic layer was separated. The obtained organic layer was washed with water, and the insoluble matter was removed by filtration again. The organic layer was separated. The obtained organic layer was washed with water and then with saturated saline, dried over anhydrous magnesium sulfate, and concentrated under reduced pressure. The residue was purified by silica gel column chromatography (eluting solvent: hexane) to give 5.83 g of the title compound. The physical property values of this compound were as follows:

$^1$H-NMR (CDCl$_3$) δ (ppm): 1.88 (d, J=6.0 Hz, 3H), 6.18 (qd, J=6.0, 16.0 Hz, 1H), 6.24 (d, J=16.0 Hz, 1H), 6.85-6.96 (m, 2H).

Synthesis of (1S,2S)-1-(3,4,5-trifluorophenyl)propane-1,2-diol 1,2,3-Trifluoro-5-((E)-propenyl)benzene (5.83 g) was added to a solution mixture of tert-butanol (170 mL) and water (170 mL) of AD-Mix-α (47.5 g) and methanesulfonamide (3.22 g) under ice-cooling. This reaction solution was stirred at 5° C. overnight. Then, sodium sulfite (51 g) was added to the reaction solution, and the resulting mixture was stirred at room temperature for 1 hr. The reaction solution was extracted with methylene chloride three times. All the organic layers were combined and washed with a 2 N sodium hydroxide aqueous solution. The sodium hydroxide layer was re-extracted with methylene chloride. All the organic layers were combined, dried over anhydrous magnesium sulfate, and concentrated under reduced pressure. The residue was purified by silica gel column chromatography (hexane:ethyl acetate=9:1 to 1:1) to give 5.54 g of the title compound. The physical property values of this compound were as follows:

$^1$H-NMR (CDCl$_3$) δ (ppm): 1.12 (d, J=6.4 Hz, 3H), 2.20 (brs, 1H), 2.79 (brs, 1H), 3.78 (qd, J=6.4, 6.4 Hz, 1H), 4.34 (d, J=6.4 Hz, 1H), 6.96-7.05 (m, 2H).

Synthesis of (1R,2S)-1-azido-1-(3,4,5-trifluorophenyl)propan-2-ol

In nitrogen atmosphere, a sodium hydroxide pellet (110 mg) was added to a dimethyl carbonate solution (15 mL) of (1S,2S)-1-(3,4,5-trifluorophenyl)propane-1,2-diol (5.54 g). This reaction solution was stirred at 70° C. for 45 min. Then, the external temperature of the reaction solution was increased to 100° C. and dimethyl carbonate in the solution was removed by blowing nitrogen. Further, dimethyl carbonate (5 mL) was added to the residue, and then the dimethyl carbonate was removed by blowing nitrogen. Then, THF was added to the residue, and the insoluble matter was removed by Celite filtration. The filtrate was concentrated under reduced pressure to give 6.13 g of a carbonated substance.

In nitrogen atmosphere, water (0.5 mL) and sodium azide (1.92 g) were added to a DMF solution (20 mL) of the given carbonated substance. This reaction solution was stirred at 110° C. overnight. The reaction solution was cooled to room temperature, and diethylether was added thereto. The organic layer was separated, washed with water (three times) and then with saturated saline, dried over anhydrous magnesium sulfate, and concentrated under reduced pressure. The residue was purified by silica gel column chromatography (hexane:ethyl acetate=19:1 to 9:1) to give 5.16 g of the title compound. The physical property values of this compound were as follows:

$^1$H-NMR (CDCl$_3$) δ (ppm): 1.14 (d, J=6.4 Hz, 3H), 1.79 (brs, 1H), 3.97 (qd, J=6.4, 4.8 Hz, 1H), 4.42 (d, J=4.8 Hz, 1H), 6.96-7.05 (m, 2H).

Synthesis of [(1R,2S)-2-hydroxy-1-(3,4,5-trifluorophenyl)propyl]carbamic acid tert-butyl ester In nitrogen atmosphere, triphenylphosphine (5.85 g) was added to a THF solution (75 mL) of (1R,2S)-1-azido-1-(3,4,5-trifluorophenyl)propan-2-ol (5.16 g). This reaction solution was stirred at room temperature for 10 min, then water (5 mL) was added the reaction solution. This mixture was stirred at 60° C. for 3.5 hr. The reaction solution was cooled to room temperature, and then di-tert-butylcarbonate (5.35 g) was added to the reaction solution. The resulting reaction solution was stirred at room temperature for 45 min and then concentrated under reduced pressure. The obtained residue was purified by silica gel column chromatography (toluene:ethyl acetate=9:1) to give 5.88 g of the title compound. The physical property values of this compound were as follows:

$^1$H-NMR (CDCl$_3$) δ (ppm): 1.07 (d, J=6.4 Hz, 3H), 1.41 (s, 9H), 4.10 (brs, 1H), 4.47 (brs, 1H), 5.44 (brs, 1H), 6.92-7.01 (m, 2H).

Synthesis of 4-nitrobenzoic acid (1R,2R)-2-tert-butoxycarbonylamino-1-methyl-2-(3,4,5-trifluorophenyl)ethyl ester In nitrogen atmosphere, diisopropyl azodicarboxylate (6 mL) was dropwise added to a THF solution (100 mL) of [(1R,2S)-2-hydroxy-1-(3,4,5-trifluorophenyl)propyl]carbamic acid tert-butyl ester (5.88 g), 4-nitrobenzoic acid (4.84 g), and triphenylphosphine (7.59 g) under ice-cooling. This reaction solution was stirred at room temperature for 2 hr and concentrated under reduced pressure. The obtained residue was purified by silica gel column chromatography (toluene:ethyl acetate=97:3) to give a powder. The obtained powder was triturated with toluene-hexane to give 6.69 g of the title compound. The physical property values of this compound were as follows:

$^1$H-NMR (CDCl$_3$) δ (ppm): 1.37 (s, 9H), 1.38 (d, J=6.4 Hz, 3H), 4.85 (brs, 1H), 5.16 (d, J=9.2 Hz, 1H), 5.41 (qd, J=6.4, 6.0 Hz, 1H), 6.92-7.01 (m, 2H), 8.16 (d, J=8.8 Hz, 2H), 8.29 (d, J=8.8 Hz, 2H).

Synthesis of [(1R,2R)-2-hydroxy-1-(3,4,5-trifluorophenyl)propyl]carbamic acid tert-butyl ester A potassium carbonate powder (6.43 g) was added to a solution mixture of methanol (90 mL) and THF (10 mL) of 4-nitrobenzoic acid (1R,2R)-2-tert-butoxycarbonylamino-1-methyl-2-(3,4,5-trifluorophenyl)ethyl ester (7.03 g). This reaction solution was stirred at room temperature for 1 hr. Then, ethyl acetate and water were added to the reaction solution, and the organic layer was separated. The obtained organic layer was washed with saturated saline twice, dried over anhydrous magnesium sulfate, and concentrated under reduced pressure. To the obtained residue, diethylether was added. The insoluble matter was removed by filtration and the filtrate was concentrated. The obtained residue was purified by silica gel column chromatography (toluene ethyl acetate=6:1) to give 4.49 g of the title compound. The physical property values of this compound were as follows:

$^1$H-NMR (CDCl$_3$) δ (ppm): 1.28 (d, J=6.4 Hz, 3H), 1.44 (s, 9H), 4.01 (brs, 1H), 4.48 (brs, 1H), 5.35 (brs, 1H), 6.90-7.00 (m, 2H).

Synthesis of [(1R,2R)-1-amino-1-(3,4,5-trifluorophenyl)propan-2-ol hydrochloride A 4 N hydrochloric acid ethyl acetate solution (20 mL) was added to an ethyl acetate solution (50 mL) of [(1R,2R)-2-hydroxy-1-(3,4,5-trifluorophenyl)propyl]carbamic acid tert-butyl ester (4.49 g). This reaction solution was stirred at room temperature for 5 hr. The reaction solution was concentrated under reduced pressure to give 3.5 g of the title compound. The physical property values of this compound were as follows:

ESI-MS; m/z 206 [M$^+$+H].

Synthesis of 1-[(1R,2R)-2-hydroxy-1-(3,4,5-trifluorophenyl)propyl]-3-{1-[3-methoxy-4-(4-methyl-1H-imidazol-1-yl)phenyl]-(E)-methylidene}piperidin-2-one IPEA (4 mL), HOBT (1.11 g), and EDC (1.57 g) were added to a DMF solution (40 mL) of (E)-5-chloro-2-[3-methoxy-4-(4-methyl-1H-imidazol-1-yl)benzylidene]valeric acid trifluoroacetate (CAS Registry No. 870850-40-1, 3.69 g) and (1R,2R)-1-amino-1-(3,4,5-trifluorophenyl)propan-2-ol hydrochloride (1.98 g). This reaction solution was stirred at room temperature for 3.5 hr, and ethyl acetate and a saturated sodium hydrogencarbonate aqueous solution were added thereto. The organic layer was separated, dried over magnesium sulfate, and concentrated under reduced pressure. The obtained solid was suspended in diisopropyl ether and collected by filtration to give 3.16 g of a condensed substance. To a DMF solution (50 mL) of this condensed substance (3.16 g), sodium hydride (containing 40% mineral oil, 278 mg) was added at 0° C. The resulting reaction solution was stirred at room temperature for 15 min, and ethyl acetate and water were added thereto. The organic layer was separated, dried over magnesium sulfate, and concentrated under reduced pressure. The residue was purified by silica gel column chromatography (carrier: Chromatorex NH, eluting solvent: heptane to ethyl acetate) to give 2.3 g of the title compound. The physical property values of this compound were as follows:

$^1$H-NMR (CDCl$_3$) δ (ppm): 1.31 (d, J=6.0 Hz, 3H), 1.76-1.96 (m, 2H), 2.31 (s, 3H), 2.78-2.85 (m, 2H), 3.23-3.30 (m, 1H), 3.49-3.57 (m, 1H), 3.86 (s, 3H), 4.43-4.51 (m, 1H), 5.24 (d, J=7.6 Hz, 1H), 6.93 (brs, 1H), 7.03 (brs, 1H), 7.05 (t, J=10.0 Hz, 2H), 7.08 (brd, J=7.2 Hz, 1H), 7.25 (d, J=7.2 Hz, 1H), 7.73 (s, 1H), 7.85 (s, 1H).

Synthesis of 3-{4-{1-[(1R,2R)-2-hydroxy-1-(3,4,5-trifluorophenyl)propyl]-2-oxopiperidin-(3E)-ylidenemethyl}-2-methoxyphenyl}-5-methyl-1-(phosphonooxymethyl)-3H-imidazol-1-ium trifluoroacetate A DME solution (3 mL) of 1-[(1R,2R)-2-hydroxy-1-(3,4,5-trifluorophenyl)propyl]-3-{1-[3-methoxy-4-(4-methyl-1H-imidazol-1-yl)phenyl]-(E)-methylidene}piperidin-2-one (62 mg), chloromethyl di-tert-butylphosphate (CAS Registry No. 229625-50-7, 50 mg), sodium iodide (19 mg), and IPEA (0.05 mL) were stirred at 80° C. for 3 hr. This reaction solution was allowed to cool to room temperature and concentrated under reduced pressure. To a chloroform solution (1 mL) of the obtained residue, TFA (1 mL) was added. The resulting mixture was stirred at room temperature for 30 min and concentrated under reduced pressure. The residue was purified by reversed phase C18 silica gel column chromatography (developing solvent: water-acetonitrile system containing 0.1% trifluoroacetic acid) to give 31 mg of the title compound. The physical property values of this compound were as follows:

ESI-MS; m/z 596 [M$^+$]. $^1$H-NMR (CD$_3$OD) δ (ppm): 1.27 (d, J=6.4 Hz, 3H), 1.68-1.80 (m, 1H), 1.90-2.01 (m, 1H), 2.53 (s, 3H), 2.76-2.85 (m, 2H), 3.25-3.39 (m, 1H), 3.62-3.72 (m, 1H), 3.94 (s, 3H), 4.35-4.45 (m, 1H), 5.53 (d, J=7.6 Hz, 1H), 5.87 (d, J=9.6 Hz, 2H), 7.10-7.20 (m, 4H), 7.40 (s, 1H), 7.51 (d, J=8.4 Hz, 1H), 7.79 (s, 1H), 9.37 (s, 1H).

Example 5

Synthesis of 3-[2-fluoro-4-[(S)-4-[(1R,2R)-2-hydroxy-1-(3,4,5-trifluorophenyl)propyl]-6-methyl-3-oxomorpholin-(2Z)-ylidenemethyl]phenyl]-5-methyl-1-phosphonooxymethyl-3H-imidazol-1-ium trifluoroacetate

[Formula 29]

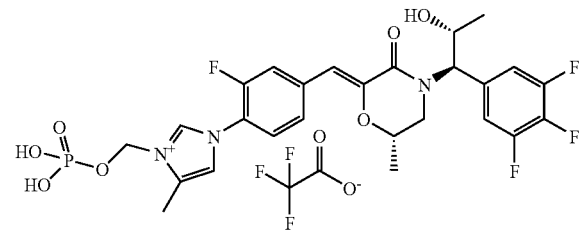

Synthesis of 3-fluoro-4-(4-methyl-1H-imidazol-1-yl)benzaldehyde

4-Methylimidazole (46.4 g) and potassium carbonate (78.0 g) were added to a DMF solution (533 mL) of 3,4-difluorobenzaldehyde (40.0 g) at room temperature. This reaction solution was stirred at 90° C. for 6 hr and then was allowed to cool to room temperature. To the reaction solution, ethyl acetate and water were added. The organic layer was separated, washed with saturated saline, dried over magnesium sulfate, and concentrated under reduced pressure. The residue was purified by silica gel column chromatography (eluting solvent: heptane-ethyl acetate system) and further solidified with tert-butylmethylether to give 10.1 g of the title compound. The physical property values of this compound were as follows:

$^1$H-NMR (CDCl$_3$) δ (ppm): 2.33 (d, J=0.8 Hz, 3H), 7.07 (brs, 1H), 7.57 (dd, J=7.2, 7.2 Hz, 1H), 7.76-7.82 (m, 2H), 7.87 (brs, 1H), 10.01 (d, J=1.6 Hz, 1H).

Synthesis of [(1R,2R)-2-(tert-butyldiphenylsilanyloxy)-1-(3,4,5-trifluorophenyl)propyl]carbamic acid tert-butyl ester In nitrogen atmosphere, tert-butyldiphenylsilyl chloride (2.0 mL) was added dividedly four times to a DMF solution (3 mL) of [(1R,2R)-2-hydroxy-1-(3,4,5-trifluorophenyl)propyl]-carbamic acid tert-butyl ester (610 mg) and imidazole (817 mg). This reaction solution was stirred at room temperature for 3 hr. To the reaction solution, ethyl acetate and water were added. The organic layer was separated, washed with 1 N hydrochloric acid, water, a saturated sodium hydrogencarbonate aqueous solution, and saturated saline in this order. The organic layer was dried over anhydrous magnesium sulfate and concentrated under reduced pressure. The residue was purified by silica gel column chromatography (eluting solvent: hexane:diethylether=49:1 to 19:1) to give 684 mg of the title compound. The physical property values of this compound were as follows:

$^1$H-NMR (CDCl$_3$) δ (ppm): 0.95 (s, 9H) 1.13 (d, J=6.4 Hz, 3H), 1.47 (s, 9H), 4.02 (brs, 1H), 4.46 (brs, 1H), 5.34 (brs, 1H), 6.69-6.80 (m, 2H), 7.28-7.46 (m, 8H), 7.55 (d, J=8.4 Hz, 2H).

Synthesis of (1R,2R)-2-tert-butyldiphenylsilanyloxy-1-(3,4,5-trifluorophenyl)propylamine Trifluoroacetic acid (0.5 mL) was added to a methylene chloride solution (2 mL) of [(1R,2R)-2-tert-butyldiphenylsilanyloxy-1-(3,4,5-trifluorophenyl)propyl]carbamic acid tert-butyl ester (370 mg). This reaction solution was stirred at room temperature for 11 hr. To this reaction solution, a saturated sodium hydrogencarbonate aqueous solution and ethyl acetate were added. The organic layer was separated, washed with a saturated sodium hydrogencarbonate aqueous solution and then with saturated saline. Then, the organic layer was concentrated under reduced pressure to give 275 mg of the title compound. The physical property values of this compound were as follows:

$^1$H-NMR (CDCl$_3$) δ (ppm): 0.93 (d, J=6.4 Hz, 3H), 1.02 (s, 9H), 3.81 (d, J=4.8 Hz, 1H), 3.91 (dq, J=4.8, 6.0 Hz, 1H), 6.88-6.97 (m, 2H), 7.32-7.46 (m, 6H), 7.57 (d, J=8.0 Hz, 2H), 7.55 (d, J=8.0 Hz, 2H).

Synthesis of (S)-1-[(1R,2R)-2-tert-butyldiphenylsilanyloxy-1-(3,4,5-trifluorophenyl)propylamino]propan-2-ol A diethyl ether solution (1 mL) of (S)-(−)-propylene oxide (0.1 mL) and (1R,2R)-2-tert-butyldiphenylsilanyloxy-1-(3,4,5-trifluorophenyl)propylamine (212 mg) was added to a diethyl ether suspension (1 mL) of lithium perchlorate (750 mg). This reaction solution was stirred in nitrogen atmosphere at room temperature overnight. To this reaction solution, methylene chloride and iced-water were added. The organic layer was separated, and the water was re-extracted with methylene chloride. The organic layers were combined, dried over anhydrous magnesium sulfate, and concentrated under reduced pressure. The obtained residue was purified by silica gel column chromatography (eluting solvent; ethyl acetate:heptane=9:1 to 4:1) to give 172 mg of the title compound. The physical property values of this compound were as follows:

$^1$H-NMR (CDCl$_3$) δ (ppm): 0.83 (d, J=6.0 Hz, 3H), 1.06 (s, 9H), 1.08 (m, 3H), 2.20-2.50 (m, 3H), 3.47 (brs, 1H), 3.59 (brs, 1H), 3.86 (brs, 1H), 6.78-6.95 (m, 2H), 7.36-7.48 (m, 6H), 7.67 (d, J=6.8 Hz, 4H).

Synthesis of (S)-4-[(1R,2R)-2-tert-butyldiphenylsilanyloxy-1-(3,4,5-trifluorophenyl)propyl]-6-methylmorpholin-2,3-dione In nitrogen atmosphere, oxalyl chloride (45 μL) was dropwise added to a methylene chloride solution (2 mL) of (S)-1-[(1R,2R)-2-tert-butyldiphenylsilanyloxy-1-(3,4,5-trifluorophenyl)propylamino]propan-2-ol (171 mg), TEA (0.17 mL), and 4-(N,N-dimethylamino)pyridine (8 mg) under ice-cooling. This reaction solution was stirred under ice-cooling for 2 hr. To the reaction solution, iced-water and ethyl acetate were added. The organic layer was separated, washed with water, 1 N hydrochloric acid, water, a saturated sodium hydrogencarbonate aqueous solution, and saturated saline in this order. Then, the organic layer was dried over anhydrous magnesium sulfate and concentrated under reduced pressure. The residue was purified by silica gel column chromatography (eluting solvent; heptane:ethyl acetate=9:1 to 3:1) to give 96 mg of the title compound. The physical property values of this compound were as follows:

$^1$H-NMR (CDCl$_3$) δ (ppm): 1.02 (s, 9H), 1.19 (d, J=6.0 Hz, 3H), 1.28 (d, J=6.4 Hz, 3H), 3.20 (dd, J=5.6, 13.2 Hz, H), 3.68 (dd, J=2.4, 13.2 Hz, 1H), 4.42 (dq, J=5.6, 6.0 Hz, 1H) 4.62 (ddq, J=2.4, 5.6, 6.4 Hz, 1H), 5.51 (d, J=5.6 Hz, 1H), 6.82-6.94 (m, 2H), 7.40-7.54 (m, 6H), 7.62 (d, J=8.0 Hz, 2H), 7.67 (d, J=8.0 Hz, 2H).

Synthesis of (S)-4-[(1R,2R)-2-tert-butyldiphenylsilanyloxy-1-(3,4,5-trifluorophenyl)propyl]-2-hydroxy-6-methylmorpholin-3-one In nitrogen atmosphere, a THF solution (0.25 mL) of 1.06 M lithium tri-sec-butyl borohydride was dropwise added to a THF solution (3 mL) of (S)-4-[(1R,2R)-2-tert-butyldiphenylsilanyloxy-1-(3,4,5-trifluorophenyl)propyl]-6-methylmorpholin-2,3-dione (95 mg) at −20° C. This reaction solution was stirred at −20° C. for 30 min. To this reaction solution, a 5 N sodium hydroxide aqueous solution (0.03 mL) and a 30% hydrogen peroxide aqueous solution (0.07 mL) were added. This reaction solution was stirred under ice-cooling for 1 hr. A sodium hydrogensulfite powder (20 mg) was added to the reaction solution, and this reaction solution was stirred at room temperature for 30 min. To this reaction solution, saturated saline and ethyl acetate were added. The organic layer was separated, washed with saturated saline, dried over anhydrous magnesium sulfate, and concentrated under reduced pressure. The obtained residue was purified by silica gel column chromatography (eluting solvent; heptane ethyl acetate=1:1) to give 93 mg of the title compound. The physical property values of this compound were as follows:

$^1$H-NMR (CDCl$_3$) δ (ppm): 1.01 (s, 9H), 1.11 (d, J=6.0 Hz, 3H), 1.19 (d, J=6.4 Hz, 3H), 2.88 and 2.99 (dd, J=12.0, 12.0 Hz, 1H), 3.12 and 3.48 (dd, J=2.4, 12.0 Hz, 1H), 3.16 and 3.91 (d, J=2.8 Hz, 1H), 4.35-4.55 (m, 2H), 5.11 and 5.30 (d, J=3.6 Hz, 1H), 5.40 and 5.49 (d, J=6.8 Hz, 1H), 6.79-6.94 (m, 2H), 7.38-7.54 (m, 6H), 7.65 (d, J=8.0 Hz, 2H), 7.69 (d, J=8.0 Hz, 2H).

Synthesis of (Z)-(S)-2-[1-[3-fluoro-4-(4-methyl-1H-imidazol-1-yl)phenyl]methylidene]-4-[(1R,2R)-2-hydroxy-1-(3,4,5-trifluorophenyl)propyl]-6-methylmorpholin-3-one In nitrogen atmosphere, an acetonitrile solution (70 mL) of (S)-4-[(1R,2R)-2-tert-butyldiphenylsilanyloxy-1-(3,4,5-trifluorophenyl)propyl]-2-hydroxy-6-methylmorpholin-3-one (2.16 g) and triphenylphosphonium bromide (1.61 g) was heated under reflux for 1 hr. The reaction solution was concentrated under reduced pressure. To an ethanol solution (80 mL) of the obtained residue, 3-fluoro-4-(4-methyl-1H-imidazol-1-yl)benzaldehyde (869 mg) and TEA (2.68 mL) were added. This reaction solution was stirred in nitrogen atmosphere at room temperature for 10 hr and concentrated under reduced pressure. A solution mixture of trifluoroacetic acid (30 mL) and methylene chloride (30 mL) of the obtained residue was stirred at room temperature for 13 hr. The reaction solution was poured into a saturated sodium hydrogencarbonate aqueous solution. The resulting mixture was extracted with ethyl acetate. The organic layer was washed with a saturated sodium hydrogencarbonate aqueous solution and then with saturated saline, and concentrated under reduced pressure. The obtained residue was purified by silica gel column chromatography (carrier: Chromatorex NH, eluting solvent; heptane:ethyl acetate=1:1 to 0:1) and further solidified with heptane-ethyl acetate to give 1.32 g of the title compound. The physical property values of this compound were as follows:

$^1$H-NMR (CDCl$_3$) δ (ppm): 1.33 (d, J=6.4 Hz, 3H), 1.42 (d, J=6.0 Hz, 3H), 2.30 (s, 3H), 3.19 (dd, J=12.4, 9.2 Hz, 1H), 3.63 (dd, J=12.4, 2.0 Hz, 1H), 4.44-4.49 (m, 2H), 5.36 (d, J=6.8 Hz, 1H), 6.80 (s, 1H), 6.97 (s, 1H), 7.09 (dd, J=8.4, 6.4 Hz, 2H), 7.29 (t, J=8.4 Hz, 1H), 7.44 (dd, J=8.4, 2.0 Hz, 1H), 7.71 (dd, J=12.8, 1.2 Hz, 1H), 7.74 (s, 1H).

Synthesis of 3-[2-fluoro-4-[(S)-4-[(1R,2R)-2-hydroxy-1-(3,4,5-trifluorophenyl)propyl]-6-methyl-3-oxomorpholin-(2Z)-ylidenemethyl]phenyl]-5-methyl-1-phosphonooxymethyl-3H-imidazol-1-ium trifluoroacetate An acetone solution (0.5 mL) of (Z)-(S)-4-[(1R,2R)-2-hydroxy-1-(3,4,5-trifluorophenyl)propyl]-2-[1-[3-methoxy-4-(4-methyl-1H-imidazol-1-yl)phenyl]methylidene]-6-methylmorpholin-3-one (25 mg), chloromethyl di-tert-butylphosphate (CAS Register No. 229625-50-7, 20 mg), sodium iodide (23 mg), and IPEA (0.01 mL) was stirred at 60° C. for 2 hr. The reaction solution was allowed to cool to room temperature, and the insoluble matter was removed by filtration. The filtrate was concentrated under reduced pressure. To the obtained residue, a solvent mixture of methylene chloride and TFA (1:1, 2 mL) was added. The reaction solution was stirred at room temperature for 1 hr and concentrated under reduced pressure. The residue was purified by reversed phase C18 silica gel column chromatography (developing solvent: 50% acetonitrile aqueous solution containing 0.1% trifluoroacetic acid) to give 14 mg of the title compound. The physical property values of this compound were as follows:

ESI-MS; m/z 600 [M$^+$]. $^1$H-NMR (CD$_3$OD) δ (ppm): 1.19 (d, J=5.2 Hz, 3H), 1.39 (d, J=6.4 Hz, 3H), 2.54 (s, 3H), 3.20-3.30 (m, 1H), 3.89 (brd, J=12.0 Hz, 1H), 4.43-4.61 (m, 2H), 5.39 (d, J=8.0 Hz, 1H), 5.96 (brd, J=12.0 Hz, 2H), 6.75 (s, 1H), 7.22-7.34 (m, 2H), 7.58-7.70 (m, 2H), 7.77 (s, 1H), 7.89 (d, J=12.8 Hz, 1H), 9.53 (s, 1H).

Example 6

Synthesis of 3-{2-methoxy-4-[(3S,8aS)-5-oxo-3-(3,4,5-trifluorophenyl)hexahydroindolizin-(6E)-ylidenemethyl]phenyl}-5-methyl-1-phosphonooxymethyl-3H-imidazol-1-ium trifluoroacetate

[Formula 30]

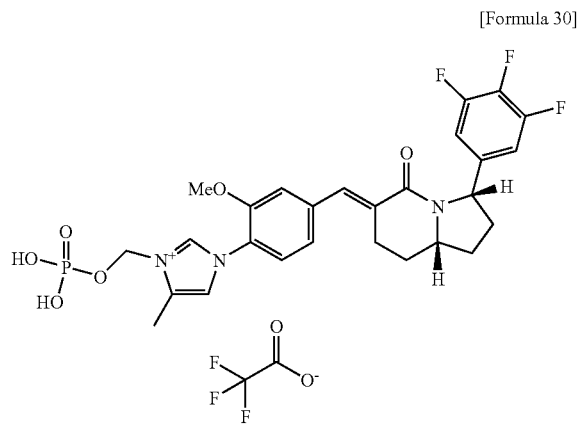

Synthesis of (2R,5S)-5-(3,4,5-trifluorophenyl)pyrrolidine-2-carboxylic acid ethyl ester 3,4,5-Trifluorophenyl magnesium bromide (0.35 M diethylether solution, 55 mL) was dropwise added to a tetrahydrofuran solution (100 mL) of (R)-5-oxo-pyrrolidine-1,2-dicarboxylic acid 1-tert-butyl ester 2-ethyl ester (CAS Register No. 128811-48-3, 4.1 g) over 20 min at −40° C. This reaction solution was stirred at −40° C. for 5 hr. To this solution, a saturated ammonium chloride aqueous solution and ethyl acetate were added. The reaction solution was heated to room temperature. The organic layer was separated, washed with saturated saline, dried over anhydrous magnesium sulfate, and concentrated under reduced pressure. The residue was purified by silica gel column chromatography (heptane ethyl acetate=1:0 to 1:1) to give 4.8 g of (R)-2-tert-butoxycarbonylamino-5-oxo-5-(3,4,5-trifluorophenyl)pentanoic acid ethyl ester. A 4 N hydrochloric acid ethyl acetate solution (30 mL) was added to an ethyl acetate solution (30 mL) of the obtained (R)-2-tert-butoxycarbonylamino-5-oxo-5-(3,4,5-trifluorophenyl)pentanoic acid ethyl ester. This solution was stirred for 16 hr. The reaction solution was concentrated under reduced pressure. To the residue, ethyl acetate and a saturated sodium hydrogencarbonate aqueous solution were added. The organic layer was separated, dried over anhydrous magnesium sulfate, and concentrated under reduced pressure.

To an ethyl acetate solution (50 mL) of the residue, 10% palladium-carbon (100 mg) was added. The resulting reaction solution was stirred under 1 atm of hydrogen atmosphere for 6 hr. The reaction solution was filtered through Celite. The filtrate was concentrated under reduced pressure to give 2.91 g of the title compound. The physical property values of this compound were as follows:

ESI-MS; m/z 274 [M$^+$+H].

Synthesis of [(2R,5S)-5-(3,4,5-trifluorophenyl)pyrrolidin-2-yl]methanol

LAH (483 mg) was added to a THF solution (50 mL) of (2R,5S)-5-(3,4,5-trifluorophenyl)pyrrolidine-2-carboxylic acid ethyl ester (2.91 g) over 1 hr at −15° C. The resulting reaction solution was stirred at −15° C. for 19 hr. To the reaction solution, water (0.5 mL), a 5 N sodium hydroxide aqueous solution (0.5 mL), and water (1.5 mL) were added in this order. The resulting mixture was stirred at room temperature for 30 min and then filtered through Celite. The filtrate was concentrated under reduced pressure to give 2.4 g of the title compound. The physical property values of this compound were as follows:

ESI-MS; m/z 232 [M$^+$+H]. $^1$H-NMR (CDCl$_3$) δ (ppm): 1.51-1.63 (m, 1H), 1.66-1.77 (m, 1H), 1.89-2.00 (m, 1H), 2.10-2.20 (m, 1H), 3.43 (dd, J=10.0, 5.6 Hz, 1H), 3.47-3.55 (m, 1H), 3.64 (dd, J=10.0, 3.6 Hz, 1H), 4.23 (t, J=8.0 Hz, 1H), 7.02 (t, J=8.0 Hz, 2H).

Synthesis of (E)-3-[(2R,5S)-1-(3-butenoyl)-5-(3,4,5-trifluorophenyl)pyrrolidin-2-yl]acrylic acid ethyl ester Triethylamine (1.95 mL) and BOPCl (2.85 g) were added to a THF solution (50 mL) of [(2R,5S)-5-(3,4,5-trifluorophenyl)pyrrolidin-2-yl]methanol (2.17 g) and vinylacetic acid (0.67 mL). The resulting reaction solution was stirred at room temperature for 12 hr. To the reaction solution, a solution mixture of toluene and THF (1:1) and a 1 N hydrochloric acid aqueous solution were added. The organic layer was separated, washed with a 1 N sodium hydroxide aqueous solution, dried over anhydrous magnesium sulfate, and concentrated under reduced pressure to give a residue.

A methylene chloride solution (5 mL) of DMSO (1.17 g) was dropwise added to a methylene chloride solution (15 mL) of oxalyl chloride (1.77 g) at −78° C. The resulting reaction solution was stirred at −78° C. for 20 min. To this reaction solution, a dichloromethane solution (10 mL) of the above-given residue was dropwise added at −78° C. The resulting reaction solution was stirred at −78° C. for 70 min. Triethylamine (6.5 mL) was dropwise added to this solution, and the resulting reaction solution was stirred at −78° C. for 1 hr. To the reaction solution, a solution mixture of toluene and THF (1:1) and a saturated ammonium chloride aqueous solution were added. The resulting mixture was heated to room temperature, and the organic layer was separated. The obtained organic layer was washed with a 1 N hydrochloric acid aqueous solution, a saturated sodium hydrogencarbonate aqueous solution, and saturated saline in this order, and dried over anhydrous magnesium sulfate, and then concentrated under reduced pressure to give a residue.

Triethylphosphonoacetate (3.7 mL) was added to a THF suspension (70 mL) of sodium hydride (containing 40% mineral oil, 746 mg) at 0° C. The resulting reaction solution was stirred at 0° C. for 1 hr. To this reaction solution, a THF solution (30 mL) of the above-given residue, and the resulting reaction solution was stirred at room temperature for 1 hr. To the reaction solution, ethyl acetate and a saturated ammonium chloride aqueous solution were added. The organic layer was separated, dried over anhydrous magnesium sulfate, and concentrated under reduced pressure. The residue was purified by silica gel column chromatography (heptane:ethyl acetate=1:0 to 1:1) to give 1.33 g of the title compound. The physical property values of this compound were as follows:

ESI-MS; m/z 368 [M$^+$+H]

Synthesis of (3S,8aR)-3-(3,4,5-trifluorophenyl)-2,3,6,8a-tetrahydro-1H-indolizin-5-one A methylene chloride solution (60 mL) of (E)-3-[(2R,5S)-1-(3-butenoyl)-5-(3,4,5-trifluorophenyl)pyrrolidin-2-yl]acrylic acid ethyl ester (1.33 g) and Grubbs catalyst second generation (153 mg) was heated under reflux for 2 hr. The reaction solution was allowed to cool to room temperature, and then triethylamine (0.5 mL) was added thereto. The resulting mixture was stirred for 1 hr and concentrated under reduced pressure. The residue was purified by silica gel column chromatography (heptane:ethyl acetate=1:1 to 0:1) to give 680 mg of the title compound. The physical property values of this compound were as follows:

ESI-MS; m/z 268 [M$^+$+H]. $^1$H-NMR (CDCl$_3$) δ (ppm): 1.74-1.86 (m, 2H), 2.10-2.18 (m, 1H), 2.29-2.42 (m, 1H), 2.95-3.00 (m, 2H) 4.22-4.32 (m, 1H), 5.01 (d, J=9.2 Hz, 1H), 5.98-6.05 (m, 1H), 6.07-6.32 (m, 1H), 6.67-6.76 (m, 2H).

Synthesis of (3S,8aR)-3-(3,4,5-trifluorophenyl)hexahydroindolizin-5-one

Platinum oxide (100 mg) was added to a methanol solution (20 mL) of (3S,8aR)-3-(3,4,5-trifluorophenyl)-2,3,6,8a-tetrahydro-1H-indolizin-5-one (680 mg). The resulting reaction solution was stirred under 1 atm of hydrogen atmosphere at room temperature for 2.5 hr. The reaction solution was filtered through Celite. The filtrate was concentrated under reduced pressure to give 684 mg of the title compound. The physical property values of this compound were as follows:

ESI-MS; m/z 270 [M$^+$+H].

Synthesis of (E)-(3S)-(3,4,5-trifluorophenyl)-6-[3-methoxy-4-(4-methyl-1H-imidazol-1-yl)benzylidene]-(9S)-hexahydroindolizin-5-one Trimethylsilyl iodide (0.542 mL) was dropwise added to a methylene chloride solution (15 mL) of (3S,8aR)-3-(3,4,5-trifluorophenyl)hexahydroindolizin-5-one (684 mg) and N,N,N',N'-tetramethylethylenediamine (1.34 mL) at 0° C. The resulting reaction solution was stirred at 0° C. for 30 min, and then iodine (967 mg) was added thereto at 0° C. The resulting reaction solution was stirred at 0° C. for 1 hr. To the reaction solution, a saturated sodium thiosulfate aqueous solution and ethyl acetate were added. The resulting mixture was heated to room temperature, and the organic layer was separated. The obtained organic layer was washed with saturated saline, dried over anhydrous magnesium sulfate, and concentrated under reduce pressure. A triethyl phosphite solution (5 mL) of the residue was stirred at 120° C. for 1 hr. The reaction solution was allowed to cool to room temperature and concentrated under reduced pressure. To a solution mixture of THF (15 mL) and ethanol (3 mL) of the residue, 3-methoxy-4-(4-methyl-1H-imidazol-1-yl)benzaldehyde (549 mg) and lithium hydroxide monohydrate (319 mg) were added. The resulting reaction solution was stirred at room temperature for 15 hr, and ethyl acetate and saturated saline were added thereto. The organic layer was separated, dried over anhydrous magnesium sulfate, and concentrated under reduced pressure. The residue was purified by silica gel column chromatography (carrier: Chromatorex NH, eluting solvent; heptane and ethyl acetate (1:1) to ethyl acetate and then to ethyl acetate and methanol (9:1)) to give 762 mg of the title compound. The physical property values of this compound were as follows:

ESI-MS; m/z 468 [M$^+$+H]. $^1$H-NMR (CDCl$_3$) δ (ppm): 1.65-1.87 (m, 3H), 2.06-2.14 (m, 1H), 2.30-2.39 (m, 5H), 2.69-2.80 (m, 1H), 3.15 (brt, J=16.8 Hz, 1H), 3.76-3.85 (m, 1H), 3.86 (s, 3H), 5.10 (d, J=8.8 Hz, 1H), 6.79 (dd, J=8.4, 6.4 Hz, 2H), 6.95 (s, 1H), 7.05 (brs, 1H), 7.08 (brd, J=8.0 Hz, 1H), 7.26 (d, J=8.0 Hz, 1H), 7.74 (brs, 1H), 7.85 (s, 1H).

Synthesis of 3-{2-methoxy-4-[(3S,8aS)-5-oxo-3-(3,4,5-trifluorophenyl)hexahydroindolizin-(6E)-ylidenemethyl]phenyl}-5-methyl-1-phosphonooxymethyl-3H-imidazol-1-ium trifluoroacetate A DME solution (5 mL) of (E)-(3S)-(3,4,5-trifluorophenyl)-6-[3-methoxy-4-(4-methyl-1H-imidazol-1-yl)benzylidene]-(9S)-hexahydroindolizin-5-one (130 mg), chloromethyl di-tert-butylphosphate (CAS Registry No. 229625-50-7, 108 mg), sodium iodide (125 mg), and IPEA (0.05 mL) was stirred at 80° C. for 2.5 hr. The reaction solution was allowed to cool to room temperature and concentrated under reduced pressure. TFA (1 mL) was added to a chloroform solution (1 mL) of the obtained residue. The resulting mixture was stirred at room temperature for 1 hr and then concentrated under reduced pressure. The residue was purified by reversed phase C18 silica gel column chromatography (developing solvent: water-acetonitrile system containing 0.1% trifluoroacetic acid) to give 80 mg of the title compound. The physical property values of this compound were as follows:

ESI-MS; m/z 578 [M$^+$]. $^1$H-NMR (CD$_3$OD) δ (ppm): 1.70-1.87 (m, 3H), 2.08-2.16 (m, 1H), 2.33-2.48 (m, 2H), 2.53 (s, 3H), 2.80-2.93 (m, 1H), 3.10-3.20 (m, 1H), 3.85-3.95 (m, 1H), 3.96 (s, 3H), 5.12 (d, J=8.8 Hz, 1H), 5.90 (d, J=12.8 Hz, 2H), 6.92-7.00 (m, 2H), 7.26 (dd, J=8.4, 1.2 Hz, 1H), 7.33 (d, J=1.2 Hz, 1H), 7.59 (d, J=8.4 Hz, 1H), 7.66 (brs, 1H), 7.67 (brs, 1H), 9.40 (d, J=1.6 Hz, 1H).

Example 7

Synthesis of 3-{4-{(S)-4-[(S)-1-(2,6-difluoropyridin-3-yl)ethyl]-6-methyl-3-oxomorpholin-(2Z)-ylidenemethyl}-2-methoxyphenyl}-5-methyl-1-phosphonooxymethyl-3H-imidazol-1-ium chloride

[Formula 31]

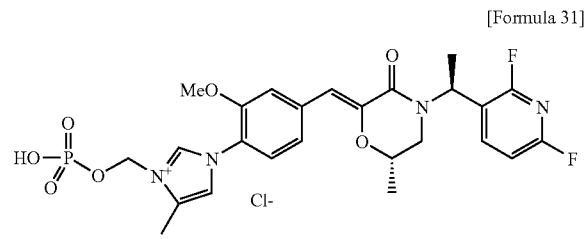

Synthesis of 1-(2,6-difluoropyridin-3-yl)ethanol

In nitrogen atmosphere, diisopropylamine (134 mL) was dropwise added to a solution mixture of an n-butyl lithium hexane solution (2.62 M, 368 mL) and tetrahydrofuran (800 mL) at −60° C. or below. The resulting reaction solution was stirred at −60° C. for 30 min, and then a tetrahydrofuran solution (100 mL) of 2,6-difluoropyridine (100 g) was dropwise added thereto at −60° C. or below. The resulting reaction solution was stirred at the same temperature for 1 hr, and then acetoaldehyde (97.6 mL) was dropwise added thereto. Then, a 2 N hydrochloric acid aqueous solution (1000 mL) was dropwise added to the reaction solution, and further ethyl acetate (1000 mL) and toluene (1000 mL) were added thereto. The organic layer was separated and concentrated under reduced pressure to give 129 g of the title compound. The physical property values of this compound were as follows:

$^1$H-NMR (CDCl$_3$) δ (ppm): 1.51 (d, J=5.6 Hz, 3H), 2.00 (s, 1H), 5.13-5.16 (m, 1H), 6.84 (dd, J=8.0, 2.1 Hz, 1H), 8.05 (dd, J=16.0, 8.0 Hz, 1H).

Synthesis of (S)-1-[(S)-1-(2,6-difluoropyridin-3-yl) ethylamino]propan-2-ol (+)-di-p-toluoyl-D-tartrate salt A toluene solution (300 mL) of 1-(2,6-difluoropyridin-3-yl)ethanol (216 g) was added to a toluene solution (1500 mL) of thionyl bromide (337 g) under ice-cooling. The resulting reaction solution was stirred at room temperature for 3 hr, and then iced-water and toluene were added thereto. The organic layer was separated, washed with water (1000 mL) three times, dried over anhydrous magnesium sulfate, and filtered through a silica gel pad, and (S)-1-amino-2-propanol (157 g), cesium carbonate (1.28 kg), and DMF (2500 mL) were added thereto. The resulting reaction solution was stirred at room temperature overnight. The reaction solution was filtered, and the filtrate was concentrated under reduced pressure. The residue was diluted with ethanol (1000 mL), and an ethanol solution (500 mL) of (+)-di-p-toluoyl-D-tartrate (152 g) was added thereto. The resulting reaction solution was stirred at room temperature for 1 hr. The precipitated crystal was filtered and washed with ethanol. The crystal was dried at 80° C. for 2 hr and suspended in a solvent mixture of ethanol (2000 mL) and heptane (1000 mL). The resulting suspension was heated to and stirred at 80° C. After 1 hr, the reaction solution was allowed to cool to room temperature. The precipitated crystal was filtered, washed with ethanol, and dried at 80° C. overnight to give 155 g of the title compound. The physical property values of this compound were as follows:

$^1$H-NMR (DMSO-d6) δ (ppm): 1.02 (d, J=6.0 Hz, 6H), 1.37 (d, J=6.8 Hz, 6H), 2.36 (s, 6H), 2.37-2.51 (m, 4H), 3.67-3.71 (m, 2H), 4.14-4.16 (m, 2H), 5.65 (s, 2H), 7.21 (dd, J=8.0, 2.0 Hz, 2H), 7.31 (d, J=8.4, Hz, 4H), 7.82 (d, J=8.4 Hz, 4H), 8.27 (dd, J=17.6, 8.0 Hz, 2H).

Synthesis of (S)-4-[(S)-1-(2,6-difluoropyridin-3-yl) ethyl]-6-methylmorpholin-2,3-dione A 5 N sodium hydroxide aqueous solution (450 mL), water (1000 mL), and 50% toluene-THF (2000 mL) were added to (S)-1-[(S)-1-(2,6-difluoropyridin-3-yl)ethylamino]propan-2-ol (+)-di-p-toluoyl-D-tartrate (199 g). The organic layer was separated. The water layer was extracted with 50% toluene-THF (800 mL) three times. All the organic layers were combined and concentrated under reduced pressure. To the residue, diethyl oxalate (200 mL) was added. The resulting reaction solution was heated to and stirred at 140 to 150° C. After 3 hr, the reaction solution was diluted with toluene (500 mL) and cooled with ice while stirring. The precipitated crystal was filtered, washed with toluene and diethyl ether, and dried in air to give 103 g of the title compound. The physical property values of this compound were as follows:

$^1$H-NMR (CDCl$_3$) δ (ppm): 1.43 (d, J=6.8 Hz, 3H), 1.70 (d, J=6.8 Hz, 3H), 3.36 (dd, J=13.2, 8.8 Hz, 1H), 3.52 (dd, J=13.2, 2.1 Hz, 1H), 4.72-4.78 (m, 1H), 5.59 (q, J=6.8 Hz, 1H), 6.88 (dd, J=8.0, 2.8 Hz, 1H), 8.01 (dd, J=16.8, 8.0 Hz, 1H).

Synthesis of (S)-4-[(S)-1-(2,6-difluoropyridin-3-yl) ethyl]-2-hydroxy-6-methylmorpholin-3-one A THF solution (20 mL) of 1 M lithium tri-s-butyl borohydride was dropwise added to a THF solution of (S)-4-[(S)-1-(2,6-difluoropyridin-3-yl)ethyl]-6-methylmorpholin-2,3-dione (4.5 g) at −50° C. or below. The resulting reaction solution was stirred for 2 hr. To the reaction solution, a 5 N sodium hydroxide aqueous solution (1.66 mL) and 30% hydrogen peroxide aqueous solution (6.78 mL) were added in this order at −10° C. or below. The resulting reaction solution was stirred for 1 hr, and then sodium hydrogensulfite (520 mg) was added thereto. The resulting reaction solution was stirred for 30 min, and then saturated saline and 50% toluene-THF were added thereto. The organic layer was separated, and the water layer was extracted with 50% toluene-THF. All the organic layers were combined and concentrated under reduced pressure. The residue was purified by silica gel column chromatography (heptane:ethyl acetate=1:1 to 0:1) to give 4.52 g of the title compound. The physical property values of this compound were as follows:

$^1$H-NMR (CDCl$_3$) δ (ppm): 1.25 (d, J=6.8 Hz, 2.58H), 1.30 (d, J=6.8 Hz, 0.42H), 1.60 (d, J=6.8 Hz, 2.58H), 1.62 (d, J=6.8 Hz, 0.42H), 2.90 (dd, J=12.8, 8.8 Hz, 0.86H), 3.09 (dd, J=12.8, 8.8 Hz, 0.14H), 3.11 (dd, J=12.8, 2.1 Hz, 0.86H), 3.31 (dd, J=12.8, 2.1 Hz, 0.14H), 4.39-4.49 (m, 1H), 5.14 (s, 0.14H), 5.30 (s, 0.86H), 5.50 (q, J=6.8 Hz, 0.14H), 5.71 (q, J=6.8 Hz, 0.86H), 6.87 (dd, J=8.0, 2.8 Hz, 1H), 7.96 (dd, J=16.8, 8.0 Hz, 1H).

Synthesis of (Z)-(S)-4-[(S)-1-(2,6-difluoropyridin-3-yl)ethyl]-2-{1-[3-methoxy-4-(4-methyl-1H-imidazol-1-yl)phenyl]methylidene}-6-methylmorpholin-3-one Triphenylphosphonium bromide (6.52 g) was added to an acetonitrile solution of (S)-4-[(S)-1-(2,6-difluoropyridin-3-yl)ethyl]-2-hydroxy-6-methylmorpholin-3-one (4.3 g). The resulting reaction solution was heated under reflux for 1 hr, and triethylamine (5.28 mL) and 3-methoxy-4-(4-methyl-1H-imidazol-1-yl)benzaldehyde (3.42 g) were added thereto. The resulting reaction solution was heated under reflux for 1.5 hr and concentrated under reduced pressure. The residue was diluted with a 2 N hydrochloric acid aqueous solution and ethyl acetate. The water layer was separated, and the organic layer was washed with a 2 N hydrochloric acid aqueous solution. All the water layers were combined and alkalinized with a concentrated sodium hydroxide aqueous solution. The alkaline aqueous solution was extracted with ethyl acetate. The organic layer was separated, washed with saturated sodium hydrogencarbonate, dried over anhydrous magnesium sulfate, and concentrated under reduced pressure. The residue was purified by silica gel column chromatography (carrier: Chromatorex NH, eluting solvent; heptane:ethyl acetate=1:1 to 0:1) to give 4.06 g of the title compound. The physical property values of this compound were as follows:

ESI-MS; m/z 455 [M$^+$+H]. $^1$H-NMR (CDCl$_3$) δ (ppm): 1.44 (d, J=6.4 Hz, 3H), 1.67 (d, J=7.2 Hz, 3H), 2.31 (s, 3H), 3.23 (dd, J=12.8, 10.0 Hz, 1H), 3.42 (dd, J=12.8, 2.8 Hz, 1H), 3.84 (s, 3H), 4.37 (m, 1H), 5.74 (q, J=7.2 Hz, 1H), 6.81 (s, 1H), 6.87 (dd, J=8.0, 2.8 Hz, 1H), 6.93 (dd, J=1.2, 1.2 Hz, 1H), 7.20 (d, J=8.0 Hz, 1H), 7.31 (dd, J=8.4, 1.6 Hz, 1H), 7.50 (d, J=1.6 Hz, 1H), 7.77 (s, 1H), 8.00 (m, 1H).

Synthesis of 3-{4-{(S)-4-[(S)-1-(2,6-difluoropyridin-3-yl)ethyl]-6-methyl-3-oxomorpholin-(2Z)-ylidenemethyl}-2-methoxyphenyl}-5-methyl-1-phosphonooxymethyl-3H-imidazol-1-ium chloride Chloromethyl di-tert-butylphosphate (427 mg), sodium iodide (494 mg), and diisopropylethylamine (47.1 µL) were added to an acetone solution (10 mL) of (Z)-(S)-4-[(S)-1-(2,6-difluoropyridin-3-yl)ethyl]-2-{1-[3-methoxy-4-(4-methyl-1H-imidazol-1-yl)phenyl]methylidene}-6-methylmorpholin-3-one (500 mg). The resulting reaction solution was heated under reflux for 1 hr and then filtered. The filtrate was concentrated under reduced pressure. To the residue, trifluoroacetic acid (3 mL) was added. The resulting reaction solution was stirred at room temperature for 30 min, concentrated under reduced pressure. The residue was diluted with ethyl acetate and adjusted to a pH of 8 to 9 by a sodium hydroxide aqueous solution and a saturated sodium hydrogencarbonate aqueous solution. The organic layer was separated. The water layer was acidified with concentrated hydrochloric acid and diluted with chloroform. The precipitated oily matter was collected and solidified with ethyl acetate to give 129 mg of the title compound. The physical property values of this compound were as follows:
$^1$H-NMR (DMSO-$d_6$) δ (ppm): 1.33 (d, J=6.4 Hz, 3H), 1.56 (d, J=7.2 Hz, 3H), 2.43 (s, 3H), 2.99 (dd, J=12.8, 9.2 Hz, 1H), 3.53 (dd, J=12.8, 1.6 Hz, 1H), 3.87 (s, 3H), 4.40-4.43 (m, 1H), 5.85-5.89 (m, 3H), 6.73 (s, 1H), 7.25 (dd, J=8.4, 2.4 Hz, 1H), 7.47-7.55 (m, 2H), 7.73 (s, 1H), 7.85 (s, 1H), 8.27 (dd, J=17.6, 8.4 Hz, 1H), 9.68 (s, 1H).

Example 8

Synthesis of 3-{4-[(3S,8aS)-3-(4-chlorophenyl)-5-oxohexahydroindolizin-(6E)-ylidenemethyl]-2-methoxyphenyl}-5-methyl-1-(phosphonooxymethyl)-3H-imidazol-1-ium trifluoroacetate

[Formula 32]

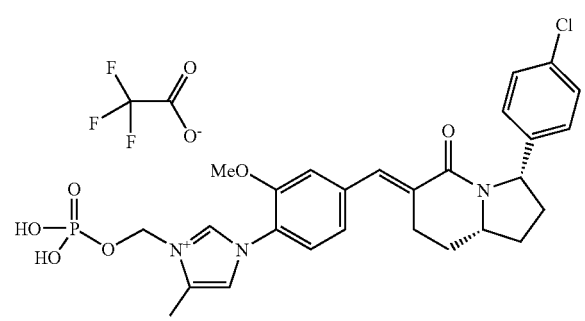

Synthesis of (R)-2-tert-butoxycarbonylamino-5-(4-chlorophenyl)-5-oxopentanoic acid ethyl ester 4-Chlorophenyl magnesium bromide (1.0 M diethylether solution, 17.1 mL) was dropwise added to a tetrahydrofuran solution (100 mL) of (R)-5-oxopyrrolidin-1,2-dicarboxylic acid 1-tert-butyl ester 2-ethyl ester (CAS Register No. 128811-48-3, 4.0 g) over 20 min at −40° C. The resulting reaction solution was stirred while heating from −40° C. to 0° C. for 1 hr. To this solution, water was gradually added at 0° C. The reaction solution was extracted with ethyl acetate. The extract solution was washed with saturated saline, dried over anhydrous magnesium sulfate, and concentrated under reduced pressure. The residue was purified by silica gel column chromatography (heptane-ethyl acetate system) to give 5.6 g of the title compound as a colorless oily substance. The physical property values of this compound were as follows:
ESI-MS; m/z 392 [M$^+$+Na]. $^1$H-NMR (CDCl$_3$) δ (ppm): 1.28 (t, J=7.2 Hz, 3H), 1.42 (s, 9H), 2.00-2.50 (m, 2H), 2.95-3.20 (m, 2H), 4.10-4.50 (m, 2H), 4.10-5.20 (m, 2H), 7.41-7.47 (m, 2H), 7.86-7.92 (m, 2H).

Synthesis of (R)-5-(4-chlorophenyl)-3,4-dihydro-2H-pyrrole-2-carboxylic acid ethyl ester A 4 N hydrochloric acid-ethyl acetate solution (30 mL) was dropwise added to an ethyl acetate solution (30 mL) of (R)-2-tert-butoxycarbonylamino-5-(4-chlorophenyl)-5-oxopentanoic acid ethyl ester (5.6 g) at room temperature. The resulting reaction solution was stirred at room temperature for 2 hr and concentrated under reduced pressure to give 5.0 g of a yellow oily substance. To an ethyl acetate solution (100 mL) of this crude product, a saturated sodium hydrogencarbonate aqueous solution (100 mL) was dropwise added. The resulting reaction solution was stirred at room temperature for 20 min and then extracted with ethyl acetate. The extract solution was washed with saturated saline, dried over anhydrous magnesium sulfate, and concentrated under reduced pressure to give 3.5 g of the title compound as a light yellow oily substance. The physical property values of this compound were as follows:
ESI-MS; m/z 525 [2M$^+$+Na]. $^1$H-NMR (CDCl$_3$) δ (ppm): 1.32 (t, J=7.2 Hz, 3H), 2.18-2.43 (m, 2H), 2.90-3.03 (m, 1H), 3.05-3.20 (m, 1H), 4.25 (q, J=7.2 Hz, 2H), 4.85-4.95 (m, 1H), 7.36-7.41 (m, 2H), 7.79-7.85 (m, 2H).

Synthesis of (2R,5S)-5-(4-chlorophenyl)pyrrolidine-1,2-dicarboxylic acid 1-tert-butyl ester 2-ethyl ester Sodium borohydride (1.05 g) was added to a methanol (80 mL)-acetic acid (20 mL) solution of (R)-5-(4-chlorophenyl)-3,4-dihydro-2H-pyrrole-2-carboxylic acid ethyl ester (3.5 g) at −45° C. over 5 min. The resulting reaction solution was stirred for 3 hr while heating from −45° C. to 0° C. To the reaction solution, a disodium hydrogenphosphate was added. The resulting reaction solution was stirred at room temperature for 20 min, and the organic solvent was evaporated under reduced pressure. The residue was extracted with ethyl acetate. The organic layer was washed with a sodium hydrogencarbonate aqueous solution, dried over anhydrous magnesium sulfate, and concentrated under reduced pressure to give 3.6 g of a yellow oily substance. To a dichloromethane solution (50 mL) of the obtained oily substance, triethylamine (7.49 mL) and di-tert-butyl dicarbonate (3.76 g) were added. The resulting reaction solution was stirred at room temperature for 1 hr and then poured into iced-water. The resulting mixture was extracted with ethyl acetate. The extract solution was washed with saturated saline, dried over anhydrous magnesium sulfate, and concentrated under reduced pressure. The residue was purified by silica gel column chromatography (heptane-ethyl acetate system) to give 3.3 g of the title compound as a yellow oily substance. The physical property values of this compound were as follows:
ESI-MS; m/z 376 [M$^+$+Na]. $^1$H-NMR (CDCl$_3$) δ (ppm): 1.17 and 1.41 (s, 9H), 1.26-1.38 (m, 3H), 1.84-2.10 (m, 2H), 2.16-2.36 (m, 2H), 4.20-4.30 (m, 2H), 4.30-5.00 (m, 2H), 7.25-7.35 (m, 2H), 7.45-7.60 (m, 2H).

Synthesis of (2S,5R)-2-(4-chlorophenyl)-5-((E)-2-methoxycarbonylvinyl)pyrrolidine-1-carboxylic acid tert-butyl ester Lithium borohydride (813 mg) was added to a tetrahydrofuran solution (50 mL) of (2R,5S)-5-(4-chlorophenyl)pyrrolidine-1,2-dicarboxylic acid 1-tert-butyl ester 2-ethyl ester (3.3 g) at 0° C. The resulting reaction solution was stirred at room temperature for 12 hr and then poured into iced-water. The resulting mixture was extracted with ethyl acetate. The extract solution was washed with saturated saline, dried over anhydrous magnesium sulfate, and concentrated under reduced pressure to give 3.0 g of an alcohol compound as a yellow oily substance. DMSO (1.09 mL) was dropwise added to a dichloromethane solution (40 mL) of oxalyl chloride (1.24 mL) at −70° C. The resulting reaction solution was stirred at −70° C. for 3 min. To this reaction solution, a dichloromethane solution (20 mL) of the above-given alcohol compound (3.0 g) was dropwise added at −60° C. The resulting reaction solution was stirred at −60° C. for 15 min. To this solution, triethylamine (10.7 mL) was dropwise added. The resulting reaction solution was stirred for 30 min while heating from −60° C. to 0° C. and then poured into water. The resulting mixture was extracted with ethyl acetate. The extract solution was washed with saturated saline, dried over anhydrous magnesium sulfate, and concentrated under reduce pressure to give 3.0 g of aldehyde compound as a light yellow oily substance. Sodium hydride (60% oily substance, 0.579 g) was added to a DMF solution (20 mL) of trimethylphosphonoacetate (2.63 g) at room temperature. The resulting reaction solution was stirred for 20 min and then added to a DMF solution (10 mL) of the above-given aldehyde compound (3.0 g) at room temperature. The resulting reaction solution was stirred at room temperature for 1 hr and poured into water. The resulting mixture was extracted with ethyl acetate. The extract solution was washed with saturated saline, dried over anhydrous magnesium sulfate, and concentrated under reduced pressure. The residue was purified by silica gel column chromatography (heptane-ethyl acetate system) to give 2.8 g of the title compound as a yellow oily substance. The physical property values of this compound were as follows:

ESI-MS; m/z 388 [M$^+$+Na]. $^1$H-NMR (CDCl$_3$) δ (ppm): 1.00-1.50 (m, 9H), 1.75-1.95 (m, 2H), 2.05-2.20 (m, 1H), 2.20-2.35 (m, 1H), 3.77 (s, 3H), 4.30-5.00 (m, 2H), 5.95-6.10 (m, 1H), 6.95-7.05 (m, 1H), 7.18 (d, J=8.4 Hz, 2H), 7.30 (d, J=8.4 Hz, 2H).

Synthesis of (E)-3-[(2R,5S)-1-(3-butenoyl)-5-(4-chlorophenyl)pyrrolidin-2-yl]acrylic acid methyl ester A 4 N hydrochloric acid-ethyl acetate solution (19.4 mL) was dropwise added to an ethyl acetate solution (5 mL) of (2S,5R)-2-(4-chlorophenyl)-5-((E)-2-methoxycarbonylvinyl)pyrrolidine-1-carboxylic acid tert-butyl ester (2.8 g) at room temperature. The resulting reaction solution was stirred at 50° C. for 30 min and then concentrated under reduced pressure to give 2.5 g of a yellow solid. Diethyl cyanophosphonate (1.97 mL) was dropwise added to a DMF solution (40 mL) of the given yellow solid (2.5 g), vinylacetic acid (1.1 mL), and triethylamine (3.63 mL) at 0° C. The resulting reaction solution was stirred at 0° C. for 2 hr and then poured into iced-water. The resulting mixture was extracted with ethyl acetate. The extract solution was washed with a 1 N hydrochloric acid aqueous solution, a saturated sodium hydrogencarbonate aqueous solution, and saturated saline in this order; dried over anhydrous magnesium sulfate; and concentrated under reduced pressure. The residue was purified by silica gel column chromatography (heptane-ethyl acetate system) to give 2.2 g of the title compound as a yellow oily substance. The physical property values of this compound were as follows:

ESI-MS; m/z 334 [M$^+$+H]. $^1$H-NMR (CDCl$_3$) δ (ppm): 1.30-3.20 (m, 6H), 3.76 and 3.79 (s, 3H), 4.60-5.20 (m, 4H), 5.70-6.20 (m, 2H), 6.90-7.40 (m, 5H).

Synthesis of (3S,8aR)-3-(4-chlorophenyl)-2,3,6,8a-tetrahydro-1H-indolizin-3-one

Grubbs catalyst second generation (559 mg) was added to a dichloromethane solution (100 mL) of (E)-3-[(2R,5S)-1-(3-butenoyl)-5-(4-chlorophenyl)pyrrolidin-2-yl]acrylic acid methyl ester (2.2 g). The resulting reaction solution was heated under reflux for 5 hr in nitrogen atmosphere and then allowed to cool to room temperature. To the reaction solution, triethylamine (4 mL) was added. The resulting reaction solution was stirred for 20 min and concentrated under reduced pressure. The residue was purified by silica gel column chromatography (heptane-ethyl acetate system) to give 1.3 g of the title compound as a brown oily substance. The physical property values of this compound were as follows:

ESI-MS; m/z 248 [M$^+$+H]. $^1$H-NMR (CDCl$_3$) δ (ppm): 1.70-1.90 (m, 2H), 2.05-2.15 (m, 1H), 2.25-2.45 (m, 1H), 2.90-3.05 (m, 2H), 4.20-4.35 (m, 1H), 5.10 (d, J=8.8 Hz, 1H), 5.98-6.04 (m, 1H), 6.06-6.12 (m, 1H), 7.00-7.08 (m, 2H), 7.20-7.28 (m, 2H).

Synthesis of (3S,8aS)-3-(4-chlorophenyl)-hexahydroindolizin-5-one

Platinum oxide (151 mg) was added to a methanol solution (50 mL) of (3S,8aR)-3-(4-chlorophenyl)-2,3,6,8a-tetrahydro-1H-indolizin-3-one (1.3 g). The resulting reaction solution was stirred in hydrogen atmosphere at room temperature for 5 hr. The platinum oxide was removed by filtration from the reaction solution, and the filtrate was concentrated under reduced pressure. The residue was purified by silica gel column chromatography (heptane-ethyl acetate system) to give 1.0 g of the title compound as a light brown solid. The physical property values of this compound were as follows:

ESI-MS; m/z 250 [M$^+$+H]. $^1$H-NMR (CDCl$_3$) δ (ppm): 1.50-1.90 (m, 4H), 1.90-2.10 (m, 2H), 2.15-2.50 (m, 4H), 3.52-3.65 (m, 1H), 5.08 (d, J=8.8 Hz, 1H), 7.06 (d, J=8.4 Hz, 2H), 7.25 (d, J=8.4 Hz, 2H).

Synthesis of [(3S,8aR)-3-(4-chlorophenyl)-5-oxooctahydroindolizin-6-yl]phosphonic acid diethyl ester Trimethylsilyl iodide (0.763 mL) was dropwise added to a dichloromethane solution (40 mL) of (3S,8aS)-3-(4-chlorophenyl)hexahydroindolizin-5-one (1.0 g) and N,N,N',N'-tetramethylethylenediamine (2.05 mL) at 0° C. The resulting reaction solution was stirred at 0° C. for 30 min, and iodine (1.36 g) was added thereto at 0° C. The resulting reaction solution was stirred at 0° C. for 40 min and then poured into an iced-sodium thiosulfate aqueous solution. The resulting mixture was extracted with ethyl acetate. The extract solution was washed with 1 N hydrochloric acid and saturated saline, dried over hydrous magnesium sulfate, and concentrated under reduced pressure to give an iodinated compound.

A triethyl phosphite solution (20 mL) of the given iodinated compound was stirred at 130° C. for 2 hr, cooled to room temperature, and concentrated under reduced pressure to give 2.5 g of the title compound. The physical property values of this compound were as follows:

ESI-MS; m/z 386 [M$^+$+H]

Synthesis of (E)-(3S,8aR)-3-(4-chlorophenyl)-6-[3-methoxy-4-(4-methyl-1H-imidazol-1-yl)benzylidene]hexahydroindolizin-5-one Lithium hydroxide (355 mg) was added to a solution mixture of tetrahydrofuran (8 mL)-ethanol (30 mL) of 3-methoxy-4-(4-methyl-1H-imidazol-1-yl)benzaldehyde (875 mg) and [(3S,8aR)-3-(4-chlorophenyl)-5-oxooctahydroindolizin-6-yl]phosphonic acid diethyl ester (2.5 g). The resulting reaction solution was stirred under light-shielded conditions at room temperature for 5 hr and then poured into iced-water. The resulting mixture was extracted with ethyl acetate. The extract solution was washed with saturated saline, dried over anhydrous magnesium sulfate, and concentrated under reduced pressure. The residue was purified by silica gel column chromatography (heptane-ethyl acetate system) to give 1.43 g of the title compound as a colorless solid. The physical property values of this compound were as follows:

ESI-MS; m/z 448 [M$^+$+H]. $^1$H-NMR (CDCl$_3$) δ (ppm): 1.66-1.88 (m, 3H), 2.02-2.12 (m, 1H), 2.26-2.40 (m, 2H), 2.30 (s, 3H), 2.68-2.82 (m, 1H), 3.10-3.20 (m, 1H), 3.76-3.90 (m, 1H), 3.85 (s, 3H), 5.20 (d, J=8.8 Hz, 1H), 6.94 (s, 1H), 7.02-7.16 (m, 2H), 7.12 (d, J=8.4 Hz, 2H), 7.20-7.34 (m, 1H), 7.28 (d, J=8.4 Hz, 2H), 7.72 (d, J=1.6 Hz, 1H), 7.76 (d, J=2.0 Hz, 1H).

Synthesis of 1-[4-{(E)-{(3S,8aS)-3-(4-chlorophenyl)-5-oxohexahydroindolizin-6-ylidene}methyl}-2-methoxyphenyl]-4-methyl-3-[(phosphonooxy)methyl]-3H-imidazol-1-ium trifluoroacetate In nitrogen atmosphere, (E)-(3S,8aS)-3-(4-chlorophenyl)-6-[3-methoxy-4-(4-methyl-1H-imidazol-1-yl)benzylidene] hexahydroindolizin-5-one (50 mg) was added to an acetone solution (4 mL) of chloromethyl di-tert-butylphosphate (43.5 mg), sodium iodide (50.4 mg), and N,N-diisopropylethylamine (4.88 μL). The resulting reaction solution was stirred at 60° C. for 1 hr and then cooled with water. The insoluble matter in the reaction solution was removed by filtration, and the filtrate was concentrated under reduced pressure. To a dichloromethane solution (2 mL) of the residue, trifluoloacetatic acid (0.5 mL) was added. The resulting reaction solution was stirred at room temperature for 1 hr and concentrated under reduced pressure. The residue was purified by reversed phase C18 silica gel column chromatography (developing solvent: water-acetonitrile system containing 0.1% trifluoroacetic acid) to give 32 mg of the title compound as a colorless solid. The physical property values of this compound were as follows:

ESI-MS; m/z 558 [M$^+$]. $^1$H-NMR (CD$_3$OD) δ (ppm): 1.70-1.90 (m, 3H), 2.05-2.15 (m, 1H), 2.30-2.50 (m, 2H), 2.53 (s, 3H), 2.80-2.95 (m, 1H), 3.05-3.20 (m, 1H), 3.85-4.00 (m, 1H), 3.95 (s, 3H), 5.18 (d, J=9.2 Hz, 1H), 5.96 (d, J=12.4 Hz, 2H), 7.18 (d, J=8.4 Hz, 2H), 7.25 (d, J=8.4 Hz, 1H), 7.31 (d, J=8.4 Hz, 2H), 7.32 (s, 1H), 7.59 (d, J=8.4 Hz, 1H), 7.62 (s, 1H), 7.69 (s, 1H), 9.45 (s, 1H).

Example 9

Synthesis of 3-{4-{(S)-4-[(1R,2R)-1-(3,4-difluorophenyl)-2-hydroxypropyl]-6-methyl-3-oxomorpholin-(2Z)-ylidenemethyl}-2-fluorophenyl}-5-methyl-1-phosphonooxymethyl-3H-imidazol-1-ium trifluoroacetate

[Formula 33]

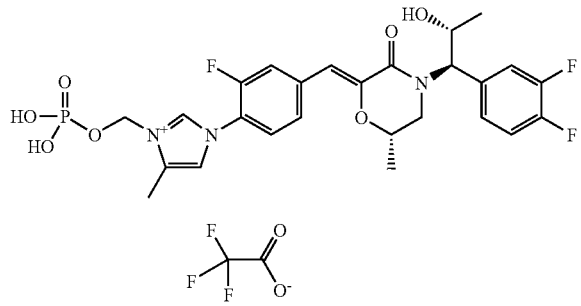

Synthesis of (S)-4-[(1R,2R)-1-(3,4-difluorophenyl)-2-hydroxypropyl]-2-{1-[3-fluoro-4-(4-methyl-1H-imidazol-1-yl)phenyl]-(Z)-methylidene}-6-methyl-morpholin-3-one By using 1-bromo-3,4-difluolobenzene as the starting material, 1.15 g of the title compound was obtained according to the same method as that in Example 4. The physical property values of this compound were as follows:

$^1$H-NMR (CDCl$_3$) δ (ppm): 1.31 (d, J=6.4 Hz, 3H), 1.41 (d, J=6.8 Hz, 3H), 2.20 (d, J=6.4 Hz, 1H), 2.30 (s, 3H), 3.15 (dd, J=12.8, 9.6 Hz, 1H), 3.57 (dd, J=12.8, 2.4 Hz, 1H), 4.42-4.48 (m, 2H), 5.38 (d, J=7.6 Hz, 1H), 6.80 (s, 1H), 6.97 (s, 1H), 7.12-7.18 (m, 2H), 7.26-7.31 (m, 2H), 7.44 (dd, J=8.4, 2.0 Hz, 1H), 7.71 (dd, J=12.8, 1.6 Hz, 1H), 7.73 (s, 1H).

Synthesis of 3-{4-[(3S,8aS)-3-(4-chlorophenyl)-5-oxohexahydroindolizin-(6E)-ylidenemethyl]-2-methoxyphenyl}-5-methyl-1-(phosphonooxymethyl)-3H-imidazol-1-ium trifluoroacetate A DME solution (5 mL) of (S)-4-[(1R,2R)-1-(3,4-difluorophenyl)-2-hydroxypropyl]-2-{1-[3-fluoro-4-(4-methyl-1H-imidazol-1-yl)phenyl]-(Z)-methylidene}-6-methylmorpholin-3-one (100 mg), chloromethyl di-tert-butylphosphate (CAS Registry No. 229625-50-7, 82 mg), sodium iodide (95 mg), and IPEA (0.04 mL) was stirred at 80° C. for 2 hr. The reaction solution was allowed to cool to room temperature and concentrated under reduced pressure. To a chloroform solution (1 mL) of the obtained residue, TFA (1 mL) was added. The resulting mixture was stirred at room temperature for 1 hr and then concentrated under reduced pressure. The residue was purified by reversed phase C18 silica gel column chromatography (developing solvent: water-acetonitrile system containing 0.1% trifluoroacetic acid) to give 90 mg of the title compound. The physical property values of this compound were as follows:

ESI-MS; m/z 582 [M$^+$]. $^1$H-NMR (CD$_3$OD) δ (ppm): 1.25 (d, J=6.0 Hz, 3H), 1.41 (d, J=6.8 Hz, 3H), 2.54 (s, 3H), 3.18 (dd, J=13.2, 9.6 Hz, 1H), 3.82 (dd, J=13.2.2.4 Hz, 1H), 4.40-4.48 (m, 1H), 4.51-4.61 (m, 1H), 5.53 (d, J=7.6 Hz, 1H), 5.93

(brd, J=12.4 Hz, 2H), 6.74 (brs, 1H), 7.16-7.24 (m, 2H), 7.30-7.38 (m, 1H), 7.52-7.64 (m, 3H), 7.83 (d, J=13.2 Hz, 1H), 9.53 (s, 1H).

Example 10

Synthesis of 3-{2-methoxy-4-[(6S,9aS)-4-oxo-6-(3,4,5-trifluorophenyl)hexahydroquinolizin-(3E)-ylidenemethyl]phenyl}-5-methyl-1-(phosphonooxymethyl)-3H-imidazol-1-ium trifluoroacetate

[Formula 34]

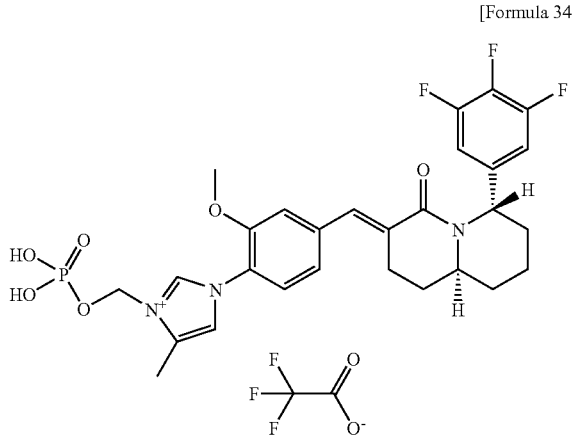

Synthesis of 1-(4-bromobutyl)-2-(3,4,5-trifluorophenyl)-2,3-dihydro-1H-pyridin-4-one According to the method disclosed in Tetrahedron Letters, 1986, 27, 4549-4552, 1.02 g of the title compound was given by using 4-methoxypyridine (1.52 mL), 3,4,5-trifluorophenyl magnesium bromide (0.3 M, THF solution, 50 mL), and 4-bromobutyryl chloride (1.74 mL). The physical property values of this compound were as follows:
$^1$H-NMR (CDCl$_3$) δ (ppm): 2.24-2.31 (m, 2H), 2.77-2.88 (m, 3H), 3.06-3.18 (m, 1H), 3.51-3.55 (m, 2H), 5.48 (brd, J=8.0 Hz, 1H), 5.98 (brs, 1H), 6.82-6.90 (m, 2H), 7.72 (brs, 1H).

Synthesis of (4S*,9aR*)-4-(3,4,5-trifluorophenyl)hexahydroquinolizin-2,6-dione

According to the method disclosed in Journal of Organic Chemistry, 1993, 58, 4198-4199, 331 mg of the title compound was given by using 1-(4-bromobutyryl)-2-(3,4,5-trifluorophenyl)-2,3-dihydro-1H-pyridin-4-one (1.15 g), tributyltin hydride (973 μL), and AIBN (201 mg). The physical property values of this compound were as follows:
$^1$H-NMR (CDCl$_3$) δ (ppm): 1.61-1.69 (m, 1H), 1.72-1.82 (m, 1H), 1.87-1.97 (m, 1H), 1.99-2.07 (m, 1H), 2.23-2.31 (m, 1H), 2.39 (ddd, J=14.8, 3.2, 1.6 Hz, 1H), 2.47-2.57 (m, 2H), 2.81 (ddd, J=15.2, 7.2, 0.8 Hz, 1H), 2.92 (ddd, J=15.2, 2.4, 1.6 Hz, 1H), 3.52-3.59 (m, 1H), 6.45 (brd, J=7.2 Hz, 1H), 6.88-6.92 (m, 2H).

Synthesis of (6S*,9aR*)-8-hydroxy-6-(3,4,5-trifluorophenyl)octahydroquinolizin-4-one A methanol solution (10 mL) of (6S*,9aR*)-4-(3,4,5-trifluorophenyl)hexahydroquinolizin-2,6-dione (331 mg) was cooled to 0° C., and sodium borohydride (64.1 mg) was added thereto. The resulting reaction solution was stirred for 1 hr, and then water and ethyl acetate were added thereto. The organic layer was separated, washed with saturated saline, dried over anhydrous magnesium sulfate, and concentrated under reduced pressure to give 340 mg of a crude alcohol compound. The physical property values of this compound were as follows:
$^1$H-NMR (CDCl$_3$) δ (ppm): 1.57-1.64 (m, 1H), 1.70-2.00 (m, 3H), 2.00-2.12 (m, 1H), 2.20-2.60 (m, 5H), 3.28-3.35 (m, ½H), 3.81-3.89 (m, 1H), 4.23-4.26 (m, ½H), 5.91 (brd, J=6.4 Hz, ½H), 6.15 (brd, J=4.8 Hz, ½H), 6.80-6.94 (m, 2H).

Synthesis of (6S*,9aS*)-6-(3,4,5-trifluorophenyl)octahydroquinolizin-4-one

A methylene chloride solution (5 mL) of (6S*,9aR*)-8-hydroxy-6-(3,4,5-trifluorophenyl)octahydroquinolizin-4-one (161 mg) was cooled to 0° C., and triethylamine (450 μL) and methanesulfonyl chloride (125 μL) were added thereto. The resulting reaction solution was stirred at room temperature for 4.5 hr, and then water and ethyl acetate were added thereto. The organic layer was separated, washed with saturated saline, dried over anhydrous magnesium sulfate, and concentrated under reduced pressure to give 203 mg of a crude mesyl compound. To an NMP solution (5.0 mL) of the given crude mesyl compound (203 mg), sodium borohydride (204 mg) was added. The resulting reaction solution was heated to 100° C. and then stirred for 2.5 hr. The reaction solution was cooled to room temperature, and water and ethyl acetate were added thereto. The organic layer was separated, washed with saturated saline, dried over anhydrous magnesium sulfate, and concentrated under reduced pressure. The residue was purified by silica gel column chromatography (eluting solvent: heptane-ethyl acetate system) to give 79 mg of the title compound. The physical property values of this compound were as follows:
$^1$H-NMR (CDCl$_3$) δ (ppm): 1.38-2.00 (m, 6H), 2.10-2.22 (m, 1H), 2.25-2.34 (m, 1H), 2.42-2.62 (m, 2H), 2.74-2.80 (m, 1H), 3.19-3.30 (m, 2H), 6.00-6.05 (brs, 1H), 6.79-6.83 (m, 2H).

Synthesis of (E)-(6S*,9aS*)-6-(3,4,5-trifluorophenyl)-3-[3-methoxy-4-(4-methyl-1H-imidazol-1-yl)benzylidene]octahydroquinolizin-4-one An LDA (1.5 M, THF solution, 372 μL) was added to a THF solution (2.0 mL) of (6S*,9aR*)-6-(3,4,5-trifluorophenyl)octahydroquinolizin-4-one (79 mg) at 0° C. The resulting reaction solution was stirred at 0° C. for 1 hr, and then a THF solution (1 mL) of 3-methoxy-4-(4-methyl-1H-imidazol-1-yl)benzaldehyde (66.4 mg) was added thereto. The resulting reaction solution was further stirred at 0° C. for 30 min, and water and ethyl acetate were added thereto. The organic layer was separated, dried with magnesium sulfate, and concentrated under reduced pressure to give 88 mg of a crude aldol adduct. A methylene chloride solution (3.0 mL) of the crude aldol adduct (88 mg) was cooled to 0° C., and triethylamine (147 μL) and methanesulfonyl chloride (40.9 μL) were added thereto. The resulting reaction solution was stirred at room temperature for 2.5 hr, and sodium methoxide (28%, methanol solution, 102 μL) and ethanol (1.0 mL) were added thereto. The resulting reaction solution was stirred at room temperature for 40 min, and then water and ethyl acetate were added thereto. The organic layer was separated, washed with saturated saline, dried over anhydrous magnesium sulfate, and concentrated under reduced pressure. The residue was purified by silica gel column chromatography (eluting solvent: heptane-ethyl acetate system to ethyl acetate-methanol system) to give 72 mg of a mixture of a crude aldol adduct and the title compound. The given mixture (72 mg) was dissolved in methylene chloride (3.0 mL) again. The resulting reaction solution was cooled to 0° C., and then triethylamine (147 µL) and methanesulfonyl chloride (61.3 µL) were added thereto. The resulting reaction solution was stirred at room temperature for 4 hr and 15 min, and sodium methoxide (28%, methanol solution, 102 µL) and ethanol (1.0 mL) were added thereto. The resulting reaction solution was stirred at room temperature for 2 hr and 15 min, and water and ethyl acetate were added thereto. The organic layer was separated, washed with saturated saline, dried over anhydrous magnesium sulfate, and concentrated under reduced pressure. The residue was purified by silica gel column chromatography (eluting solvent: heptane-ethyl acetate system to ethyl acetate-methanol system) to give 54.0 mg of the title compound. The physical property values of this compound were as follows:

$^1$H-NMR (CDCl$_3$) δ (ppm): 1.51-1.80 (m, 5H), 1.88-2.06 (m, 2H), 2.26-2.34 (m, 1H), 2.33 (s, 3H), 2.69-2.76 (m, 1H), 2.86-2.96 (m, 1H), 3.40-3.46 (m, 1H), 3.88 (s, 3H), 6.12-6.16 (brs, 1H), 6.86-6.91 (m, 2H), 6.96 (brs, 1H), 7.03-7.05 (m, 2H), 7.26-7.30 (m, 1H), 7.78-7.84 (brs, 1H), 7.83 (s, 1H).

Synthesis of (E)-(6S,9aS)-6-(3,4,5-trifluorophenyl)-3-[3-methoxy-4-(4-methyl-1H-imidazol-1-yl)benzylidene]-octahydroquinolizin-4-one and (E)-(6R,9aR)-6-(3,4,5-trifluorophenyl)-3-[3-methoxy-4-(4-methyl-1H-imidazol-1-yl)benzylidene]octahydroquinolizin-4-one The above-given racemic (E)-(6S*,9aS*)-6-(3,4,5-trifluorophenyl)-3-[3-methoxy-4-(4-methyl-1H-imidazol-1-yl)benzylidene]octahydroquinolizin-4-one (54 mg) was fractioned into an optically active title compound having a retention time of 6.6 min (18.6 mg: >99% ee) and an optically active title compound having a retention time of 7.8 min (21.0 mg: >95% ee) by Daicel CHIRALPAK™ AD-H (2 cm×25 cm, mobile phase; hexane ethanol=50:50).

The physical property values of the optically active title compound having a retention time of 6.6 min were as follows:

$^1$H-NMR (CDCl$_3$) δ (ppm): 1.51-1.80 (m, 5H), 1.88-2.06 (m, 2H), 2.26-2.34 (m, 1H), 2.33 (s, 3H), 2.69-2.76 (m, 1H), 2.86-2.96 (m, 1H), 3.40-3.46 (m, 1H), 3.88 (s, 3H), 6.12-6.16 (brs, 1H), 6.86-6.91 (m, 2H), 6.96 (brs, 1H), 7.03-7.05 (m, 2H), 7.26-7.30 (m, 1H), 7.78-7.84 (brs, 1H), 7.83 (s, 1H).

The physical property values of the optically active title compound having a retention time of 7.8 min were as follows:

$^1$H-NMR (CDCl$_3$) δ (ppm): 1.51-1.80 (m, 5H), 1.88-2.06 (m, 2H), 2.26-2.34 (m, 1H), 2.33 (s, 3H), 2.69-2.76 (m, 1H), 2.86-2.96 (m, 1H), 3.40-3.46 (m, 1H), 3.88 (s, 3H), 6.12-6.16 (brs, 1H), 6.86-6.91 (m, 2H), 6.96 (brs, 1H), 7.03-7.05 (m, 2H), 7.26-7.30 (m, 1H), 7.78-7.84 (brs, 1H), 7.83 (s, 1H).

Synthesis of 3-{2-methoxy-4-[(6S,9aS)-4-oxo-6-(3,4,5-trifluorophenyl)hexahydroquinolizin-(3E)-ylidenemethyl]phenyl}-5-methyl-1-(phosphonooxymethyl)-3H-imidazol-1-ium trifluoroacetate The title compound (28 mg) was obtained as a colorless solid by using (E)-(6S,9aS)-6-(3,4,5-trifluorophenyl)-3-[3-methoxy-4-(4-methyl-1H-imidazol-1-yl)benzylidene]octahydroquinolizin-4-one (130 mg) by the same method as that in Example 1. The physical property values of this compound were as follows:

ESI-MS; m/z 592 [M$^+$]. $^1$H-NMR (CD$_3$OD) δ (ppm): 1.56-1.78 (m, 3H), 1.88-1.98 (m, 1H), 2.02-2.12 (m, 1H), 2.38-2.45 (m, 1H), 2.53 (s, 3H), 2.74-2.83 (m, 1H), 2.90-2.98 (m, 1H), 3.50-3.57 (m, 2H), 3.66-3.68 (m, 1H), 3.97 (s, 3H), 5.93 (d, J=12.3 Hz, 2H), 6.01 (brs, 1H), 7.01-7.05 (m, 2H), 7.21 (d, J=8.4 Hz, 1H), 7.31 (s, 1H), 7.60 (d, J=8.4 Hz, 1H), 7.68 (s, 1H), 7.75 (s, 1H), 9.42 (s, 1H).

Example 11

Synthesis of 3-{2-methoxy-4-[(4R,9aS)-6-oxo-4-(3,4,5-trifluorophenyl)hexahydropyrido[2,1-c][1,4]oxazin-(7E)-ylidenemethyl]phenyl}-5-methyl-1-phosphonooxymethyl-3H-imidazol-1-ium trifluoroacetate

[Formula 35]

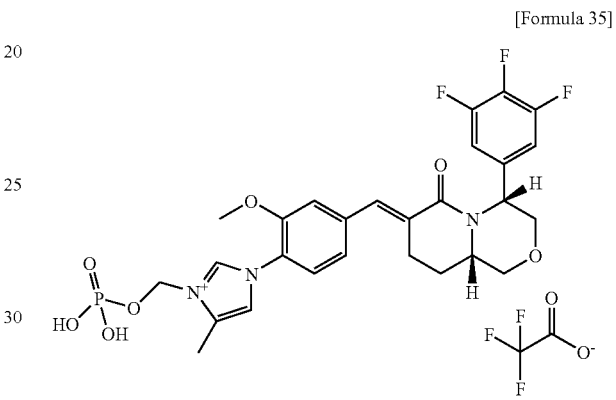

Synthesis of (S)-5-benzyloxymethylmorpholin-3-one

Bromoacetyl chloride (5.06 mL) was added to a solution mixture of toluene (100 mL) and a 2 N sodium hydroxide aqueous solution (100 mL) of (R)-(+)-2-amino-3-benzyloxy-1-propanol (10 g) under ice-cooling. The resulting reaction solution was stirred at 0° C. for 30 min and then further stirred at 60° C. for 1 hr. The reaction solution was cooled to room temperature, and a solution mixture of toluene and THF (1:1) was added thereto. The organic layer was separated, dried over anhydrous magnesium sulfate, and concentrated under reduced pressure. The residue was purified by silica gel column chromatography (eluting solvent: heptane-ethyl acetate system) to give 1.36 g of the title compound. The physical property values of this compound were as follows:

$^1$H-NMR (CDCl$_3$) δ (ppm): 3.42 (t, J=9.2 Hz, 1H), 3.54 (dd, J=9.2, 5.2 Hz, 1H), 3.62 (dd, J=12.0, 6.0 Hz, 1H), 3.75 (m, 1H), 3.86 (dd, J=12.0, 4.0 Hz, 1H), 4.12 (d, J=16.8 Hz, 1H), 4.18 (d, J=16.8 Hz, 1H), 4.53 (s, 2H), 6.29 (bs, 1H), 7.28-7.40 (m, 5H).

Synthesis of (S)-3-benzyloxymethyl-5-oxomorpholine-4-carboxylic acid tert-butyl ester Triethylamine (1.72 mL), 4-dimethylaminopyridine (189 mg), and di-tert-butyl dicarbonate (2.02 g) were added to an acetonitrile solution (25 mL) of (S)-5-benzyloxymethylmorpholin-3-one (1.36 g). The resulting reaction solution was stirred at room temperature for 2 hr, and then saturated saline and ethyl acetate were added thereto. The organic layer was separated, dried over anhydrous magnesium sulfate, and concentrated under reduced pressure. The residue was purified by silica gel column chromatography (eluting solvent: heptane-ethyl acetate system) to give 1.65 g of the title compound. The physical property values of this compound were as follows:

¹H-NMR (CDCl₃) δ (ppm): 1.50 (s, 9H), 3.57 (dd, J=8.8, 4.8 Hz, 1H), 3.68-3.75 (m, 2H), 4.08-4.28 (m, 4H), 4.53 (d, J=12.0 Hz, 1H), 4.58 (d, J=12.0 Hz, 1H), 7.25-7.36 (m, 5H).

Synthesis of {(S)-1-benzyloxymethyl-2-[2-oxo-2-(3,4,5-trifluorophenyl)ethoxy]ethyl}carbamic acid tert-butyl ester 1-Bromo-3,4,5-trifluorobenzene (446 μL) was dropwise added to a diethylether suspension (5 mL) of magnesium (249 mg) over 10 min at 40° C. The resulting reaction solution was stirred at 40° C. for 1 hr and then dropwise added to a tetrahydrofuran solution (30 mL) of (S)-3-benzyloxymethyl-5-oxomorpholine-4-carboxylic acid tert-butyl ester (1.1 g) over 10 min at −40° C. The resulting reaction solution was stirred at −40° C. for 1 hr, and a saturated ammonium chloride aqueous solution was gradually added dropwise thereto at −40° C. The resulting reaction solution was warmed up to room temperature, and then ethyl acetate was added thereto. The organic layer was separated, washed with saturated saline, dried over anhydrous magnesium sulfate, and concentrated under reduced pressure. The residue was purified by silica gel column chromatography (heptane-ethyl acetate system) to give 952 mg of the title compound. The physical property values of this compound were as follows:

¹H-NMR (CDCl₃) δ (ppm): 1.43 (s, 9H), 3.54 (dd, J=9.2, 6.0 Hz, 1H), 3.61-3.71 (m, 3H), 3.96 (m, 1H), 4.51 (s, 2H), 4.61 (s, 2H), 5.02 (m, 1H), 7.21-7.35 (m, 5H), 7.50-7.62 (m, 2H).

Synthesis of [(3S,5R)-5-(3,4,5-trifluorophenyl)morpholin-3-yl]methanol

A 4 N hydrochloric acid-ethyl acetate solution (30 mL) was added to an ethyl acetate solution (30 mL) of {(S)-1-benzyloxymethyl-2-[2-oxo-2-(3,4,5-trifluorophenyl)ethoxy]ethyl}carbamic acid tert-butyl ester (3.55 g) at room temperature. The resulting reaction solution was stirred at room temperature for 1 hr and then concentrated under reduced pressure. To a methanol solution (50 mL) of the obtained residue, 10% palladium-carbon (containing 50% water, 167 mg) was added. The resulting reaction solution was stirred in hydrogen atmosphere at room temperature for 18 hr, and the palladium carbon in the reaction solution was removed by filtration. The filtrate was concentrated under reduced pressure, and a saturated sodium hydrogencarbonate aqueous solution and ethyl acetate were added thereto. The organic layer was separated, washed with saturated saline, dried over anhydrous magnesium sulfate, and concentrated under reduced pressure. The residue was purified by silica gel column chromatography (eluting solvent: heptane-ethyl acetate system) to give 1.52 g of the title compound. The physical property values of this compound were as follows:

¹H-NMR (CDCl₃) δ (ppm): 3.13-3.22 (m, 2H), 3.34 (dd, J=10.8, 10.4 Hz, 1H), 3.53 (dd, J=10.8, 6.4 Hz, 1H), 3.67 (dd, J=10.8, 4.0 Hz, 1H), 3.77 (dd, J=10.8, 3.2 Hz, 1H), 3.85 (dd, J=10.8, 3.2 Hz, 1H), 3.96 (dd, J=10.4, 3.2 Hz, 1H), 7.02-7.25 (m, 2H).

Synthesis of 1-[(3S,5R)-3-hydroxymethyl-5-(3,4,5-trifluorophenyl)morpholin-4-yl]-(3-buten)-1-one Vinyl acetate (0.784 mL), BOPCl (2.35 g), and triethylamine (1.71 mL) were added in this order to a THF solution (50 mL) of [(3S,5R)-5-(3,4,5-trifluorophenyl)morpholin-3-yl]methanol (1.52 g) at room temperature. The resulting reaction solution was stirred at room temperature for 2 hr, and then a 1 N hydrochloric acid aqueous solution and ethyl acetate were added thereto. The organic layer was separated, washed with a 1 N sodium hydroxide aqueous solution and then with saturated saline, dried over anhydrous magnesium sulfate, and concentrated under reduced pressure. The residue was purified by silica gel column chromatography (eluting solvent: heptane-ethyl acetate system) to give 1.66 g of the title compound. The physical property values of this compound were as follows:

ESI-MS; m/z 316 [M⁺+H]. ¹H-NMR (CDCl₃) δ (ppm): 3.30 (m, 3H), 3.46 (m, 1H), 3.65 (dd, J=12.0, 4.0 Hz, 1H), 3.76 (dd, J=12.8, 4.0 Hz, 1H), 3.80 (m, 1H), 3.99 (d, J=12.0 Hz, 1H), 4.48 (d, J=12.8 Hz, 1H), 5.15-5.29 (m, 2H), 5.64 (m, 1H), 6.01 (m, 1H), 7.25-7.30 (m, 2H).

Synthesis of (E)-3-[(3S,5R)-4-(3-butenoyl)-5-(3,4,5-trifluorophenyl)morpholin-3-yl]acrylic acid methyl ester Oxalyl chloride (0.664 mL) was dropwise added to a dichloromethane solution (40 mL) of dimethylsulfoxide (0.576 mL) at −78° C. The resulting reaction solution was stirred at −78° C. for 20 min, and then a dichloromethane solution (10 mL) of 1-[(3S,5R)-3-hydroxymethyl-5-(3,4,5-trifluorophenyl)morpholin-4-yl]-(3-buten)-1-one (1.6 g) was dropwise added thereto at −78° C. The resulting reaction solution was stirred at −78° C. for 30 min, and triethylamine (3.54 mL) was dropwise added thereto. The resulting reaction solution was stirred at −78° C. for 30 min, and a saturated ammonium chloride aqueous solution was added thereto. The resulting reaction solution was warmed up to room temperature, and ethyl acetate was added thereto. The organic layer was separated, washed with saturated saline, dried over anhydrous magnesium sulfate, and concentrated under reduced pressure to give a crude aldehyde substance. Sodium hydride (60% dispersion in mineral oil, 0.304 g) was added to a solution mixture of THF (35 mL) and DMF (8 mL) of trimethylphosphonoacetate (1.46 mL) at 0° C. The resulting reaction solution was stirred at room temperature for 30 min, and a THF solution (5 mL) of the above-given crude aldehyde substance was added thereto at 0° C. The resulting reaction solution was stirred at room temperature for 30 min, and a saturated ammonium chloride aqueous solution and ethyl acetate were added thereto. The organic layer was separated, dried over anhydrous magnesium sulfate, and concentrated under reduced pressure. The residue was purified by silica gel column chromatography (eluting solvent: heptane-ethyl acetate system) to give 1.24 g of the title compound. The physical property values of this compound were as follows:

ESI-MS; m/z 370 [M⁺+H]

Synthesis of (4R,9aS)-4-(3,4,5-trifluorophenyl)-3,4,7,9a-tetrahydro-1H-pyrido[2,1-c][1,4]oxazin-6-one Grubbs catalyst second generation (285 mg) was added to a dichloromethane solution (100 mL) of (E)-3-[(3S,5R)-4-(3-butenoyl)-5-(3,4,5-trifluorophenyl)morpholin-3-yl]acrylic acid methyl ester (1.24 g). The resulting reaction solution was heated under reflux for 1.5 hr in nitrogen atmosphere. The reaction solution was cooled to room temperature, and triethylamine (3 mL) was added thereto. The resulting reaction solution was stirred for 10 min and concentrated under reduced pressure. The residue was purified by silica gel column chromatography (heptane-ethyl acetate system) to give 250 mg of the title compound. The physical property values of this compound were as follows:

ESI-MS; m/z 284 [M++H]. ¹H-NMR (CDCl₃) δ (ppm): 2.91-3.11 (m, 2H), 3.62-3.69 (m, 2H), 4.06 (dd, J=11.2, 4.0 Hz, 1H), 4.22 (dd, J=12.0, 3.2 Hz, 1H), 4.50-4.60 (m, 1H), 4.76-4.80 (m, 1H), 5.57-5.61 (m, 1H), 5.93-6.01 (m, 1H), 6.83-6.95 (m, 2H).

Synthesis of (4R,9aS)-4-(3,4,5-trifluorophenyl)hexahydropyrido[2,1-c][1,4]oxazin-6-one Platinum oxide (20.1 mg) was added to a methanol solution (6 mL) of (4R,9aS)-4-(3,4,5-trifluorophenyl)-3,4,7,9a-tetrahydro-1H-pyrido[2,1-c][1,4]oxazin-6-one (250 mg). The resulting reaction solution was stirred at room temperature for 2 hr in hydrogen atmosphere and then filtered through Celite. The filtrate was concentrated under reduced pressure to give 252 mg of the title compound. The physical property values of this compound were as follows:
ESI-MS; m/z 286 [M++H].

Synthesis of [(4R,9aS)-6-oxo-4-(3,4,5-trifluorophenyl)octahydropyrido[2,1-c][1,4]oxazin-7-yl]phosphonic acid diethyl ester In nitrogen atmosphere, trimethylsilyle iodide (0.188 mL) was added to a methylene chloride solution (6 mL) of (4R,9aS)-4-(3,4,5-trifluorophenyl)hexahydropyrido[2,1-c][1,4]oxazin-6-one (252 mg) and N,N,N',N'-tetramethylethylenediamine (0.466 mL) at 0° C. The resulting reaction solution was stirred under ice-cooling for 30 min, and iodine (336 mg) was added thereto under ice-cooling. The resulting reaction solution was stirred under ice-cooling for 1 hr, and ethyl acetate and a saturated sodium thiosulfate aqueous solution were added thereto. The organic layer was separated, washed with saturated saline, dried over magnesium sulfate, and concentrated under reduced pressure to give a crude iodinated substance. To the given crude iodinated substance, triethyl phosphite (3 mL) was added. The resulting mixture was stirred at 120° C. for 2 hr, allowed to cool to room temperature, and then concentrated under reduced pressure to give 372 mg of the title compound. The physical property values of this compound were as follows:
ESI-MS; m/z 422 [M++H].

Synthesis of (E)-(4R,9aS)-7-[3-methoxy-4-(4-methyl-1H-imidazol-1-yl)benzylidene]-4-(3,4,5-trifluorophenyl)hexahydropyrido[2,1-c][1,4]oxazin-6-one Lithium hydroxide monohydrate (63.4 mg) was added to a solution mixture of tetrahydrofuran (6 mL) and ethanol (2 mL) of [(4R,9aS)-6-oxo-4-(3,4,5-trifluorophenyl)octahydropyrido[2,1-c][1,4]oxazin-7-yl]phosphonic acid diethyl ester (372 mg) and 3-methoxy-4-(4-methyl-1H-imidazol-1-yl)benzaldehyde (229 mg) at room temperature. The resulting reaction solution was stirred at room temperature for 2 hr, and ethyl acetate and water were added thereto. The organic layer was separated, washed with saturated saline, dried over magnesium sulfate, and concentrated under reduced pressure. The residue was purified by silica gel column chromatography (carrier: Chromatorex NH, eluting solvent: heptane-ethyl acetate system) to give 163.2 mg of the title compound. The physical property values of this compound were as follows:
ESI-MS; m/z 484 [M++H]. ¹H-NMR (CDCl₃) δ (ppm): 1.60-1.75 (m, 1H), 1.96-2.02 (m, 1H), 2.30 (s, 3H), 2.72-2.83 (m, 1H), 3.12-3.20 (m, 1H), 3.62 (t, J=11.6 Hz, 1H), 3.86 (s, 3H), 3.86 (dd, J=4.8, 12.4 Hz, 1H), 3.96 (dd, J=4.0, 11.6 Hz, 1H), 4.10-4.17 (m, 1H), 4.32 (dd, J=3.6, 12.4 Hz, 1H), 5.02 (dd, J=3.6, 4.8 Hz, 1H), 6.93-6.94 (m, 1H), 6.96-7.05 (m, 4H), 7.26-7.29 (m, 1H), 7.73 (d, J=1.6 Hz, 1H), 7.76 (d, J=2.4 Hz, 1H).

Synthesis of 3-{2-methoxy-4-[(4R,9aS)-6-oxo-4-(3,4,5-trifluorophenyl)hexahydropyrido[2,1-c][1,4]oxazin-(7E)-ylidenemethyl]phenyl}-5-methyl-1-phosphonooxymethyl-3H-imidazol-1-ium trifluoroacetate Chloromethyl di-tert-butylphosphate (CAS Registry No. 229625-50-7, 20.1 mg), sodium iodide (23.2 mg), and IPEA (8.86 μL) were added to a DME solution (1 mL) of (E)-(4R,9aS)-7-[3-methoxy-4-(4-methyl-1H-imidazol-1-yl)benzylidene]-4-(3,4,5-trifluorophenyl)hexahydropyrido[2,1-c][1,4]oxazin-6-one (25 mg). The resulting reaction solution was stirred at 80° C. for 2 hr. The reaction solution was allowed to cool to room temperature and concentrated under reduced pressure. To a chloroform solution (0.5 mL) of the obtained residue, TFA (0.5 mL) was added. The resulting mixture was stirred at room temperature for 2 hr and concentrated under reduced pressure. The residue was purified by reversed phase C18 silica gel column chromatography (developing solvent: water-acetonitrile system containing 0.1% trifluoroacetic acid) to give 10.5 mg of the title compound. The physical property values of this compound were as follows:
ESI-MS; m/z 594 [M+]. ¹H-NMR (CD₃OD) δ (ppm): 1.63-1.73 (m, 1H), 2.00-2.03 (m, 1H), 2.53 (s, 3H), 2.82-2.90 (m, 1H), 3.09-3.14 (m, 1H), 3.62-3.68 (m, 1H), 3.89 (dd, J=12.4, 4.0 Hz, 1H), 3.95 (s, 3H), 3.9-3.98 (m, 1H), 4.26-4.32 (m, 1H), 4.40 (dd, J=3.6, 12.0 Hz, 1H), 5.04 (s, 1H), 5.94 (d, J=12.4 Hz, 2H), 7.10-7.15 (m, 2H), 7.22 (d, J=7.6 Hz, 1H), 7.31 (s, 1H), 7.59 (d, J=8.4 Hz, 1H), 7.66 (brs, 1H), 7.68 (s, 1H), 9.43 (s, 1H).

Example 12

Synthesis of 3-{4-{(S)-4-[(1R,2R)-2-hydroxy-1-(3,4,5-trifluorophenyl)propyl]-6-methyl-3-oxomorpholin-(2Z)-ylidenemethyl}-2-methoxyphenyl}-5-methyl-1-(phosphonooxymethyl)-3H-imidazol-1-ium trifluoroacetate

[Formula 36]

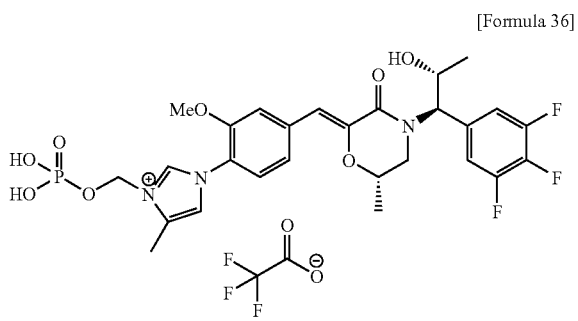

Synthesis of 1,2,3-trifluoro-5-((E)-propenyl)benzene

In nitrogen atmosphere, tetrakistriphenylphosphine palladium(0) (4.66 g) and cesium fluoride (21.4 g) were added to a solution mixture of dioxane (95 mL) and water (5 mL) of 1-bromo-3,4,5-trifluorobenzene (8.5 g) and trans-1-propen-1-ylboronic acid (4.1 g). The resulting reaction solution was stirred at 80° C. for 5 hr and then cooled to room temperature, and hexane and water were added thereto. The insoluble matter was removed by filtration. The organic layer of the filtrate was separated and washed with water. The insoluble matter was removed by filtration again. The filtrate was washed with water and then with saturated saline, dried over anhydrous magnesium sulfate, and concentrated under reduced pressure. The residue was purified by silica gel column chromatography (hexane) to give 5.83 g of the title compound. The physical property values of this compound were as follows:

$^1$H-NMR (CDCl$_3$) δ (ppm): 1.88 (d, J=6.0 Hz, 3H), 6.18 (qd, J=6.0, 16.0 Hz, 1H), 6.24 (d, J=16.0 Hz, 1H), 6.85-6.96 (m, 2H).

Synthesis of (1S,2S)-1-(3,4,5-trifluorophenyl)propane-1,2-diol

To an ice-cooled solution mixture of tert-butanol (170 mL) and water (170 mL) of AD-Mix-α (47.5 g) and methanesulfonamide (3.22 g), 1,2,3-trifluoro-5-((E)-propenyl)benzene (5.83 g) was added. The resulting reaction solution was stirred at 5° C. overnight, and then sodium sulfite (51 g) was added thereto. The resulting reaction solution was stirred at room temperature for 1 hr, and then extracted with methylene chloride three times. The organic layers were combined and washed with a 2 N sodium hydroxide aqueous solution. The sodium hydroxide layer was re-extracted with methylene chloride. The organic layers were combined, dried over anhydrous magnesium sulfate, and concentrated under reduced pressure. The obtained crude product was purified by silica gel column chromatography (hexane:ethyl acetate=9:1 to 1:1) to give 5.54 g of the title compound. The physical property values of this compound were as follows:

$^1$H-NMR (CDCl$_3$) δ (ppm): 1.12 (d, J=6.4 Hz, 3H), 2.20 (brs, 1H), 2.79 (brs, 1H), 3.78 (qd, J=6.4, 6.4 Hz, 1H), 4.34 (d, J=6.4 Hz, 1H), 6.96-7.05 (m, 2H).

Synthesis of (1R,2S)-1-azido-1-(3,4,5-trifluorophenyl)propan-2-ol

In nitrogen atmosphere, a sodium hydroxide pellet (110 mg) was added to a dimethyl carbonate solution (15 mL) of (1S,2S)-1-(3,4,5-trifluorophenyl)propane-1,2-diol (5.54 g). The resulting reaction solution was stirred at 70° C. for 45 min. Then, the dimethyl carbonate in the reaction solution was removed by blowing nitrogen at 100° C. Further, dimethyl carbonate (5 mL) was added to the residue, and the dimethyl carbonate was removed from the reaction solution by blowing nitrogen. To the residue, THF was added. The insoluble matter of the resulting mixture was removed by filtration through Celite, and the filtrate was concentrated under reduced pressure to give 6.13 g of a carbonated substance.

In nitrogen atmosphere, water (0.5 mL) and sodium azide (1.92 g) were added to a DMF solution (20 mL) of the given carbonated substance. The resulting reaction solution was stirred at 110° C. overnight, then cooled to room temperature, and diethylether was added thereto. The organic layer was separated, washed with water three times and then with saturated saline, dried over anhydrous magnesium sulfate, and concentrated under reduced pressure. The residue was purified by silica gel column chromatography (hexane:ethyl acetate=19:1 to 9:1) to give 5.16 g of the title compound. The physical property values of this compound were as follows:

$^1$H-NMR (CDCl$_3$) δ (ppm): 1.14 (d, J=6.4 Hz, 3H), 1.79 (brs, 1H), 3.97 (qd, J=6.4, 4.8 Hz, 1H), 4.42 (d, J=4.8 Hz, 1H), 6.96-7.05 (m, 2H).

Synthesis of [(1R,2S)-2-hydroxy-1-(3,4,5-trifluorophenyl)propyl]carbamic acid tert-butyl ester In nitrogen atmosphere, triphenylphosphine (5.85 g) was added to a THF solution (75 mL) of (1R,2S)-1-azido-1-(3,4,5-trifluorophenyl)propan-2-ol (5.16 g). The resulting reaction solution was stirred at room temperature for 10 min, and then water (5 mL) was added thereto. The resulting reaction solution was stirred at 60° C. for 3.5 hr, then cooled to room temperature, and di-tert-butyl dicarbonate (5.35 g) was added thereto. The resulting reaction solution was stirred at room temperature for 45 min and then concentrated under reduced pressure. The obtained residue was purified by silica gel column chromatography (toluene:ethyl acetate=9:1) to give 5.88 g of the title compound. The physical property values of this compound were as follows:

$^1$H-NMR (CDCl$_3$) δ (ppm): 1.07 (d, J=6.4 Hz, 3H), 1.41 (s, 9H), 4.10 (brs, 1H), 4.47 (brs, 1H), 5.44 (brs, 1H), 6.92-7.01 (m, 2H).

Synthesis of 4-nitrobenzoic acid (1R,2R)-2-tert-butoxycarbonylamino-1-methyl-2-(3,4,5-trifluorophenyl)ethyl ester In nitrogen atmosphere, diisopropylazodicarboxylate (6 mL) was dropwise added under ice-cooling to a THF solution (100 mL) of [(1R,2S)-2-hydroxy-1-(3,4,5-trifluorophenyl)propyl]carbamic acid tert-butyl ester (5.88 g), 4-nitrobenzoic acid (4.84 g), and triphenylphosphine (7.59 g). The resulting reaction solution was stirred at room temperature for 2 hr and then concentrated under reduced pressure. The residue was purified by silica gel column chromatography (toluene:ethyl acetate=97:3), and then the obtained powder was triturated with toluene-hexane to give 6.69 g of the title compound. The physical property values of this compound were as follows:

$^1$H-NMR (CDCl$_3$) δ (ppm): 1.37 (s, 9H), 1.38 (d, J=6.4 Hz, 3H), 4.85 (brs, 1H), 5.16 (d, J=9.2 Hz, 1H), 5.41 (qd, J=6.4, 6.0 Hz, 1H), 6.92-7.01 (m, 2H), 8.16 (d, J=8.8 Hz, 2H), 8.29 (d, J=8.8 Hz, 2H).

Synthesis of [(1R,2R)-2-hydroxy-1-(3,4,5-trifluorophenyl)propyl]carbamic acid tert-butyl ester A potassium carbonate powder (6.43 g) was added to a solution mixture of methanol (90 mL) and THF (10 mL) of 4-nitrobenzoic acid (1R,2R)-2-tert-butoxycarbonylamino-1-methyl-2-(3,4,5-trifluorophenyl)ethyl ester (7.03 g). The resulting reaction solution was stirred at room temperature for 1 hr, and ethyl acetate and water were added thereto. The organic layer was separated, washed with saturated saline twice, dried over anhydrous magnesium sulfate, and concentrated under reduced pressure. To the obtained residue, diethylether was added. The insoluble matter was removed by filtration, and the filtrate was concentrated. The residue was purified by silica gel column chromatography (toluene:ethyl acetate=6:1) to give 4.49 g of the title compound. The physical property values of this compound were as follows:

$^1$H-NMR (CDCl$_3$) δ (ppm): 1.28 (d, J=6.4 Hz, 3H), 1.44 (s, 9H), 4.01 (brs, 1H), 4.48 (brs, 1H), 5.35 (brs, 1H), 6.90-7.00 (m, 2H).

Synthesis of [(1R,2R)-2-(tert-butyldiphenylsilanyloxy)-1-(3,4,5-trifluorophenyl)propyl]carbamic acid tert-butyl ester In nitrogen atmosphere, tert-butyldiphenylsilyl chloride (2.0 mL) was added dividedly four times to a DMF solution (3 mL) of [(1R,2R)-2-hydroxy-1-(3,4,5-trifluorophenyl)-propyl]carbamic acid tert-butyl ester (610 mg) and imidazole (817 mg). The resulting reaction solution was stirred at room temperature for 3 hr, and ethyl acetate and water were added thereto. The organic layer was separated and washed with 1 N hydrochloric acid, water, a saturated sodium hydrogencarbonate aqueous solution, and saturated saline in this order. Then, the organic layer was dried over anhydrous magnesium sulfate and concentrated under reduced pressure. The residue was purified by silica gel column chromatography (hexane:diethyleter=49:1 to 19:1) to give 684 mg of the title compound. The physical property values of this compound were as follows:

$^1$H-NMR (CDCl$_3$) δ (ppm): 0.95 (s, 9H) 1.13 (d, J=6.4 Hz, 3H), 1.47 (s, 9H), 4.02 (brs, 1H), 4.46 (brs, 1H), 5.34 (brs, 1H), 6.69-6.80 (m, 2H), 7.28-7.46 (m, 8H), 7.55 (d, J=8.4 Hz, 2H).

Synthesis of (1R,2R)-2-tert-butyldiphenylsilanyloxy-1-(3,4,5-trifluorophenyl)propylamine Trifluoroacetic acid (0.5 mL) was added to a methylene chloride solution (2 mL) of [(1R,2R)-2-tert-butyldiphenylsilanyloxy-1-(3,4,5-trifluorophenyl)propyl]carbamic acid tert-butyl ester (370 mg). The resulting reaction solution was stirred at room temperature for 11 hr, and a saturated sodium hydrogencarbonate aqueous solution and ethyl acetate were added thereto. The organic layer was separated, washed with a saturated sodium hydrogencarbonate aqueous solution and with saturated saline in this order, and concentrated under reduced pressure to give 275 mg of the title compound. The physical property values of this compound were as follows:

$^1$H-NMR (CDCl$_3$) δ (ppm): 0.93 (d, J=6.4 Hz, 3H), 1.02 (s, 9H), 3.81 (d, J=4.8 Hz, 1H), 3.91 (dq, J=4.8, 6.0 Hz, 1H), 6.88-6.97 (m, 2H), 7.32-7.46 (m, 6H), 7.57 (d, J=8.0 Hz, 2H), 7.55 (d, J=8.0 Hz, 2H).

Synthesis of (S)-1-[(1R,2R)-2-tert-butyldiphenylsilanyloxy-1-(3,4,5-trifluorophenyl)propylamino]propan-2-ol A diethylether solution (1 mL) of (S)-(–)-propylene oxide (0.1 mL) and (1R,2R)-2-tert-butyldiphenylsilanyloxy-1-(3,4,5-trifluorophenyl)propylamine (212 mg) was added to a diethylether suspension (1 mL) of lithium perchlorate (750 mg). The resulting reaction solution was stirred in nitrogen atmosphere at room temperature overnight, and then methylene chloride and iced-water were added thereto. The resulting mixture was stirred. The organic layer was separated, and the water layer was re-extracted with methylene chloride. The organic layers were combined, dried over anhydrous magnesium sulfate, and concentrated under reduced pressure. The obtained residue was purified by silica gel column chromatography (heptane: ethyl acetate=9:1 to 4:1) to give 172 mg of the title compound. The physical property values of this compound were as follows:

$^1$H-NMR (CDCl$_3$) δ (ppm): 0.83 (d, J=6.0 Hz, 3H), 1.06 (s, 9H), 1.08 (m, 3H), 2.20-2.50 (m, 3H), 3.47 (brs, 1H), 3.59 (brs, 1H), 3.86 (brs, 1H), 6.78-6.95 (m, 2H), 7.36-7.48 (m, 6H), 7.67 (d, J=6.8 Hz, 4H).

Synthesis of (S)-4-[(1R,2R)-2-tert-butyldiphenylsilanyloxy-1-(3,4,5-trifluorophenyl)propyl]-6-methyl-morpholin-2,3-dione In nitrogen atmosphere, oxalyl chloride (45 μL) was dropwise added under ice-cooling to a methylene chloride solution (2 mL) of (S)-1-[(1R,2R)-2-tert-butyldiphenylsilanyloxy-1-(3,4,5-trifluorophenyl)propylamino]propan-2-ol (171 mg), TEA (0.17 mL), and 4-(N,N-dimethylamino)pyridine (8 mg). The resulting reaction solution was stirred at the same temperature for 2 hr, and then iced-water and ethyl acetate were added thereto. The organic layer was separated and washed with water, 1 N hydrochloric acid, water, a saturated sodium hydrogencarbonate aqueous solution, and saturated saline in this order. Then, the organic layer was dried over anhydrous magnesium sulfate and concentrated under reduced pressure. The residue was purified by silica gel column chromatography (heptane:ethyl acetate=9:1 to 3: 1) to give 96 mg of the title compound. The physical property values of this compound were as follows:

$^1$H-NMR (CDCl$_3$) δ (ppm): 1.02 (s, 9H), 1.19 (d, J=6.0 Hz, 3H), 1.28 (d, J=6.4 Hz, 3H), 3.20 (dd, J=5.6, 13.2 Hz, 1H), 3.68 (dd, J=2.4, 13.2 Hz, 1H), 4.42 (dq, J=5.6, 6.0 Hz, 1H) 4.62 (ddq, J=2.4, 5.6, 6.4 Hz, 1H), 5.51 (d, J=5.6 Hz, 1H), 6.82-6.94 (m, 2H), 7.40-7.54 (m, 6H), 7.62 (d, J=8.0 Hz, 2H), 7.67 (d, J=8.0 Hz, 2H).

Synthesis of (S)-4-[(1R,2R)-2-tert-butyl-diphenylsilanyloxy-1-(3,4,5-trifluorophenyl)propyl]-2-hydroxy-6-methylmorpholin-3-one In nitrogen atmosphere, a THF solution (0.25 mL) of 1.06 M lithium tri-sec-butyl borohydride was dropwise added at –20° C. to a THF solution (3 mL) of (S)-4-[(1R,2R)-2-tert-butyldiphenylsilanyloxy-1-(3,4,5-trifluorophenyl)propyl]-6-methylmorpholin-2,3-dione (95 mg). The resulting reaction solution was stirred at –20° C. for 30 min. To the reaction solution, a 5 N sodium hydroxide aqueous solution (0.03 mL) and a 30% hydrogen peroxide aqueous solution (0.07 mL) were added in this order. The resulting reaction solution was stirred under ice-cooling for 1 hr, and a sodium hydrogensulfite powder (20 mg) was added thereto. The resulting reaction solution was stirred at room temperature for 30 min, and then saturated saline and ethyl acetate were added thereto. The organic layer was separated, washed with saturated saline, dried over anhydrous magnesium sulfate, and concentrated under reduced pressure. The residue was purified by silica gel column chromatography (heptane:ethyl acetate=1:1) to give 93 mg of the title compound. The physical property values of this compound were as follows:

$^1$H-NMR (CDCl$_3$) δ (ppm): 1.01 (s, 9H), 1.11 (d, J=6.0 Hz, 3H), 1.19 (d, J=6.4 Hz, 3H), 2.88 and 2.99 (t, J=12.0 Hz, 1H), 3.12 and 3.48 (dd, J=2.4, 12.0 Hz, 1H), 3.16 and 3.91 (d, J=2.8 Hz, 1H), 4.35-4.55 (m, 2H), 5.11 and 5.30 (d, J=3.6 Hz, 1H), 5.40 and 5.49 (d, J=6.8 Hz, 1H), 6.79-6.94 (m, 2H), 7.38-7.54 (m, 6H), 7.65 (d, J=8.0 Hz, 2H), 7.69 (d, J=8.0 Hz, 2H).

Synthesis of (Z)-(S)-4-[(1R,2R)-2-hydroxy-1-(3,4,5-trifluorophenyl)propyl]-2-[1-[3-methoxy-4-(4-methyl-1H-imidazol-1-yl)phenyl]methylidene]-6-methylmorpholin-3-one In nitrogen atmosphere, an acetonitrile solution (4 mL) of (S)-4-[(1R,2R)-2-tert-butyl-diphenylsilanyloxy-1-(3,4,5-trifluorophenyl)propyl]-2-hydroxy-6-methyl-morpholin-3-one (92 mg) and triphenylphosphine hydrobromide (68 mg) was heated under reflux for 1 hr. The solvent of the reaction solution was evaporated under reduced pressure. To an ethanol solution (4 mL) of the obtained residue, 3-methoxy-4-(4-methyl-1H-imidazol-1-yl)benzaldehyde (40 mg) and TEA (0.12 mL) were added. The resulting reaction solution was stirred in nitrogen atmosphere at room temperature overnight and then concentrated under reduced pressure. To the obtained residue, trifluoroacetic acid (1 mL) was added. The resulting reaction solution was stirred at room temperature for 2 hr and then poured into a saturated sodium hydrogencarbonate aqueous solution. The resulting mixture was extracted with ethyl acetate. The organic layer was washed with a saturated sodium hydrogencarbonate aqueous solution and then with saturated saline and concentrated under reduced pressure. The residue was purified by silica gel column chromatography (carrier: Chromatorex NH, eluting solvent; heptane:ethyl acetate=1:1 to 0:1) to give 61.9 mg of the title compound. The physical property values of this compound were as follows:

ESI-MS; m/z 502 [M⁺+H]. ¹H-NMR (CDCl₃) δ (ppm): 1.33 (d, J=6.0 Hz, 3H), 1.42 (d, J=6.0 Hz, 3H), 2.34 (s, 3H), 3.20 (dd, J=9.6, 12.8 Hz, 1H), 3.61 (dd, J=2.4, 12.8 Hz, 1H), 3.85 (s, 3H), 4.42-4.52 (m, 2H), 5.35 (d, J=6.8 Hz, 1H), 6.85 (s, 1H), 6.95 (s, 1H), 7.06-7.15 (m, 2H), 7.22 (d, J=8.0 Hz, 1H), 7.33 (dd, J=1.6, 8.0 Hz, 1H), 7.53 (d, J=1.6 Hz, 1H), 7.86 (s, 1H).

Synthesis of 3-{4-{(S)-4-[(1R,2R)-2-hydroxy-1-(3,4,5-trifluorophenyl)propyl]-6-methyl-3-oxomorpholin-(2Z)-ylidenemethyl}-2-methoxyphenyl}-5-methyl-1-(phosphonooxymethyl)-3H-imidazol-1-ium trifluoroacetate In nitrogen atmosphere, (Z)-(S)-4-[(1R,2R)-2-hydroxy-1-(3,4,5-trifluorophenyl)propyl]-2-[1-[3-methoxy-4-(4-methyl-1H-imidazol-1-yl)phenyl]methylidene]-6-methylmorpholin-3-one (25 mg) was added to an acetone solution (1.5 mL) of chloromethyl di-tert-butylphosphate (CAS Registry No. 229625-50-7, 20 mg), sodium iodide (23 mg), and diisopropylamine (5 μL). The resulting reaction solution was stirred at 60° C. for 1 hr and 40 min. The reaction solution was concentrated under reduced pressure, and trifluoroacetic acid (0.3 mL) was added to the obtained residue. The resulting reaction solution was stirred at room temperature for 15 min and concentrated under reduced pressure. The residue was purified by reversed phase C18 silica gel column chromatography (developing solvent: water-acetonitrile system containing 0.1% trifluoroacetic acid) to give 19.7 mg of the title compound. The physical property values of this compound were as follows:

ESI-MS; m/z 612 [M⁺]. ¹H-NMR (CD₃OD) δ (ppm): 1.20 (d, J=6.0 Hz, 3H), 1.41 (d, J=6.0 Hz, 3H), 2.52 (s, 3H), 3.25 (dd, J=5.6, 12.8 Hz, 1H), 3.87 (dd, J=2.8, 12.8 Hz, 1H), 3.93 (s, 3H), 4.45-4.60 (m, 2H), 5.40 (d, J=8.0 Hz, 1H), 5.90 (s, 1H), 5.93 (s, 1H), 6.76 (s, 1H), 7.25-7.35 (m, 2H), 7.45 (dd, J=1.2, 8.0 Hz, 1H), 7.49 (d, J=8.0 Hz, 1H), 7.64 (d, J=2.0 Hz, 1H), 7.74 (d, J=1.2 Hz, 1H), 9.38 (d, J=2.0 Hz, 1H).

Example 13

Synthesis of 3-{4-[(6S,9aR)-6-(4-chlorophenyl)-4-oxohexahydroquinolizin-(3E)-ylidenemethyl]-2-methoxyphenyl}-5-methyl-1-phosphonooxymethyl-3H-imidazol-1-ium trifluoroacetate

[Formula 37]

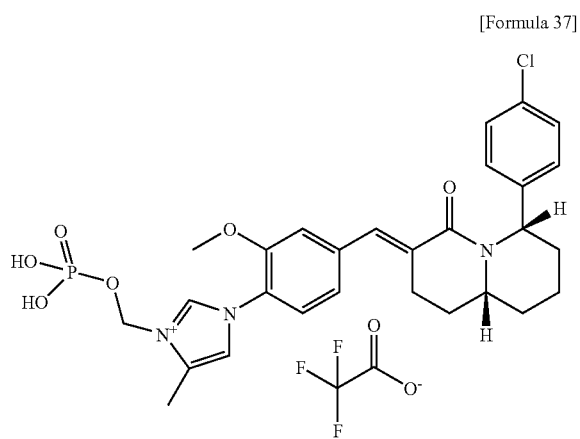

Synthesis of (2R,6S)-6-(4-chlorophenyl)piperidine-2-carboxylic acid methyl ester In nitrogen atmosphere, 4-chlorophenyl magnesium bromide (1.0 M, diethylether solution, 42 mL) was added to a THF solution (120 mL) of (R)-6-oxopiperidine-1,2-dicarboxylic acid 1-tert-butyl ester (CAS Register No. 183890-36-0, 9.00 g) over 20 min at −78° C. The resulting reaction solution was stirred at −78° C. to −40° C. for 1.5 hr and then quenched with a saturated ammonium chloride aqueous solution at −40° C. To this reaction solution, water was added. The resulting mixture was extracted with ethyl acetate. The obtained extract solution was dried over magnesium sulfate and concentrated under reduced pressure. The residue was purified by silica gel column chromatography (eluting solvent: heptane-ethyl acetate system) to give 9.53 g of (R)-2-tert-butoxycarbonylamino-6-(4-chlorophenyl)-6-oxohexanoic acid methyl ester. To an ethyl acetate solution (90 mL) of the (R)-2-tert-butoxycarbonylamino-6-(4-chlorophenyl)-6-oxohexanoic acid methyl ester (9.53 g), a 4 N hydrogen chloride-ethyl acetate solution (90 mL) was added at room temperature. The resulting reaction solution was stirred at room temperature for 12 hr and then concentrated under reduced pressure. A saturated sodium hydrogencarbonate aqueous solution was added to the residue for basification, and then chloroform was added thereto. The resulting reaction solution was stirred at room temperature for 2 hr. The organic layer was separated, dried over magnesium sulfate, and concentrated under reduced pressure. To a methanol solution (150 mL) of the residue, sodium cyano borohydride (3.29 g) and then acetic acid (4.27 mL) were added at 0° C. The resulting reaction solution was stirred at 0° C. for 1 hr and further at room temperature for 1 hr, and then a saturated sodium hydrogencarbonate aqueous solution was added thereto. The resulting mixture was extracted with chloroform. The obtained extract solution was dried over magnesium sulfate and concentrated under reduced pressure. The residue was purified by silica gel column chromatography (eluting solvent: heptane-ethyl acetate system) and further solidified from a heptane-diisopropylether system to give 2.47 g of the title compound. The physical property values of this compound were as follows:

ESI-MS; m/z 254 [M⁺+H]. ¹H-NMR (CDCl₃) δ (ppm): 1.38-1.60 (m, 3H), 1.72-1.78 (m, 1H), 1.96-2.03 (m, 1H), 2.05-2.12 (m, 1H), 2.17 (brs, 1H), 3.49 (dd, J=10.8, 2.8 Hz, 1H), 3.63 (dd, J=11.2, 2.8 Hz, 1H), 3.73 (s, 3H), 7.25-7.34 (m, 4H).

Synthesis of [(2R,6S)-6-(4-chlorophenyl)piperidin-2-yl]methanol

In nitrogen atmosphere, (2R,6S)-6-(4-chlorophenyl)piperidine-2-carboxylic acid methyl ester (2.47 g) was added to a THF suspension (50 mL) of lithium aluminium hydride (508 mg) at −20° C. The resulting reaction solution was stirred at −20° C. for 1 hr, and then water (0.51 mL), a 5 N sodium hydroxide aqueous solution (0.51 mL), and water (1.53 mL) were added thereto in this order at −20° C. The resulting reaction solution was stirred at room temperature for 15 min, and then ethyl acetate was added thereto. The resulting reaction solution was filtered through Celite, and the filtrate was concentrated under reduced pressure. The residue was purified by silica gel column chromatography (carrier: Chromatorex NH, eluting solvent: heptane-ethyl acetate system) to give 1.90 g of the title compound. The physical property values of this compound were as follows:

ESI-MS; m/z 226 [M⁺+H].

Synthesis of (6S,9aR)-6-(4-chlorophenyl)-3,6,7,8,9,9a-hexahydroquinolizin-4-one Triethylamine (2.20 mL), vinylacetic acid (1.16 mL), and BOPCl (3.47 g) were sequentially added to a THF solution of [(2R,6S)-6-(4-chlorophenyl)piperidin-2-yl]methanol (2.36 g). The resulting reaction solution was stirred at room temperature for 5 hr, and then ethyl acetate and toluene were added thereto. The organic layer was separated, washed with 0.5 N hydrochloric acid, a 0.5 N sodium hydroxide aqueous solution, a saturated sodium hydrogencarbonate aqueous solution, and saturated saline in this order, dried over magnesium sulfate, and concentrated under reduced pressure to give 1-[(2S,6R)-2-(4-chlorophenyl)-6-(hydroxymethyl)piperidin-1-yl]-(3-buten)-1-one. In nitrogen atmosphere, DMSO (1.04 mL) was added to a dichloromethane solution (70 mL) of oxalyl chloride (1.20 mL) over 5 min at −78° C. The resulting reaction solution was stirred at −78° C. for 10 min, and then a dichloromethane solution (10 mL) of the above-given 1-[(2S,6R)-2-(4-chlorophenyl)-6-(hydroxymethyl)piperidin-1-yl]-(3-buten)-1-one was added thereto over 20 min at −78° C. The resulting reaction solution was stirred at −78° C. for 20 min, and triethylamine (7.64 mL) was added thereto over 10 min at −78° C. The resulting reaction solution was stirred for 1 hr at −75° C. to −50° C. Then, the reaction solution was added to water. The resulting mixture was extracted with ethyl acetate, and the obtained extract solution was washed with saturated saline, dried over magnesium sulfate, and concentrated under reduced pressure to give a residue. Trimethyl phosphonoacetate (2.73 mL) was added to a THF (50 mL)-DMF (10 mL) solvent mixture of 60% sodium hydride (413 mg) at 0° C. The resulting reaction solution was stirred at room temperature for 30 min. To this reaction solution, a THF solution (10 mL) of the above-given residue (2.41 g) was added at 0° C. The resulting reaction solution was stirred at room temperature for 30 min, and then a cooled ammonium chloride aqueous solution was added thereto. The resulting mixture was extracted with ethyl acetate. The extract was dried over magnesium sulfate and concentrated under reduced pressure. The residue was purified by silica gel column chromatography (eluting solvent: heptane-ethyl acetate system) to give 0.65 g of a low polar isomer and 1.10 g of a high polar isomer of 3-[(2R,6S)-1-(3-butenoyl)-6-(4-chlorophenyl)piperidin-2-yl]acrylic acid methyl ester. In nitrogen atmosphere, a methylene chloride solution (60 mL) of the low polar isomer (0.65 g) of 3-[(2R, 6S)-1-(3-butenoyl)-6-(4-chlorophenyl)piperidin-2-yl]acrylic acid methyl ester and Grubbs catalyst second generation (158 mg) was stirred under reflux for 3 hr. The reaction solution was allowed to cool to room temperature, and triethylamine (0.26 mL) was added thereto. The resulting reaction solution was stirred at room temperature for 10 min and concentrated under reduced pressure. Similarly, in nitrogen atmosphere, a methylene chloride solution (100 mL) of the high polar isomer (1.10 g) of 3-[(2R,6S)-1-(3-butenoyl)-6-(4-chlorophenyl)piperidin-2-yl]acrylic acid methyl ester and Grubbs catalyst second generation (268 mg) was heated under reflux for 3 hr. The reaction solution was allowed to cool to room temperature, and triethylamine (0.44 mL) was added thereto. The resulting reaction solution was stirred at room temperature for 10 min and concentrated under reduced pressure. The residues of both isomers were combined and purified by silica gel column chromatography (eluting solvent: heptane-ethyl acetate system) to give 1.09 g of the title compound. The physical property values of this compound were as follows:

ESI-MS; m/z 262 [M$^+$+H].

Synthesis of (6S,9aR)-6-(4-chlorophenyl)-octahydroquinolizin-4-one

Platinum oxide (95 mg) was added to a methanol solution (50 mL) of (6S,9aR)-6-(4-chlorophenyl)-3,6,7,8,9,9a-hexahydroquinolizin-4-one (1.09 g). The resulting reaction solution was stirred under hydrogen atmosphere at room temperature for 1 hr and filtered through Celite. The filtrate was concentrated under reduced pressure. The residue was purified by silica gel column chromatography (eluting solvent: heptane-ethyl acetate system) to give 877 mg of the title compound. The physical property values of this compound were as follows:

ESI-MS; m/z 264 [M$^+$+H]

Synthesis of (6S,9aR)-6-(4-chlorophenyl)-3-{1-[3-methoxy-4-(4-methyl-1H-imidazol-1-yl)phenyl]-(E)-methylidene}octahydroquinolizin-4-one In nitrogen atmosphere, trimethylsilyl iodide (0.74 mL) was added to a methylene chloride solution (25 mL) of (6S, 9aR)-6-(4-chlorophenyl)-octahydroquinolizin-4-one (877 mg) and N,N,N',N'-tetramethylethylenediamine (1.76 mL) at 0° C. The resulting reaction solution was stirred at 0° C. for 30 min, and then iodine (1.26 g) was added thereto at 0° C. The resulting reaction solution was stirred at 0° C. for 1 hr, and a sodium thiosulfate aqueous solution and ethyl acetate were added thereto. The organic layer was separated, washed with saturated saline, dried over magnesium sulfate, and concentrated under reduced pressure to give (6S,9aR)-6-(4-chlorophenyl)-3-iodooctahydroquinolizin-4-one. A mixture of the (6S,9aR)-6-(4-chlorophenyl)-3-iodooctahydroquinolizin-4-one and triethyl phosphite (10 mL) was stirred at 120° C. for 2 hr. This reaction solution was allowed to cool to room temperature and then concentrated under reduced pressure to give [(6S,9aR)-6-(4-chlorophenyl)-4-oxooctahydroquinolizin-3-yl]phosphonic acid diethyl ester. To a solution mixture of tetrahydrofuran (21 mL) and ethanol (7 mL) of the [(6S,9aR)-6-(4-chlorophenyl)-4-oxooctahydroquinolizin-3-yl]phosphonic acid diethyl ester and 3-methoxy-4-(4-methyl-1H-imidazol-1-yl)benzaldehyde (869 mg), lithium hydroxide monohydrate (422 mg) was added. The resulting reaction solution was stirred at room temperature for 2 hr, and then ethyl acetate and a saturated sodium hydrogencarbonate aqueous solution were added thereto. The organic layer was separated, washed with saturated saline, dried over magnesium sulfate, and concentrated under reduced pressure. The residue was purified by silica gel column chromatography (carrier: Chromatorex NH, eluting solvent: heptane-ethyl acetate system) and then by silica gel column chromatography (eluting solvent: heptane-ethyl acetate system and then ethyl acetate-methanol system) to give 1.07 g of the title compound. The physical property values of this compound were as follows:

ESI-MS; m/z 462 [M$^+$+H]. $^1$H-NMR (CDCl$_3$) δ (ppm): 1.33-1.80 (m, 5H), 2.00-2.09 (m, 1H), 2.11-2.30 (m, 2H), 2.31 (s, 3H), 2.66-2.78 (m, 1H), 3.07-3.17 (m, 1H), 3.76-3.87 (m, 1H), 3.86 (s, 3H), 5.51 (brs, 1H), 6.92-6.95 (m, 1H), 7.02-7.07 (m, 2H), 7.20 (brd, J=8.4 Hz, 2H), 7.24-7.32 (m, 3H), 7.72 (d, J=1.6 Hz, 1H), 7.81 (brd, J=2.8 Hz, 1H).

Synthesis of 3-{4-[(6S,9aR)-6-(4-chlorophenyl)-4-oxohexahydroquinolizin-(3E)-ylidenemethyl]-2-methoxyphenyl}-5-methyl-1-phosphonooxymethyl-3H-imidazol-1-ium trifluoroacetate An acetone solution (2 mL) of (6S,9aR)-6-(4-chlorophenyl)-3-{1-[3-methoxy-4-(4-methyl-1H-imidazol-1-yl)phenyl]-(E)-methylidene}octahydroquinolizin-4-one (100 mg), chloromethyl di-tert-butylphosphate (CAS Registry No. 229625-50-7, 84 mg), sodium iodide (97 mg), and IPEA (0.01 mL) were stirred at 60° C. for 1 hr. The reaction solution was allowed to cool to room temperature. Then, the insoluble matter was removed by filtration, and the filtrate was concentrated under reduced pressure. To the obtained residue, a solvent mixture of methylene chloride and TFA (1:1, 2 mL) was added. The resulting reaction solution was stirred at room temperature for 1 hr and then concentrated under reduced pressure. The residue was purified by reversed phase C18 silica gel column chromatography (developing solvent: water-acetonitrile system containing 0.1% trifluoroacetic acid) to give 60 mg of the title compound. The physical property values of this compound were as follows:
ESI-MS; m/z 572 [M$^+$]. $^1$H-NMR (CD$_3$OD) δ (ppm): 1.27-1.38 (m, 1H), 1.49-1.84 (m, 4H), 2.05-2.13 (m, 1H), 2.18-2.40 (m, 2H), 2.53 (s, 3H), 2.77-2.89 (m, 1H), 3.05-3.13 (m, 1H), 3.87-3.95 (m, 1H), 3.96 (s, 3H), 5.42-5.46 (m, 1H), 5.92 (d, J=12.8 Hz, 2H), 7.21-7.25 (m, 1H), 7.25-7.29 (m, 2H), 7.30-7.35 (m, 3H), 7.60 (d, J=8.0 Hz, 1H), 7.66-7.70 (m, 2H), 9.41 (d, J=1.6 Hz, 1H).

Example 14

Synthesis of 3-{2-methoxy-4-[(1S,6R,9aR)-1-methyl-4-oxo-6-(3,4,5-trifluorophenyl)tetrahydro-[1,4]oxazino[3,4-c][1,4]oxazine-(3Z)-ylidenemethyl]phenyl}-5-methyl-1-phosphonooxymethyl-3H-imidazole-1-ium trifluoroacetate

[Formula 38]

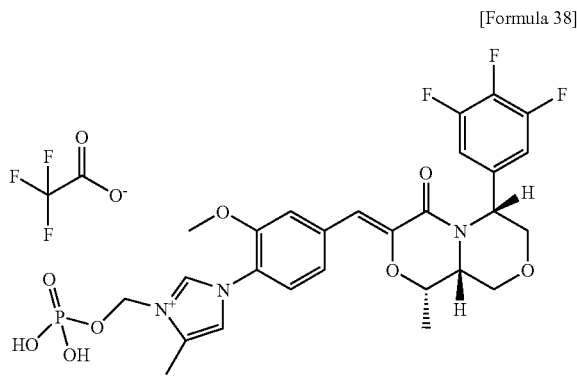

Synthesis of (R)-5-((R)-1-benzyloxyethyl)morpholine-3-one

To a solution of ((1R,2R)-2-benzyloxy-1-hydroxymethylpropyl)carbamic acid t-butyl ester (83.1 g, CAS No. 133565-43-2) in toluene (400 mL) was added tetrabutylammonium hydrogen sulfate (24.1 g) in 50% aqueous sodium hydroxide (400 mL). t-Butylbromoacetate (125 mL) was dropwise added to the resultant solution while cooling with ice, and this solution was stirred at the same temperature for 3 hours. Then, water (500 mL) and toluene (500 mL) was added to the solution. The organic layer was separated and washed with brine. The organic layer was then dried over anhydrous magnesium sulfate. Solvent was removed by distillation under reduced pressure, to thereby obtain a crude product (122.5 g) containing ((2R,3R)-3-benzyloxy-2-t-butylcarbonylaminobutoxy)acetic acid t-butyl ester. To a solution of the obtained crude product (118g) in dichloromethane (315 mL) was added trifluoroacetic acid (315 mL), and the resultant solution was stirred for 2 hours at room temperature. Solvent was removed by distillation under reduced pressure, and the resultant product was diluted with methanol (350 mL). To the resultant solution was dropwise added thionyl chloride (96.9 mL) while cooling with ice, and then the solution was stirred for 1 hour at room temperature. Solvent was removed by distillation under reduced pressure, and the resultant product was diluted with methanol (315 mL). To the resultant solution was then dropwise added sodium methoxide (165 mL, 28% methanol solution) while cooling with ice. Solvent was removed by distillation under reduced pressure, and the resultant product was diluted with ethyl acetate and water. The organic layer was partitioned and successively washed with 1 N hydrochloric acid and brine. The organic layer was then dried over anhydrous magnesium sulfate. Solvent was removed by distillation under reduced pressure, and the resulting product was purified by silica gel column chromatography (ethyl acetate), to thereby obtain the titled compound (61.57 g). The physical properties of the compound were as follows.
ESI-MS; m/z 236 [M$^+$+H]. $^1$H-NMR (CDCl$_3$) δ (ppm): 1.21 (d, J=5.6 Hz, 3H), 3.44-3.52 (m, 3H), 3.90-4.95 (m, 1H), 4.04-4.21 (m, 2H), 4.40 (d, J=11.2 Hz, 1H), 4.66 (d, J=11.2 Hz, 1H), 6.51 (brs, 1H), 7.28-7.38 (m, 5H).

Synthesis of (R)-3-((R)-1-benzyloxyethyl)-5-oxomorpholine-4-carboxylic acid t-butyl ester To a solution of (R)-5-((R)-1-benzyloxyethyl)morpholine-3-one (61.6 g) in acetonitrile (600 mL) was successively added di-t-butyldicarbonate (74.4 g), triethylamine (72.6 mL) and 4-dimethylaminopyridine (1.6 g), and the resultant solution was stirred for 4 hours at room temperature. To the solution was then added imidazole (8.92 g), and the reaction mixture was stirred for 30 minutes at room temperature. Solvent was removed by distillation under reduced pressure, and the resulting product was diluted with ethyl acetate. The ethyl acetate solution was washed 3 times with cooled 0.1 N hydrochloric acid, followed by washing with brine. The organic layer was then dried over anhydrous magnesium sulfate. Solvent was removed by distillation under reduced pressure. The formed solid was washed with hexane, to thereby obtain the titled compound (69.97 g). The physical properties of the compound were as follows.
$^1$H-NMR (CDCl$_3$) δ (ppm): 1.27 (d, J=6.0 Hz, 3H), 1.46 (s, 9H), 3.74 (dd, J=12.4, 3.2 Hz, 1H), 3.77-3.84 (m, 1H), 4.09-4.22 (m, 4H), 4.49 (d, J=12.0 Hz, 1H), 4.60 (d, J=12.0 Hz, 1H), 7.25-7.34 (m, 5H).

Synthesis of ((2R,3R)-3-benzyloxy-2-t-butoxycarbonyl-aminobutoxy)acetic acid

To a solution of (R)-3-((R)-1-benzyloxyethyl)-5-oxomorpholine-4-carboxylic acid t-butyl ester (40 g) in methanol (250 mL) was added 2 N aqueous sodium hydroxide (250 mL), and the resultant solution was stirred for 3 hours at room temperature. The methanol was removed by distillation under reduced pressure, and the resulting product was diluted with ether. The water layer was partitioned and then washed with ether. The pH of the water layer was adjusted to about 4 using 5% aqueous citric acid. The resultant solution was twice extracted using ethyl acetate, and the organic layer was then washed twice with water. The organic layer was dried over anhydrous magnesium sulfate. Solvent was removed by distillation under reduced pressure, to thereby obtain the titled compound (42.1 g). The physical properties of the compound were as follows.

ESI-MS; m/z 376 [M$^+$+Na]. $^1$H-NMR (CDCl$_3$) δ (ppm): 1.24 (d, J=6.4 Hz, 3H), 1.44 (s, 9H), 3.54-3.63 (m, 2H), 3.77-3.80 (brm, 2H), 4.04 (s, 1H), 4.04 (s, 1H), 4.38 (d, J=11.6 Hz, 1H), 4.61 (d, J=11.2 Hz, 1H), 4.98 (brd, J=3.6 Hz, 1H), 7.25-7.36 (m, 5H).

Synthesis of {(1R,2R)-2-benzyloxy-1-[(methoxymethylcarbamoyl)methoxymethyl]propyl}carbamic acid t-butyl ester To a solution of ((2R,3R)-3-benzyloxy-2-t-butoxycarbonylaminobutoxy)acetic acid (42.1 g) in DMF (400 mL) was successively added N,N-diisopropylethylamine (41 mL), N,O-dimethylhydroxyamine hydrochloride (17.4 g), EDCI (34.3 g) and HOBt (24.1 g), and the resultant solution was stirred for 16 hours at room temperature. Solvent was removed by distillation under reduced pressure, and the resultant product was diluted with ethyl acetate and water. The organic layer was partitioned, washed with brine, and then dried over anhydrous magnesium sulfate. Solvent was removed by distillation under reduced pressure. After passing the residue through a silica pad (silica gel 500 cc), the filtrate was concentrated by distillation under reduced pressure, to thereby obtain the titled compound (46.0 g). The physical properties of the compound were as follows.

ESI-MS; m/z 419 [M$^+$+Na]. $^1$H-NMR (CDCl$_3$) δ (ppm): 1.23 (d, J=6.4 Hz, 3H), 1.43 (s, 9H), 3.17 (s, 3H), 3.58 (dd, J=9.6, 5.6 Hz, 1H), 3.63-3.64 (m, 1H), 3.66 (s, 3H), 3.78-3.84 (m, 1H), 3.90-3.98 (m, 1H), 4.24 (s, 2H), 4.48 (d, J=11.2 Hz, 1H), 4.61 (d, J=11.2 Hz, 1H), 5.02 (d, J=8.4 Hz, 1H), 7.25-7.33 (m, 5H).

Synthesis of {(1R,2R)-2-benzyloxy-1-[2-oxo-2-(3,4,5-trifluorophenyl)ethoxymethyl]propyl}carbamic acid t-butyl ester

Preparation of 3,4,5-trifluorophenylmagnesium bromide

Under a nitrogen atmosphere, 1-bromo-3,4,5-trifluorophenyl (7.47 mL) was added to a suspension of magnesium (1.59 g) and iodine (one piece) in diethyl ether (65 mL) while heating. Once refluxing had stopped, the solution was stirred at room temperature for 1 hour. Under a nitrogen atmosphere, a solution of {(1R,2R)-2-benzyloxy-1-[(methoxymethylcarbamoyl)methoxymethyl]propyl}carbamic acid t-butyl ester (10 g) in tetrahydrofuran (200 mL) was cooled to −50° C., and the above-prepared 3,4,5-trifluorophenylmagnesium bromide was dropped thereto. The temperature of the solution was raised over 4 hours from −40° C. to 0° C., and then the solution was diluted with saturated aqueous ammonium chloride. The resultant solution was extracted using ethyl acetate. The organic layer was washed with brine, and then dried over anhydrous magnesium sulfate. Solvent was removed by distillation under reduced pressure, and the resulting residue was passed through a silica pad (carrier: silica gel, 300 cc; elution solvent: ethyl acetate, 1.5 L). The filtrate was concentrated by distillation under reduced pressure, to thereby obtain a crude product (13.89 g) containing the titled compound. The physical properties of this crude product were as follows.

$^1$H-NMR (CDCl$_3$) δ (ppm): 1.23 (d, J=6.4 Hz, 3H), 1.43 (s, 9H), 3.55-3.62 (m, 2H), 3.79-3.86 (m, 2H), 4.39 (d, J=11.2 Hz, 1H), 4.58-4.63 (m, 3H), 4.89 (brd, J=9.6 Hz, 1H), 7.24-7.34 (m, 5H), 7.57 (dd, J=7.6, 6.4 Hz, 2H).

Synthesis of (R)-1-[(3R,5R)-5-(3,4,5-trifluorophenyl)-morpholine-3-yl]ethanol To a solution of {(1R,2R)-2-benzyloxy-1-[2-oxo-2-(3,4,5trifluorophenyl)ethoxymethyl]-propyl}carbamic acid t-butyl ester (13.9 g, purity: about 84.9%) in ethyl acetate (20 mL) was added a 4 N hydrochloric acid/ethyl acetate solution (63 mL), and the resultant solution was stirred at room temperature for 5 hours. Solvent was removed by distillation under reduced pressure, and to the resultant product in methanol (100 ml) was added 10% palladium-carbon (1 g, 50% water content). Under a hydrogen atmosphere, the reaction mixture was stirred for 10 hours. The catalyst was filtered off over Celite. To the resultant product was added methanol (100 ml) and 20% palladium hydroxide-carbon (1 g), and under a hydrogen atmosphere, the reaction mixture was stirred for 8 hours. The catalyst was filtered off over Celite, and solvent was removed by distillation under reduced pressure. The residue was passed through a silica pad (carrier: silica gel, 500 cc; elution solvent: 5% triethylamine/ethyl acetate, 6 L), and the filtrate was then concentrated by distillation under reduced pressure. The residue was diluted with ethyl acetate. The resultant solution was washed with brine, and then dried over anhydrous magnesium sulfate. Solvent was removed by distillation under reduced pressure, to thereby obtain the titled compound (3.97 g). The physical properties of the compound were as follows. ESI-MS; m/z 262 [M$^+$+H]. $^1$H-NMR (CDCl$_3$) δ (ppm): 1.22 (d, J=6.8 Hz, 3H), 1.93 (brs, 1H), 2.88 (ddd, J=10.0, 6.8, 3.6 Hz, 1H), 3.14 (dd, J=11.2, 10.0 Hz, 1H), 3.31 (dd, J=10.4, 10.4 Hz, 1H), 3.64 (ddd, J=12.4, 6.0, 6.0 Hz, 1H), 3.76 (dd, J=11.2, 3.2 Hz, 1H), 3.83 (dd, J=11.2, 3.2 Hz, 1H), 3.91 (dd, J=10.0, 3.2 Hz, 1H), 7.05 (dd, J=8.0, 6.4 Hz, 2H).

Synthesis of (S)-1-[(3R,5R)-5-(3,4,5-trifluorophenyl)morpholine-3-yl]ethanol Under a nitrogen atmosphere, to a tetrahydrofuran (50 mL) solution containing (R)-1-[(3R,5R)-5-(3,4,5-trifluorophenyl)morpholine-3-yl]ethanol (2.25 g), triphenylphosphine (4.51 g) and 4-nitrobenzoic acid (2.88 g) was dropwise added diisopropyl azodicarboxylate (3.39 mL) while cooling with ice. The resultant solution was stirred at the same temperature for 30 minutes, and then at room temperature for 2 hours. The reaction solution was diluted with water and ethyl acetate, and the organic layer was partitioned. The organic layer was washed with brine, and then dried over anhydrous magnesium sulfate. Solvent was removed by distillation under reduced pressure, and the resulting residue was crudely purified by silica gel column chromatography (heptane/ethyl acetate 8/2→1/1), to thereby obtain a crude product (3.6 g) of 4-nitrobenzoic acid (S)-1-[(3R,5R)-5-(3,4,5-trifluorophenyl)morpholine-3-yl]ethyl ester. A solution of the obtained crude product (3.53 g) in methanol (300 mL) was added sodium methoxide (4.39 mL, 28% methanol solution), and the resultant solution was stirred at room temperature for 1 hour. Solvent was removed by distillation under reduced pressure, and the resultant product was diluted with ethyl acetate and water. The organic layer was partitioned, washed with brine, and then dried over anhydrous magnesium sulfate. Solvent was removed by distillation under reduced pressure, and the resulting residue was purified by silica gel column chromatography (heptane/ethyl acetate 9/1→1/1), to thereby obtain the titled compound (1.19 g). The physical properties of the compound were as follows.

ESI-MS; m/z 262 [M$^+$+H]. $^1$H-NMR (CDCl$_3$) δ (ppm): 1.22 (d, J=6.8 Hz, 3H), 2.29 (brs, 1H), 3.03 (ddd, J=10.4, 3.6, 3.6 Hz, 1H), 3.14 (dd, J=11.2, 10.4 Hz, 1H), 3.42 (dd, J=10.8, 10.8 Hz, 1H), 3.73-3.79 (m, 2H), 3.79-4.00 (m, 2H), 7.05 (dd, J=8.0, 7.2 Hz, 2H).

Synthesis of (1S,6R,9aR)-1-methyl-6-(3,4,5-trifluorophenyl)tetrahydro[1,4]oxazino[3,4-c][1,4]oxazine-3,4-dione To a solution consisting of (S)-1-[(3R,5R)-5-(3,4,5-trifluorophenyl)morpholine-3-yl]ethanol (1.18 g) and pyridine (5 mL) in dichloromethane (20 mL) was dropwise added oxalyl chloride (1.18 mL) while cooling with ice. The resultant solution was stirred at the same temperature for 30 minutes, and then at room temperature for 1 hour. The reaction solution was diluted with water, and the organic layer was partitioned. The organic layer was then dried over anhydrous magnesium sulfate. Solvent was removed by distillation under reduced pressure, and the resulting residue was purified by silica gel column chromatography (heptane/ethyl acetate→ethyl acetate), to thereby obtain the titled compound (912 mg). The physical properties of the compound were as follows. ESI-MS; m/z 316 [M$^+$+H]. $^1$H-NMR (CDCl$_3$) δ (ppm): 1.54 (d, J=7.2 Hz, 3H), 3.50 (dd, J=11.6, 11.6 Hz, 1H), 3.68 (dd, J=12.4, 8.0 Hz, 1H), 4.06 (dd, J=11.6, 4.4 Hz, 1H), 4.18 (dd, J=12.4, 4.8 Hz, 1H), 4.49 (ddd, J=12.0, 4.4, 4.0 Hz, 1H), 4.64-4.70 (m, 1H), 4.78 (dd, J=8.4, 5.2 Hz, 1H), 7.01 (dd, J=8.0, 6.4 Hz, 2H).

Synthesis of (Z)-(1S,6R,9aR)-3-[3-methoxy-4-(4-methyl-1H-imidazole-1-yl)benzylidene]-1-methyl-6-(3,4,5-trifluorophenyl)tetrahydro[1,4]oxazino[3,4-c][1,4]oxazine-4-one A tetrahydrofuran (25 mL) solution containing (1S,6R,9aR)-1-methyl-6-(3,4,5-trifluorophenyl)tetrahydro[1,4]oxazino[3,4-c][1,4]oxazine-3,4-dione (912 mg) was cooled to −30° C., and to the solution was then dropwise added L-Selectride (4.0 mL, 1.02 M tetrahydrofuran solution). The resultant solution was stirred for 2 hours in the range of −20° C. to −30° C. To the reaction solution was added 5 N aqueous sodium hydroxide (606 μL), and the mixture was then stirred for 20 minutes in the range of −20° C. to 0° C. To the solution was added hydrogen peroxide water (294 μL, 35% aqueous), and the mixture was then stirred for 20 minutes at 0° C. To the resultant solution was then added sodium bisulfite (316 mg), and the mixture was then stirred at room temperature for 20 minutes. The resultant solution was then diluted with ethyl acetate and brine, and the organic layer was partitioned. The organic layer was then dried over anhydrous magnesium sulfate, and solvent was removed by distillation under reduced pressure. A solution of the residue and triphenylphosphonium bromide (1.06 g) in acetonitrile (25 mL) was heated to reflux for 2 hours. The temperature of the solution was returned to room temperature. To the solution was added 3-methoxy-4-(4-methyl-1H-imidazole-1-yl)benzaldehyde (723 mg) and triethylamine (841 μL), and the reaction mixture was then stirred for 12 hours at room temperature. Solvent was removed by distillation under reduced pressure, and the resultant product was then diluted with ethyl acetate and brine. The organic layer was partitioned and then dried over anhydrous magnesium sulfate. Solvent was removed by distillation under reduced pressure, and the resulting residue was coarsely purified by silica gel column chromatography (carrier: Chromatorex NH; elution solvent: hexane/ethyl acetate→ethyl acetate). The resultant product was then further crystallized using a mixed solvent of ether/ethyl acetate/heptane (4/1/20), to thereby obtain the titled compound (714 mg). The physical properties of the compound were as follows.

$^1$H-NMR (CDCl$_3$) δ (ppm): $^1$H-NMR (CDCl$_3$) δ (ppm): 1.49 (d, J=6.4 Hz, 3H), 2.29 (s, 3H), 3.50 (dd, J=11.6, 11.6 Hz, 1H), 3.68 (dd, J=12.4, 8.0 Hz, 1H), 3.84 (s, 3H), 4.03 (dd, J=11.2, 4.0 Hz, 1H), 4.19 (dd, J=12.0, 4.8 Hz, 1H), 4.41 (ddd, J=11.6, 3.6, 3.6 Hz, 1H), 4.54 (dq, J=13.2, 3.2 Hz, 1H), 4.79 (dd, J=8.0, 4.8 Hz, 1H), 6.83 (s, 1H), 6.92 (s, 1H), 7.03 (dd, J=8.0, 6.4 Hz, 2H), 7.20 (d, J=8.8 Hz, 1H), 7.35 (s, 1H), 7.36 (d, J=6, 8 Hz, 1H), 7.72 (s, 1H).

Synthesis of 3-{2-methoxy-4-[(1S,6R,9aR)-1-methyl-4-oxo-6-(3,4,5-trifluorophenyl)tetrahydro-[1,4]oxazino[3,4-c][1,4]oxazine-(3Z)-ylidenemethyl]phenyl}-5-methyl-1-phosphonooxymethyl-3H-imidazole-1-ium trifluoroacetate A solution consisting of (Z)-(1S,6R,9aR)-3-[3-methoxy-4-(4-methyl-1H-imidazole-1-yl)benzylidene]-1-methyl-6-(3,4,5-trifluorophenyl)tetrahydro-[1,4]oxazino[3,4-c][1,4]oxazine-4-one (95 mg), chloromethyl ditertiary butyl phosphate (CAS No. 229625-50-7, 73.7 mg), sodium iodide (85.4 mg) and IPEA (8.2 μL) in acetone (3 mL) was heated to reflux for 3 hours. The reaction solution was left to cool to room temperature, and then concentrated under reduced pressure. To a solution of the obtained residue in chloroform (2 mL) was added TFA (2 mL), and the resultant mixture was stirred for 2 hours at room temperature. The reaction solution was then concentrated under reduced pressure, and the residue was purified using reversed-phase system C18 silica gel column chromatography (eluting solvent: 0.1% trifluoroacetic-acid-containing water/acetonitrile system), to thereby obtain the titled compound (53 mg). The physical properties of the compound were as follows. ESI-MS; m/z 610 [M$^+$]. $^1$H-NMR (CD$_3$OD) δ (ppm): 1.50 (d, J=6.8 Hz, 3H), 2.52 (d, J=0.8 Hz, 3H), 3.56 (dd, J=11.6, 8.0 Hz, 1H), 3.69 (dd, J=12.0, 8.4 Hz, 1H), 3.93 (s, 3H), 4.06 (dd, J=11.2, 4.4 Hz, 1H), 4.20 (dd, J=12.4, 4.8 Hz, 1H), 4.45-4.50 (m, 1H), 4.66-4.72 (m, 1H), 4.80 (dd, J=8.0, 5.2 Hz, 1H), 5.94 (d, J=12.8 Hz, 2H), 6.76 (s, 1H), 7.17 (dd, J=8.8, 6.4 Hz, 2H), 7.50 (d, J=8.4 Hz, 1H), 7.53 (d, J=8.4 Hz, 1H), 7.64 (s, 1H), 7.67 (s, 1H), 9.41 (s, 1H).

Example 15

Synthesis of 3-{4-[(1S,6R,9aR)-6-(4-chlorophenyl)-1-methyl-4-oxotetrahydro[1,4]oxazino[3,4-c][1,4]oxazine-(3Z)-ylidenemethyl]-2-methoxyphenyl}-5-methyl-1-phosphonooxymethyl-3H-imidazole-1-ium trifluoroacetate

[Formula 39]

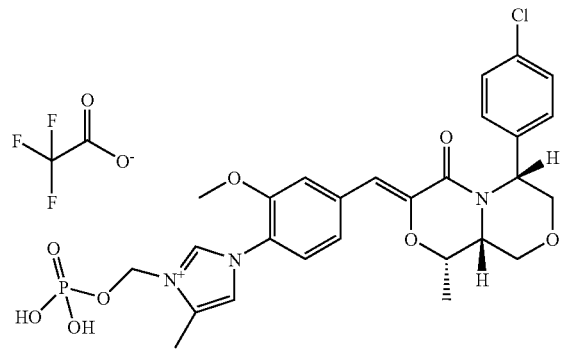

Synthesis of {(1R,2R)-2-benzyloxy-1-[2-(4-chlorophenyl)-2-oxoethoxymethyl]propyl}carbamic acid t-butyl ester A solution of {(1R,2R)-2-benzyloxy-1-[(methoxymethylcarbamoyl)methoxymethyl]propyl}carbamic acid t-butyl ester (2.42 g) in tetrahydrofuran (50 mL) was cooled to −40° C. and to the mixture was then dropwise added 4-chlorophenylmagnesium bromide (18.3 mL, 1 M tetrahydrofuran solution). The resultant solution was stirred for 1 hour at –40° C., after which the temperature was slowly raised to 0° C. The solution was then diluted with saturated aqueous ammonium chloride. The resultant solution was extracted using ethyl acetate. The organic layer was washed with brine, and then dried over anhydrous magnesium sulfate. Solvent was removed by distillation under reduced pressure, and the resulting residue was purified by silica gel column chromatography (heptane/ethyl acetate 9/1→1/1), to thereby obtain the titled compound (2.61 g). The physical properties of this crude product were as follows.

ESI-MS; m/z 470 [M$^+$+Na]. $^1$H-NMR (CDCl$_3$) δ (ppm): 1.23 (d, J=6.4 Hz, 3H), 1.43 (s, 9H), 3.55-3.65 (m, 2H), 3.79-3.86 (m, 2H), 4.39 (d, J=11.2 Hz, 1H), 4.58-4.64 (m, 3H), 4.92 (brd, J=9.2 Hz, 1H), 7.25-7.32 (m, 5H), 7.41 (d, J=8.4 Hz, 2H), 7.84 (d, J=8.4z, 2H).

Synthesis of {(3R,5R)-3-((R)-1-benzyloxyethyl)-5-(4-chlorophenyl)morpholine

A solution of {(1R,2R)-2-benzyloxy-1-[2-(4-chlorophenyl)-2-oxoethoxymethyl]propyl}carbamic acid t-butyl ester (2.61 g) in a 4 N hydrochloric acid/ethyl acetate solution (40 mL) was stirred at room temperature for 1 hour. Solvent was removed by distillation under reduced pressure, and the resultant product was diluted with methanol (30 ml). While cooling with ice, to the stirring solution was added sodium cyanoborohydride (733 mg), and the resultant solution was stirred overnight at room temperature. Solvent was removed by distillation under reduced pressure. The resultant product was diluted with ethyl acetate. This solution was successively washed with saturated sodium bicarbonate water and brine, and the organic layer was then dried over anhydrous magnesium sulfate. Solvent was removed by distillation under reduced pressure, and the resulting residue was purified by silica gel column chromatography (heptane/ethyl acetate 95/5→3/2), to thereby obtain the titled compound (1.435 g). The physical properties of this crude product were as follows.

ESI-MS; m/z 332 [M$^+$+H]. $^1$H-NMR (CDCl$_3$) δ (ppm): 1.20 (d, J=6.4 Hz, 3H), 2.59 (brs, 1H), 2.97 (ddd, J=10.4, 8.4, 3.2 Hz, 1H), 3.18 (dd, J=10.4, 10.4 Hz, 1H), 3.24 (dd, J=10.8, 10.8 Hz, 1H), 3.37-3.44 (m, 1H), 3.74 (dd, J=10.8, 3.2 Hz, 1H), 3.85 (dd, J=10.8, 3.2 Hz, 1H), 3.87 (dd, J=10.4, 3.2 Hz, 1H), 4.42 (d, J=11.2 Hz, 1H), 4.64 (d, J=11.2 Hz, 1H), 7.26-7.31 (m, 9H).

Synthesis of (R)-1-[(3R,5R)-5-(4-chlorophenyl)-morpholine-3-yl]ethanol

To a solution of (3R,5R)-3-((R)-1-benzyloxyethyl)-5-(4-chlorophenyl)morpholine (1.44 g) in a dichloromethane (20 mL) was added trimethylsilyl iodide (3.07 mL), and the resultant solution was stirred at room temperature for 10 hours. To this solution was further added trimethylsilyl iodide (3.07 mL), and the mixture was stirred at room temperature for 4 days. To the solution was again added trimethylsilyl iodide (3.07 mL), and the mixture was stirred at room temperature for 1 day. To the solution was further added trimethylsilyl iodide (3.07 mL), and the reaction mixture was stirred at room temperature for 10 hours. The resultant solution was diluted with 5 N aqueous sodium hydroxide. The organic layer was partitioned and then dried over anhydrous magnesium sulfate. The resulting product was purified by silica gel column chromatography (heptane/ethyl acetate), to thereby obtain the titled compound (903 mg). The physical properties of this crude product were as follows.

$^1$H-NMR (CDCl$_3$) δ (ppm): 1.21 (d, J=6.0 Hz, 3H), 2.90 (ddd, J=10.0, 5.6, 2.4 Hz, 1H), 3.22 (dd, J=10.4, 10.4 Hz, 1H), 3.36 (dd, J=10.8, 10.8 Hz, 1H), 3.60-3.67 (m, 1H), 3.77 (dd, J=10.8, 3.2 Hz, 1H), 3.86 (dd, J=10.8, 3.2 Hz, 1H), 3.96 (dd, J=10.4z, 3.2 Hz, 1H), 7.26-7.36 (m, 4H).

Synthesis of 4-nitrobenzoic acid (S)-1-[(3R,5R)-5-(4-chlorophenyl)morpholine-3-yl]ethyl ester Under a nitrogen atmosphere, to a tetrahydrofuran (20 mL) solution containing (R)-1-[(3R,5R)-5-(4-chlorophenyl)morpholine-3-yl]ethanol (903 mg), triphenylphosphine (1.81 g) and 4-nitrobenzoic acid (1.16 g) was dropwise added diisopropyl azodicarboxylate (1.36 mL) while cooling with ice. The resultant solution was stirred at the same temperature for 30 minutes, and then at room temperature for 2 hours. The reaction solution was diluted with water and ethyl acetate, and the organic layer was partitioned. The organic layer was washed with brine, and then dried over anhydrous magnesium sulfate. Solvent was removed by distillation under reduced pressure, and the resulting residue was purified by silica gel column chromatography (heptane/ethyl acetate 9/1→8/2→7/3), to thereby obtain the titled compound (1.46 g). The physical properties of the compound were as follows.

$^1$H-NMR (CDCl$_3$) δ (ppm): 1.44 (d, J=6.4 Hz, 3H), 3.21 (dd, J=10.8, 10.8 Hz, 1H), 3.32 (ddd, J=10.0, 4.8, 2.4 Hz, 1H), 3.40 (dd, J=10.4, 10.4 Hz, 1H), 3.78 (dd, J=10.8, 3.2 Hz, 1H), 3.97-4.02 (m, 2H), 5.18-5.24 (m, 1H), 7.28 (d, J=8.4 Hz, 2H), 7.33 (d, J=8.4 Hz, 2H), 8.19 (d, J=8.8 Hz, 2H), 8.30 (d, J=8.8 Hz, 2H).

Synthesis of (S)-1-[(3R,5R)-5-(4-chlorophenyl)-morpholine-3-yl]ethanol

To a solution of 4-nitrobenzoic acid (S)-1-[(3R,5R)-5-(4-chlorophenyl)morpholine-3-yl]ethyl ester (1.46 g mg) in methanol (40 mL) was added sodium methoxide (1.9 mL, 28% methanol solution), and the resultant solution was stirred at room temperature for 1 hour. Solvent was removed by distillation under reduced pressure, and the resultant product was diluted with ethyl acetate and water. The organic layer was partitioned and washed with brine. The organic layer was then dried over anhydrous magnesium sulfate. Solvent was removed by distillation under reduced pressure, and the resulting residue was purified by silica gel column chromatography (heptane/ethyl acetate 9/1→1/3), to thereby obtain the titled compound (833 mg). The physical properties of the compound were as follows.

ESI-MS; m/z 242 [M$^+$+H]. $^1$H-NMR (CDCl$_3$) δ (ppm): 1.22 (d, J=6.8 Hz, 3H), 2.49 (brs, 1H), 3.03 (ddd, J=10.0, 3.2, 3.2 Hz, 1H), 3.20 (dd, J=10.4, 10.4 Hz, 1H), 3.46 (dd, J=3.2, 3.2 Hz, 1H), 3.74-3.79 (m, 2H), 3.96 (dd, J=11.2, 3.2 Hz, 1H), 4.03 (dd, J=10.0, 3.2 Hz, 1H), 7.28-7.35 (m, 4H).

Synthesis of (1S,6R,9aR)-6-(4-chlorophenyl)-1-methyltetrahydro[1,4]oxazino[3,4-c][1,4]oxazine-3,4-dione To a solution consisting of (S)-1-[(3R,5R)-5-(4-chlorophenyl)morpholine-3-yl]ethanol (833 g) and pyridine (4 mL) in dichloromethane (15 mL) was dropwise added oxalyl chloride (833 μL) while cooling with ice. The resultant solution was stirred at the same temperature for 30 minutes, and then at room temperature for 1 hour. The reaction solution was diluted with water, and the organic layer was partitioned. The organic layer was then dried over anhydrous magnesium sulfate. Solvent was removed by distillation under reduced pressure, and the resulting residue was purified by silica gel column chromatography (heptane/ethyl acetate→ethyl acetate), to thereby obtain the titled compound (686 mg). The physical properties of the compound were as follows. ESI-MS; m/z 296 [M$^+$+H]. $^1$H-NMR (CDCl$_3$) δ (ppm): 1.51 (d, J=6.4 Hz, 3H), 3.52 (dd, J=12.0, 12.0 Hz, 1H), 3.78 (dd, J=12.4, 8.0 Hz, 1H), 4.02 (dd, J=11.6, 4.4 Hz, 1H), 4.18 (dd, J=12.4, 4.8 Hz, 1H), 4.51 (ddd, J=11.2, 4.0, 4.0 Hz, 1H), 4.61-4.67 (m, 1H), 4.89 (dd, J=8.0, 4.8 Hz, 1H), 7.32 (s, 4H).

Synthesis of (Z)-(1S,6R,9aR)-6-(4-chlorophenyl)-3-{1-[3-methoxy-4-(4-methyl-1H-imidazole-1-yl)phenyl]methylidene}-1-methyltetrahydro[1,4]-oxazino[3,4-c][1,4]oxazine-4-one A tetrahydrofuran (20 mL) solution containing (1S,6R,9aR)-6-(4-chlorophenyl)-1-methyltetrahydro-[1,4]oxazino[3,4-c][1,4]oxazine-3,4-dione (685 mg) was cooled to −30° C., and L-Selectride (3.01 mL, 1.02 M tetrahydrofuran solution) was then dropped thereto. The resultant solution was stirred for 2 hours in the range of −20° C. to −30° C. To the reaction solution was added 5 N aqueous sodium hydroxide (460 μL), and the reaction mixture was stirred for 20 minutes in the range of −20° C. to 0° C. To the resultant solution was then added hydrogen peroxide water (221 μL, 35% aqueous), and the mixture was stirred for 20 minutes at 0° C. To the resultant solution was then added sodium bisulfite (237 mg), and the mixture was stirred at room temperature for 20 minutes. The resultant solution was then diluted with ethyl acetate and brine, and the organic layer was partitioned. The organic layer was then dried over anhydrous magnesium sulfate, and solvent was removed by distillation under reduced pressure. A solution of the residue and triphenylphosphonium bromide (796 mg) in acetonitrile (19.4 mL) was heated to reflux for 2 hours. The temperature of the solution was returned to room temperature. To the solution was then added 3-methoxy-4-(4-methyl-1H-imidazole-1-yl)benzaldehyde (543 mg) and triethylamine (633 μL), and the resultant solution was stirred for 12 hours at room temperature. Solvent was removed by distillation under reduced pressure, and the resultant product was then diluted with ethyl acetate and brine. The organic layer was partitioned and then dried over anhydrous magnesium sulfate. Solvent was removed by distillation under reduced pressure, and the resulting residue was purified by silica gel column chromatography (carrier: Chromatorex NH; elution solvent: hexane/ethyl acetate→ethyl acetate), to thereby obtain the titled compound (640 mg). The physical properties of the compound were as follows.

ESI-MS; m/z 480 [M$^+$+H]. $^1$H-NMR (CDCl$_3$) δ (ppm): 1.48 (d, J=6.4 Hz, 3H), 2.29 (s, 3H), 3.51 (dd, J=11.2, 11.2 Hz, 1H), 3.74 (dd, J=12.0, 8.0 Hz, 1H), 3.83 (s, 3H), 3.99 (dd, J=11.2, 4.0 Hz, 1H), 4.18 (dd, J=12.4, 4.8 Hz, 1H), 4.41 (ddd, J=11.6, 4.0, 4.0 Hz, 1H), 4.50-4.56 (m, 1H), 4.86 (dd, J=8.0, 4.4 Hz, 1H), 7.82 (s, 1H), 6.91 (s, 1H), 7.18 (d, J=8.8 Hz, 1H), 7.32-7.35 (m, 6H), 7.69 (s, 1H).

Synthesis of 3-{4-[(1S,6R,9aR)-6-(4-chlorophenyl)-1-methyl-4-oxotetrahydro[1,4]oxazino[3,4-c][1,4]oxazine-(3Z)-ylidenemethyl]-2-methoxyphenyl}-5-methyl-1-phosphonooxymethyl-3H-imidazole-1-ium trifluoroacetate A solution consisting of (Z)-(1S,6R,9aR)-6-(4-chlorophenyl)-3-{1-[3-methoxy-4-(4-methyl-1H-imidazole-1-yl)phenyl]methylidene}-1-methyltetrahydro[1,4]oxazino[3,4-c][1,4]oxazine-4-one (93 mg), chloromethyl ditertiary butyl phosphate (CAS No. 229625-50-7, 72.1 mg), sodium iodide (83.6 mg) and IPEA (8.0 μL) in acetone (3 mL) was heated to reflux for 3 hours. The reaction solution was left to cool to room temperature, and then concentrated under reduced pressure. To a solution of the obtained residue in chloroform (2 mL) was added TFA (2 mL), and the resultant mixture was stirred for 2 hours at room temperature. The reaction solution was then concentrated under reduced pressure, and the residue was purified using reversed-phase system C18 silica gel column chromatography (eluting solvent: 0.1% trifluoroacetic-acid-containing water/acetonitrile system), to thereby obtain the titled compound (53 mg). The physical properties of the compound were as follows. ESI-MS; m/z 590 [M$^+$]. $^1$H-NMR (CD$_3$OD) δ (ppm): 1.49 (d, J=6.8 Hz, 3H), 2.52 (s, 3H), 3.56-2.62 (m, 1H), 3.73 (dd, J=12.0, 8.0 Hz, 1H), 3.92 (s, 3H), 4.04 (dd, J=11.2, 4.0 Hz, 1H), 4.19 (dd, J=12.4, 4.8 Hz, 1H), 4.49 (ddd, J=11.2, 4.0, 4.0 Hz, 1H), 4.66-4.70 (m, 1H), 4.85 (dd, J=8.0, 5.2 Hz, 1H), 5.98 (d, J=12.4 Hz, 2H), 6.72 (s, 1H), 7.34 (d, J=8.8 Hz, 2H), 7.38 (d, J=8.8 Hz, 2H), 7.48 (d, J=8.4 Hz, 1H), 7.52 (d, J=8.4 Hz, 1H), 7.63 (s, 1H), 7.68 (s, 1H), 9.43 (d, J=1.2 Hz, 1H).

Example 16

Synthesis of 3-{2-methoxy-4-[(1S,6S,8aR)-1-methyl-4-oxo-6-(3,4,5-trifluorophenyl)tetrahydropyrrolo[2,1-c][1,4]oxazine-(3Z)-ylidenemethyl]phenyl}-5-methyl-1-phosphonooxymethyl-3H-imidazole-1-ium trifluoroacetate

[Formula 40]

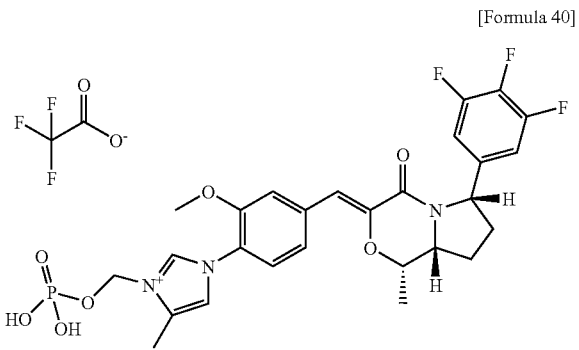

Synthesis of (R)-5-oxopyrrolidine-1,2-dicarboxylic acid 1-t-butyl ester 2-ethyl ester To a tetrahydrofuran (200 mL) solution containing D-pyroglutamic acid ethyl ester (20 g), triethylamine (35.2 mL) and di-t-butyldicarbonate (30.5 g) was added 4-dimethylaminopyridine (1.55 g), and the resultant solution was stirred for 5 hours at room temperature. To the solution was then added imidazole (1.3 g), and the reaction mixture was stirred for 30 minutes at room temperature. Solvent was removed by distillation under reduced pressure, and the resulting product was diluted with ethyl acetate. The ethyl acetate solution was successively washed 3 times with 0.2 N hydrochloric acid, and then washed with brine. The organic layer was then dried over anhydrous magnesium sulfate. Solvent was removed by distillation under reduced pressure, to thereby obtain the titled compound (31.08 g). The physical properties of the compound were as follows.

¹H-NMR (CDCl₃) δ (ppm): 1.30 (t, J=7.2 Hz, 3H), 1.49 (s, 9H), 1.99-2.06 (m, 1H), 2.26-2.37 (m, 1H), 2.44-2.52 (m, 1H), 2.58-2.68 (m, 1H), 4.23 (q, J=7.2 Hz, 2H), 4.59 (dd, J=9.6, 3.2 Hz, 1H).

Synthesis of (R)-2-t-butoxycarbonylamino-5-oxo-5-(3,4,5-trifluorophenyl)valeric acid ethyl ester Preparation of 3,4,5-trifluorophenylmagnesium bromide Under a nitrogen atmosphere, 1-bromo-3,4,5-trifluorophenyl (2 mL) was added to a suspension of magnesium (1.7 g) and iodine (one piece) in diethyl ether (60 mL), and the resultant solution was heated. To the solution was then dropwise added 1-bromo-3,4,5-trifluorophenyl (5.6 mL). Once refluxing had stopped, the solution was stirred at room temperature for 1 hour.

Under a nitrogen atmosphere, a solution of (R)-5-oxopyrrolidine-1,2-dicarboxylic acid 1-t-butyl ester 2-ethyl ester (15 g) in tetrahydrofuran (200 mL) was dropwise added to the above-prepared 3,4,5-trifluorophenylmagnesium bromide at −40° C. The solution was stirred at the same temperature for 1 hour, and then diluted with saturated aqueous ammonium chloride. The resultant solution was extracted using ethyl acetate. The organic layer was washed with brine, and then dried over anhydrous magnesium sulfate. Solvent was removed by distillation under reduced pressure, and the resulting residue was passed through a silica pad (carrier: Chromatorex 400 cc; elution solvent: ethyl acetate). The filtrate was concentrated under reduced pressure to thereby obtain the titled compound (22.34 g). The physical properties of the compound were as follows.

ESI-MS; m/z 412 [M⁺+Na].

Synthesis of (R)-5-(3,4,5-trifluorophenyl)-3,4-dihydro-2H-pyrrole-2-carboxylic acid ethyl ester To a solution of (R)-2-t-butoxycarbonylamino-5-oxo-5-(3,4,5-trifluorophenyl)valeric acid ethyl ester (22.2 g) in ethyl acetate (30 mL) was added 4 N hydrochloric acid/ethyl acetate (163 mL), and the resultant solution was stirred at room temperature for 3 hours. Solvent was removed by distillation under reduced pressure, and the resulting residue was diluted with ethyl acetate and sodium bicarbonate water. The organic layer was partitioned, washed with brine, and then dried over anhydrous magnesium sulfate. Solvent was removed by distillation under reduced pressure, to thereby obtain the titled compound (12.4 g). The physical properties of this crude product were as follows.

ESI-MS; m/z 272 [M⁺+H]. ¹H-NMR (CDCl₃) δ (ppm): 1.32 (t, J=7.2 Hz, 3H), 2.24-2.31 (m, 1H), 2.33-2.43 (m, 1H), 2.86-2.95 (m, 1H), 3.03-3.12 (m, 1H), 4.23 (q, J=7.2 Hz, 2H), 4.87-4.92 (m, 1H), 7.51 (dd, J=8.4, 6.4 Hz, 2H).

Synthesis of (2R,5S)-5-(3,4,5-trifluorophenyl)-pyrrolidine-2-carboxylic acid ethyl ester To a solution of (R)-5-(3,4,5-trifluorophenyl)-3,4-dihydro-2H-pyrrole-2-carboxylic acid ethyl ester (12.4 g) in ethanol (170 mL) was added 10% palladium-carbon (1.2 g, 50% water content). Under a hydrogen atmosphere, the reaction mixture was stirred for 16 hours at room temperature. The catalyst was filtered off over Celite. The obtained filtrate was concentrated, to thereby obtain the titled compound (11.98 g). The physical properties of the compound were as follows.

¹H-NMR (CDCl₃) δ (ppm): 1.31 (t, J=7.2 Hz, 3H), 1.61-1.69 (m, 1H), 2.05-2.21 (m, 3H), 3.93 (dd, J=8.0, 5.6 Hz, 1H), 4.19 (dd, J=7.2, 7.2 Hz, 1H), 4.22 (q, J=7.2 Hz, 2H), 7.11 (dd, J=8.4, 6.4 Hz, 2H).

Synthesis of (2R,5S)-5-(3,4,5-trifluorophenyl)-pyrrolidine-1,2-dicarboxylic acid 1-t-butyl ester 2-ethyl ester A dimethylformamide (120 mL) solution containing (2R,5S)-5-(3,4,5-trifluorophenyl)pyrrolidine-2-carboxylic acid ethyl ester (11.98 g), triethylamine (10.5 mL) and di-t-butyl-dicarbonate (13.4 g) was stirred for 5 hours at room temperature. To the reaction mixture was then added imidazole (1.79 g), and the mixture was stirred for 20 minutes at room temperature. The resultant solution was then diluted with water and ethyl acetate, and the organic layer was partitioned. The organic layer was successively washed with 0.2 N hydrochloric acid (twice) and brine, and then dried over anhydrous magnesium sulfate. Solvent was removed by distillation under reduced pressure, and the resulting residue was passed through a silica pad. The filtrate was concentrated under reduced pressure to thereby obtain the titled compound (16.4 g). The physical properties of the compound were as follows.

ESI-MS; m/z 396 [M⁺+Na].

Synthesis of (S)-2-((R)-hydroxylmethyl)-5-(3,4,5-trifluorophenyl)pyrrolidine-1-carboxylic acid t-butyl ester To a solution of (2R,5S)-5-(3,4,5-trifluorophenyl)pyrrolidine-1,2-dicarboxylic acid 1-t-butyl ester 2-ethyl ester (6 g) in tetrahydrofuran (80 mL) was added lithium borohydride (554 mg) while cooling with ice. The resultant solution was stirred at the same temperature for 30 minutes, and then at room temperature for 13 hours. The reaction solution was diluted with water and ethyl acetate, and the organic layer was partitioned. The organic layer was washed with brine and then dried over anhydrous magnesium sulfate. Solvent was removed by distillation under reduced pressure, and the resulting product was purified by silica gel column chromatography (heptane/ethyl acetate), to thereby obtain the titled compound (4.65 g). The physical properties of the compound were as follows.

ESI-MS; m/z 354 [M⁺+Na]. ¹H-NMR (CDCl₃) δ (ppm): 1.26 (s, 9H), 1.78-1.83 (m, 1H), 2.01-2.06 (m, 2H), 2.24-2.30 (m, 1H), 3.71-3.83 (m, 2H), 4.08-4.14 (m, 1H), 4.46 (brs, 1H), 4.75 (dd, J=10.8, 10.8 Hz, 1H), 6.88 (dd, J=8.0, 6.4 Hz, 2H).

Synthesis of (S)-2-((R)-1-hydroxylethyl-5-(3,4,5-trifluorophenyl)pyrrolidine-1-carboxylic acid t-butyl ester A tetrahydrofuran (90 mL) solution containing dimethylsulfoxide (1.68 mL) was cooled to −78° C. and oxalyl chloride (1.88 mL) was then dropwise added thereto. After the solution was stirred at the same temperature for 5 minutes, a solution of (S)-2-((R)-hydroxylmethyl)-5-(3,4,5-trifluorophenyl)pyrrolidine-1-carboxylic acid t-butyl ester (4.65 g) in tetrahydrofuran (10 mL) was added to the solution. After the reaction mixture was stirred at the same temperature for 40 minutes, triethylamine (8.7 mL) was added to the reaction mixture. This solution was then stirred for 1 hour in the range of −78° C. to room temperature. The reaction solution was diluted with aqueous ammonium chloride and ethyl acetate, and the organic layer was partitioned. The organic layer was washed with brine and then dried over anhydrous magnesium sulfate. Solvent was removed by distillation under reduced pressure. The residue was diluted with tetrahydrofuran (100 mL), and the resultant solution was cooled to −78° C. To the reaction solution was dropwise added methylmagnesium bromide (17.3 mL, 0.97 M tetrahydrofuran solution). The solution was then stirred at the same temperature for 1 hour. The reaction solution was diluted with aqueous ammonium chloride and ethyl acetate, and the organic layer was partitioned. The organic layer was washed with brine and then dried over anhydrous magnesium sulfate. Solvent was removed by distillation under reduced pressure. The residue was purified by silica gel column chromatography (heptane/ethyl acetate), to thereby obtain the titled compound (3.71 g). The physical properties of this crude product were as follows.

ESI-MS; m/z 368 [M$^+$+Na].

Synthesis of (R)-1-[(S)-5-(3,4,5-trifluorophenyl)-pyrrolidine-2-yl]ethanol

To a solution of (S)-2-((R)-1-hydroxylethyl-5-(3,4,5-trifluorophenyl)pyrrolidine-1-carboxylic acid t-butyl ester (3.71 g) in ethyl acetate (20 mL) was added 4 N hydrochloric acid/ethyl acetate (26.8 mL), and the resultant solution was stirred at room temperature for 2 hours. Solvent was removed by distillation under reduced pressure, and the resultant product was diluted with 5 N aqueous sodium hydroxide and dichloromethane. The organic layer was partitioned and then dried over anhydrous magnesium sulfate. Solvent was removed by distillation under reduced pressure, to thereby obtain the titled compound (2.6 g). The physical properties of this crude product were as follows.

ESI-MS; m/z 246 [M$^+$+H].

Synthesis of (1S,4R,6S)-1-methyl-6-(3,4,5-trifluorophenyl)tetrahydropyrrole[2,1-c][1,4]oxazine-3,4-dione A solution of (R)-1-[(S)-5-(3,4,5-trifluorophenyl)pyrrolidine-2-yl]ethanol (2.6 g) in diethyl oxalate (14.3 mL) was stirred at 120° C. for 4 hours. The temperature of the solution was then returned to room temperature, and solvent was removed by distillation under reduced pressure. The resulting residue was purified by silica gel column chromatography (heptane/ethyl acetate→ethyl acetate), to thereby obtain the titled compound (860 mg). The physical properties of the compound were as follows.

$^1$H-NMR (CDCl$_3$) δ (ppm): 1.54 (d, J=6.8 Hz, 3H), 1.84-1.95 (m, 1H), 2.15-2.23 (m, 2H), 2.43-2.54 (m, 1H), 4.39-4.44 (m, 1H), 4.87-4.93 (m, 1H), 5.08 (d, J=9.2 Hz, 1H), 6.92-7.00 (m, 2H).

Synthesis of (Z)-(1S,6S,8aR)-3-[3-methoxy-4-(4-methyl-1H-imidazole-1-yl)benzylidene]-1-methyl-6-(3,4,5-trifluorophenyl)tetrahydropyrrole[2,1-c][1,4]oxazine-4-one To a tetrahydrofuran (25 mL) solution containing (1S,4R,6S)-1-methyl-6-(3,4,5-trifluorophenyl)tetrahydropyrrole[2,1-c][1,4]oxazine-3,4-dione (860 mg) was dropwise added L-Selectride (3.78 mL, 1.02 M tetrahydrofuran solution) while cooling with ice. The resultant solution was stirred for 1 hour at the same temperature. The reaction solution was diluted with 5 N aqueous sodium hydroxide (570 µL), and stirred for 20 minutes at 0° C. To the resultant solution was then added hydrogen peroxide water (279 µL, 35% aqueous), and the reaction mixture was stirred for 20 minutes at 0° C. To the resultant solution was then added sodium bisulfite (298 mg), and the mixture was stirred at room temperature for 20 minutes. The resultant solution was then diluted with ethyl acetate and brine, and the organic layer was partitioned. The organic layer was then dried over anhydrous magnesium sulfate, and solvent was removed by distillation under reduced pressure. A solution of the residue and triphenylphosphonium bromide (1 g) in acetonitrile (25 mL) was heated to reflux for 1 hour. The temperature of the solution was returned to room temperature. To the solution was then added 3-methoxy-4-(4-methyl-1H-imidazole-1-yl)benzaldehyde (683 mg) and triethylamine (796 µL), and the resultant solution was stirred for 10 hours at room temperature. The resultant solution was then diluted with ethyl acetate and brine, and the organic layer was partitioned. The organic layer was then dried over anhydrous magnesium sulfate. Solvent was removed by distillation under reduced pressure, and the resulting residue was purified by silica gel column chromatography (twice; carrier: Chromatorex NH, elution solvent: heptane/ethyl acetate→ethyl acetate, and carrier: Chromatorex, elution solvent: heptane/ethyl acetate→ethyl acetate→ethyl acetate/methanol), to thereby obtain the titled compound (700 mg). The physical properties of the compound were as follows.

ESI-MS; m/z 484 [M$^+$+H]. $^1$H-NMR (CDCl$_3$) δ (ppm): 1.48 (d, J=6.8 Hz, 3H), 1.77-1.88 (m, 1H), 2.00-2.05 (m, 1H), 2.11-2.17 (m, 1H), 2.29 (s, 3H), 2.35-2.46 (m, 1H), 3.84 (s, 3H), 4.24 (ddd, J=9.2, 4.8, 4.8 Hz, 1H), 4.78-4.84 (m, 1H), 5.06 (d, J=9.6 Hz, 1H), 6.81 (s, 1H), 6.92 (dd, J=1.2, 1.2 Hz, 1H), 6.94 (dd, J=8.4, 6.0 Hz, 2H), 7.19 (d, J=8.0 Hz, 1H), 7.38 (s, 1H), 7.40 (dd, J=8.0, 1.6 Hz, 1H), 7.70 (d, J=1.2 Hz, 1H).

Synthesis of 3-{2-methoxy-4-[(1S,6S,8aR)-1-methyl-4-oxo-6-(3,4,5-trifluorophenyl)tetrahydropyrrolo[2,1-c][1,4]oxazine-(3Z)-ylidenemethyl]phenyl}-5-methyl-1-phosphonooxymethyl-3H-imidazole-1-ium trifluoroacetate A solution consisting of (Z)-(1S,6S,8aR)-3-[3-methoxy-4-(4-methyl-1H-imidazole-1-yl)benzylidene]-1-methyl-6-(3,4,5-trifluorophenyl)tetrahydropyrrole-[2,1-c][1,4]oxazine-4-one (100 mg), chloromethyl ditertiary butyl phosphate (CAS No. 229625-50-7, 77.5 mg), sodium iodide (89.8 mg) and IPEA (8.6 µL) in acetone (3 mL) was heated to reflux for 3 hours. The reaction solution was left to cool to room temperature, and then concentrated under reduced pressure. To a solution of the obtained residue in chloroform (2 mL) was added TFA (2 mL), and the resultant mixture was stirred for 2 hours at room temperature. The reaction solution was then concentrated under reduced pressure, and the resulting residue was purified using reversed-phase system C18 silica gel column chromatography (eluting solvent: 0.1% trifluoroacetic-acid-containing water/acetonitrile system), to thereby obtain the titled compound (65 mg). The physical properties of the compound were as follows.

ESI-MS; m/z 594 [M$^+$]. $^1$H-NMR (CD$_3$OD) δ (ppm): 1.48 (d, J=6.8 Hz, 3H), 1.88-2.04 (m, 2H), 2.14-2.20 (m, 1H), 2.42-2.52 (m, 1H), 2.53 (s, 3H), 3.94 (s, 3H), 4.32 (ddd, J=11.6, 5.2, 4.0 Hz, 1H), 4.91-4.97 (m, 1H), 5.10 (d, J=11.2 Hz, 1H), 5.98 (d, J=12.4 Hz, 2H), 6.76 (s, 1H), 7.11 (dd, J=8.4, 6.8 Hz, 2H), 7.50 (d, J=8.4 Hz, 1H), 7.56 (d, J=8.8 Hz, 1H), 7.68 (s, 1H), 7.69 (s, 1H), 9.44 (d, J=1.2 Hz, 1H)

Example 17

Synthesis of 3-{4-[(1S,6R,9aR)-6-(3,4-difluorophenyl)-1-methyl-4-oxotetrahydro[1,4]oxazino[3,4-c][1,4]oxazine-(3Z)-ylidenemethyl]-2-methoxyphenyl}-5-methyl-1-phosphonooxymethyl-3H-imidazole-1-ium trifluoroacetate

[Formula 41]

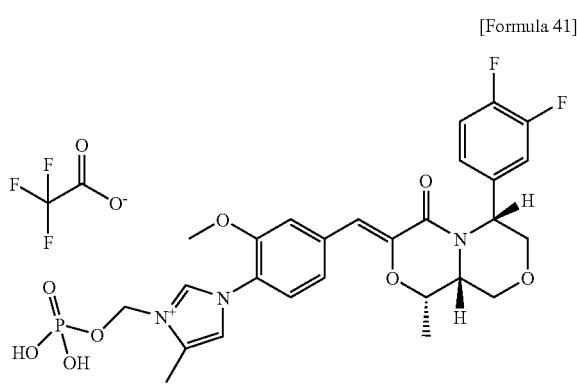

Synthesis of {(S)-2-benzyloxy-1-[2-(3,4-difluorophenyl)-2-oxoethoxymethyl]ethyl}carbamic acid t-butyl ester

Preparation of 3,4-difluorophenylmagnesium bromide

Under a nitrogen atmosphere, 1-bromo-3,4-difluorobenzene (1.46 mL) was dropwise added to a tetrahydrofuran (60 mL) suspension containing magnesium (1.47 g) and iodine (one piece), and the resultant solution was heated. Once the reaction had started, 1-bromo-3,4-difluorobenzene (10.2 mL) was dropwise added thereto, and the resultant solution was stirred at room temperature for another 1 hour.

Under a nitrogen atmosphere, a solution of (S)-3-benzyloxymethyl-5-oxomorpholine-4-carboxylic acid t-butyl ester (16.2 g) in tetrahydrofuran (100 mL) was cooled to −40° C., and the above-prepared 3,4-difluorophenylmagnesium bromide was dropwise added thereto. After stirring at the same temperature for 30 minutes, the solution was diluted with saturated aqueous ammonium chloride. The resultant solution was extracted using ethyl acetate. The organic layer was washed with brine, and then dried over anhydrous magnesium sulfate. Solvent was removed by distillation under reduced pressure, to thereby obtain the titled compound (22.2 g). The physical properties of this crude product were as follows.

ESI-MS; m/z 458 [M++Na].

Synthesis of (3R,5S)-3-(3,4-difluorophenyl)-5-hydroxymethylmorpholine-4-carboxylic acid 9H-fluorene-9-ylmethyl ester To a solution of {(S)-2-benzyloxy-1-[2-(3,4-difluorophenyl)-2-oxoethoxymethyl]ethyl}carbamic acid t-butyl ester (26.8 g) in ethyl acetate (50 mL) was added a 4 N hydrochloric acid/ethyl acetate solution (100 mL), and the resultant solution was stirred at room temperature for 2.5 hours. Solvent was removed by distillation under reduced pressure, and the resultant product was twice subjected to azeotropy with toluene. The resulting residue was diluted with a mixed solvent of ether/heptane (1/1, 300 mL) to form a solid. The supernatant was decanted off, and the residue solid was dried under reduced pressure. To a solution of the residue solid in methanol (200 ml) was added 10% palladium-carbon (9.1 g, 50% water content). Under a hydrogen atmosphere, this mixture was stirred for 18 hours. The catalyst was then filtered off, and the filtrate was concentrated by distillation under reduced pressure. The resulting product was then diluted with ethyl acetate and saturated sodium bicarbonate water. The organic layer was partitioned, washed with brine, and then dried over anhydrous magnesium sulfate. Solvent was removed by distillation under reduced pressure. The resultant residue was diluted with tetrahydrofuran (120 mL) and saturated sodium bicarbonate water (120 mL). To this solution was added 9-fluorenylmethyl chloroformate (16.6 g) while cooling with ice. The temperature of the solution was returned to room temperature, and the solution was then stirred for 14 hours. The reaction solution was diluted with ethyl acetate and water, and the organic layer was partitioned. The organic layer was washed with brine, and then dried over anhydrous magnesium sulfate. Solvent was removed by distillation under reduced pressure, and the resulting residue was diluted with ethyl acetate (50 mL) and heptane (5 mL). The resultant solution was then left to stand for 4 days at 4° C. The precipitated solid was collected by filtering, to thereby obtain the titled compound (7.19 g). The filtrate was purified by silica gel column chromatography (hexane/ethyl acetate 4/1→1/1), and again solidified using ethyl acetate. The titled compound (3.69 g) was collected by filtering. The physical properties of the compound were as follows.

ESI-MS; m/z 452 [M++H].

Synthesis of (3R,5R)-3-(3,4-difluorophenyl)-5-(1-hydroxyethyl)morpholine-4-carboxylic acid 9H-fluorene-9-ylmethyl ester Under a nitrogen atmosphere, a tetrahydrofuran (35 mL) solution containing dimethylsulfoxide (530 µL) was cooled to −78° C. To the reaction solution was then dropwise added oxalyl chloride (608 µL), and this solution was stirred at the same temperature for 5 minutes. A solution of tetrahydrofuran (25 mL) containing (3R,5S)-3-(3,4-difluorophenyl)-5-hydroxymethylmorpholine-4-carboxylic acid 9H-fluorene-9-ylmethyl ester (2.5 g) was then dropwise added thereto, and the solution was stirred at the same temperature for 30 minutes. To the reaction solution was then added triethylamine (3.7 mL), and the reaction mixture was stirred at the same temperature for 30 minutes followed by stirring at room temperature for 1 hour. The resultant solution was diluted with saturated aqueous ammonium chloride, and this solution was extracted with ethyl acetate. The organic layer was dried over anhydrous magnesium sulfate. Solvent was removed by distillation under reduced pressure. The resultant residue was diluted with tetrahydrofuran (15 mL), and the resultant solution was cooled to −78° C. To the reaction solution was dropwise added methylmagnesium bromide (8.33 mL, 0.97 M tetrahydrofuran solution), and the resultant solution was stirred at the same temperature for 1 hour. The solution was then diluted with saturated aqueous ammonium chloride and ethyl acetate, and the organic layer was partitioned. The organic layer was washed with brine and then dried over anhydrous magnesium sulfate. Solvent was removed by distillation under reduced pressure. The residue was purified by silica gel column chromatography (heptane/ethyl acetate 95/5→1/1), to thereby obtain the titled compound (950 mg). The physical properties of this crude product were as follows.

ESI-MS; m/z 488 [M++Na]

Synthesis of 1-[(3R,5R)-5-(3,4-difluorophenyl)morpholine-3-yl]ethanol

To a solution of (3R,5R)-3-(3,4-difluorophenyl)-5-(1-hydroxyethyl)morpholine-4-carboxylic acid 9H-fluorene-9-ylmethyl ester (950 mg) in acetonitrile (16 mL) was added diethylamine (4 mL), and the resultant solution was stirred for 1 hour at room temperature. The reaction solution was then diluted with toluene (20 mL), and solvent was removed by distillation under reduced pressure. The resulting residue was purified by silica gel column chromatography (heptane/ethyl acetate 4/1→1/1), to thereby obtain the titled compound (424 mg). The physical properties of this crude product were as follows.

ESI-MS; m/z 244 [M$^+$+H]. $^1$H-NMR (CDCl$_3$) δ (ppm): 1.22 (d, J=6.4 Hz, 3H), 3.00-3.48 (m, 3H), 3.73-3.80 (m, 2H), 3.90-4.03 (m, 2H), 7.08-7.12 (m, 2H), 7.24-7.29 (m, 1H).

Synthesis of (1S,6R,9aR)-6-(3,4-difluorophenyl)-1-methyltetrahydro-[1,4]oxazino[3,4-c][1,4]oxazine-3,4-dione To a solution consisting of 1-[(3R,5R)-5-(3,4-difluorophenyl)morpholine-3-yl]ethanol (424 mg) and pyridine (2 mL) in dichloromethane (8 mL) was dropwise added oxalyl chloride (417 μL) while cooling with ice. The resultant solution was stirred at the same temperature for 30 minutes. The reaction solution was diluted with water, and the organic layer was partitioned. The organic layer was then dried over magnesium sulfate. Solvent was removed by distillation under reduced pressure, and the resulting residue was purified by silica gel column chromatography (heptane/ethyl acetate 9/1→1/4), to thereby obtain the titled compound (353 mg). The physical properties of the compound were as follows.

ESI-MS; m/z 298 [M$^+$+H]. $^1$H-NMR (CDCl$_3$) δ (ppm): 1.52 (d, J=6.4 Hz, 3H), 3.51 (dd, J=11.6, 11.6 Hz, 1H), 3.74 (dd, J=10.8, 8.4 Hz, 1H), 4.05 (dd, J=11.2, 4.4 Hz, 1H), 4.18 (dd, J=12.4, 4.0 Hz, 1H), 4.54 (ddd, J=11.6, 4.0, 4.0 Hz, 1H), 4.66 (dq, J=13.2, 3.2 Hz, 1H), 4.86 (dd, J=7.2, 5.6 Hz, 1H), 7.13-7.23 (m, 3H).

Synthesis of (Z)-(1S,6R,9aR)-6-(3,4-difluorophenyl)-3-[3-methoxy-4-(4-methyl-1H-imidazole-1-yl)benzylidene]-1-methyltetrahydro[1,4]oxazino[3,4-c][1,4]oxazine-4-one A tetrahydrofuran (10 mL) solution containing (1S,6R,9aR)-6-(3,4-difluorophenyl)-1-methyltetrahydro-[1,4]oxazino[3,4-c][1,4]oxazine-3,4-dione (353 mg) was cooled to −30° C., and L-Selectride (1.55 mL, 1.06 M tetrahydrofuran solution) was dropwise added thereto. The resultant solution was stirred for 2 hours in the range of −20° C. to −30° C. To the reaction solution was added 5 N aqueous sodium hydroxide (235 μL), and this solution was stirred for 20 minutes in the range of −20° C. to 0° C. To the resultant solution was then added hydrogen peroxide water (114 μL, 35% aqueous), and the reaction mixture was stirred for 20 minutes at 0° C. To the resultant solution was then added sodium bisulfite (122 mg), and the mixture was stirred for 20 minutes at room temperature. The resultant solution was then diluted with ethyl acetate and brine, and the organic layer was partitioned. The organic layer was then dried over anhydrous magnesium sulfate, and solvent was removed by distillation under reduced pressure. A solution of the residue and triphenylphosphonium bromide (410 mg) in acetonitrile (10 mL) was heated to reflux for 2 hours. The temperature of the solution was returned to room temperature. To the solution was then added 3-methoxy-4-(4-methyl-1H-imidazole-1-yl)benzaldehyde (280 mg) and triethylamine (326 μL), and the resultant solution was stirred for 12 hours at room temperature. Solvent was removed by distillation under reduced pressure. The resultant product was then diluted with ethyl acetate and brine, and the organic layer was partitioned. Solvent was removed by distillation under reduced pressure, and the resulting residue was purified by silica gel column chromatography (carrier: Chromatorex NH; elution solvent: hexane/ethyl acetate→ethyl acetate), to thereby obtain the titled compound (270 mg). The physical properties of the compound were as follows.

ESI-MS; m/z 482 [M$^+$+H]. $^1$H-NMR (CDCl$_3$) δ (ppm): 1.48 (d, J=6.4 Hz, 3H), 2.29 (s, 3H), 3.51 (dd, J=11.2, 11.2 Hz, 1H), 3.73 (dd, J=12.4, 8.4z, 1H), 3.83 (s, 3H), 4.00 (dd, J=11.6, 4.0 Hz, 1H), 4.19 (dd, J=12.0, 4.8 Hz, 1H), 4.41 (ddd, J=11.6, 3.6, 3.6 Hz, 1H), 4.53 (dq, J=13.2, 2.8 Hz, 1H), 4.85 (dd, J=8.4, 4.4 Hz, 1H), 6.82 (s, 1H), 6.91 (s, 1H), 7.10-7.23 (m, 4H), 7.33-7.36 (m, 2H), 7.69 (d, J=1.6 Hz, 1H).

Synthesis of 3-{4-[(1S,6R,9aR)-6-(3,4-difluorophenyl)-1-methyl-4-oxotetrahydro[1,4]oxazino[3,4-c][1,4]oxazine-(3Z)-ylidenemethyl]-2-methoxyphenyl}-5-methyl-1-phosphonooxymethyl-3H-imidazole-1-ium trifluoroacetate A solution consisting of (Z)-(1S,6R,9aR)-6-(3,4-difluorophenyl)-3-[3-methoxy-4-(4-methylimidazole-1-yl)benzylidene]-1-methyltetrahydro[1,4]oxazino[3,4-c][1,4]oxazine-4-one (30 mg), chloromethyl ditertiary butyl phosphate (CAS No. 229625-50-7, 23.3 mg), sodium iodide (26.9 mg) and IPEA (2.6 μL) in acetone (1 mL) was heated to reflux for 3 hours. The reaction solution was left to cool to room temperature, and then concentrated under reduced pressure. To a solution of the obtained residue in chloroform (2 mL) was added TFA (2 mL), and the resultant mixture was stirred for 2 hours at room temperature. The reaction solution was then concentrated under reduced pressure, and the residue was purified using reversed-phase system C18 silica gel column chromatography (eluting solvent: 0.1% trifluoroacetic-acid-containing water/acetonitrile system), to thereby obtain the titled compound (11 mg). The physical properties of the compound were as follows. ESI-MS; m/z 592 [M$^+$]. $^1$H-NMR (CD$_3$OD) δ (ppm): 1.49 (d, J=6.4 Hz, 3H), 2.52 (s, 3H), 3.58 (dd, J=11.2 Hz, 1H), 3.74 (dd, J=12.4, 8.0 Hz, 1H), 3.93 (s, 3H), 4.05 (dd, J=11.2, 4.4 Hz, 1H), 4.21 (dd, J=12.0, 4.8 Hz, 1H), 4.50 (ddd, J=11.6, 4.0, 4.0 Hz, 1H), 4.69 (dd, J=6.8, 3.2 Hz, 1H), 4.83-4.88 (m, 1H), 5.96 (d, J=12.4 Hz, 2H), 6.75 (s, 1H), 7.21-7.33 (m, 3H), 7.49 (d, J=8.4 Hz, 1H), 7.53 (d, J=8.4 Hz, 1H), 7.64 (s, 1H), 7.67 (s, 1H), 9.42 (s, 1H).

Example 18

Synthesis of 3-{4-[(6R,9aR)-1,1-dimethyl-4-oxo-6-(3,4,5-trifluorophenyl)tetrahydro[1,4]oxazino[3,4-c][1,4]oxazine-(3Z)-ylidenemethyl]-2-methoxyphenyl}-5-methyl-1-phosphonooxymethyl-3H-imidazole-1-ium trifluoroacetate

[Formula 42]

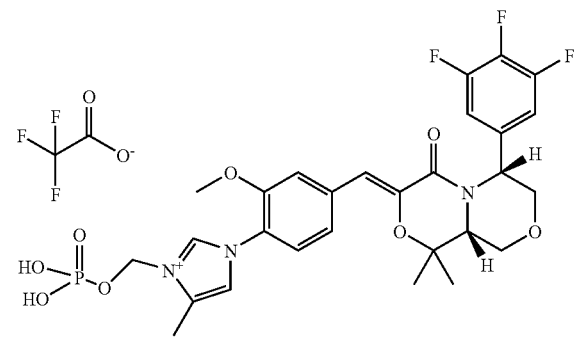

Synthesis of (3R,5R)-3-((R)-1-hydroxyethyl)-5-(3,4,5-trifluorophenyl)morpholine-4-carboxylic acid benzyl ester To a solution of (R)-1-[(3R,5R)-5-(3,4,5-trifluorophenyl)morpholine-3-yl]ethanol (2 g) in tetrahydrofuran (20 mL) was added saturated sodium bicarbonate water (20 mL) and benzyl chloroformate (1.31 mL). After stirring the reaction solution at room temperature for 16 hours, benzyl chloroformate (1.33 mL) was further added thereto, and the mixture was then stirred for another 20 hours. The resultant solution was diluted with water and ethyl acetate. The organic layer was partitioned, washed with brine, and then dried over anhydrous magnesium sulfate. Solvent was removed by distillation under reduced pressure, and the resulting residue was purified by silica gel column chromatography (heptane/ethyl acetate), to thereby obtain the titled compound (880 mg). The physical properties of this crude product were as follows.

$^1$H-NMR (CDCl$_3$) δ (ppm): 1.14 (d, J=7.2 Hz, 3H), 3.58-3.64 (m, 1H), 3.68 (dd, J=12.4, 4.0 Hz, 1H), 3.82 (dd, J=12.4, 4.0 Hz, 1H), 3.85 (dd, J=8.0, 4.0 Hz, 1H), 3.92 (d, J=12.0 Hz, 1H), 4.39 (d, J=12.8 Hz, 1H), 5.17 (brm, 1H), 5.20 (d, J=12.4 Hz, 1H), 5.27 (d, J=12.4 Hz, 1H), 7.28-7.38 (m, 7H).

Synthesis of (3R,5R)-3-acetyl-5-(3,4,5-trifluorophenyl)morpholine-4-carboxylic acid benzyl ester A solution of dimethylsulfoxide (0.22 mL) in tetrahydrofuran (15 mL) was cooled to −78° C. and then oxalyl chloride (246 μL) was dropwise added thereto. The resultant solution was stirred at the same temperature for 5 minutes, and to the reaction mixture was then dropwise added a solution of (3R,5R)-3-((R)-1-hydroxyethyl)-5-(3,4,5-trifluorophenyl)morpholine-4-carboxylic acid benzyl ester (880 mg) in tetrahydrofuran (5 mL). The resultant solution was stirred at the same temperature for 1 hour, and triethylamine (1.54 mL) was then added thereto. The temperature of this solution was returned to room temperature. The solution was then stirred for 1 hour. The reaction solution was diluted with aqueous ammonium chloride and ethyl acetate, and the organic layer was partitioned. The organic layer was dried over anhydrous magnesium sulfate. Solvent was removed by distillation under reduced pressure. The resultant product was purified by silica gel column chromatography (heptane/ethyl acetate), to thereby obtain the titled compound (800 mg). The physical properties of this crude product were as follows.

$^1$H-NMR (CDCl$_3$) δ (ppm): 1.63 (s, 3H), 3.62 (dd, J=11.6, 4.4 Hz, 1H), 3.85 (dd, J=12.4, 4.4 Hz, 1H), 4.19 (d, J=12.0 Hz, 1H), 4.42 (brm, 1H), 4.65 (d, J=12.0 Hz, 1H), 5.09 (brs, 1H), 5.21 (d, J=11.6 Hz, 1H), 5.29 (d, J=11.6 Hz, 1H), 7.24-7.38 (m, 7H).

Synthesis of 1-[(3R,5R)-5-(3,4,5-trifluorophenyl)morpholine-3-yl]ethanone

A suspension of (3R,5R)-3-acetyl-5-(3,4,5-trifluorophenyl)morpholine-4-carboxylic acid benzyl ester (800 mg) and 10% palladium-carbon (79.2 mg, 50% water content) in ethanol (15 mL) was stirred under a hydrogen atmosphere for 15 minutes. The catalyst was filtered off over Celite. The obtained filtrate was concentrated, to thereby obtain the titled compound (529 mg). The physical properties of the compound were as follows.

ESI-MS; m/z 260 [M$^+$+H].

Synthesis of 2-[(3R,5R)-5-(3,4,5-trifluorophenyl)morpholine-3-yl]propane-2-ol To a solution of 1-[(3R,5R)-5-(3,4,5-trifluorophenyl)morpholine-3-yl]ethanone (529 mg) in tetrahydrofuran (25 mL) was, under a nitrogen atmosphere, dropwise added methylmagnesium bromide (0.97 M tetrahydrofuran solution, 4.63 mL) at 0° C. The resultant solution was stirred for 1 hour at the same temperature, and then diluted with aqueous ammonium chloride and ethyl acetate. The organic layer was partitioned, washed with brine, and then dried over anhydrous magnesium sulfate. Solvent was removed by distillation under reduced pressure, and the resulting residue was purified by silica gel column chromatography (heptane/ethyl acetate), to thereby obtain the titled compound (330 mg). The physical properties of this crude product were as follows.

ESI-MS; m/z 276 [M$^+$+H]. $^1$H-NMR (CDCl$_3$) δ (ppm): 1.25 (s, 6H), 2.00 (s, 1H), 2.17 (brs, 1H), 2.91 (dd, J=10.8, 3.2 Hz, 1H), 3.11 (dd, J=10.8, 10.8 Hz, 1H), 3.35 (dd, J=10.8, 10.8 Hz, 1H), 3.73 (dd, J=10.8, 3.2 Hz, 1H), 3.90-3.97 (m, 2H), 7.06 (dd, J=8.4, 6.4 Hz, 2H).

Synthesis of (6R,9aR)-1,1-dimethyl-6-(3,4,5-trifluorophenyl)tetrahydro[1,4]oxazino[3,4-c][1,4]oxazine-3,4-dione To a solution of 2-[(3R,5R)-5-(3,4,5-trifluorophenyl)morpholine-3-yl]propane-2-ol (330 mg) and pyridine (2 mL) in chloroform (10 mL) was dropwise added oxalyl chloride (205 μL) while cooling with ice. The resultant solution was stirred at the same temperature for 1 hour, and then stirred for another 2 hours at room temperature. The resultant solution was diluted with water, and the organic layer was partitioned. The organic layer was washed with brine and then dried over anhydrous magnesium sulfate. Solvent was removed by distillation under reduced pressure. The resultant residue was purified by silica gel column chromatography (heptane/ethyl acetate), to thereby obtain the titled compound (260 mg). The physical properties of this crude product were as follows.

ESI-MS; m/z 330 [M$^+$+H]. $^1$H-NMR (CDCl$_3$) δ (ppm): 1.50 (S, 3H), 1.55 (s, 3H), 3.52 (dd, J=11.6, 11.6 Hz, 1H), 3.72 (dd, J=12.0, 7.6 Hz, 1H), 4.07 (dd, J=11.2, 4.4 Hz, 1H), 4.18 (dd, J=12.4, 4.8 Hz, 1H), 4.24 (dd, J=11.2, 4.4 Hz, 1H), 4.84 (dd, J=8.0, 4.8 Hz, 1H), 7.03 (dd, J=8.0, 6.4 Hz, 2H).

Synthesis of (6R,9aR)-3-[1-[3-methoxy-4-(4-methyl-1H-imidazole-1-yl)phenylmeth-(Z)-ylidene]-1,1-dimethyl-6-(3,4,5-trifluorophenyl)tetrahydro-[1,4]oxazino[3,4-c][1,4]oxazine-4-one To a tetrahydrofuran (10 mL) solution containing (6R,9aR)-1,1-dimethyl-6-(3,4,5-trifluorophenyl)tetrahydro[1,4]oxazino[3,4-c][1,4]oxazine-3,4-dione (260 mg) was dropwise added L-Selectride (1.14 mL, 1.02 M tetrahydrofuran solution) while cooling with ice. The resultant solution was stirred for 1 hour at the same temperature. To the reaction solution was added 5 N aqueous sodium hydroxide (173 μL), and the mixture was stirred for 20 minutes at the same temperature. To the solution was then added hydrogen peroxide water (305 μL, 35% aqueous), and the reaction mixture was stirred for 20 minutes at the same temperature. To the solution was then added sodium bisulfite (328 mg), and the mixture was stirred for 20 minutes at room temperature. The solution was then diluted with ethyl acetate and brine, and the organic layer was partitioned. The organic layer was then dried over anhydrous magnesium sulfate, and solvent was removed by distillation under reduced pressure. A solution of the residue and triphenylphosphonium bromide (302 mg) in acetonitrile (10 mL) was heated to reflux for 1 hour. The temperature of the solution was returned to room temperature. To the solution was then added 3-methoxy-4-(4-methyl-1H-imidazole-1-yl)benzaldehyde (206 mg) and triethylamine (240 μL), and the resultant solution was stirred for 20 hours at room temperature. Solvent was removed by distillation under reduced pressure. The resultant product was then diluted with ethyl acetate and brine, and the organic layer was partitioned. The organic layer was then dried over anhydrous magnesium sulfate. Solvent was removed by distillation under reduced pressure, and the resulting residue was purified by silica gel column chromatography (elution solvent: heptane/ethyl acetate→ethyl acetate), to thereby obtain the titled compound (210 mg). The physical properties of the compound were as follows.

ESI-MS; m/z 514 [M$^+$+H]. $^1$H-NMR (CDCl$_3$) δ (ppm): 1.49 (s, 3H), 1.52 (s, 3H), 2.29 (d, J=1.2 Hz, 3H), 3.50 (dd, J=7.2, 7.2 Hz, 1H), 3.71 (dd, J=12.4, 7.6 Hz, 1H), 3.85 (s, 3H), 4.05 (dd, J=11.2, 4.4 Hz, 1H), 4.15 (dd, J=12.0, 4.4 Hz, 1H), 4.20 (dd, J=12.4, 4.4 Hz, 1H), 4.85 (dd, J=7.6, 4.8 Hz, 1H), 6.81 (s, 1H), 6.93 (dd, J=0.8, 0.8 Hz, 1H), 7.04 (dd, J=8.0, 6.4 Hz, 2H), 7.21 (d, J=8.4 Hz, 1H), 7.30 (dd, J=8.4, 6.4 Hz, 1H), 7.48 (d, J=1.6 Hz, 1H), 7.71 (d, J=1.2 Hz, 1H)

Synthesis of 3-{4-[(6R,9aR)-1,1-dimethyl-4-oxo-6-(3,4,5-trifluorophenyl)tetrahydro[1,4]oxazino[3,4-c][1,4]oxazine-(3Z)-ylidenemethyl]-2-methoxyphenyl}-5-methyl-1-phosphonooxymethyl-3H-imidazole-1-ium trifluoroacetate A solution consisting of (6R,9aR)-3-[1-[3-methoxy-4-(4-methyl-1H-imidazole-1-yl)phenylmeth-(Z)-ylidene]-1,1-dimethyl-6-(3,4,5-trifluorophenyl)tetrahydro-[1,4]oxazino[3,4-c][1,4]oxazine-4-one (60 mg), chloromethyl ditertiary butyl phosphate (CAS No. 229625-50-7, 46.5 mg), sodium iodide (53.9 mg) and IPEA (5.2 μL) in acetone (2 mL) was heated to reflux for 3 hours. The reaction solution was left to cool to room temperature, and then concentrated under reduced pressure. To a solution of the obtained residue in chloroform (2 mL) was added TFA (2 mL), and the resultant mixture was stirred for 2 hours at room temperature. The reaction solution was then concentrated under reduced pressure, and the residue was purified using reversed-phase system C18 silica gel column chromatography (eluting solvent: 0.1% trifluoroacetic-acid-containing water/acetonitrile system), to thereby obtain the titled compound (15 mg). The physical properties of the compound were as follows. ESI-MS; m/z 624 [M$^+$]. $^1$H-NMR (CD$_3$OD) δ (ppm): 1.53 (s, 3H), 1.55 (s, 3H), 2.53 (s, 3H), 3.57-3.64 (m, 1H), 3.71 (dd, J=12.0, 8.0 Hz, 1H), 3.94 (s, 3H), 4.09 (dd, J=11.6, 4.8 Hz, 1H), 4.20 (dd, J=12.0, 4.8 Hz, 1H), 4.27 (dd, J=11.2, 4.4 Hz, 1H), 4.84 (dd, J=11.6, 4.8 Hz, 1H), 6.02 (d, J=12.8 Hz, 2H), 6.74 (s, 1H), 7.17 (dd, J=8.8, 6.4 Hz, 2H), 7.46-7.52 (m, 2H), 7.70 (s, 1H), 7.74 (s, 1H), 9.46 (s, 1H).

The present inventors have conducted the following tests for showing the usefulness of compounds represented by Formula (I) of the present invention.

Test Example 1

Solubility Test

Several milligram of each compound to be tested was precisely weighed, and 0.1 to 1.3 mL of the following test solutions were each added to the compound. The resulting mixture was stirred for several tens of seconds to several minutes for dispersing or dissolving the compound. Then, the supernatant was collected by centrifugation or filtration through a membrane. The concentration of the compound in the supernatant was quantitatively measured by an HPLC-UV method as an apparent solubility of the compound to each test solution.

pH 5: Diluted McIlvaine buffer solution (KANTO Chemical Co. Inc.)

pH 7: GIBCO™ Dulbecco's phosphate-buffered saline (Invitrogen Corporation)

Tables 1, 2 and 3 show the results.

TABLE 1

| Compound being tested | Solubility at pH 5 (mg/mL) | Solubility at pH 7 (mg/mL) |
|---|---|---|
| Example 2 | >10 | >10 |
| Example 3 | 1.24 | 1.12 |
| Example 4 | >10 | >10 |
| Example 5 | 0.32 | 0.46 |
| Example 7 | >10 | >10 |
| Example 8 | 0.96 | 1.69 |
| Example 9 | 3.45 | 4.72 |

TABLE 2

| Compound being tested | Solubility at pH 5 (mg/mL) | Solubility at pH 7 (mg/mL) |
|---|---|---|
| Example 6 | 9.14 | 8.89 |
| Example 10 | 9.59 | 9.76 |
| Example 11 | 7.68 | 8.11 |
| Example 12 | 3.44 | 1.83 |
| Example 13 | 9.33 | 9.15 |

TABLE 3

| Compound being tested | Solubility at pH 5 (mg/mL) | Solubility at pH 7 (mg/mL) |
|---|---|---|
| Example 14 | >10 | >10 |
| Example 15 | >10 | >10 |
| Example 16 | 1.15 | 1.12 |
| Example 17 | >10 | 7.55 |
| Example 18 | >10 | >10 |

As is obvious from the results shown in Tables 1, 2 and 3, the solubility of the compounds according to the present invention is significantly high.

Test Example 2

Evaluation of In Vitro Conversion

An aqueous solution of human placental alkaline phosphatase (5000 Units/L) was prepared and pre-incubated for 5 min. To this solution, each compound to be tested was added so that the final concentration of the compound was 0.1 mg/mL. The resulting reaction solution was incubated for 10 min, and then the same quantity of ice-cooled acetonitrile was added thereto. The resulting reaction solution was stirred to terminate the reaction. Then, the reaction solution was centrifuged and the obtained supernatant was analyzed by HPLC. It was confirmed from the results that each compound of the present invention was converted into the active parent compound in vitro.

Test Example 3

Evaluation of In Vivo Conversion

Each compound to be tested was orally administered to a rat, and plasma concentrations of the compound were monitored for 24 hr after the administration. Blood samples were collected longitudinally by drawing about 0.2 mL of blood sample from a jugular vein with a heparin-treated syringe each time. Plasma was prepared by centrifuging each blood sample and analyzed by an HPLC-MS method. It was confirmed from the results that each compound of the present invention was converted into an active parent compound in vivo.

The compound or its pharmacologically acceptable salt represented by Formula (I) of the present invention has an activity to decrease Aβ40 and Aβ42 synthesis and therefore is useful as a prodrug of a cinnamide compound which is a preventive or therapeutic agent for neurodegenerative diseases, such as Alzheimer's disease and Down syndrome, caused by Aβ.

The invention claimed is:

1. A compound represented by Formula (I) or its pharmacologically acceptable salt:

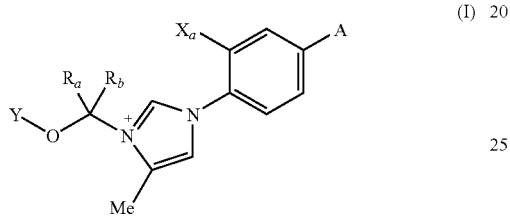

(I)

wherein
$R_a$ and $R_b$ are the same or different and each denote a hydrogen atom or a C1-6 alkyl group;
$X_a$ denotes a methoxy group or a fluorine atom;
Y denotes —CO—(O)$_n$—$R_c$·$M_a^-$, wherein $R_c$ denotes a C1-6 alkyl group, 6- to 14-membered aromatic hydrocarbon ring group, 5- to 14-membered aromatic heterocyclic group, 6- to 14-membered non-aromatic hydrocarbon ring group, or 5- to 14-membered non-aromatic heterocyclic group, which may be substituted with the same or different 1 to 5 substituents selected from Substituent Group A1; n is 0 or 1; and $M_a^-$ denotes an anion, —P(=O)(OR$_d$)$_2$·$M_a^-$, wherein $R_d$ denotes a C1-6 alkyl group which may be substituted with the same or different 1 to 3 substituents selected from Substituent Group A2, and $M_a^-$ denotes an anion, —P(=O)(OH)$_2$·$M_a^-$, wherein $M_a^-$ denotes an anion, —P(=O)(—O$^-$)(OH), or —P(=O)(—O$^-$)(—O$^-$·$M_b^+$), wherein $M_b^+$ denotes a cation;
A is represented by Formula (A-1):

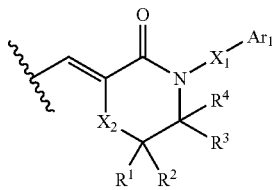

(A-1)

wherein
(a) $R^1$, $R^2$, $R^3$, and $R^4$ are the same or different and each denote a hydrogen atom or a C1-6 alkyl group, $X_1$ denotes a C1-6 alkylene group which may be substituted with 1 to 3 hydroxy or C1-6 alkyl groups which may be substituted with 1 to 3 hydroxy groups, $X_2$ denotes an oxygen atom or a methylene group which may be substituted with 1 or 2 C1-6 alkyl groups, and $Ar_1$ denotes —$X_{1-a}$—$Ar_{1-a}$, wherein $Ar_{1-a}$ denotes a 6- to 14-membered aromatic hydrocarbon ring or 5- to 14-membered aromatic heterocyclic group, which may be substituted with the same or different 1 to 3 substituents selected from Substituent Group A2, and $X_{1-a}$ denotes a single bond or an oxygen atom; or (b) $R^1$, $R^2$, $R^3$, $R^4$, and $X_2$ are the same as defined above, and $Ar_1$-$X_1$— denotes a C3-8 cycloalkyl group which has a methylene group which may be substituted with an oxygen atom condensed with a benzene ring which may be substituted with the same or different 1 to 3 substituents selected from Substituent Group A2, or A is represented by Formula (A-2):

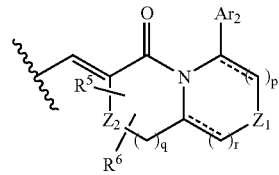

(A-2)

wherein ⁼ denotes a single bond or a double bond; $Ar_2$ denotes a 6- to 14-membered aromatic hydrocarbon ring or 5- to 14-membered aromatic heterocyclic group, which may be substituted with the same or different 1 to 3 substituents selected from Substituent Group A2; $R^5$ and $R^6$ are the same or different and each denote a substituent selected from Substituent Group A2; $Z_1$ and $Z_2$ are the same or different and each denote a methylene or vinylene group, which may be substituted with the same or different 1 or 2 substituents selected from Substituent Group A2, an oxygen atom, or an imino group which may be substituted with a C1-6 alkyl or C1-6 acyl group; and p, q, and r are the same or different and each denote an integer of 0 to 2, wherein Substituent Group A1 consists of (1) hydroxy groups, (2) cyano groups, (3) C3-8 cycloalkoxy groups, (4) C1-6 alkoxy groups which may be each substituted with 1 to 3 substituents selected from the group consisting of halogen atoms, hydroxy groups, cyano groups, C3-8 cycloalkyl groups, and C3-8 cycloalkoxy groups, (5) amino groups which may be each substituted with 1 or 2 C1-6 alkyl groups which may be each substituted with 1 to 3 halogen atoms, (6) carbamoyl groups which may be each substituted with 1 or 2 C1-6 alkyl groups which may be each substituted with 1 to 3 halogen atoms, (7) carboxyl groups, (8) pyridinyl groups, and (9) sugar residues; and Substituent Group A2 consists of (1) halogen atoms, (2) hydroxy groups, (3) cyano groups, (4) C3-8 cycloalkyl groups, (5) C3-8 cycloalkoxy groups, (6) C1-6 alkyl groups which may be each substituted with 1 to 3 substituents selected from the group consisting of halogen atoms, hydroxy groups, cyano groups, C3-8 cycloalkyl groups, C1-6 alkoxy groups, and C3-8 cycloalkoxy groups, (7) C1-6 alkoxy groups which may be each substituted with 1 to 3 substituents selected from the group consisting of halogen atoms, hydroxy groups, cyano groups, C3-8 cycloalkyl groups, and C3-8 cycloalkoxy groups, (8) amino groups which may be each substituted with 1 or 2 C1-6 alkyl groups which may be each substituted with 1 to 3 halogen atoms, and (9) carbamoyl groups which may be each substituted with 1 or 2 C1-6 alkyl groups which may be each substituted with 1 to 3 halogen atoms.

2. The compound or its pharmacologically acceptable salt according to claim 1, wherein $X_a$ denotes a methoxy group.

3. The compound or its pharmacologically acceptable salt according to claim 1, wherein $X_a$ denotes a fluorine atom.

4. The compound or its pharmacologically acceptable salt according to claim 1, wherein Y denotes —P(=O) (OH)$_2$·$M_a^-$, wherein $M_a^-$ denotes an anion, —P(=O) (—O$^-$) (OH), or —P(=O) (—O$^-$) (—O$^-$·$M_b^+$), wherein $M_b^+$ denotes a cation.

5. The compound or its pharmacologically acceptable salt according to claim 1, wherein $Ar_1$ denotes a 6- to 14-membered aromatic hydrocarbon ring or 5- to 14-membered aromatic heterocyclic group which may be substituted with the same or different 1 to 3 substituents selected from the aforementioned Substituent Group A2.

6. The compound or its pharmacologically acceptable salt according to claim 1, wherein $Ar_1$ denotes a phenyl or pyridinyl group, which may be substituted with the same or different 1 to 3 substituents selected from the aforementioned Substituent Group A2.

7. The compound or its pharmacologically acceptable salt according to claim 1, wherein $Ar_1$ denotes a phenyl group, a pyridinyl group, or a phenyl or pyridinyl group which has been substituted with 1 to 3 halogen atoms.

8. The compound or its pharmacologically acceptable salt according to claim 1, wherein $X_1$ denotes =CH—CH(OH)—$R^7$, wherein $R^7$ denotes a C1-6 alkyl group).

9. The compound or its pharmacologically acceptable salt according to claim 1, wherein $X_2$ denotes a methylene group.

10. The compound or its pharmacologically acceptable salt according to claim 1, wherein $X_2$ denotes an oxygen atom.

11. The compound or its pharmacologically acceptable salt according to claim 1, wherein $Z_1$ and $Z_2$ are the same or different and each denote an oxygen atom or a methylene group which may be substituted with 1 or 2 of C1-6 alkyl groups, halogen atoms, and hydroxy groups; and $R^5$ and $R^6$ are the same or different and each denote a C1-6 alkyl group, a halogen atom, or a hydrogen atom.

12. The compound or its pharmacologically acceptable salt according to claim 11, wherein $Z_1$ and $Z_2$ are the same or different and each denote a methylene group which may be substituted with 1 or 2 of C1-6 alkyl groups, halogen atoms, and hydroxy groups; and p, q, and r are each 1.

13. The compound or its pharmacologically acceptable salt according to claim 11, wherein $Z_1$ and $Z_2$ are the same or different and each denote a methylene group which may be substituted with 1 or 2 of C1-6 alkyl groups, halogen atoms, and hydroxy groups; p and q are each 1; and r is 0.

14. The compound or its pharmacologically acceptable salt according to claim 11, wherein $Z_1$ denotes a methylene group which may be substituted with 1 or 2 of C1-6 alkyl groups, halogen atoms, and hydroxy groups; $Z_2$ denotes an oxygen atom; and p, q, and r are each 1.

15. The compound or its pharmacologically acceptable salt according to claim 11, wherein $Z_1$ denotes an oxygen atom; $Z_2$ denotes a methylene group which may be substituted with 1 or 2 of C1-6 alkyl groups, halogen atoms, and hydroxy groups; and p, q, and r are each 1.

16. The compound or its pharmacologically acceptable salt according to claim 11, in which $Z_1$ denotes an oxygen atom; $Z_2$ denotes an oxygen atom; and p, q, and r are each 1.

17. The compound or its pharmacologically acceptable salt according to claim 11, wherein $Ar_2$ denotes a phenyl group which has been substituted with 1 to 3 halogen atoms.

18. The compound or its pharmacologically acceptable salt according to claim 11, wherein $Ar_2$ denotes a phenyl group which has been substituted with 2 or 3 halogen atoms.

19. The compound or its pharmacologically acceptable salt according to claim 1, wherein $R^5$ and $R^6$ are the same or different and each denote 1 or 2 of C1-6 alkyl groups, halogen atoms, and hydrogen atoms.

20. The compound or its pharmacologically acceptable salt according to claim 1, which is selected from the following group consisting of:

1) 3-{4-{1-[(S)-1-(4-fluorophenyl)ethyl]-2-oxopiperidin-(3E)-ylidenemethyl}-2-methoxyphenyl}-5-methyl-1-(phosphonooxymethyl)-3H-imidazol-1-ium trifluoroacetate, 2) 1-acetoxymethyl-3-{4-{1-[(S)-1-(4-fluorophenyl)ethyl]-2-oxopiperidin-(3E)-ylidenemethyl}-2-methoxyphenyl}-5-methyl-3H-imidazol-1-ium iodide, 3) 3-{4-{1-[(1R,2R)-2-hydroxy-1-(3,4,5-trifluorophenyl)propyl]-2-oxopiperidin-(3E)-ylidenemethyl}-2-methoxyphenyl}-5-methyl-1-(phosphonooxymethyl)-3H-imidazol-1-ium trifluoroacetate, 4) 3-[2-fluoro-4-[(S)-4-[(1R,2R)-2-hydroxy-1-(3,4,5-trifluorophenyl)propyl]-6-methyl-3-oxomorpholin-(2Z)-ylidenemethyl]phenyl]-5-methyl-1-phosphonooxymethyl-3H-imidazol-1-ium trifluoroacetate, 5) 3-{2-methoxy-4-[(3S,8aS)-5-oxo-3-(3,4,5-trifluorophenyl)hexahydroindolizin-(6E)-ylidenemethyl]phenyl}-5-methyl-1-phosphonooxymethyl-3H-imidazol-1-ium trifluoroacetate, 6) 3-{4-{(S)-4-[(S)-1-(2,6-difluoropyridin-3-yl)ethyl]-6-methyl-3-oxomorpholin-(2Z)-ylidenemethyl}-2-methoxyphenyl}-5-methyl-1-phosphonooxymethyl-3H-imidazol-1-ium chloride, 7) 3-{4-[(3S,8aS)-3-(4-chlorophenyl)-5-oxohexahydroindolizin-(6E)-ylidenemethyl]-2-methoxyphenyl}-5-methyl-1-(phosphonooxymethyl)-3H-imidazol-1-ium trifluoroacetate, 8) 3-{4-{(S)-4-[(1R,2R)-1-(3,4-difluorophenyl)-2-hydroxypropyl]-6-methyl-3-oxomorpholin-(2Z)-ylidenemethyl}-2-fluorophenyl}-5-methyl-1-phosphonooxymethyl-3H-imidazol-1-ium trifluoroacetate, 9) 3-{2-methoxy-4-[(6S,9aS)-4-oxo-6-(3,4,5-trifluorophenyl)hexahydroquinolizin-(3E)-ylidenemethyl]phenyl}-5-methyl-1-(phosphonooxymethyl)-3H-imidazol-1-ium trifluoroacetate, 10) 3-{2-methoxy-4-[(4R,9aS)-6-oxo-4-(3,4,5-trifluorophenyl)hexahydropyrido[2,1-c][1,4]oxazin-(7E)-ylidenemethyl]phenyl}-5-methyl-1-phosphonooxymethyl-3H-imidazol-1-ium trifluoroacetate, 11) 3-{4-{(S)-4-[(1R,2R)-2-hydroxy-1-(3,4,5-trifluorophenyl)propyl]-6-methyl-3-oxomorpholin-(2Z)-ylidenemethyl}-2-methoxyphenyl}-5-methyl-1-(phosphonooxymethyl)-3H-imidazol-1-ium trifluoroacetate, 12) 3-{4-[(6S,9aR)-6-(4-chlorophenyl)-4-oxohexahydroquinolizin-(3E)-ylidenemethyl]-2-methoxyphenyl}-5-methyl-1-phosphonooxymethyl-3H-imidazol-1-ium trifluoroacetate, 13) 3-{2-methoxy-4-[(1S,6R,9aR)-1-methyl-4-oxo-6-(3,4,5-trifluorophenyl)tetrahydro-[1,4]oxazino[3,4-c][1,4]oxazine-(3Z)-ylidenemethyl]phenyl}-5-methyl-1-phosphonooxymethyl-3H-imidazole-1-ium trifluoroacetate, 14) 3-{4-[(1S,6R,9aR)-6-(4-chlorophenyl)-1-methyl-4-oxotetrahydro[1,4]oxazino[3,4-c][1,4]oxazine-(3Z)- ylidenemethyl]-2-methoxyphenyl}-5-methyl-1-phosphonooxymethyl-3H-imidazole-1-ium trifluoroacetate, 15) 3-{2-methoxy-4-[(1S,6S,8aR)-1-methyl-4-oxo-6-(3,4,5-trifluorophenyl)tetrahydropyrrolo[2,1-c][1,4]oxazine-(3Z)-ylidenemethyl]phenyl}-5-methyl-1-phosphonooxymethyl-3H-imidazole-1-ium trifluoroacetate, 16) 3-{4-[(1S,6R,9aR)-6-(3,4-difluorophenyl)-1-methyl-4-oxotetrahydro[1,4]oxazino[3,4-c][1,4]oxazine-(3Z)-ylidenemethyl]-2-methoxyphenyl}-5-methyl-1-phosphonooxymethyl-3H-imidazole-1-ium trifluoroacetate, and 17) 3-{4-[(6R,9aR)-1,1-dimethyl-4-oxo-6-(3,4,5-trifluorophenyl)tetrahydro[1,4]oxazino[3,4-c][1,4]oxazine-(3Z)-ylidenemethyl]-2-methoxyphenyl}-5-methyl-1-phosphonooxymethyl-3H-imidazole-1-ium trifluoroacetate.

21. The compound according to the claim 1, which is selected from the following group consisting of:

1) 1-{4-[(E)-{1-[(1S)-1-(4-fluorophenyl)ethyl]-2-oxopiperidin-3-ylidene}methyl]-2-methoxyphenyl}-4-methyl-1H-imidazol-3-iomethyl monohydrogen phosphate, 2) 1-{4-[(E)-{1-[(1R,2R)-2-hydroxy-1-(3,4,5-trifluorophenyl)propyl]-2-oxopiperidin-3-ylidene}methyl]-2-methoxyphenyl}-4-methyl-1H-imidazol-3-iomethyl monohydrogen phosphate, 3) 1-{2-fluoro-4-[(Z)-{(6S)-4-[(1R,2R)-2-hydroxy-1-(3,4,5-trifluorophenyl)propyl]-6-methyl-3-oxomorpholin-2-ylidene}methyl]phenyl}-4-methyl-1H-imidazol-3-iomethyl monohydrogen phosphate, 4) 1-(2-methoxy-4-{(E)-[(3S,8aS)-5-oxo-3-(3,4,5-trifluorophenyl)hexahydroindolizin-6(5H)-ylidene]methyl}phenyl)-4-methyl-1H-imidazol-3-iomethyl monohydrogen phosphate, 5) 1-{4-[(Z)-{(6S)-4-[(1S)-1-(2,6-difluoropyridin-3-yl)ethyl]-6-methyl-3-oxomorpholin-2-ylidene}methyl]-2-methoxyphenyl}-4-methyl-1H-imidazol-3-iomethyl monohydrogen phosphate, 6) 1-(4-{(E)-[(3S,8aS)-3-(4-chlorophenyl)-5-oxohexahydroindolizin-6(5H)-ylidene]methyl}-2-methoxyphenyl)-4-methyl-1H-imidazol-3-iomethyl monohydrogen phosphate, 7) 1-{4-[(Z)-{(6S)-4-[(1R,2R)-1-(3,4-difluorophenyl)-2-hydroxypropyl]-6-methyl-3-oxomorpholin-2-ylidene}methyl]-2-fluorophenyl}-4-methyl-1H-imidazol-3-iomethyl monohydrogen phosphate, 8) 1-(2-methoxy-4-{(E)-[(6S,9aS)-4-oxo-6-(3,4,5-trifluorophenyl)hexahydro-2H-quinolizin-3(4H)-ylidene]methyl}phenyl)-4-methyl-1H-imidazol-3-iomethyl monohydrogen phosphate, 9) 1-(2-methoxy-4-{(E)-[(4R,9aS)-6-oxo-4-(3,4,5-trifluorophenyl)hexahydropyrido[2,1-c][1,4]oxazin-7(6H)-ylidene]methyl}phenyl)-4-methyl-1H-imidazol-3-iomethyl monohydrogen phosphate, 10) 1-{4-[(Z)-{(6S)-4-[(1R,2R)-2-hydroxy-1-(3,4,5-trifluorophenyl)propyl]-6-methyl-3-oxomorpholin-2-ylidene}methyl]-2-methoxyphenyl}-4-methyl-1H-imidazol-3-iomethyl monohydrogen phosphate, 11) 1-(4-{(E)-[(6S,9aR)-6-(4-chlorophenyl)-4-oxohexahydro-2H-quinolizin-3(4H)-ylidene]methyl}-2-methoxyphenyl)-4-methyl-1H-imidazol-3-iomethyl monohydrogen phosphate, 12) 1-(2-methoxy-4-{(Z)-[(1S,6R,9aR)-1-methyl-4-oxo-6-(3,4,5-trifluorophenyl)tetrahydro-1H-[1,4]oxazino[3,4-c][1,4]oxazin-3(4H)-ylidene]methyl}phenyl)-4-methyl-1H-imidazol-3-iomethyl monohydrogen phosphate, 13) 1-(4-{(Z)-[(1S,6R,9aR)-6-(4-chlorophenyl)-1-methyl-4-oxotetrahydro-1H-[1,4]oxazino[3,4-c][1,4]oxazin-3(4H)-ylidene]methyl}-2-methoxyphenyl)-4-methyl-1H-imidazol-3-iomethyl monohydrogen phosphate, 14) 1-(2-methoxy-4-{(Z)-[(1S,6S,8aS)-1-methyl-4-oxo-6-(3,4,5-trifluorophenyl)tetrahydro-1H-pyrrolo[2,1-c][1,4]oxazin-3(4H)-ylidene]methyl}phenyl)-4-methyl-1H-imidazol-3-iomethyl monohydrogen phosphate, 15) 1-(4-{(Z)-[(1S,6R,9aR)-6-(3,4-difluorophenyl)-1-methyl-4-oxotetrahydro-1H-[1,4]oxazino[3,4-c][1,4]oxazin-3(4H)-ylidene]methyl}-2-methoxyphenyl)-4-methyl-1H-imidazol-3-iomethyl monohydrogen phosphate and 16) 1-(4-{(Z)-[(6R,9aR)-1,1-dimethyl-4-oxo-6-(3,4,5-trifluorophenyl)tetrahydro-1H-[1,4]oxazino[3,4-c][1,4]oxazin-3(4H)-ylidene]methyl}-2-methoxyphenyl)-4-methyl-1H-imidazol-3-iomethyl monohydrogen phosphate.

22. A drug containing a compound or its pharmacologically acceptable salt according to any one of claims 1 to 21 as an active ingredient.

* * * * *